US010005738B2

(12) United States Patent
Lai et al.

(10) Patent No.: US 10,005,738 B2
(45) Date of Patent: *Jun. 26, 2018

(54) SALTS OF AN EPIDERMAL GROWTH FACTOR RECEPTOR KINASE INHIBITOR

(71) Applicant: Celgene CAR LLC, Pembroke (BM)

(72) Inventors: Mei Lai, Longmont, CO (US); Steven Richard Witowski, Cumming, GA (US); Richland Wayne Tester, Marlborough, MA (US); Kwangho Lee, Daejeon (KR)

(73) Assignee: Celgene CAR LLC, Pembroke (BM)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/401,637

(22) Filed: Jan. 9, 2017

(65) Prior Publication Data
US 2017/0217904 A1    Aug. 3, 2017

Related U.S. Application Data

(63) Continuation of application No. 14/822,366, filed on Aug. 10, 2015, now Pat. No. 9,540,335, which is a continuation of application No. 13/801,191, filed on Mar. 13, 2013, now Pat. No. 9,108,927.

(60) Provisional application No. 61/611,400, filed on Mar. 15, 2012.

(51) Int. Cl.
| | | |
|---|---|---|
| *C07D 239/49* | (2006.01) | |
| *C07D 239/48* | (2006.01) | |
| *C07C 55/02* | (2006.01) | |
| *C07C 55/07* | (2006.01) | |
| *C07C 62/02* | (2006.01) | |
| *C07C 309/04* | (2006.01) | |
| *C07C 309/05* | (2006.01) | |
| *C07C 309/27* | (2006.01) | |
| *C07C 309/29* | (2006.01) | |
| *C07C 309/30* | (2006.01) | |
| *C07C 309/35* | (2006.01) | |

(52) U.S. Cl.
CPC ............ *C07D 239/48* (2013.01); *C07C 55/02* (2013.01); *C07C 55/07* (2013.01); *C07C 62/02* (2013.01); *C07C 309/04* (2013.01); *C07C 309/05* (2013.01); *C07C 309/27* (2013.01); *C07C 309/29* (2013.01); *C07C 309/30* (2013.01); *C07C 309/35* (2013.01); *C07B 2200/13* (2013.01)

(58) Field of Classification Search
CPC .......................... C07D 239/49; C07D 239/48
See application file for complete search history.

(56) References Cited

U.S. PATENT DOCUMENTS

| | | |
|---|---|---|
| 3,609,152 A | 9/1971 | Hess et al. |
| 4,032,637 A | 6/1977 | Spiegel et al. |
| 4,337,341 A | 6/1982 | Zimmerman |
| 4,879,303 A | 11/1989 | Davison et al. |
| 5,453,510 A | 9/1995 | Hill et al. |
| 5,958,935 A | 9/1999 | Davis et al. |
| 6,093,716 A | 7/2000 | Davis et al. |
| 6,114,333 A | 9/2000 | Davis et al. |
| 6,127,376 A | 10/2000 | Davey et al. |
| 6,160,010 A | 12/2000 | Uckun et al. |
| 6,262,088 B1 | 7/2001 | Phillips |
| 6,469,168 B1 | 10/2002 | Ratzne Simonek et al. |
| 6,579,983 B1 | 6/2003 | Batchelor et al. |
| 6,593,326 B1 | 7/2003 | Bradbury et al. |
| 6,838,464 B2 | 1/2005 | Pease et al. |
| 6,908,906 B2 | 6/2005 | Takita et al. |
| 6,939,874 B2 | 9/2005 | Harmange et al. |
| 7,060,827 B2 | 6/2006 | Singh et al. |
| 7,122,542 B2 | 10/2006 | Singh et al. |
| 7,125,879 B2 | 10/2006 | Guillemont et al. |
| 7,176,212 B2 | 2/2007 | Breault et al. |
| 7,202,033 B2 | 4/2007 | Prescott et al. |
| 7,241,769 B2 | 7/2007 | Stadtmueller et al. |
| 7,282,504 B2 | 10/2007 | Armistead et al. |
| 7,329,671 B2 | 2/2008 | Singh et al. |
| 7,329,672 B2 | 2/2008 | Singh et al. |
| 7,332,484 B2 | 2/2008 | Singh et al. |
| 7,435,814 B2 | 10/2008 | Singh et al. |
| 7,452,879 B2 | 11/2008 | Singh et al. |
| 7,485,724 B2 | 2/2009 | Singh et al. |
| 7,491,732 B2 | 2/2009 | Li et al. |
| 7,498,435 B2 | 3/2009 | Singh et al. |
| 7,504,396 B2 | 3/2009 | Nunes et al. |
| 7,514,444 B2 | 4/2009 | Honigberg et al. |
| 7,514,445 B2 | 4/2009 | Freyne et al. |
| 7,514,446 B2 | 4/2009 | Davis-Ward et al. |
| 7,528,143 B2 | 5/2009 | Noronha et al. |
| 7,531,548 B2 | 5/2009 | Guillemont et al. |
| 7,550,460 B2 | 6/2009 | Singh et al. |
| 7,557,210 B2 | 7/2009 | Singh et al. |
| 7,582,648 B2 | 9/2009 | Singh et al. |
| 7,589,200 B2 | 9/2009 | Singh et al. |
| 7,642,351 B2 | 1/2010 | Singh et al. |
| 7,655,797 B2 | 2/2010 | Singh et al. |
| 7,718,662 B1 | 5/2010 | Chen et al. |
| 7,741,330 B1 | 6/2010 | Chen et al. |
| 7,803,939 B2 | 9/2010 | Singh et al. |
| 7,820,819 B2 | 10/2010 | Singh et al. |
| 7,858,633 B2 | 12/2010 | Li et al. |

(Continued)

FOREIGN PATENT DOCUMENTS

| | | |
|---|---|---|
| CN | 87102493 A | 10/1987 |
| CN | 1359375 A | 7/2002 |

(Continued)

OTHER PUBLICATIONS

U.S. Appl. No. 13/518,833, filed Jun. 22, 2012, Gray et al.

(Continued)

*Primary Examiner* — Shirley V Gembeh
(74) *Attorney, Agent, or Firm* — Choate, Hall & Stewart LLP; Kristen C. Buteau; Michael A. Shinall

(57) ABSTRACT

The present invention provides a salt form and compositions thereof, which are useful as an inhibitor of EGFR kinases and which exhibits desirable characteristics for the same.

20 Claims, 87 Drawing Sheets

(56) References Cited

U.S. PATENT DOCUMENTS

| | | |
|---|---|---|
| 7,884,111 B2 | 2/2011 | Argade et al. |
| 8,088,781 B2 | 1/2012 | Honigberg et al. |
| 8,338,439 B2 | 12/2012 | Singh et al. |
| 8,450,335 B2 | 5/2013 | Singh et al. |
| 8,501,751 B2 | 8/2013 | Honigberg et al. |
| 8,563,568 B2 | 10/2013 | Witowski et al. |
| 8,609,679 B2 | 12/2013 | Singh et al. |
| 8,710,222 B2 | 4/2014 | Singh et al. |
| 8,796,255 B2 | 8/2014 | Lee et al. |
| 8,975,249 B2 | 3/2015 | Lee et al. |
| 9,056,839 B2 | 6/2015 | Lai |
| 9,108,927 B2 | 8/2015 | Lai et al. |
| 9,212,181 B2 | 12/2015 | Singh et al. |
| 9,238,629 B2 | 1/2016 | Lee et al. |
| 9,296,737 B2 | 3/2016 | Singh et al. |
| 9,539,255 B2 | 1/2017 | Lai |
| 9,540,335 B2 | 1/2017 | Lai et al. |
| 2004/0002395 A1 | 1/2004 | Poynor |
| 2004/0019067 A1 | 1/2004 | Armistead et al. |
| 2004/0023957 A1 | 2/2004 | Wang et al. |
| 2004/0077661 A1 | 4/2004 | Arbiser |
| 2005/0004125 A1 | 1/2005 | Freyne et al. |
| 2005/0014753 A1 | 1/2005 | Ding et al. |
| 2005/0085637 A1 | 4/2005 | Cheung et al. |
| 2005/0209221 A1 | 9/2005 | Nunes et al. |
| 2005/0272083 A1 | 12/2005 | Seshagiri |
| 2006/0030018 A1 | 2/2006 | Zuccola et al. |
| 2006/0079543 A1 | 4/2006 | Sum et al. |
| 2006/0084644 A1 | 4/2006 | Pal et al. |
| 2006/0084645 A1 | 4/2006 | Pal et al. |
| 2006/0100227 A1 | 5/2006 | Baenteli et al. |
| 2006/0148800 A1 | 7/2006 | Stadtmueller et al. |
| 2006/0160803 A1 | 7/2006 | Adams et al. |
| 2006/0247241 A1 | 11/2006 | Garcia-Echeverria et al. |
| 2006/0247262 A1 | 11/2006 | Baenteli et al. |
| 2006/0270694 A1 | 11/2006 | Wong |
| 2006/0293311 A1 | 12/2006 | Li et al. |
| 2007/0010668 A1 | 1/2007 | Davis-Ward et al. |
| 2007/0032493 A1 | 2/2007 | Foley et al. |
| 2007/0066658 A1 | 3/2007 | Chappell |
| 2007/0203161 A1 | 8/2007 | Argade et al. |
| 2007/0203162 A1 | 8/2007 | Li et al. |
| 2007/0259904 A1 | 11/2007 | Noronha et al. |
| 2008/0009484 A1 | 1/2008 | Argade et al. |
| 2008/0009494 A1 | 1/2008 | Li et al. |
| 2008/0021020 A1 | 1/2008 | Argade et al. |
| 2008/0027045 A1 | 1/2008 | Argade et al. |
| 2008/0039622 A1 | 2/2008 | Singh et al. |
| 2008/0058358 A1 | 3/2008 | Luecking et al. |
| 2008/0076921 A1 | 3/2008 | Honigberg et al. |
| 2008/0132504 A1 | 6/2008 | Garcia-Echeverria et al. |
| 2008/0139582 A1 | 6/2008 | Honigberg et al. |
| 2008/0167330 A1 | 7/2008 | Luecking et al. |
| 2008/0176866 A1 | 7/2008 | Jautelat et al. |
| 2008/0182852 A1 | 7/2008 | Johnson et al. |
| 2008/0194603 A1 | 8/2008 | Li et al. |
| 2008/0194605 A1 | 8/2008 | Heinrich et al. |
| 2008/0207613 A1 | 8/2008 | Styles et al. |
| 2008/0207913 A1 | 8/2008 | Breitenkamp et al. |
| 2008/0214501 A1 | 9/2008 | Pan et al. |
| 2008/0260754 A1 | 10/2008 | Li et al. |
| 2008/0279867 A1 | 11/2008 | Atuegbu et al. |
| 2008/0300268 A1 | 12/2008 | Singh et al. |
| 2008/0312438 A1 | 12/2008 | Singh et al. |
| 2009/0131436 A1 | 5/2009 | Imbach et al. |
| 2009/0137588 A1 | 5/2009 | Singh et al. |
| 2009/0156622 A1 | 6/2009 | Singh et al. |
| 2009/0171086 A1 | 7/2009 | Singh et al. |
| 2009/0181987 A1 | 7/2009 | Honigberg et al. |
| 2009/0215803 A1 | 8/2009 | Rice et al. |
| 2009/0286778 A1 | 11/2009 | Combs et al. |
| 2009/0298830 A1 | 12/2009 | Mann et al. |
| 2009/0318407 A1 | 12/2009 | Bauer et al. |
| 2010/0004270 A1 | 1/2010 | Honigberg et al. |
| 2010/0016296 A1 | 1/2010 | Singh et al. |
| 2010/0022561 A1 | 1/2010 | Honigberg et al. |
| 2010/0029610 A1 | 2/2010 | Singh et al. |
| 2010/0041677 A1 | 2/2010 | Honigberg et al. |
| 2010/0081679 A1 | 4/2010 | Greul et al. |
| 2010/0088912 A1 | 4/2010 | Higgs et al. |
| 2010/0173285 A1 | 7/2010 | Varmus et al. |
| 2010/0197918 A1 | 8/2010 | Singh et al. |
| 2010/0249092 A1 | 9/2010 | Singh et al. |
| 2010/0254905 A1 | 10/2010 | Honigberg et al. |
| 2011/0039868 A1 | 2/2011 | Honigberg et al. |
| 2011/0105472 A1 | 5/2011 | Greul et al. |
| 2011/0207736 A1 | 8/2011 | Gray et al. |
| 2011/0224235 A1 | 9/2011 | Honigberg et al. |
| 2011/0245156 A1 | 10/2011 | Sielecki-Dzurdz |
| 2011/0245284 A1 | 10/2011 | Greul et al. |
| 2011/0281322 A1 | 11/2011 | Honigberg et al. |
| 2012/0040968 A1 | 2/2012 | Shimada et al. |
| 2012/0065201 A1 | 3/2012 | Honigberg et al. |
| 2012/0071497 A1 | 3/2012 | Buggy et al. |
| 2012/0077832 A1 | 3/2012 | Witowski et al. |
| 2012/0083006 A1 | 4/2012 | Ramsden et al. |
| 2012/0087915 A1 | 4/2012 | Buggy et al. |
| 2012/0088912 A1 | 4/2012 | Honigberg et al. |
| 2012/0094999 A1 | 4/2012 | Gray et al. |
| 2012/0101113 A1 | 4/2012 | Honigberg et al. |
| 2012/0101114 A1 | 4/2012 | Honigberg et al. |
| 2012/0149687 A1 | 6/2012 | Lee et al. |
| 2012/0149722 A1 | 6/2012 | Lee et al. |
| 2012/0157426 A1 | 6/2012 | Lee et al. |
| 2012/0165328 A1 | 6/2012 | Honigberg et al. |
| 2012/0165332 A1 | 6/2012 | Major et al. |
| 2012/0184013 A1 | 7/2012 | Honigberg et al. |
| 2012/0184567 A1 | 7/2012 | Honigberg et al. |
| 2012/0202264 A1 | 8/2012 | Honigberg et al. |
| 2012/0270237 A9 | 10/2012 | Ramsden et al. |
| 2012/0296089 A1 | 11/2012 | Honigberg et al. |
| 2012/0316135 A1 | 12/2012 | Dalgarno et al. |
| 2012/0329130 A1 | 12/2012 | Honigberg et al. |
| 2013/0065879 A1 | 3/2013 | Singh et al. |
| 2013/0065899 A1 | 3/2013 | Singh et al. |
| 2013/0072469 A1 | 3/2013 | Singh et al. |
| 2013/0137708 A1 | 5/2013 | Garske et al. |
| 2013/0165462 A1 | 6/2013 | Singh et al. |
| 2013/0267530 A1 | 10/2013 | Lai |
| 2013/0267531 A1 | 10/2013 | Lai et al. |
| 2014/0057929 A1 | 2/2014 | Witowski et al. |
| 2014/0134265 A1 | 5/2014 | Buggy et al. |
| 2014/0142123 A1 | 5/2014 | Honigberg et al. |
| 2014/0163046 A1 | 6/2014 | Honigberg et al. |
| 2014/0187564 A1 | 7/2014 | Honigberg et al. |
| 2014/0187565 A1 | 7/2014 | Honigberg et al. |
| 2014/0213574 A1 | 7/2014 | Singh et al. |
| 2015/0025055 A1 | 1/2015 | Lee et al. |
| 2015/0246040 A1 | 9/2015 | Lee et al. |
| 2015/0344441 A1 | 12/2015 | Lai et al. |
| 2016/0022677 A1 | 1/2016 | Lai |
| 2017/0281623 A1 | 10/2017 | Lai |

FOREIGN PATENT DOCUMENTS

| | | |
|---|---|---|
| EP | 1 054 004 A1 | 11/2000 |
| JP | H0741461 A | 2/1995 |
| WO | WO-96/28427 A1 | 9/1996 |
| WO | WO-97/19065 A1 | 5/1997 |
| WO | WO-99/31073 A1 | 6/1999 |
| WO | WO-00/027825 A1 | 5/2000 |
| WO | WO-00/046203 A2 | 8/2000 |
| WO | WO-00/078731 A1 | 12/2000 |
| WO | WO-01/047897 A1 | 7/2001 |
| WO | WO-01/060816 A1 | 8/2001 |
| WO | WO-01/064654 A1 | 9/2001 |
| WO | WO-01/064655 A1 | 9/2001 |
| WO | WO-01/085699 A2 | 11/2001 |
| WO | WO-02/083653 A1 | 10/2002 |
| WO | WO-03/016306 A1 | 2/2003 |
| WO | WO-03/030909 A1 | 4/2003 |
| WO | WO-03/063794 A2 | 8/2003 |
| WO | WO-03/066601 A1 | 8/2003 |
| WO | WO-2004/014382 A1 | 2/2004 |

(56) References Cited

FOREIGN PATENT DOCUMENTS

| | | |
|---|---|---|
| WO | WO-2004/031232 A1 | 4/2004 |
| WO | WO-2004/056786 A2 | 7/2004 |
| WO | WO-2004/069812 A1 | 8/2004 |
| WO | WO-2004/074244 A2 | 9/2004 |
| WO | WO-2004/080980 A1 | 9/2004 |
| WO | WO-2004/096224 A2 | 11/2004 |
| WO | WO-2005/013996 A2 | 2/2005 |
| WO | WO-2005/016893 A2 | 2/2005 |
| WO | WO-2005/016894 A1 | 2/2005 |
| WO | WO-2005/026130 A1 | 3/2005 |
| WO | WO-2005/026158 A1 | 3/2005 |
| WO | WO-2005/063722 A1 | 7/2005 |
| WO | WO-2005/070890 A2 | 8/2005 |
| WO | WO-2006/021544 A1 | 3/2006 |
| WO | WO-2006/045066 A2 | 4/2006 |
| WO | WO-2006/053109 A1 | 5/2006 |
| WO | WO-2006/055561 A2 | 5/2006 |
| WO | WO-2006/068770 A1 | 6/2006 |
| WO | WO-2006/074057 A2 | 7/2006 |
| WO | WO-2006/078846 A1 | 7/2006 |
| WO | WO-2006/101977 A2 | 9/2006 |
| WO | WO-2006/108487 A1 | 10/2006 |
| WO | WO-2006/124874 A2 | 11/2006 |
| WO | WO-2006/128129 A2 | 11/2006 |
| WO | WO-2006/129100 A1 | 12/2006 |
| WO | WO-2006/133426 A2 | 12/2006 |
| WO | WO-2007/027238 A2 | 3/2007 |
| WO | WO-2007/048064 A2 | 4/2007 |
| WO | WO-2007/053452 A1 | 5/2007 |
| WO | WO-2007/056151 A2 | 5/2007 |
| WO | WO-2007/085833 A2 | 8/2007 |
| WO | WO-2007/089768 A2 | 8/2007 |
| WO | WO-2007/113254 A1 | 10/2007 |
| WO | WO-2007/113256 A1 | 10/2007 |
| WO | WO-2007/120339 A1 | 10/2007 |
| WO | WO-2007/120980 A2 | 10/2007 |
| WO | WO-2007/125351 A1 | 11/2007 |
| WO | WO-2008/005538 A2 | 1/2008 |
| WO | WO-2008/009458 A1 | 1/2008 |
| WO | WO-2008/025556 A1 | 3/2008 |
| WO | WO-2008/049123 A2 | 4/2008 |
| WO | WO-2008/064274 A1 | 5/2008 |
| WO | WO-2008/073687 A2 | 6/2008 |
| WO | WO-2008/074515 A1 | 6/2008 |
| WO | WO-2008/079719 A1 | 7/2008 |
| WO | WO-2008/079907 A1 | 7/2008 |
| WO | WO-2008/080964 A1 | 7/2008 |
| WO | WO-2008/080965 A2 | 7/2008 |
| WO | WO-2008/088303 A1 | 7/2008 |
| WO | WO-2008/092199 A1 | 8/2008 |
| WO | WO-2008/093687 A1 | 8/2008 |
| WO | WO-2008/107096 A1 | 9/2008 |
| WO | WO-2008/115738 A1 | 9/2008 |
| WO | WO-2008/115742 A1 | 9/2008 |
| WO | WO-2008/118822 A1 | 10/2008 |
| WO | WO-2008/118823 A2 | 10/2008 |
| WO | WO-2009/012421 A1 | 1/2009 |
| WO | WO-2009/017838 A2 | 2/2009 |
| WO | WO-2009/029682 A1 | 3/2009 |
| WO | WO-2009/032668 A2 | 3/2009 |
| WO | WO-2009/032694 A1 | 3/2009 |
| WO | WO-2009/032703 A1 | 3/2009 |
| WO | WO-2009/080638 A2 | 7/2009 |
| WO | WO-2009/105675 A1 | 8/2009 |
| WO | WO-2009/112490 A1 | 9/2009 |
| WO | WO-2009/115267 A2 | 9/2009 |
| WO | WO-2009/127642 A2 | 10/2009 |
| WO | WO-2009/132202 A2 | 10/2009 |
| WO | WO-2009/143389 A1 | 11/2009 |
| WO | WO-2009/158571 A1 | 12/2009 |
| WO | WO-2010/025833 A1 | 3/2010 |
| WO | WO-2010/081679 A2 | 7/2010 |
| WO | WO-2010/129053 A2 | 11/2010 |
| WO | WO-2011/079231 A1 | 6/2011 |
| WO | WO-2011/090760 A1 | 7/2011 |
| WO | WO-2011/140338 A1 | 11/2011 |
| WO | WO-2011/153514 A2 | 12/2011 |
| WO | WO-2012/021444 A1 | 2/2012 |
| WO | WO-2012/061299 A1 | 5/2012 |
| WO | WO-2012/061303 A1 | 5/2012 |
| WO | WO-2012/061415 A1 | 5/2012 |
| WO | WO-2012/064706 A1 | 5/2012 |
| WO | WO-2012/158843 A2 | 11/2012 |
| WO | WO-2013/138495 A1 | 9/2013 |
| WO | WO-2013/138502 A1 | 9/2013 |

OTHER PUBLICATIONS

Adeyeye, Moji, Ed., Preformulation in Solid Dosage Form Development, Chapter 2.3, Informa Healthcare, 63-80 (2008).
Aliagas-Martin, I. et al., A class of 2,4-bisanilinopyrimidine Aurora A inhibitors with unusually high selectivity against Aurora B, J. Med. Chem. 52:3300-3307 (2009).
Andrulis, I. et al., Neu/ErbB-2 amplification identifies a poor-prognosis group of women with node-negative breast cancer, J Clin Oncol 16:1340-9 (1998).
Bamborough, P. et al., N-4-Pyrimidinyl-1H-indazol-4-amine inhibitors of Lck: Indazoles as phenol isosteres with improved pharmacokinetics, Bioorg. & Med. Chem. Lett. 17:4363-4368 (2007).
Bastin, R.J. et al., Salt Selection and Optimisation Procedures for Pharmaceutical New Chemical Entities, Organic Process Research & Development, 4: 427-435, (2000).
Calvo, E. et al., Administration of CI-1033, an Irreversible Pan-erbB Tyrosine Kinase Inhibitor, Is Feasible on a 7-Day Off Schedule: A Phase I Pharmacokinetic and Food Effect Study, Clinical Cancer Research, 10: 7112-7120 (2004).
Carter, T. et al, Inhibition of drug-resistant mutants of ABL, KIT, and EGF receptor kinases, Proc. Natl. Acad. Sci. USA 102(31):11011-11016 (2005).
Clovis Oncology, Press Release, "Clovis Oncology's CO-1686 Demonstrates Compelling Clinical Activity and Progression-free Survival (PFS) in Updated Phase 1/2 Study Results in Patients with EGFR-Mutant Non-small Cell Lung Cancer (NSCLC)", May 31, 2014.
Cohen, M. et al., Structural bioinformatics-based design of selective, irreversible inhibitors, Science 308:1318-1321 (2005).
Curto, M. et al., Contact-dependent inhibition of EGFR signaling by Nf2/Merlin, J Cell Biol 177:893-903 (2007).
Ding, K. et al., Design, Synthesis and Biological Evaluation of Novel Conformationally Constrained Inhibitors Targeting Epidermal Growth Factor Receptor T790M mutant, J. Med. Chem., Just Accepted Manuscript, 1-36 (2012).
Extended European Search Report for EP11816874.9, 5 pages (dated Dec. 12, 2014).
Extended European Search Report for EP11838624.2, 5 pages (dated Jun. 6, 2014).
Extended European Search Report for EP11838628.3, 7 pages (dated Jun. 20, 2014).
Extended European Search Report for EP11839800.7, 8 pages (dated Jun. 24, 2014).
Extended European Search Report for EP13761487.1, 7 pages (dated Aug. 20, 2015).
Fabian, M. et al., a small molecule-kinase interaction map for clinical kinase inhibitors, Nature Biotechnology, 23(3): 329 (2005).
Fallon, K. et al., Constitutive activation of the neuregulin-1/erbB signaling pathway promotes the proliferation of a human peripheral neuroepithelioma cell line, J Neuro Oncol 66:273-84 (2004).
Frank, D., STAT signaling in the pathogenesis and treatment of cancer, Mol. Med. 5 :432-456 (1999).
Fry, D. et al., Specific, irreversible inactivation of the epidermal growth factor receptor and erbB2, by a new class of tyrosine kinase inhibitor, Proc. Natl. Acad. Sci. USA 95:12022-12027 (1998).
Ghoneim, K., Synthesis and evaluation of some 2-, 4-, di-substituted-6-methylpyrimidine derivatives for antimicrobial activity, J. Indian Chem. Soc. 63(10):914-917 (1986).
Ghosh, D., 2-4-bis (arylamino)-5-methylpyrimidines as antimicrobial agents, J. Med. Chem. 10(5):974 (1967).

(56) References Cited

OTHER PUBLICATIONS

Ghosh, D., 2-4-bis (arylamino)-6-methylpyrimidines as antimicrobial agents, J. Indian Chem. Soc. 58(5):512-573 (1981).
Gonzales, A. et al, Antitumor activity and pharmacokinetic properties of PF-00299804, a second-generation, irreversible pan-erbB receptor tyrosine kinase inhibitor, Mol. Cancer Ther. 7(7):1880-1889 (2008).
Gould, Philip L., Salt selection for basic drugs, International Journal of Pharmaceutics, 33:201-217 (1986).
Hur, W. et al., Clinical stage EGFR inhibitors irreversibly alkylate Bmx kinase, Bioorg. Med. Chem. Lett. 18:5916-5919 (2008).
International Search Report for PCT/US09/48784, 8 pages (dated Nov. 16, 2009).
International Search Report for PCT/US10/31714, 4 pages (dated Aug. 13, 2010).
International Search Report for PCT/US10/62432, 4 pages (dated May 26, 2011).
International Search Report for PCT/US11/58610, 4 pages (dated Mar. 27, 2012).
International Search Report for PCT/US11/58616, 3 pages (dated Mar. 27, 2012).
International Search Report for PCT/US11/59726, 3 pages (dated Mar. 20, 2012).
International Search Report of PCT/US11/46926, Publication No. WO 2012/021444 (dated Dec. 22, 2011).
International Search Report of PCT/US13/30982, 2 pages (dated May 30, 2013).
International Search Report of PCT/US13/30996, 2 pages (dated May 30, 2013).
Kirken, R., Targeting Jak3 for immune suppression and allograft acceptance, Transplant. Proc. 33 :3268-3270 (2001).
Kumar, A., et al, Structure and Clinical Relevance of the Epidermal Growth Factor Receptor in Human Cancer, Journal of Clinical Oncology 26(10):1742-1751 (2008).
Kwak, E. et al., Irreversible inhibitors of the EGF receptor may circumvent acquired resistance to gefitinib, Proc. Natl. Acad. Sci. USA 102:7665-7670 (2005).
Lajeunesse, D. et al., A systematic screen for dominant second-site modifiers of Merlin/NF2 phenotypes reveals an interaction with blistered/DSRF and scribbler, Genetics 158:667-79 (2001).
Li, D. et al., BIBW2992, an irreversible EGFR/HER2 inhibitor highly effective in preclinical lung cancer models, Oncogene 27:4702-4711 (2008).
Lin, N. and Winer, E., New targets for therapy in breast cancer: Small molecule tyrosine kinase inhibitors, Breast Cancer Res 6:204-210 (2004).
Liu, Rong, Ed., Water-Insoluble Drug Formulation, Chapter 15, CRC Press, 417-435 (2008).
Malaviya, R. et al., Targeting Janus Kinase 3 in Mast Cells Prevents Immediate Hypersensitivity Reactions and Anaphylaxis, J. Biol. Chem. 274 :27028-27038 (1999).
McClatchey, A. and Giovannini, M., Membrane organization and tumorigenesis—the NF2 tumor suppressor, Merlin, Genes Dev 19:2265-77 (2005).
Minkovsky, N. and Berezov, A., BIBW-2992, a dual receptor tyrosine kinase inhibitor for the treatment of solid tumors, Curr Opin Invest Drugs 9:1336-1346 (2008).
Morissette, S.L. et al., High-throughput crystallization: polymorphs, salts, co-crystals and solvates of pharmaceutical solids, Advanced Drug Delivery Reviews, 56: 275-300 (2004).
Morris, K.R. et al., An integrated approach to the selection of optimal salt form for a new drug candidate, International Journal of Pharmaceutics, 105: 209-217 (1994).
Ogiso, et al., Crystal Structure of the Complex of Human Epidermal Growth Factor and Receptor Extracellular Domains, Cell, vol. 110, 775-787 (2002).
Pelton, P. et al., Ruffling membrane, stress fiber, cell spreading and proliferation abnormalities in human Schwann cells, Oncogene 17:2195-2209 (1998).

PubChem CID 44594695. Feb. 1, 2010. [Retrieved from the Internet May 15, 2011: http://pubchem.ncbi.nlm.nih.gov/summary.cgi?cid=44594695&loc=ec_rcs].
Readinger, J. et al., Selective Targeting of ITK Blocks Multiple Steps of HIV Replication, Proc. Natl. Acad. Sci. USA 105: 6684-6689 (2008).
Seidel, H. et al., Pharmaceutical intervention in the JAK/STAT signaling pathway, Oncogene 19: 2645-2656 (2000).
Sequist, L., Second-Generation Epidermal Growth Factor Receptor Tyrosine Kinase Inhibitors in Non-Small Cell Lung Cancer, The Oncologist 12(3):325-330 (2007).
Serajuddin, A.T.M., Salt formation to improve drug solubility, Advanced Drug Delivery Reviews, 59:603-616 (2007).
Singh, J. et al, Structure-based design of a potent, selective, and irreversible inhibitor of the catalytic domain of the erbB receptor subfamily of protein tyrosine kinases, J. Med. Chem. 40:1130-1135 (1997).
Soria, J-C. et al., "Abstract #1354: First-In-Human Evaluation of CO-1686, an Irreversible, Highly Selective Tyrosine Kinase Inhibitor of Mutations of EGFR (Activating and T790M)," 15th World Conference on Lung Cancer, Oct. 27, 2013.
Stahl, H.P. and Wermuth, C.G., Handbook of Pharmaceutical Salts. Properties, Selection, and Use. Wiley-VCH, 265-327 (2008).
Stonecypher, M. et al., Activation of the neuregulin-1/ErbB signaling pathway promotes the proliferation of neoplastic Schwann cells in human malignant peripheral nerve sheath tumors, Oncogene 24:5589-5605 (2005).
Sudbeck, E. et al., Structure-based Design of Specific Inhibitors of Janus Kinase 3 as Apoptosis-inducing Antileukemic Agents, Clin. Cancer Res. 5: 1569-1582 (1999).
Supplementary European Search Report for EP10844293.0, 8 pages (dated Jun. 27, 2013).
Swarbrick, James and Boylan, James C., Eds., Encyclopedia of Pharmaceutical Technology 13, Marcel Dekker, NY, 453-499 (1996).
Trieu, V. et al., A specific inhibitor of janus kinase-3 increases survival in a transgenic mouse model of amyotrophic lateral sclerosis, Biochem. Biophys. Res. Commun. 267 :22-25 (2000).
Walter, A. O. et al., "Discovery of a mutant-selective covalent inhibitor of EGFR that overcomes T790M-mediated resistance in NSCLC," Cancer Discov. Dec. 2013; 3(12): 1404-1415.
Wong, K. et al, A phase I study with neratinib (HKI-272), an irreversible pan Erb B receptor tyrosine kinase inhibitor, in patients with solid tumors, Clin. Cancer Res. 15(7):2552-2558 (2009).
Written Opinion for PCT/US09/48784, 9 pages (dated Nov. 16, 2009).
Written Opinion for PCT/US10/31714, 7 pages (dated Aug. 13, 2010).
Written Opinion for PCT/US10/62432, 14 pages (dated May 26, 2011).
Written Opinion for PCT/US11/46926, 9 pages (dated Dec. 22, 2011).
Written Opinion for PCT/US11/58610, 8 pages (dated Mar. 27, 2012).
Written Opinion for PCT/US11/58616, 9 pages (dated Mar. 27, 2012).
Written Opinion for PCT/US11/59726, 7 pages (dated Mar. 20, 2012).
Written Opinion of PCT/US13/30982, 12 pages (dated May 30, 2013).
Written Opinion of PCT/US13/30996, 12 pages (dated May 30, 2013).
Zhang, J. et al., Targeting Cancer with Small Molecule Kinase Inhibitors, Nature Rev. Cancer 9:28-39 (2009).
Zhang, Y. et al., Antitumor Activity of Epidermal Growth Factor Receptor-Related Protein Is Mediated by Inactivation of ErbB Receptors and Nuclear Factor-kB in Pancreatic Cancer, Cancer Res 66:1025-1032 (2006).
Zhou, W. et al. Novel mutant-selective EGFR kinase inhibitors against EGFR T790M, Nature, 462(7276): 1070-1074 (2009).

SALTS OF AN EPIDERMAL GROWTH FACTOR RECEPTOR KINASE INHIBITOR

CROSS REFERENCE TO RELATED CASES

The present application is a continuation application of U.S. patent application Ser. No. 14/822,366, filed Aug. 10, 2015 (now U.S. Pat. No. 9,540,335), which is a continuation application of U.S. patent application Ser. No. 13/801,191, filed Mar. 13, 2013 (now U.S. Pat. No. 9,108,927), which claims priority to U.S. Provisional Application No. 61/611,400, filed Mar. 15, 2012, each of which is hereby incorporated by reference in its entirety.

FIELD OF THE INVENTION

The present invention provides salt forms of a compound useful as mutant-selective inhibitors of epidermal growth factor receptor (EGFR) kinase, including polymorphic forms of certain salts. The invention also provides pharmaceutically acceptable compositions comprising salt forms of the present invention and methods of using the compositions in the treatment of various disorders.

BACKGROUND OF THE INVENTION

Protein tyrosine kinases are a class of enzymes that catalyze the transfer of a phosphate group from ATP or GTP to a tyrosine residue located on a protein substrate. Receptor tyrosine kinases act to transmit signals from the outside of a cell to the inside by activating secondary messaging effectors via a phosphorylation event. A variety of cellular processes are promoted by these signals, including proliferation, carbohydrate utilization, protein synthesis, angiogenesis, cell growth, and cell survival.

There is strong precedent for involvement of the EGFR in human cancer because over 60% of all solid tumors over-express at least one of these proteins or their ligands. Overexpression of EGFR is commonly found in breast, lung, head and neck, bladder tumors.

Activating mutations in the tyrosine kinase domain of EGFR have been identified in patients with non-small cell lung cancer (Lin, N. U.; Winer, E. P., Breast Cancer Res 6: 204-210, 2004). The reversible inhibitors Tarceva (erlotinib) and Iressa (gefitinib) currently are first-line therapy for non-small cell lung cancer patients with activating mutations. The most common activating mutations are L858R and delE746-A750.

Additionally, in the majority of patients that relapse, acquired drug resistance, such as by mutation of gatekeeper residue T790M, has been detected in at least half of such clinically resistant patients. Moreover, T790M may also be pre-existing; there may be an independent, oncogenic role for the T790M mutation. For example, there are patients with the L858R/T790M mutation who never received gefitinib treatment. In addition, germline EGFR T790M mutations are linked with certain familial lung cancers.

Current drugs in development, including second-generation covalent inhibitors, such as BIBW2992, HKI-272 and PF-0299804, are effective against the T790M resistance mutation but exhibit dose-limiting toxicities due to concurrent inhibition of WT EGFR. Accordingly, there remains a need to find mutant-selective EGFR kinase inhibitors useful as therapeutic agents.

SUMMARY OF THE INVENTION

It has now been found that the novel benzenesulfonic acid, camphor sulfonic acid, 1,2-ethane disulfonic acid, hydrobromic acid, hydrochloric acid, maleic acid, methanesulfonic acid, naphthalene-2-sulfonic acid, 1,5-naphthalene disulfonic acid, oxalic acid, 4-toluenesulfonic acid or 2,4,6-trihydroxybenzoic acid salts of the present invention, and compositions thereof, are useful as mutant-selective inhibitors of one or more EGFR kinases and exhibits desirable characteristics for the same. In general, these salts, and pharmaceutically acceptable compositions thereof, are useful for treating or lessening the severity of a variety of diseases or disorders as described in detail herein.

DETAILED DESCRIPTION OF THE INVENTION

Figure 1:
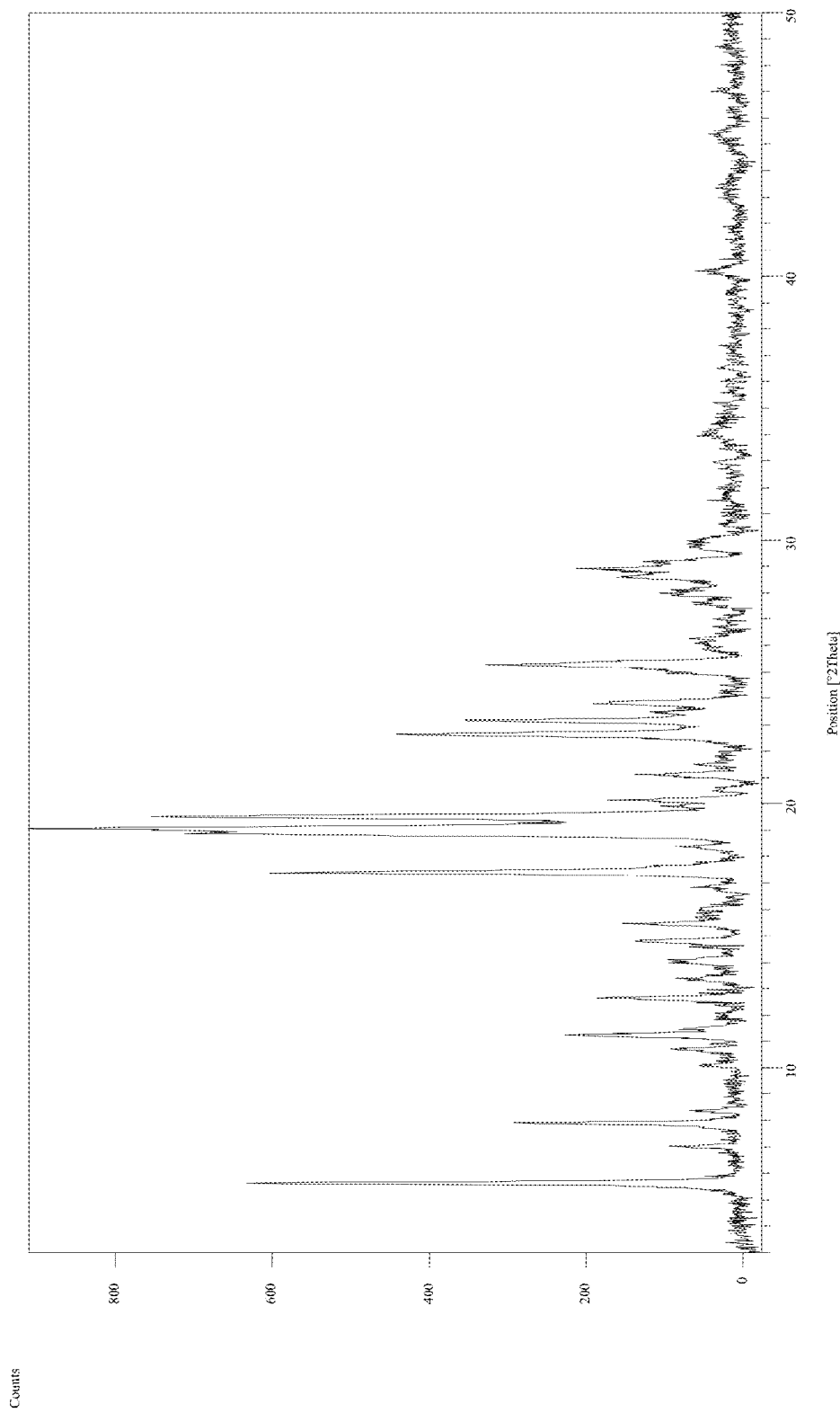
FIG. 1 depicts the x-ray powder diffraction (XRPD) pattern for a bis-besylate salt of Compound 1.

General Description of Certain Aspects of the Invention:

U.S. application Ser. No. 13/286,061, published as US 2012/0149687 on Jun. 14, 2012 ("the '061 application"), filed Oct. 31, 2011, the entirety of which is hereby incorporated herein by reference, describes certain 2,4-disubstituted pyrimidine compounds which covalently and irreversibly inhibit activity of EGFR kinase. Such compounds include compound 1:

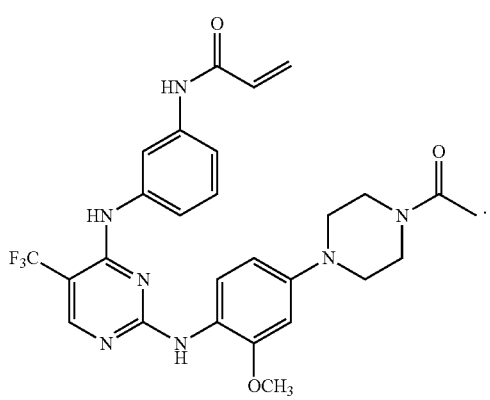

1

Compound 1 (N-(3-(2-(4-(4-acetylpiperazin-1-yl)-2-methoxyphenylamino)-5-(trifluoromethyl)pyrimidin-4-ylamino)phenyl)acrylamide)) is designated as compound number I-4 and the synthesis of compound 1 is described in detail at Example 3 of the '061 application.

Compound 1 is active in a variety of assays and therapeutic models demonstrating selective covalent, irreversible inhibition of mutant EGFR kinase (in enzymatic and cellular assays). Notably, compound 1 was found to inhibit human non-small cell lung cancer cell proliferation both in vitro and in vivo. Accordingly, compound 1 and its salts are useful for treating one or more disorders associated with activity of mutant EGFR kinase.

It would be desirable to provide a form of compound 1 that, as compared to compound 1, imparts characteristics such as improved aqueous solubility, stability and ease of formulation. Accordingly, the present invention provides several salts of compound 1.

According to one embodiment, the present invention provides a salt of compound 1, represented by compound 2:

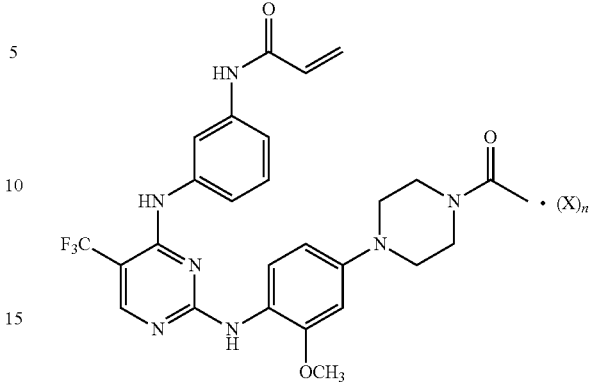

2 where:
n is 1 or 2; and
X is benzenesulfonic acid, camphor sulfonic acid, 1,2-ethane disulfonic acid, hydrobromic acid, hydrochloric acid, maleic acid, methanesulfonic acid, naphthalene-2-sulfonic acid, 1,5-naphthalene disulfonic acid, oxalic acid, 4-toluenesulfonic acid or 2,4,6-trihydroxybenzoic acid.

It will be appreciated by one of ordinary skill in the art that the acid moiety indicated as "X" and compound 1 are ionically bonded to form compound 2. It is contemplated that compound 2 can exist in a variety of physical forms. For example, compound 2 can be in solution, suspension, or in solid form. In certain embodiments, compound 2 is in solid form. When compound 2 is in solid form, said compound may be amorphous, crystalline, or a mixture thereof. Exemplary solid forms are described in more detail below.

In other embodiments, the present invention provides compound 2 substantially free of impurities. As used herein, the term "substantially free of impurities" means that the compound contains no significant amount of extraneous matter. Such extraneous matter may include excess acid "X", excess compound 1, residual solvents, or any other impurities that may result from the preparation of, and/or isolation of, compound 2. In certain embodiments, at least about 90% by weight of compound 2 is present. In certain embodiments, at least about 95% by weight of compound 2 is present. In still other embodiments of the invention, at least about 99% by weight of compound 2 is present.

According to one embodiment, compound 2 is present in an amount of at least about 95, 97, 97.5, 98.0, 98.5, 99, 99.5, 99.8 weight percent where the percentages are based on the total weight of the composition. According to another embodiment, compound 2 contains no more than about 5.0 area percent HPLC of total organic impurities and, in certain embodiments, no more than about 3.0 area percent HPLC of total organic impurities and, in certain embodiments, no more than about 1.5 area percent HPLC total organic impurities relative to the total area of the HPLC chromatogram. In other embodiments, compound 2 contains no more than about 1.0 area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 2 is also meant to include all tautomeric forms of compound 2. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

Solid Forms of Compound 2:

It has been found that compound 2 can exist in a variety of solid forms. Such forms include polymorphs and amorphous forms. The solid forms can be solvates, hydrates and unsolvated forms of compound 2. All such forms are contemplated by the present invention. In certain embodiments, the present invention provides compound 2 as a mixture of one or more solid forms of compound 2.

As used herein, the term "polymorph" refers to the different crystal structures (of solvated or unsolvated forms) in which a compound can crystallize.

As used herein, the term "solvate" refers to a crystal form with either a stoichiometric or non-stoichiometric amount of solvent. For polymorphs, the solvent is incorporated into the crystal structure. Similarly, the term "hydrate" refers to a solid form with either a stoichiometric or non-stoichiometric amount of water. For polymorphs, the water is incorporated into the crystal structure.

As used herein, the term "about", when used in reference to a degree 2-theta value refers to the stated value ±0.3 degree 2-theta (°2θ). In certain embodiments, "about" refers to ±0.2 degree 2-theta or ±0.1 degree 2-theta.

In certain embodiments, compound 2 is a crystalline solid. In other embodiments, compound 2 is a crystalline solid substantially free of amorphous compound 2. As used herein, the term "substantially free of amorphous compound 2" means that the compound contains no significant amount of amorphous compound 2. In certain embodiments, at least about 90% by weight of crystalline compound 2 is present, or at least about 95% by weight of crystalline compound 2 is present. In still other embodiments of the invention, at least about 99% by weight of crystalline compound 2 is present.

In certain embodiments, compound 2 is a benzenesulfonic acid (besylate) salt. The salt can be a mono-besylate or a bis-besylate. A besylate salt is optionally solvated or hydrated, such as a monohydrate.

According to one aspect, an unsolvated bis-besylate salt has a powder X-ray diffraction pattern substantially similar to that depicted in FIG. 1. According to one embodiment, an unsolvated bis-besylate salt is characterized by one or more peaks in its powder X-ray diffraction pattern selected from those at about 5.62, about 17.41, about 18.90, about 19.07 and about 19.52 degrees 2-theta. In some embodiments, an unsolvated bis-besylate salt is characterized by two or more peaks in its powder X-ray diffraction pattern selected from those at about 5.62, about 17.41, about 18.90, about 19.07 and about 19.52 degrees 2-theta. In certain embodiments, an unsolvated bis-besylate salt is characterized by three or more peaks in its powder X-ray diffraction pattern selected from those at about 5.62, about 17.41, about 18.90, about 19.07 and about 19.52 degrees 2-theta. In particular embodiments, an unsolvated bis-besylate salt is characterized by substantially all of the peaks in its X-ray powder diffraction pattern selected from those at about 5.62, 7.89, 11.23, 12.64, 17.41, 18.90, 19.07, 19.52, 22.63, 23.17, 25.28 and 28.92 degrees 2-theta. In an exemplary embodiment, an unsolvated bis-besylate salt is characterized by substantially all of the peaks in its X-ray powder diffraction pattern selected from those at about

| °2-Theta |
| --- |
| 3.37 |
| 3.70 |
| 5.62 |
| 7.00 |
| 7.89 |
| 8.38 |
| 9.56 |
| 10.09 |
| 10.72 |
| 10.91 |
| 11.23 |
| 11.97 |
| 12.64 |
| 12.98 |
| 13.37 |
| 14.04 |
| 14.56 |
| 14.79 |
| 15.45 |
| 16.08 |
| 16.47 |
| 16.87 |
| 17.41 |
| 18.40 |
| 18.90 |
| 19.07 |
| 19.52 |
| 19.91 |
| 20.16 |
| 20.50 |
| 21.12 |
| 21.48 |
| 21.95 |
| 22.63 |
| 23.17 |
| 23.46 |
| 23.82 |
| 24.33 |
| 24.48 |
| 24.93 |
| 25.28 |
| 25.85 |
| 26.18 |
| 26.73 |
| 27.00 |
| 27.63 |
| 27.91 |
| 28.03 |
| 28.60 |
| 28.92 |
| 29.15 |
| 29.74 |
| 29.94 |
| 30.60 |
| 31.53 |
| 32.13 |
| 32.40 |
| 32.54 |
| 32.77 |
| 32.96 |
| 34.04 |
| 35.18 |
| 35.61 |
| 35.91 |
| 36.07 |
| 36.54 |
| 36.85 |
| 37.28 |
| 38.25 |
| 38.61 |
| 39.06 |
| 39.34 |
| 40.20 |
| 41.33 |
| 41.80 |
| 41.88 |
| 42.89 |
| 43.40 |
| 43.80 |

| °2-Theta |
|---|
| 44.84 |
| 45.41 |
| 46.34 |
| 46.69 |
| 47.05 |
| 47.85 |
| 48.75 |
| 48.96 |

Figure 2:
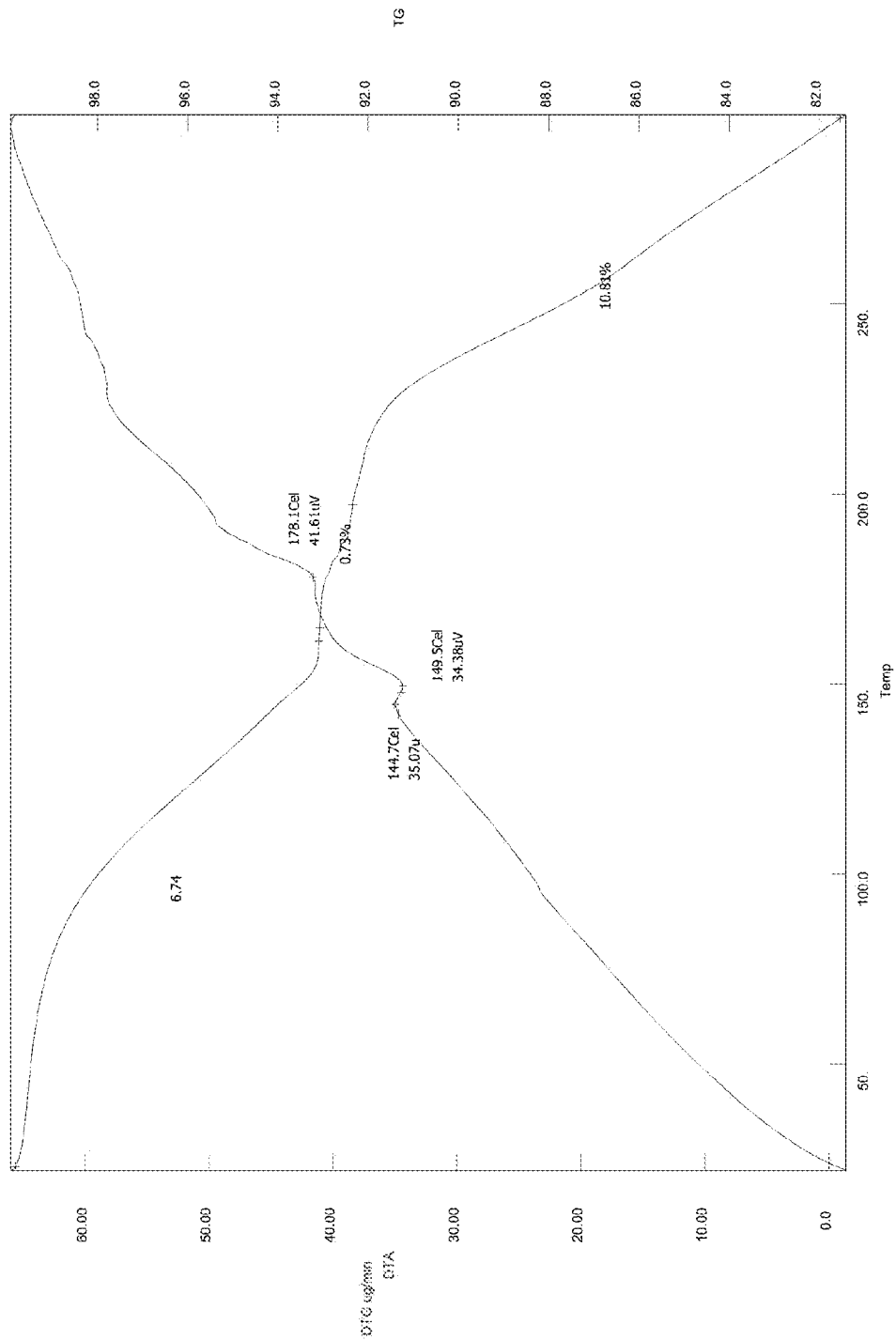
FIG. 2 depicts the thermogravimetric analysis (TGA) pattern for a bis-besylate salt of Compound 1.
Figure 3:
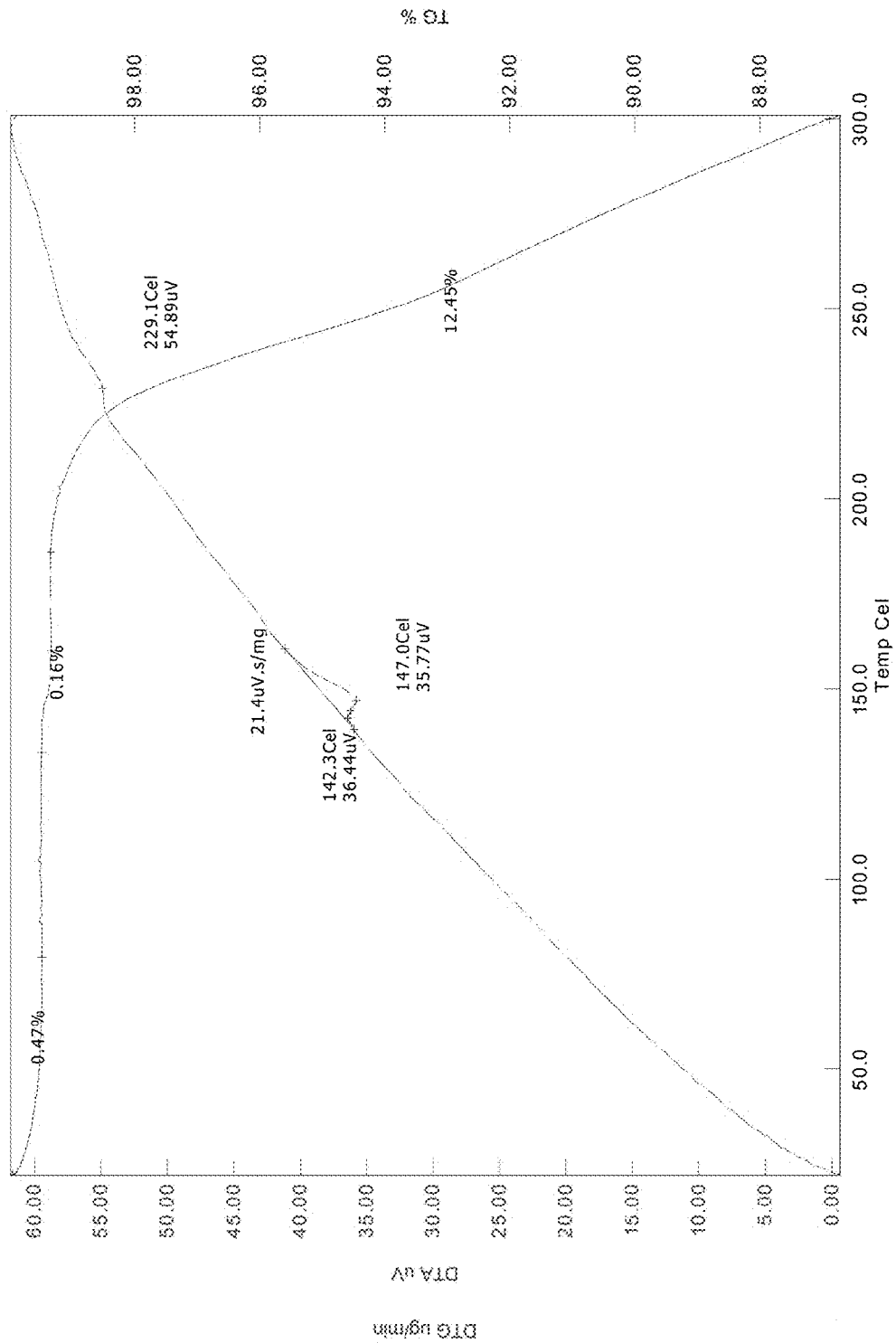
FIG. 3 depicts the thermogravimetric analysis (TGA) pattern for a further dried sample of a bis-besylate salt of Compound 1.
Figure 4:
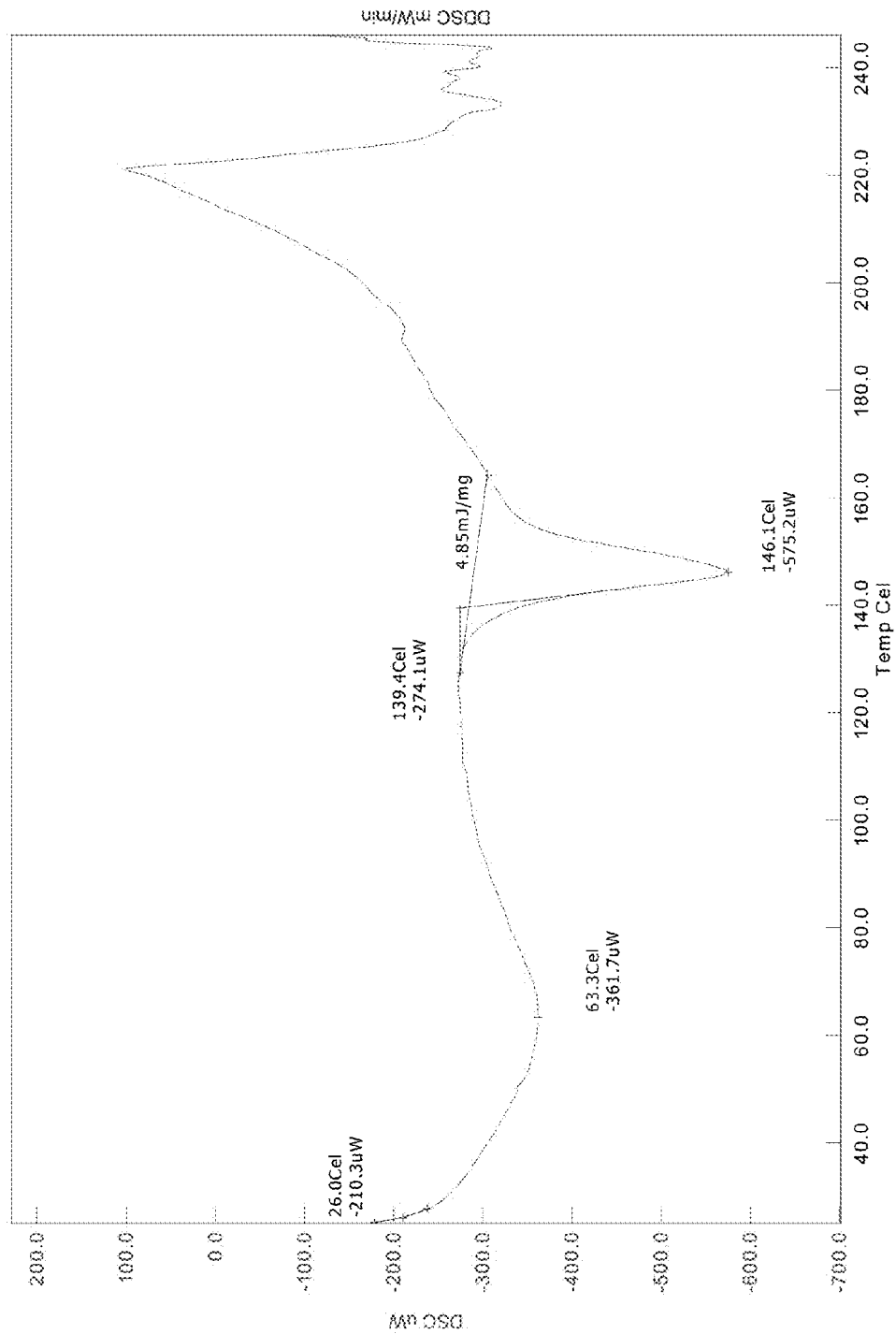
FIG. 4 depicts the differential scanning calorimetry (DSC) pattern for a bis-besylate salt of Compound 1.
Figure 5:
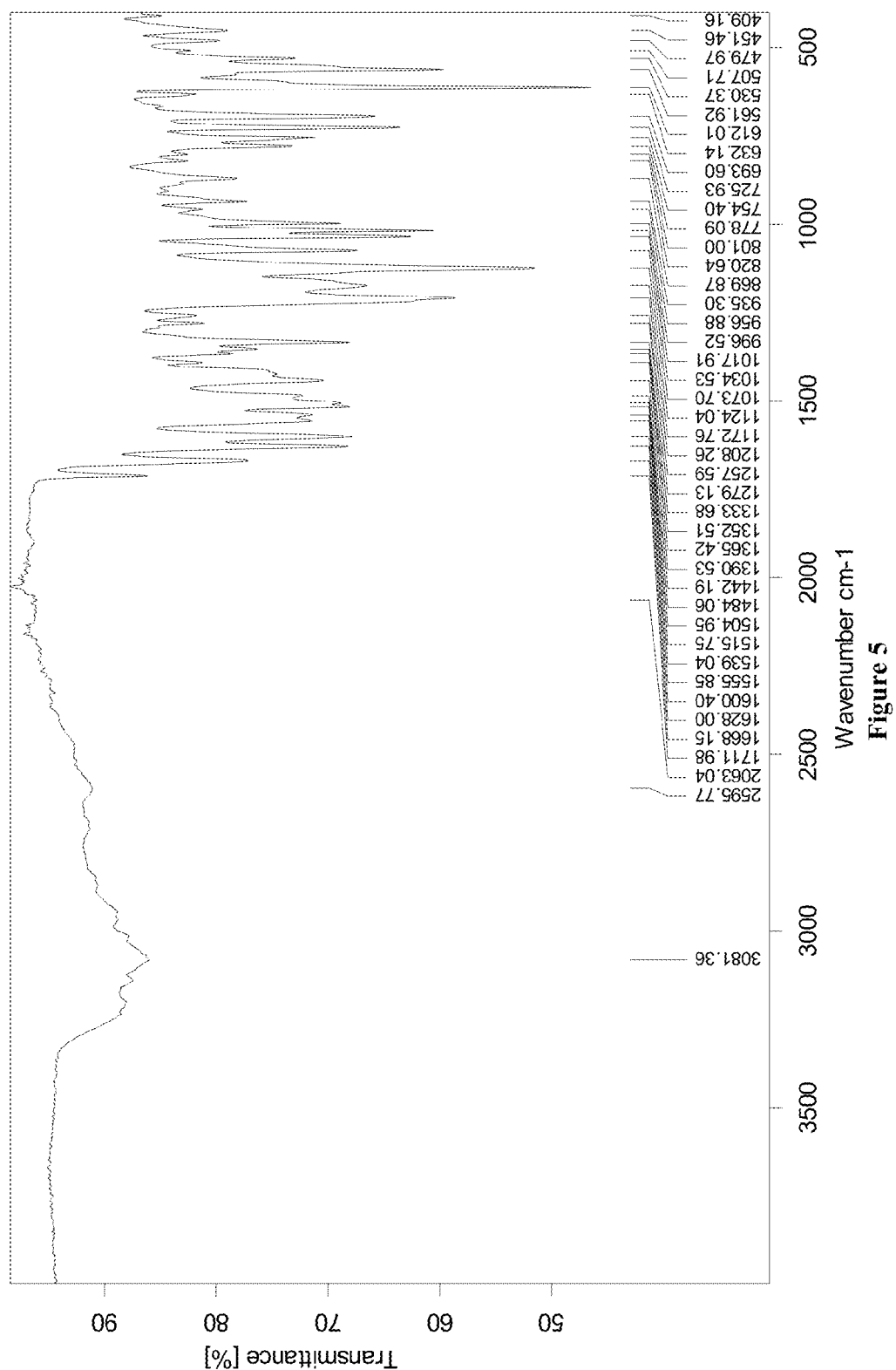
FIG. 5 depicts the infrared (IR) spectrum of a bis-besylate salt of Compound 1.
Figure 6:
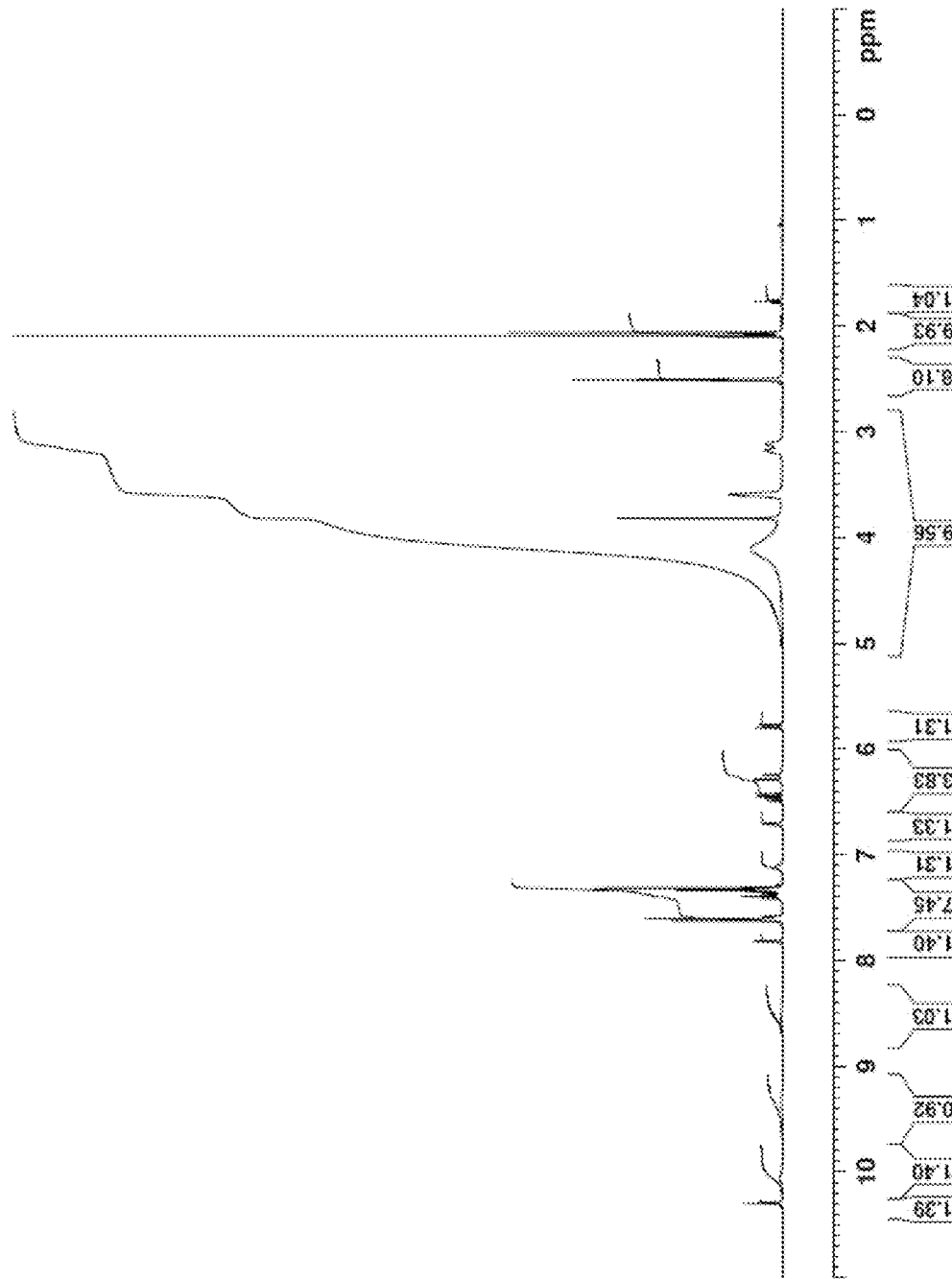
FIG. 6 depicts the $^1$H-NMR spectrum of a bis-besylate salt of Compound 1.
Figure 7:
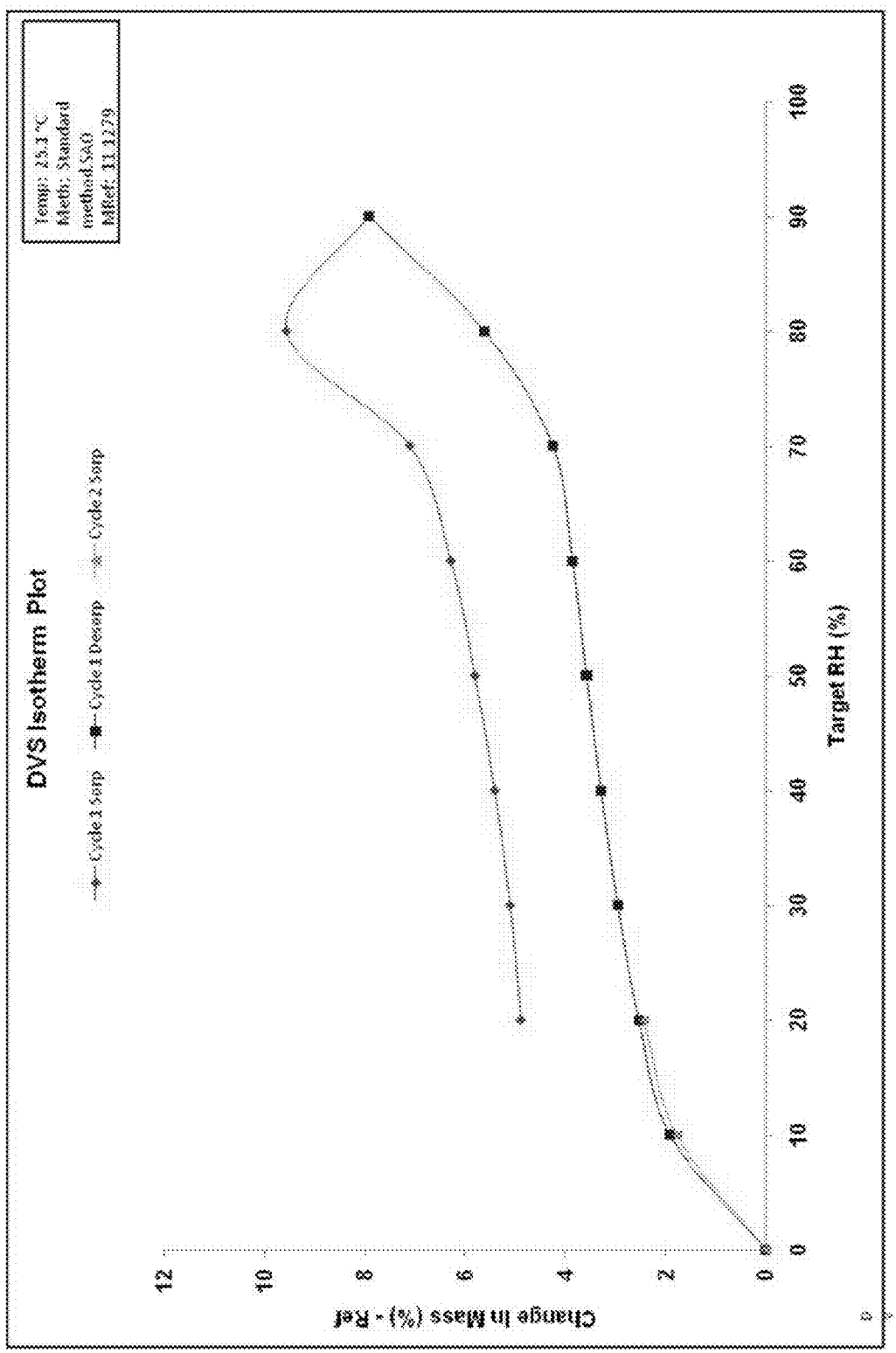
FIG. 7 depicts the dynamic vapor sorption (DVS) pattern of a bis-besylate salt of Compound 1.

According to another aspect, an unsolvated bis-besylate salt has a thermogravimetric analysis pattern substantially similar to that depicted in FIG. 2 or 3. According to yet another aspect, an unsolvated bis-besylate salt has a differential scanning calorimetry pattern substantially similar to that depicted in FIG. 4. According to a further embodiment, an unsolvated bis-besylate salt has an infrared spectrum substantially similar to that depicted in FIG. 5. According to another embodiment, an unsolvated bis-besylate salt has an $^{1}$H-NMR spectrum substantially similar to that depicted in FIG. 6. According to a further embodiment, an unsolvated bis-besylate salt has a dynamic vapour sorption pattern substantially similar to that depicted in FIG. 7. An unsolvated bis-besylate salt can be characterized by substantial similarity to two or more of these figures simultaneously.

Figure 14:
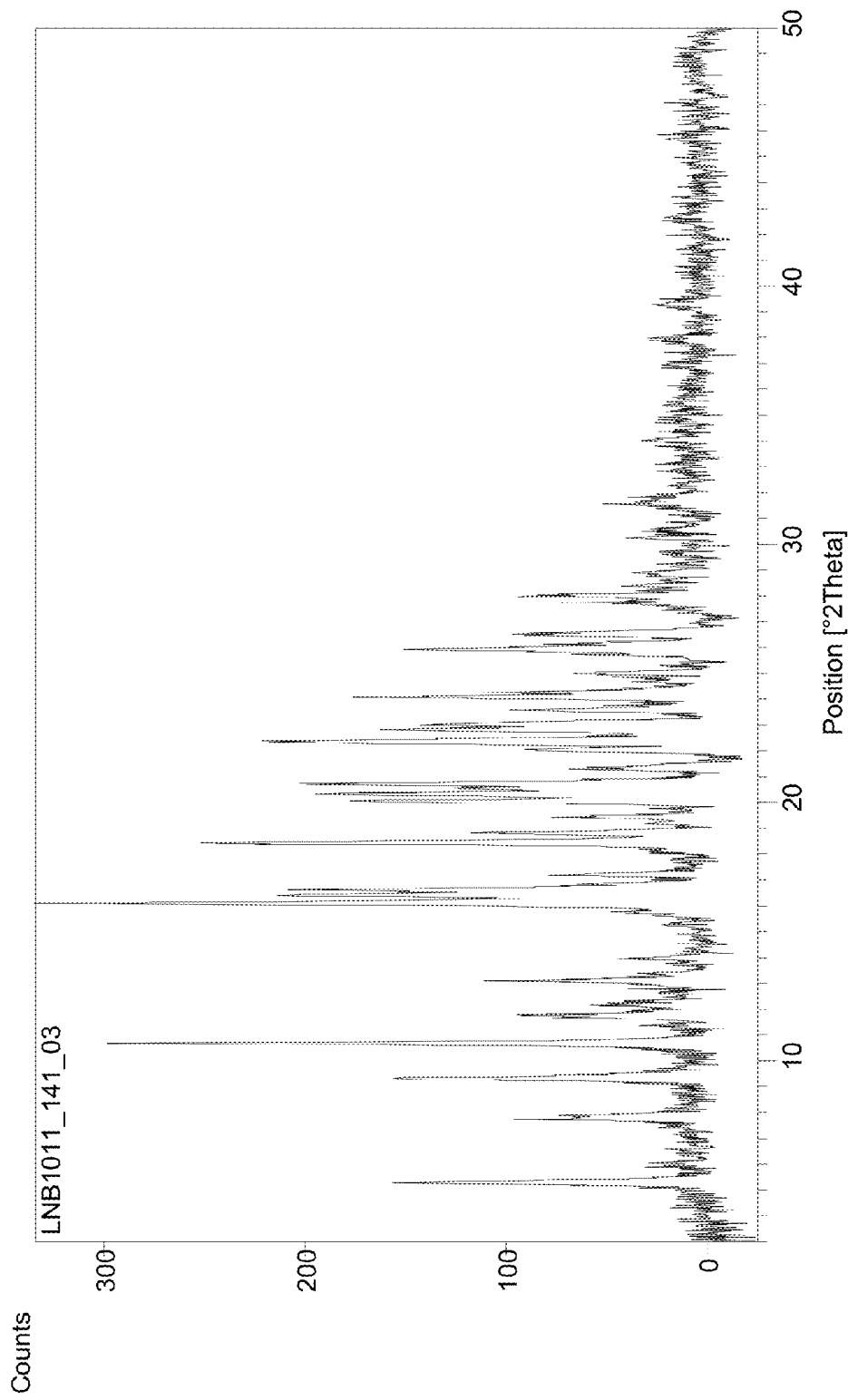
FIG. 14 depicts the XRPD pattern for a bis-besylate hydrate salt of Compound 1.

According to one aspect, a bis-besylate hydrate has a powder X-ray diffraction pattern substantially similar to that depicted in FIG. 14. According to one embodiment, a bis-besylate hydrate salt is characterized by one or more peaks in its powder X-ray diffraction pattern selected from those at about 10.68, about 16.10, about 18.44 and about 22.36 degrees 2-theta. In some embodiments, a bis-besylate hydrate salt is characterized by two or more peaks in its powder X-ray diffraction pattern selected from those at about 10.68, about 16.10, about 18.44 and about 22.36 degrees 2-theta. In certain embodiments, a bis-besylate hydrate salt is characterized by three or more peaks in its powder X-ray diffraction pattern selected from those at about 10.68, about 16.10, about 18.44 and about 22.36 degrees 2-theta. In particular embodiments, a bis-besylate hydrate salt is characterized by substantially all of the peaks in its X-ray powder diffraction pattern selected from those at about 9.33, 10.68, 16.10, 16.43, 16.64, 18.44, 20.05, 20.32, 20.74, 22.36 and 22.83 degrees 2-theta. In an exemplary embodiment, a bis-besylate hydrate salt is characterized by substantially all of the peaks in its X-ray powder diffraction pattern selected from those at about

| °2-Theta |
|---|
| 3.05 |
| 3.30 |
| 3.50 |
| 3.64 |
| 5.31 |
| 6.02 |
| 6.89 |
| 7.77 |
| 7.90 |
| 8.86 |
| 9.33 |
| 10.68 |
| 11.38 |
| 11.76 |
| 12.19 |
| 13.12 |
| 13.60 |
| 13.95 |
| 14.62 |
| 16.10 |
| 16.43 |
| 16.64 |
| 17.21 |
| 17.67 |
| 18.06 |
| 18.44 |
| 18.82 |
| 19.45 |
| 20.05 |
| 20.32 |
| 20.74 |
| 21.28 |
| 22.05 |
| 22.36 |
| 22.83 |
| 23.04 |
| 23.58 |
| 24.09 |
| 25.01 |
| 25.92 |
| 26.51 |
| 27.41 |
| 27.73 |
| 28.03 |
| 28.43 |
| 28.86 |
| 29.20 |
| 29.63 |
| 30.29 |
| 30.53 |
| 30.92 |
| 31.66 |
| 32.85 |
| 33.22 |
| 33.96 |
| 34.11 |
| 36.94 |
| 37.87 |
| 39.33 |
| 42.63 |
| 44.95 |
| 45.79 |
| 46.36 |
| 47.16 |
| 47.85 |
| 48.86 |
| 49.09 |

Figure 15:
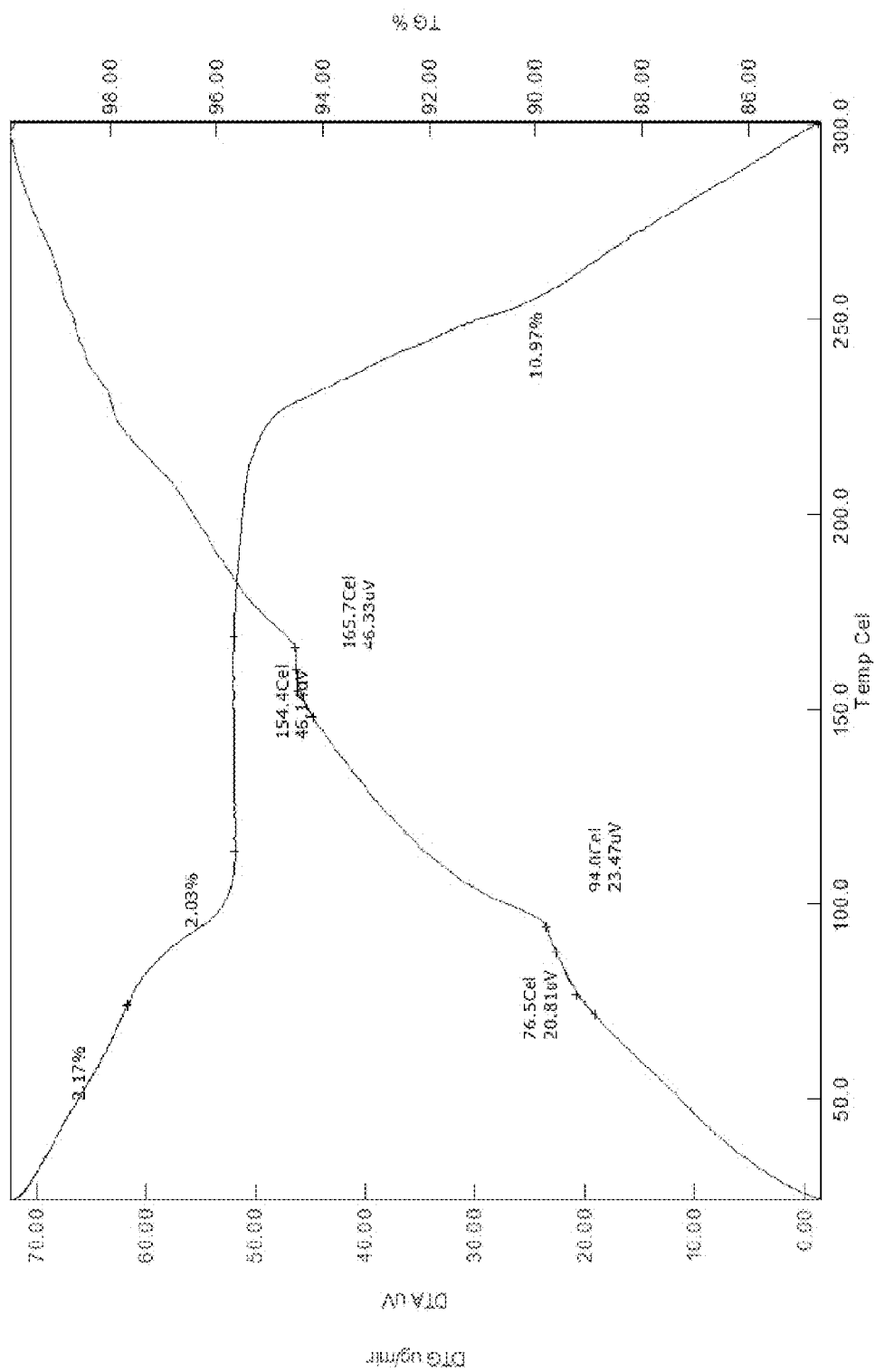
FIG. 15 depicts the TGA pattern for a bis-besylate hydrate salt of Compound 1.
Figure 17:
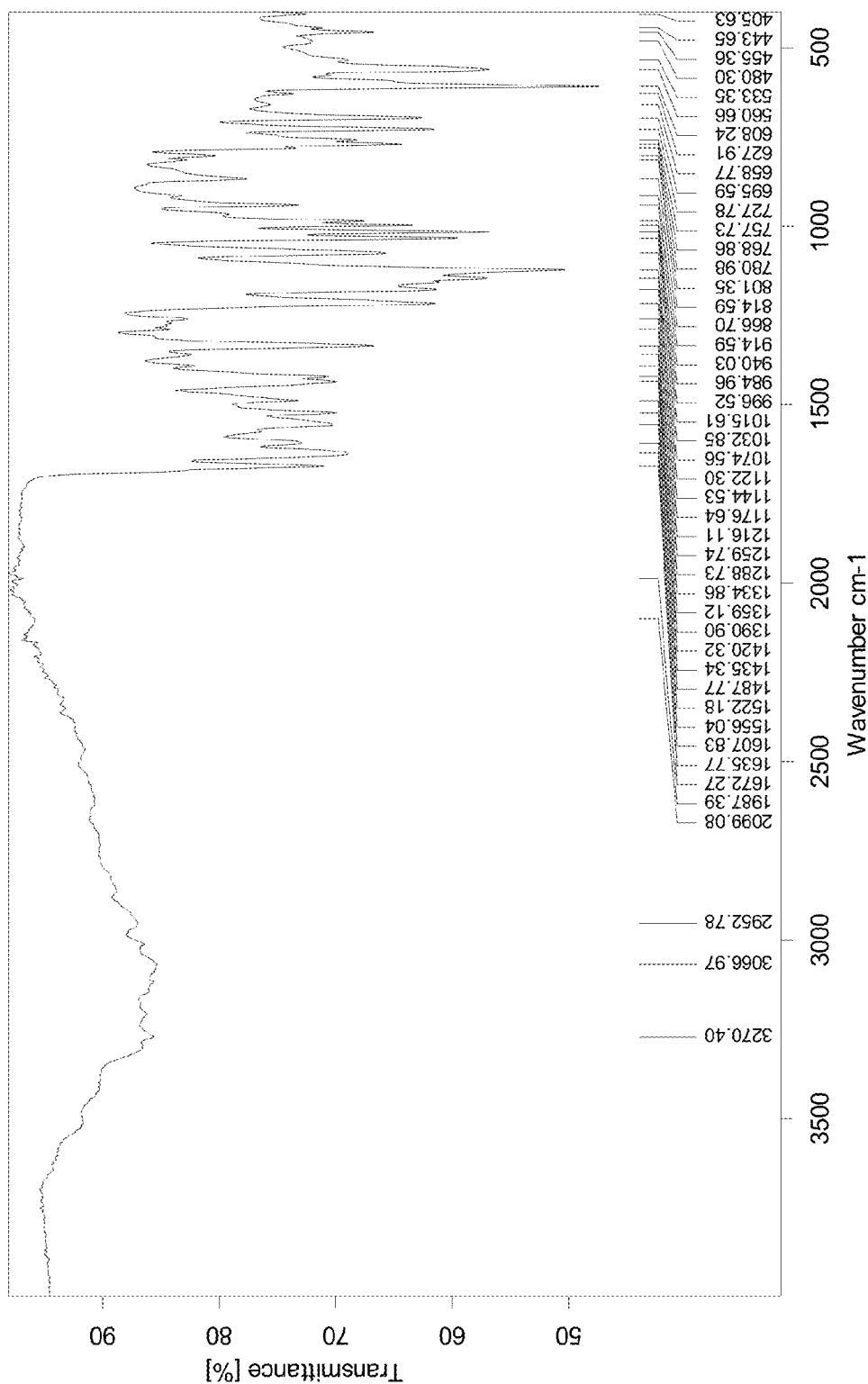
FIG. 17 depicts the IR spectrum of a bis-besylate hydrate salt of Compound 1.
Figure 18:
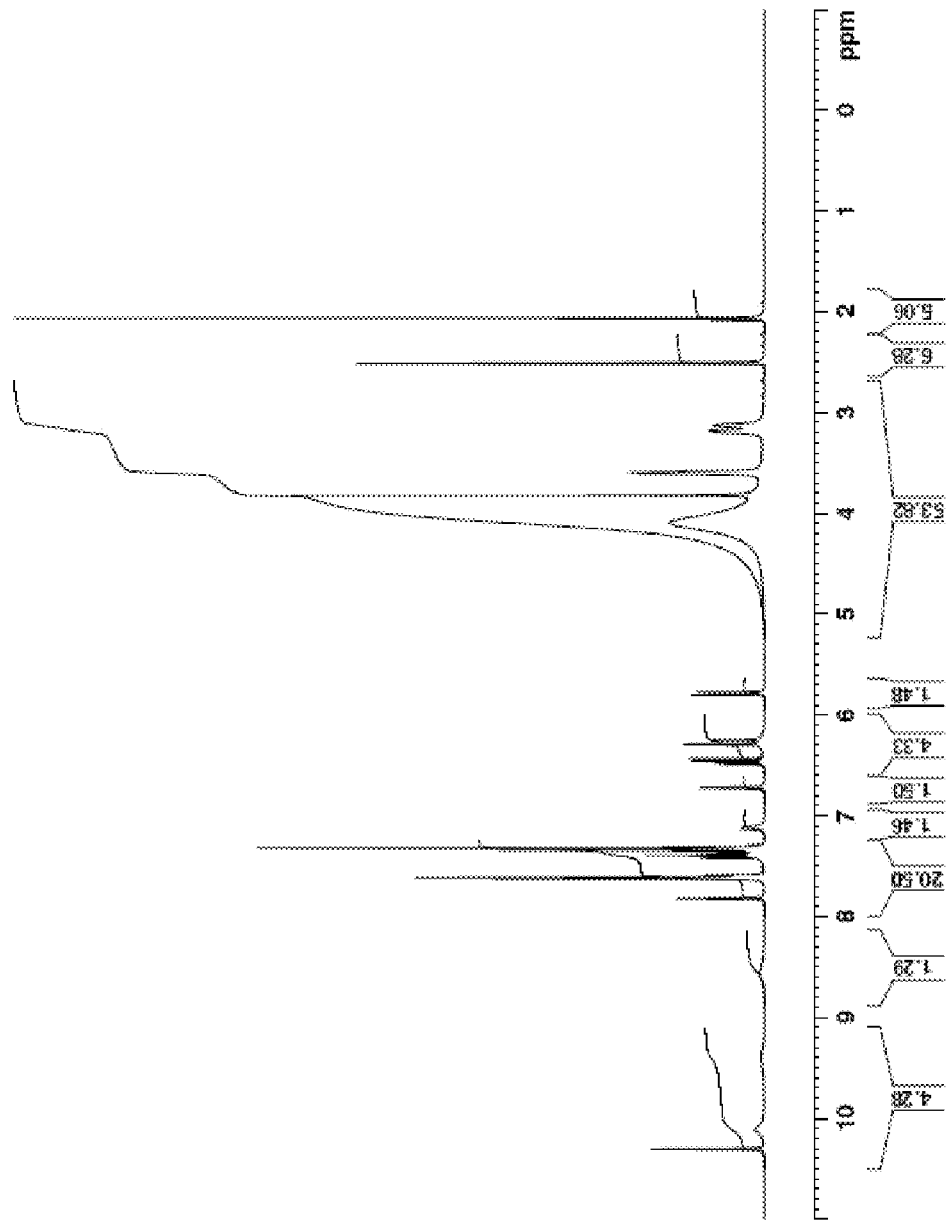
FIG. 18 depicts the $^1$H-NMR spectrum of a bis-besylate hydrate salt of Compound 1.
Figure 19:
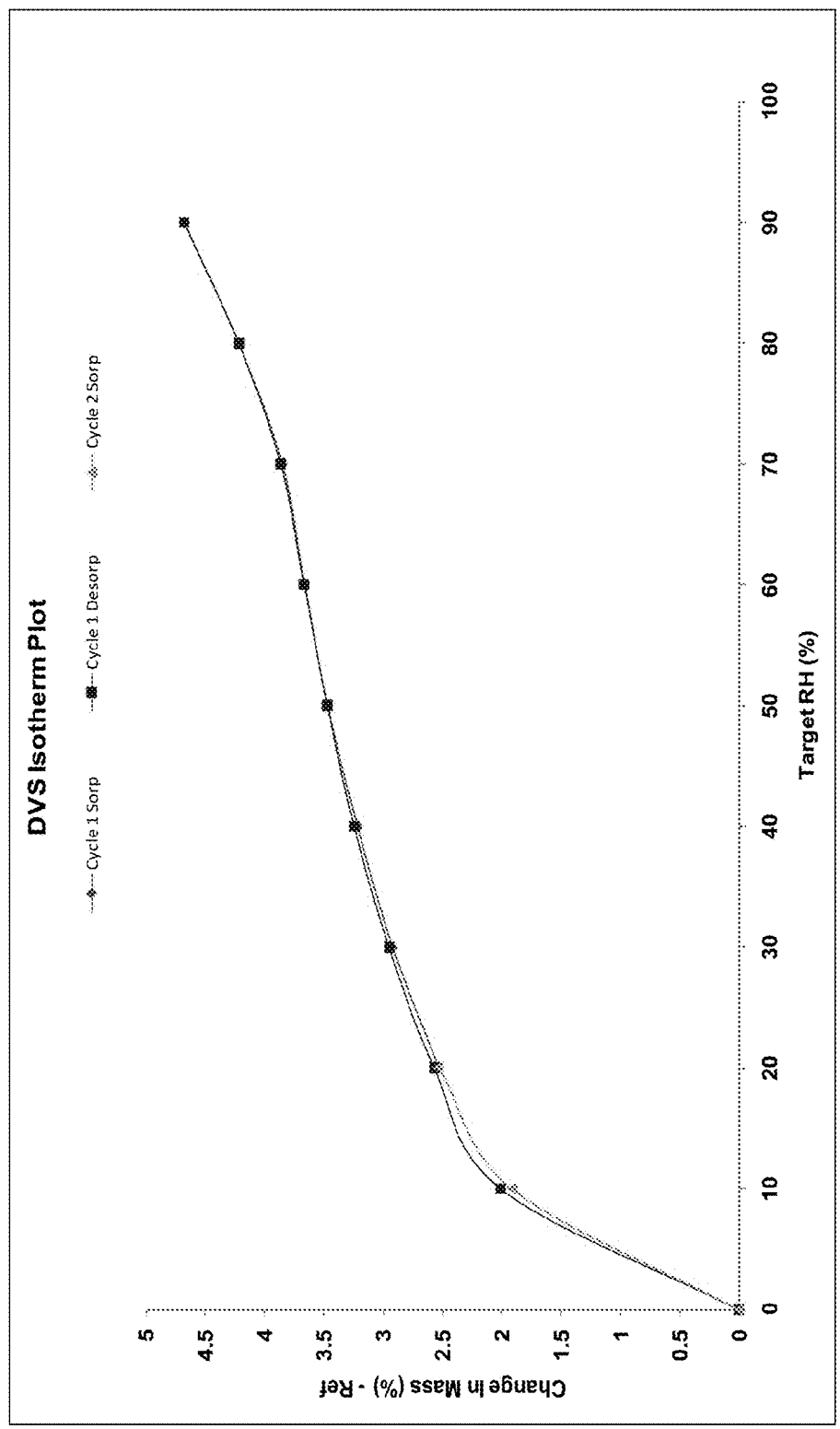
FIG. 19 depicts the DVS pattern of a bis-besylate hydrate salt of Compound 1.

According to another aspect, a bis-besylate hydrate has a thermogravimetric analysis pattern substantially similar to that depicted in FIG. 15. According to yet another aspect, a bis-besylate hydrate has a differential scanning calorimetry pattern substantially similar to that depicted in FIG. 16. According to a further embodiment, a bis-besylate hydrate has a infrared spectrum substantially similar to that depicted in FIG. 17. According to another embodiment, a bis-besylate hydrate has an $^{1}$H-NMR spectrum substantially similar to that depicted in FIG. 18. According to a further embodiment, a bis-besylate hydrate has a dynamic vapour sorption pattern substantially similar to that depicted in FIG. 19. A bis-besylate hydrate can be characterized by substantial similarity to two or more of these figures simultaneously.

In certain embodiments, compound 2 is a camphor sulfonic acid salt (e.g., camphor-10-sulfonic acid). In some embodiments, compound 2 is a mono-camphor sulfonic acid salt. In some embodiments, compound 2 is a bis-camphor sulfonic acid salt.

In certain embodiments, compound 2 is a 1,2-ethane disulfonic acid salt. In some embodiments, compound 2 is a mono-1,2-ethane disulfonic acid salt. In some embodiments, compound 2 is a bis-1,2-ethane disulfonic acid salt.

In certain embodiments, compound 2 is a hydrobromic acid salt. In some embodiments, compound 2 is an anhydrous monohydrobromic acid salt. In some embodiments, compound 2 is an anhydrous bis-hydrobromic acid salt. A hydrobromide salt is optionally solvated or hydrated. In some embodiments, compound 2 is a monohydrate hydrobromic acid salt. In some embodiments, compound 2 is a solvated hydrobromic acid salt. In some such embodiments, the solvate is selected from dimethylsulfoxide (DMSO), dimethylformamide (DMF) and 1,4-dioxane. In some embodiments, compound 2 is a hydrobromide salt selected from Form I, Form III, Form IV, Form V, Form VI, Form VII and Form VIII, each of which is described in further detail, infra.

Figure 59:
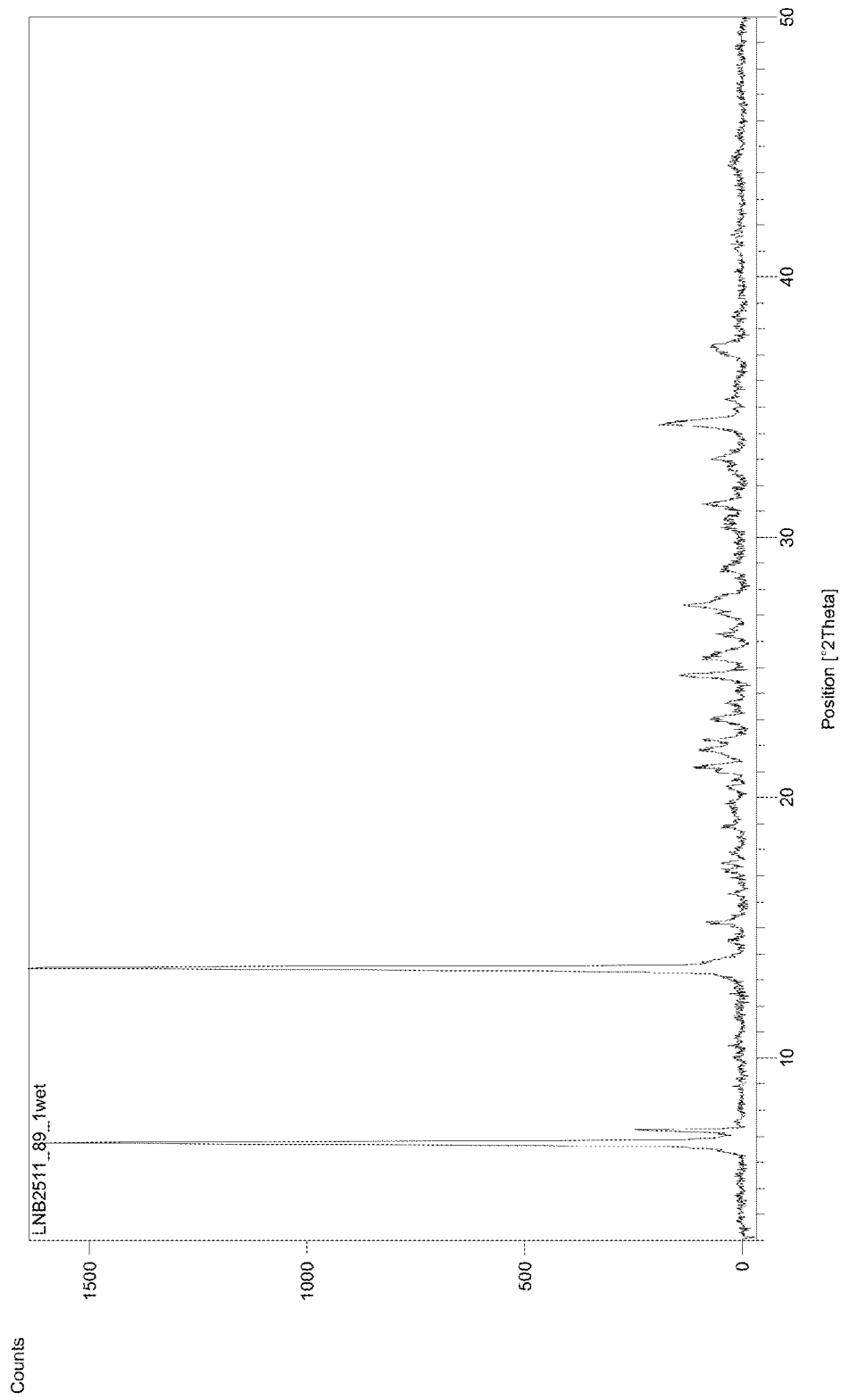
FIG. 59 depicts the XRPD pattern for a Form I hydrobromide salt of Compound 1.

In some embodiments, compound 2 is a Form I hydrobromide salt. In some such embodiments, compound 2 is an anhydrous Form I hydrobromide salt. According to one aspect, a Form I hydrobromide salt is characterized by the powder X-ray diffraction pattern substantially similar to that depicted in FIG. 60. In some embodiments, a Form I hydrobromide salt is characterized by the powder X-ray diffraction pattern substantially similar to that depicted in FIG. 59. According to one embodiment, a Form I mono-hydrobromide salt is characterized by one or more peaks in its powder X-ray diffraction pattern selected from those at about 17.39, about 19.45, about 21.41, about 23.56 and about 27.45 degrees 2-theta. In some embodiments, a Form I mono-hydrobromide salt is characterized by two or more peaks in its powder X-ray diffraction pattern selected from those at about 17.39, about 19.45, about 21.41, about 23.56 and about 27.45 degrees 2-theta. In certain embodiments, a Form I mono-hydrobromide salt is characterized by three or more peaks in its powder X-ray diffraction pattern selected from those at about 17.39, about 19.45, about 21.41, about 23.56 and about 27.45 degrees 2-theta. In some embodiments, a Form I mono-hydrobromide salt is characterized by four or more peaks in its powder X-ray diffraction pattern selected from those at about 17.39, about 19.45, about 21.41, about 23.56 and about 27.45 degrees 2-theta. In particular embodiments, a Form I mono-hydrobromide salt is characterized by an X-ray powder diffraction pattern which includes the peaks at about 9.84, 15.62, 17.39, 19.45, 20.69, 21.41, 22.38, 23.56, 25.08 and 27.45 degrees 2-theta. In an exemplary embodiment, a Form I mono-hydrobromide salt is characterized by substantially all of the peaks in its X-ray powder diffraction pattern selected from those at about

| °2-Theta |
| --- |
| 3.17 |
| 3.48 |
| 3.79 |
| 5.60 |
| 7.92 |
| 8.35 |
| 9.84 |
| 11.52 |
| 14.10 |
| 15.23 |
| 15.62 |
| 16.73 |
| 17.39 |
| 18.23 |
| 19.45 |
| 20.69 |
| 21.41 |
| 22.38 |

-continued

| °2-Theta |
| --- |
| 23.56 |
| 24.65 |
| 25.08 |
| 26.26 |
| 27.45 |
| 28.50 |
| 29.06 |
| 29.77 |
| 29.94 |
| 30.66 |
| 31.35 |
| 32.45 |
| 32.82 |
| 34.18 |
| 34.80 |
| 35.35 |
| 36.01 |
| 36.82 |
| 37.61 |
| 37.96 |
| 38.55 |
| 39.13 |
| 40.04 |
| 40.64 |
| 40.86 |
| 41.03 |
| 41.39 |
| 42.16 |
| 42.48 |
| 42.78 |
| 44.28 |
| 45.34 |
| 45.59 |
| 46.57 |
| 47.20 |
| 47.51 |

Figure 61:
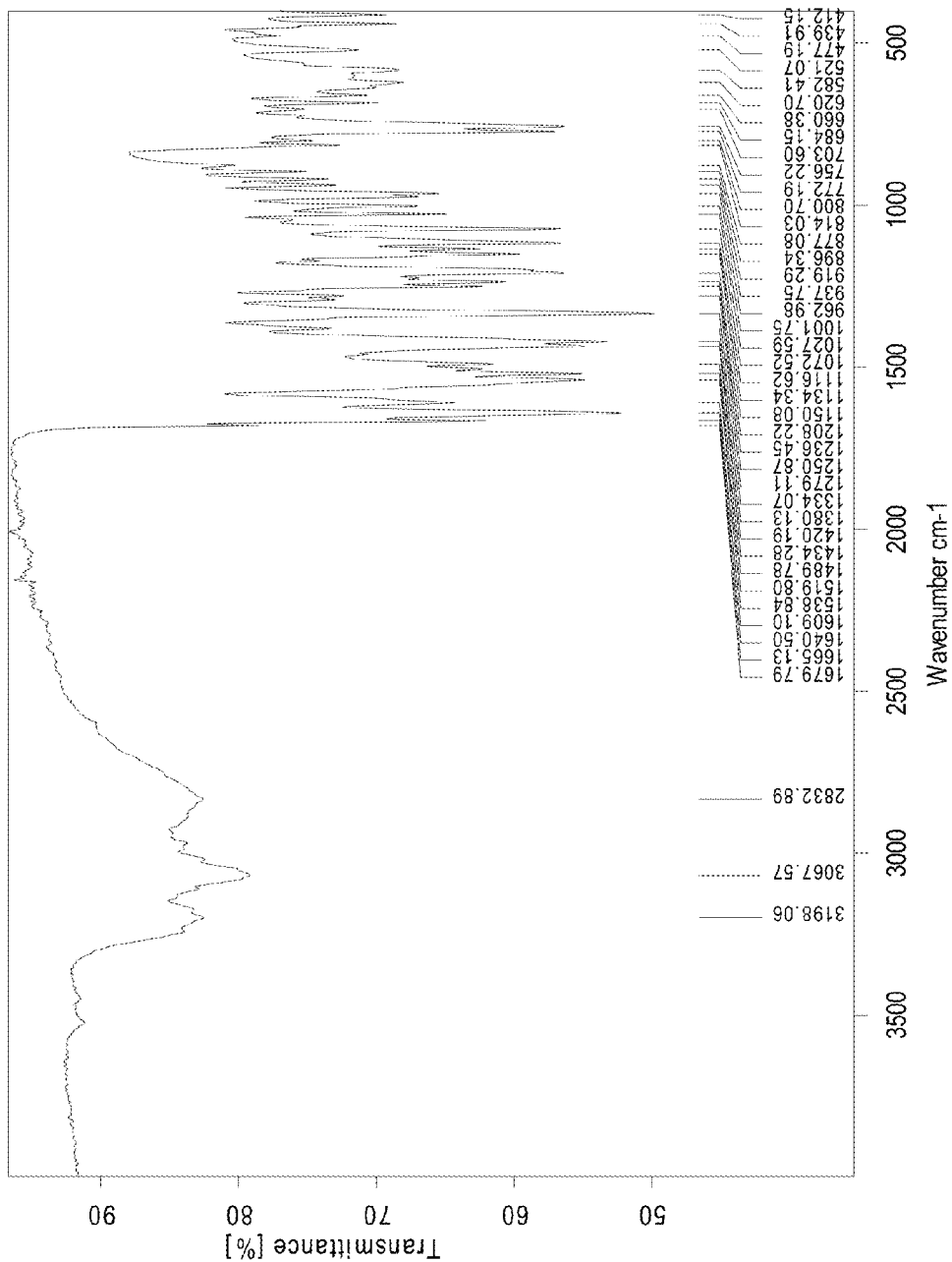
FIG. 61 depicts the IR spectrum of a Form I hydrobromide salt of Compound 1.
Figure 62:
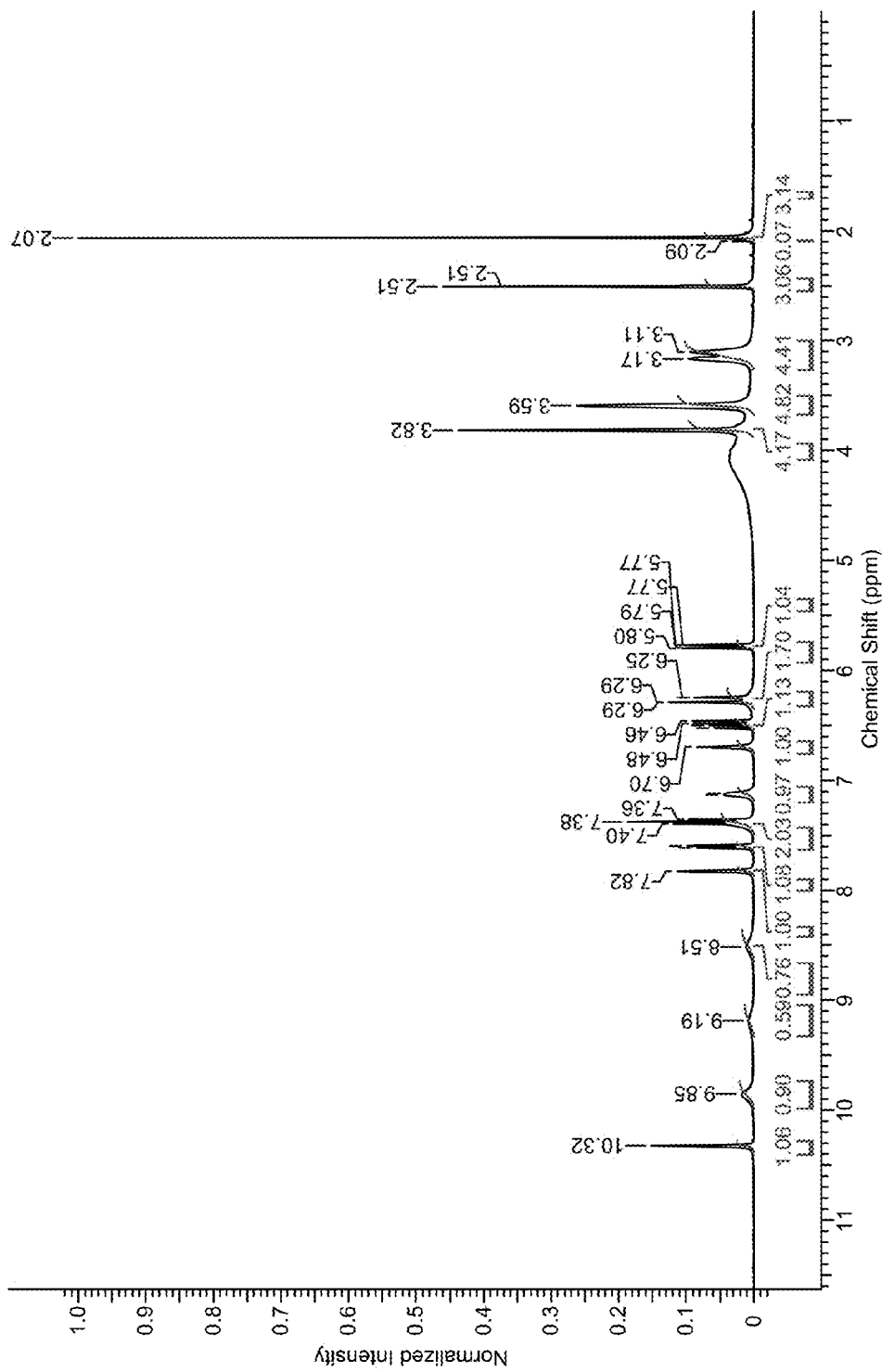
FIG. 62 depicts the $^1$H-NMR spectrum of a Form I hydrobromide salt of Compound 1.
Figure 63:
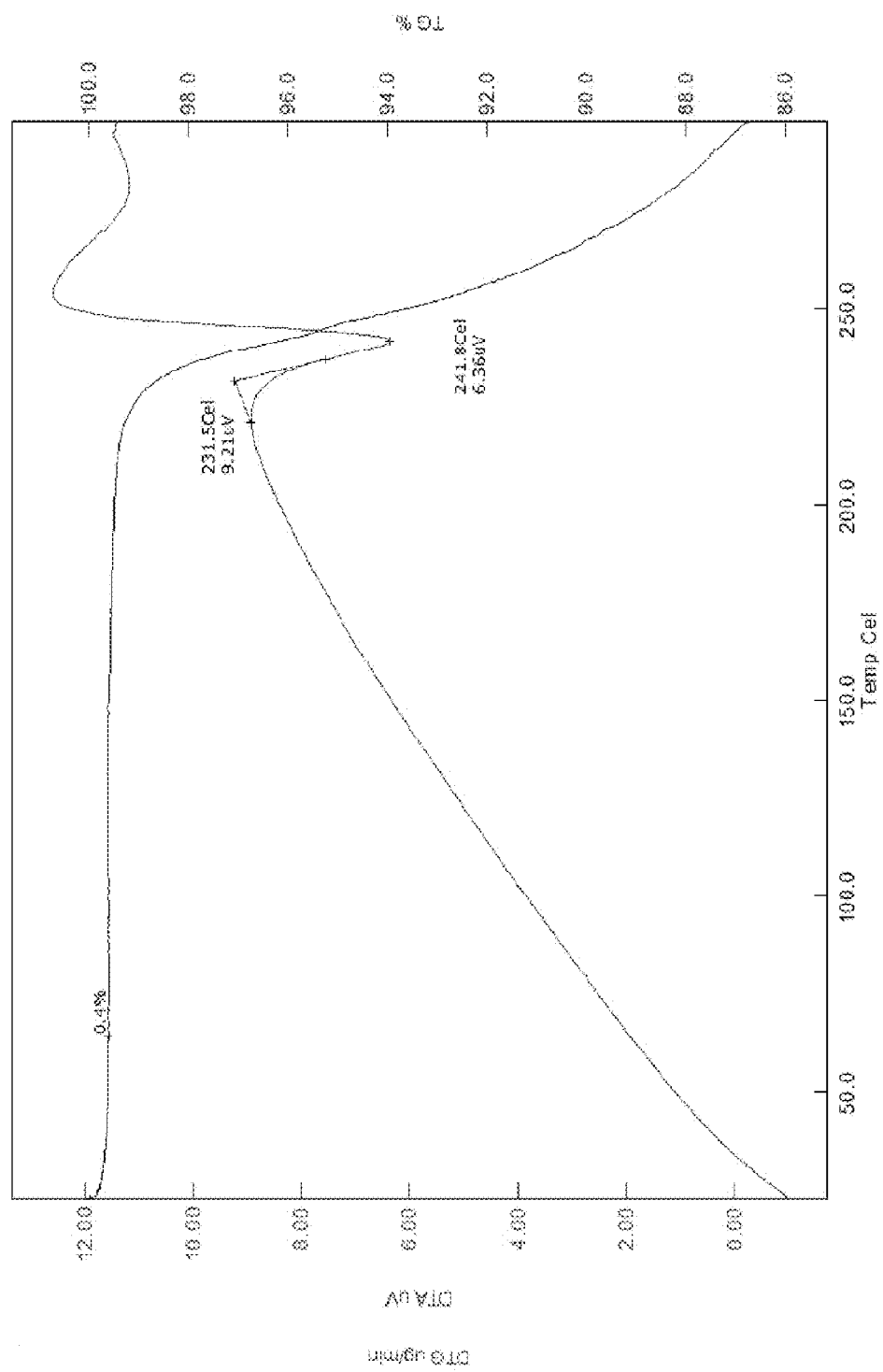
FIG. 63 depicts the TGA pattern for a Form I hydrobromide salt of Compound 1.
Figure 64:
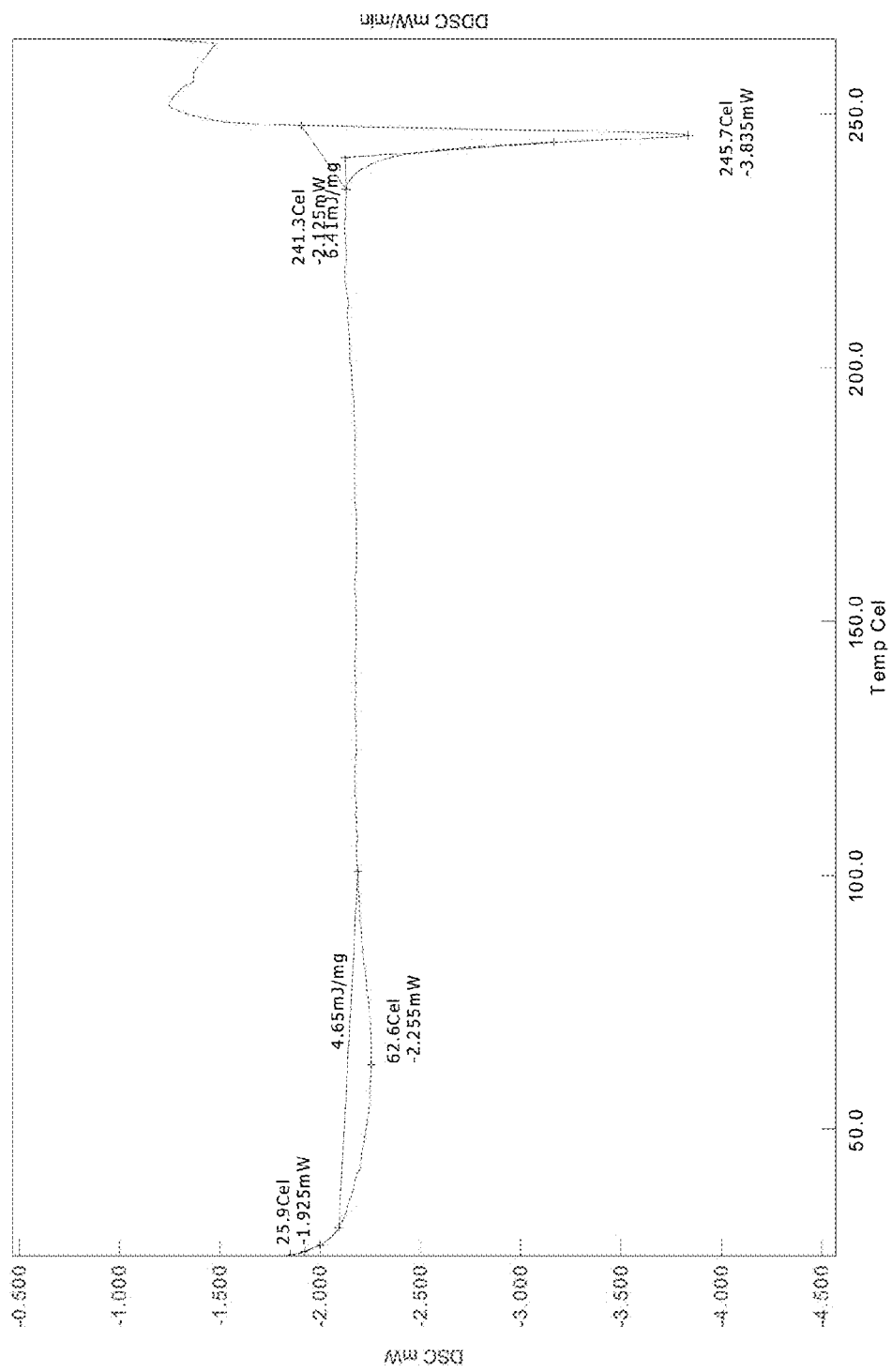
FIG. 64 depicts the DSC pattern for a Form I hydrobromide salt of Compound 1.

According to another aspect, a Form I mono-hydrobromide salt is characterized by a thermogravimetric analysis pattern substantially similar to that depicted in FIG. 63. According to yet another aspect, a Form I mono-hydrobromide salt is characterized by a differential scanning calorimetry pattern substantially similar to that depicted in FIG. 64. According to a further embodiment, a Form I mono-hydrobromide salt is characterized by an infrared spectrum substantially similar to that depicted in FIG. 61. According to another embodiment, a Form I mono-hydrobromide salt is characterized by a $^1$H-NMR spectrum substantially similar to that depicted in FIG. 62. In some embodiments, a Form I mono-hydrobromide salt is characterized by substantial similarity to two or more of these figures simultaneously.

Figure 67:
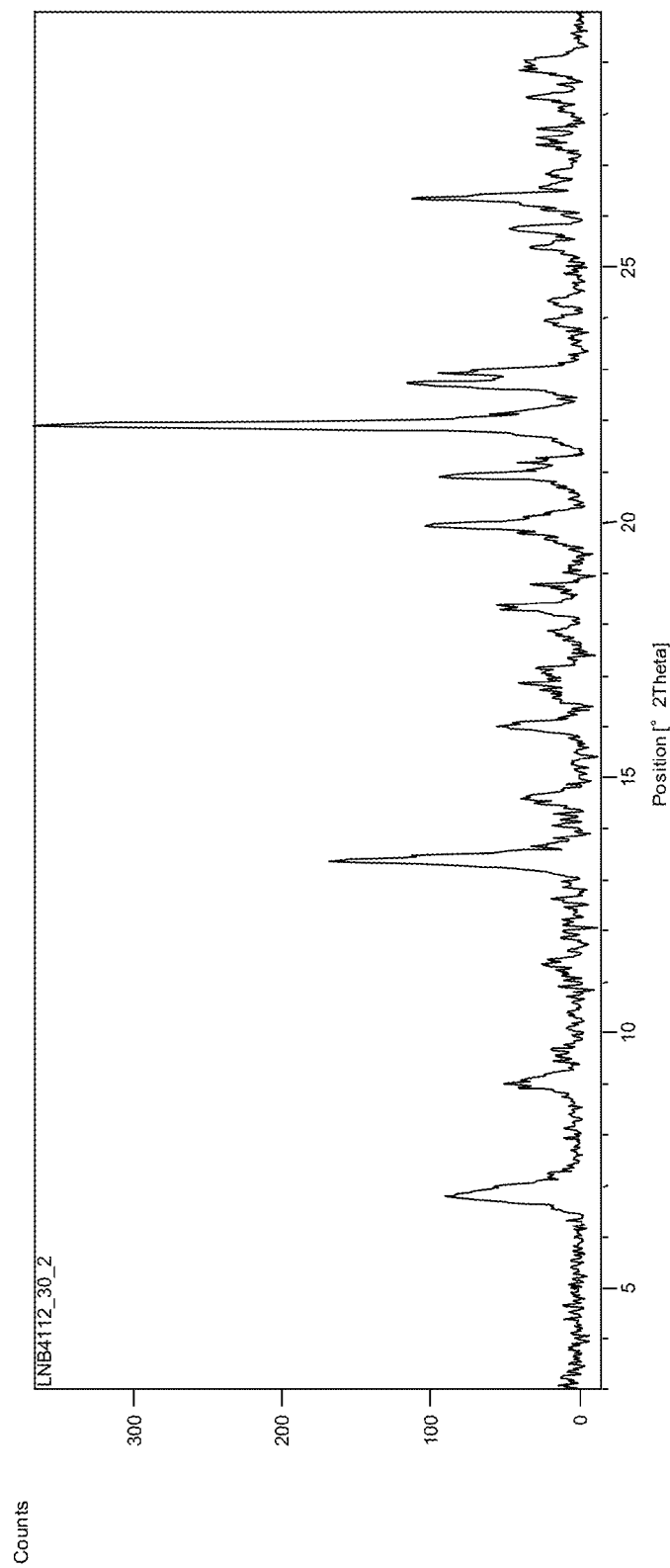
FIG. 67 depicts the XRPD pattern for a Form III hydrobromide salt of Compound 1.

In some embodiments, compound 2 is a Form III hydrobromide salt. In some such embodiments, compound 2 is an anhydrous Form III hydrobromide salt. In some embodiments, a Form III hydrobromide salt is characterized by a powder X-ray diffraction pattern substantially similar to that depicted in FIG. 67. According to one embodiment, a Form III hydrobromide salt is characterized by one or more peaks in its powder X-ray diffraction pattern selected from those at about 6.79, about 13.36, about 19.93, about 20.89, about 21.90, about 22.70, about 22.91 and about 26.34 degrees 2-theta. In some embodiments, a Form III hydrobromide salt is characterized by two or more peaks in its powder X-ray diffraction pattern selected from those at about 6.79, about 13.36, about 19.93, about 20.89, about 21.90, about 22.70, about 22.91 and about 26.34 degrees 2-theta. In certain embodiments, a Form III hydrobromide salt is characterized by three or more peaks in its powder X-ray diffraction pattern selected from those at about 6.79, about 13.36, about 19.93, about 20.89, about 21.90, about 22.70, about 22.91 and about 26.34 degrees 2-theta. In some embodiments, a Form III hydrobromide salt is characterized by four or more peaks in its powder X-ray diffraction pattern selected from those at about 6.79, about 13.36, about 19.93, about 20.89, about 21.90, about 22.70, about 22.91 and about 26.34 degrees 2-theta. In some embodiments, a Form III hydrobromide salt is characterized by five or more peaks in its powder X-ray diffraction pattern selected from those at about 6.79, about 13.36, about 19.93, about 20.89, about 21.90, about 22.70, about 22.91 and about 26.34 degrees 2-theta. In some embodiments, a Form III hydrobromide salt is characterized by six or more peaks in its powder X-ray diffraction pattern selected from those at about 6.79, about 13.36, about 19.93, about 20.89, about 21.90, about 22.70, about 22.91 and about 26.34 degrees 2-theta. In particular embodiments, a Form III hydrobromide salt is characterized by an X-ray powder diffraction pattern which includes the peaks at about 6.79, about 13.36, about 19.93, about 20.89, about 21.90, about 22.70, about 22.91 and about 26.34 degrees 2-theta. In an exemplary embodiment, a Form III hydrobromide salt is characterized by substantially all of the peaks in its X-ray powder diffraction pattern selected from those at about

| °2-Theta |
| --- |
| 6.79 |
| 8.15 |
| 8.98 |
| 9.58 |
| 10.36 |
| 11.35 |
| 13.36 |
| 14.06 |
| 14.58 |
| 15.99 |
| 16.67 |
| 17.08 |
| 17.84 |
| 18.33 |
| 18.74 |
| 19.07 |
| 19.93 |
| 20.89 |
| 21.90 |
| 22.70 |
| 22.91 |
| 23.93 |
| 24.32 |
| 25.39 |
| 25.74 |
| 26.34 |
| 27.47 |
| 28.32 |
| 28.89 |
| 30.50 |
| 30.76 |
| 31.39 |
| 31.75 |
| 32.39 |
| 32.68 |
| 33.33 |
| 33.77 |
| 34.48 |
| 34.57 |

Figure 68:
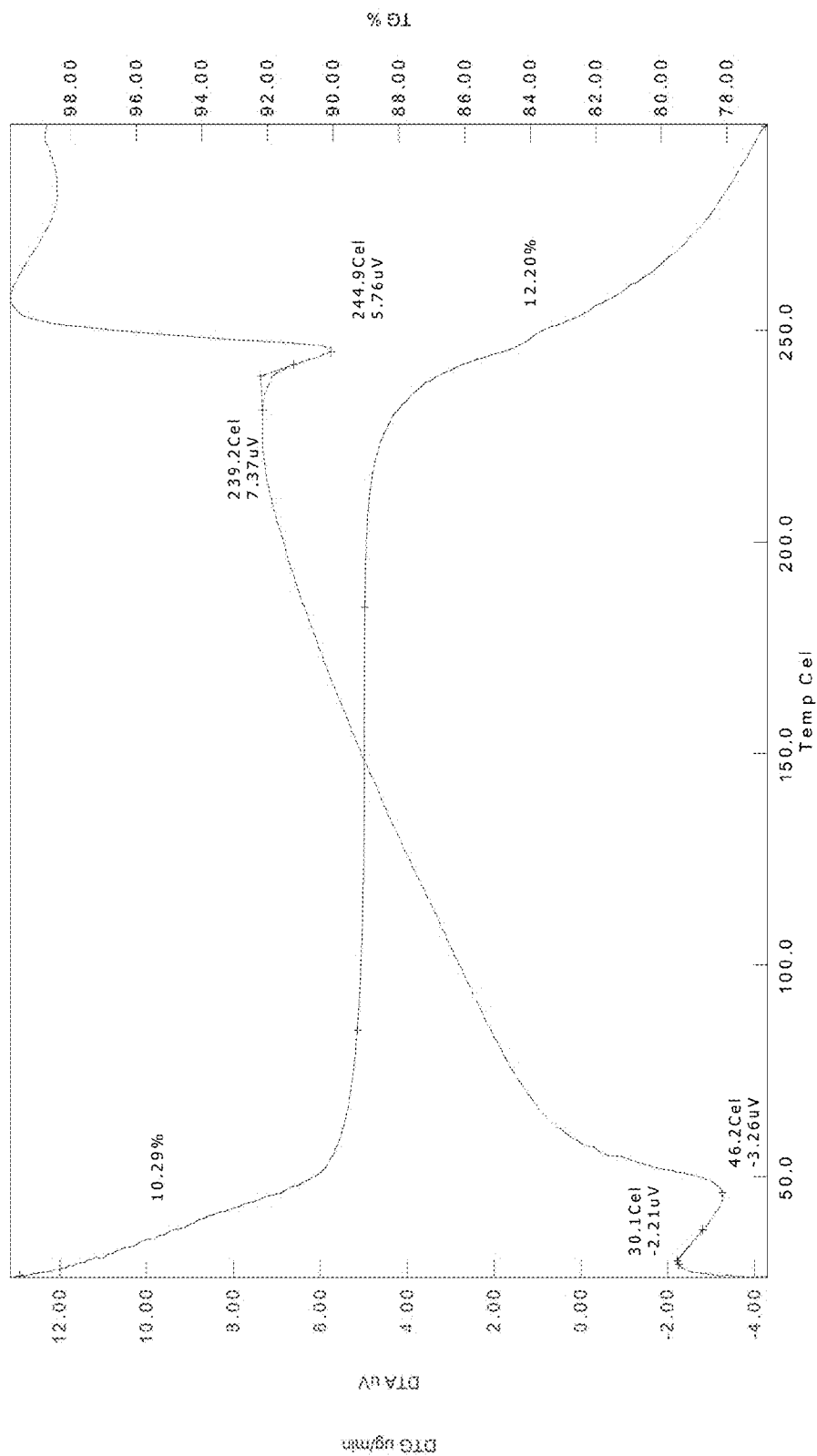
FIG. 68 depicts the TGA pattern for a Form III hydrobromide salt of Compound 1.
Figure 69:
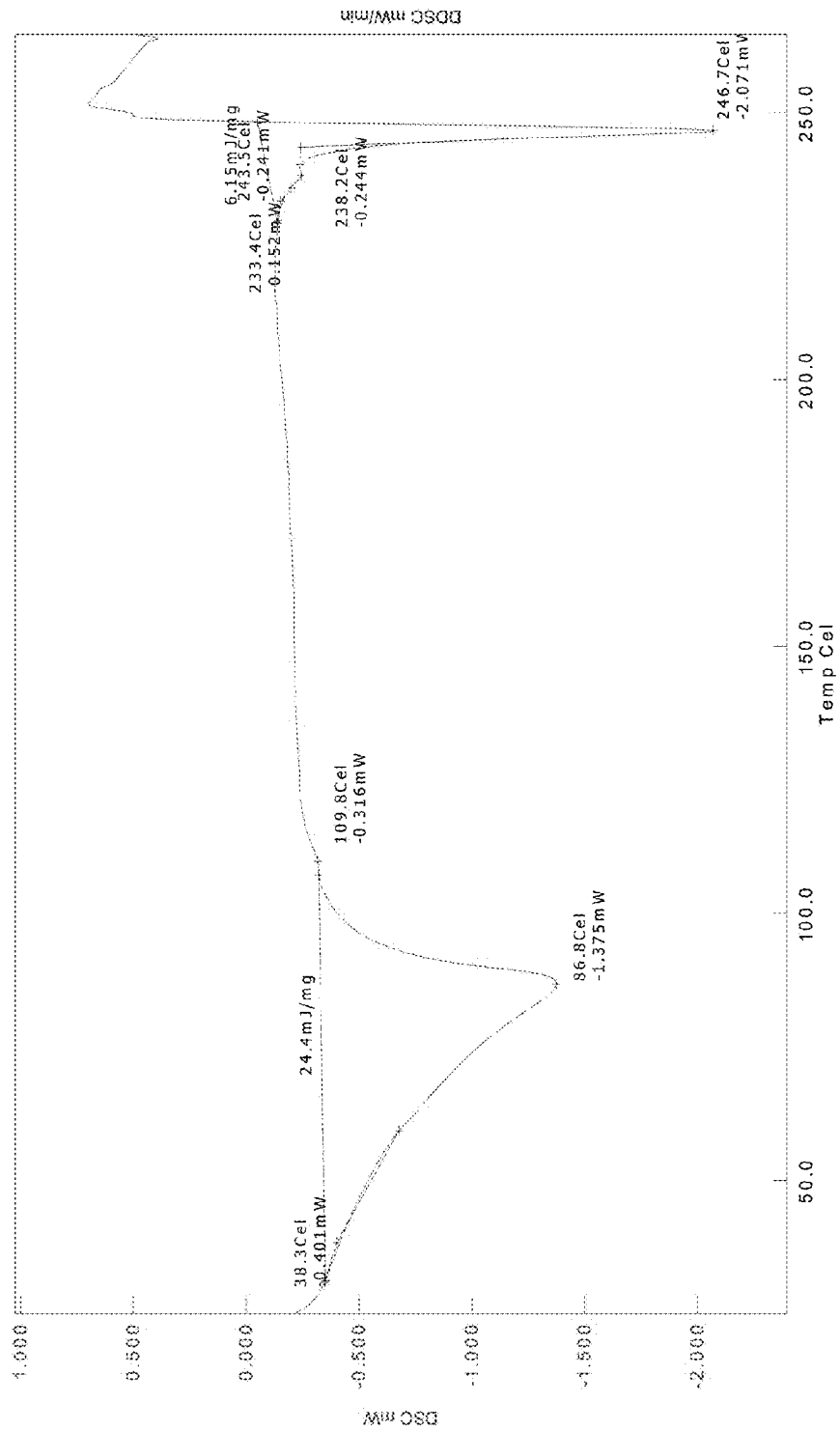
FIG. 69 depicts the DSC pattern for a Form III hydrobromide salt of Compound 1.
Figure 70:
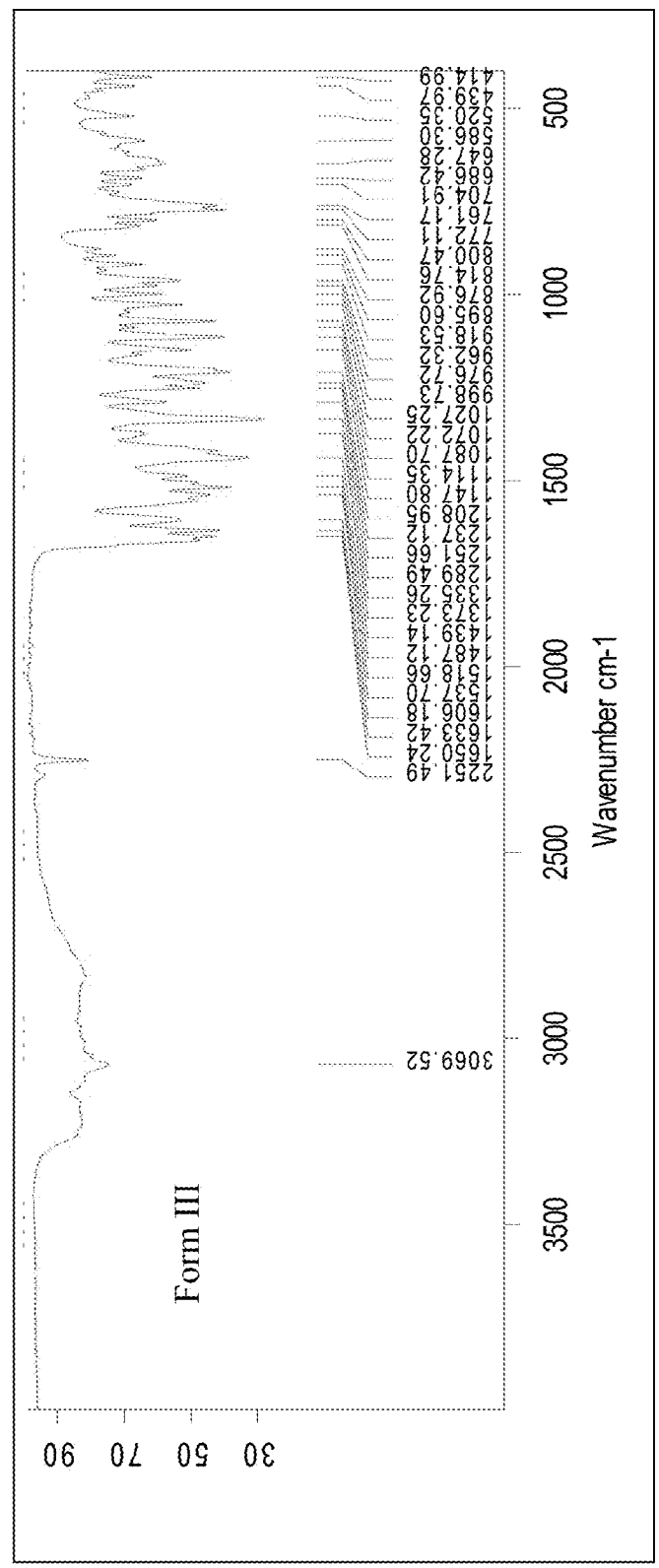
FIG. 70 depicts the IR spectrum for a Form III hydrobromide salt of Compound 1.
Figure 71:
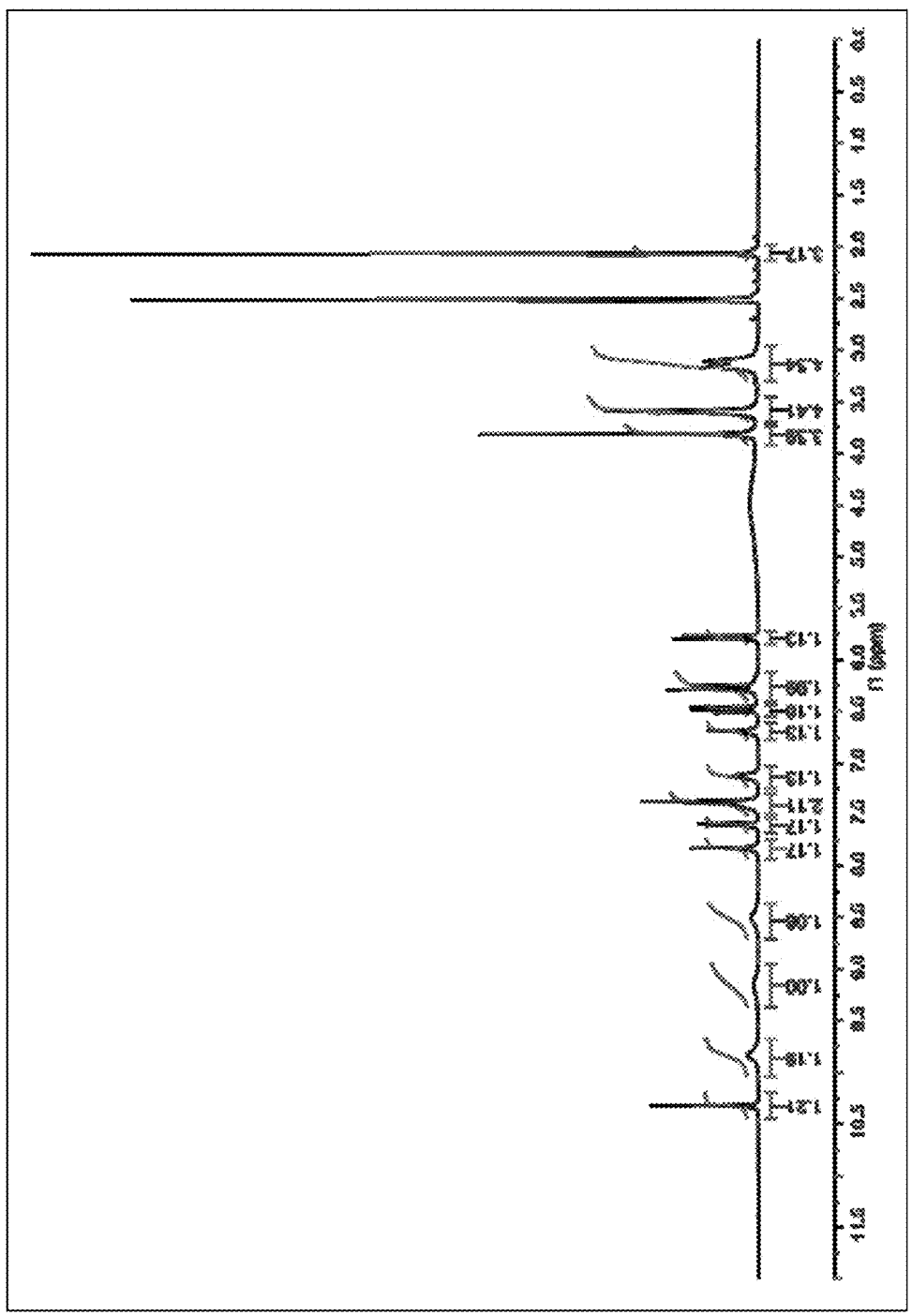
FIG. 71 depicts the $^1$H-NMR spectrum of a Form III hydrobromide salt of Compound 1.

In some embodiments, a Form III hydrobromide salt is characterized by a thermogravimetric analysis pattern substantially similar to that depicted in FIG. 68. In some embodiments, a Form III hydrobromide salt is characterized by a differential scanning calorimetry pattern substantially similar to that depicted in FIG. 69. In some embodiments, a Form III hydrobromide salt is characterized by an infrared spectrum substantially similar to that depicted in FIG. 70. In some embodiments, a Form III hydrobromide salt is characterized by a $^1$H-NMR spectrum substantially similar to that depicted in FIG. 71. In some embodiments, a Form III hydrobromide salt is characterized by substantial similarity to two or more of these figures simultaneously.

Figure 72:
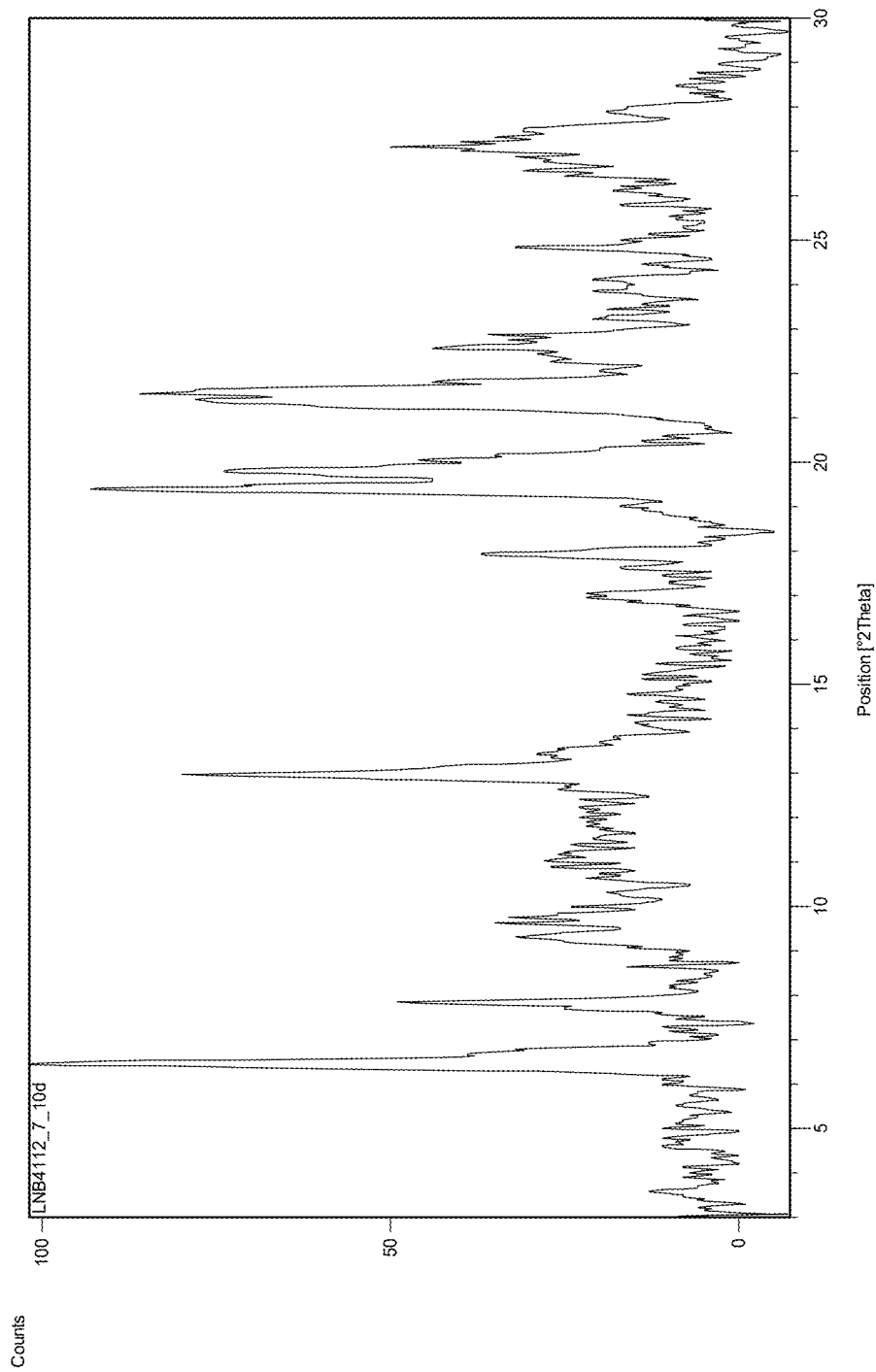
FIG. 72 depicts the XRPD pattern for a Form IV hydrobromide salt of Compound 1.

In some embodiments, compound 2 is a Form IV hydrobromide salt. In some such embodiments, a Form IV hydrobromide salt is a 1,4-dioxane solvate. In some embodiments, a Form IV hydrobromide salt is characterized by a powder X-ray diffraction pattern substantially similar to that depicted in FIG. 72. According to one embodiment, a Form IV hydrobromide salt is characterized by one or more peaks in its powder X-ray diffraction pattern selected from those at about 6.45, about 12.96, about 19.38, about 19.79, about 21.37 and about 21.58 degrees 2-theta. In some embodiments, a Form IV hydrobromide salt is characterized by two or more peaks in its powder X-ray diffraction pattern selected from those at about 6.45, about 12.96, about 19.38, about 19.79, about 21.37 and about 21.58 degrees 2-theta. In certain embodiments, a Form IV hydrobromide salt is characterized by three or more peaks in its powder X-ray diffraction pattern selected from those at about 6.45, about 12.96, about 19.38, about 19.79, about 21.37 and about 21.58 degrees 2-theta. In some embodiments, a Form IV hydrobromide salt is characterized by four or more peaks in its powder X-ray diffraction pattern selected from those at about 6.45, about 12.96, about 19.38, about 19.79, about 21.37 and about 21.58 degrees 2-theta. In some embodiments, a Form IV hydrobromide salt is characterized by five or more peaks in its powder X-ray diffraction pattern selected from those at about 6.45, about 12.96, about 19.38, about 19.79, about 21.37 and about 21.58 degrees 2-theta. In particular embodiments, a Form IV hydrobromide salt is characterized by an X-ray powder diffraction pattern which includes the peaks at about 6.45, about 12.96, about 19.38, about 19.79, about 21.37 and about 21.58 degrees 2-theta. In an exemplary embodiment, a Form IV hydrobromide salt is characterized by substantially all of the peaks in its X-ray powder diffraction pattern selected from those at about

| °2-Theta |
| --- |
| 5.99 |
| 6.45 |
| 7.23 |
| 7.84 |
| 9.31 |
| 9.71 |
| 11.07 |
| 12.96 |
| 13.42 |
| 16.34 |
| 16.55 |
| 17.00 |
| 17.93 |
| 18.99 |
| 19.38 |
| 19.79 |
| 21.37 |
| 21.58 |
| 22.65 |
| 23.23 |
| 24.10 |
| 24.82 |
| 26.539 |
| 27.12 |
| 27.89 |
| 28.43 |
| 28.74 |

Figure 73:
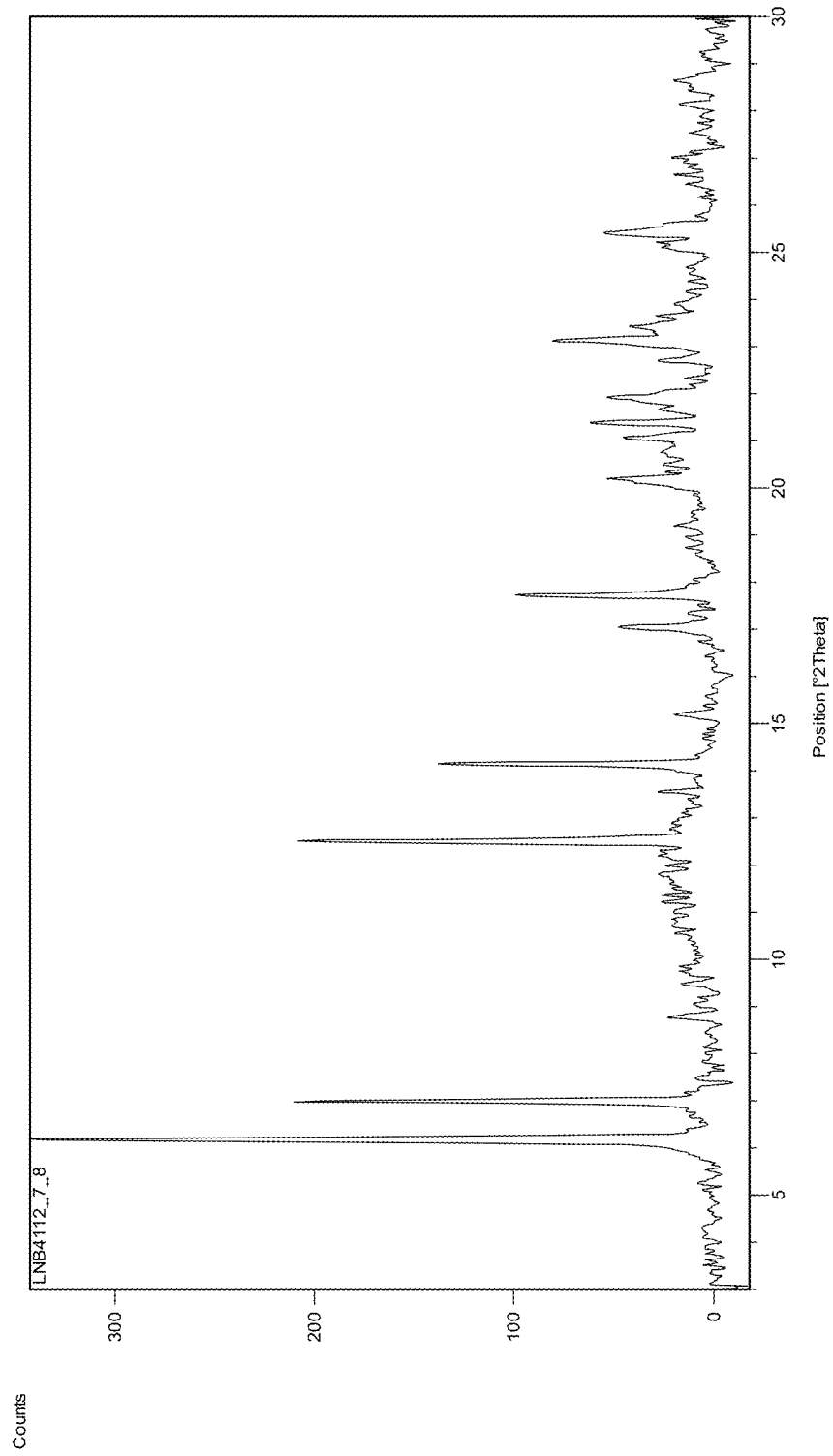
FIG. 73 depicts the XRPD pattern for a Form V hydrobromide salt of Compound 1.

In some embodiments, compound 2 is a Form V hydrobromide salt. In some such embodiments, a Form V hydrobromide salt is a N,N-dimethylformamide (DMF) solvate. In some embodiments, a Form V hydrobromide salt is characterized by a powder X-ray diffraction pattern substantially similar to that depicted in FIG. 73. According to one embodiment, a Form V hydrobromide salt is characterized by one or more peaks in its powder X-ray diffraction pattern selected from those at about 6.17, about 6.99, about 12.50, about 14.14, about 17.72 and about 23.12 degrees 2-theta. In some embodiments, a Form V hydrobromide salt is characterized by two or more peaks in its powder X-ray diffraction pattern selected from those at about 6.17, about 6.99, about 12.50, about 14.14, about 17.72 and about 23.12 degrees 2-theta. In certain embodiments, a Form V hydrobromide salt is characterized by three or more peaks in its powder X-ray diffraction pattern selected from those at about 6.17, about 6.99, about 12.50, about 14.14, about 17.72 and about 23.12 degrees 2-theta. In some embodiments, a Form V hydrobromide salt is characterized by four or more peaks in its powder X-ray diffraction pattern selected from those at about 6.17, about 6.99, about 12.50, about 14.14, about 17.72 and about 23.12 degrees 2-theta. In some embodiments, a Form V hydrobromide salt is characterized by five or more peaks in its powder X-ray diffraction pattern selected from those at about 6.17, about 6.99, about 12.50, about 14.14, about 17.72 and about 23.12 degrees 2-theta. In particular embodiments, a Form V hydrobromide salt is characterized by an X-ray powder diffraction pattern which includes the peaks at about 6.17, about 6.99, about 12.50, about 14.14, about 17.72 and about 23.12 degrees 2-theta. In an exemplary embodiment, a Form V hydrobromide salt is characterized by substantially all of the peaks in its X-ray powder diffraction pattern selected from those at about

| °2-Theta |
| --- |
| 6.17 |
| 6.99 |
| 8.76 |
| 12.50 |
| 13.56 |
| 14.14 |
| 15.19 |
| 17.03 |
| 17.72 |
| 20.20 |
| 21.06 |
| 21.38 |
| 21.66 |
| 21.90 |
| 22.33 |
| 22.70 |
| 23.12 |
| 23.41 |
| 23.66 |
| 23.88 |
| 24.16 |
| 24.57 |
| 25.15 |
| 25.41 |
| 26.64 |
| 26.97 |
| 28.12 |
| 28.42 |
| 28.61 |

Figure 74:
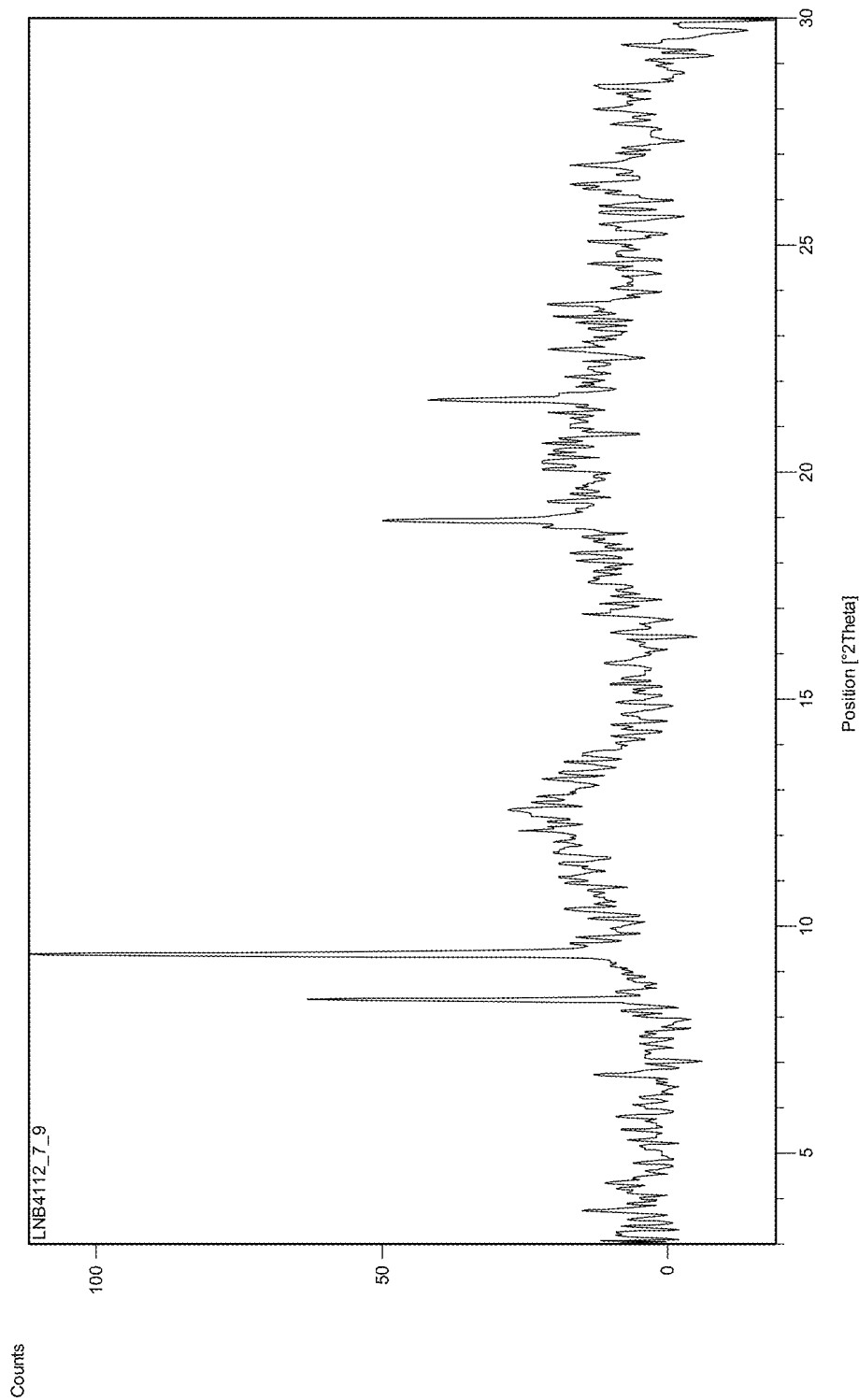
FIG. 74 depicts the XRPD pattern for a Form VI hydrobromide salt of Compound 1.

In some embodiments, compound 2 is a Form VI hydrobromide salt. In some such embodiments, a Form VI hydrobromide salt is a dimethylsulfoxide (DMSO) solvate. In some embodiments, a Form VI hydrobromide salt is characterized by a powder X-ray diffraction pattern substantially similar to that depicted in FIG. 74. According to one embodiment, a Form VI hydrobromide salt is characterized by one or more peaks in its powder X-ray diffraction pattern selected from those at about 8.38, about 9.38, about 18.93, and about 21.58 degrees 2-theta. In some embodiments, a Form VI hydrobromide salt is characterized by two or more peaks in its powder X-ray diffraction pattern selected from those at about 8.38, about 9.38, about 18.93, and about 21.58 degrees 2-theta. In certain embodiments, a Form VI hydrobromide salt is characterized by three or more peaks in its powder X-ray diffraction pattern selected from those at about 8.38, about 9.38, about 18.93, and about 21.58 degrees 2-theta. In particular embodiments, a Form VI hydrobromide salt is characterized by an X-ray powder diffraction pattern which includes the peaks at about 8.38, about 9.38, about 18.93, and about 21.58 degrees 2-theta. In an exemplary embodiment, a Form VI hydrobromide salt is characterized by substantially all of the peaks in its X-ray powder diffraction pattern selected from those at about

| °2-Theta |
| --- |
| 8.38 |
| 9.38 |
| 18.93 |
| 21.58 |

Figure 75:
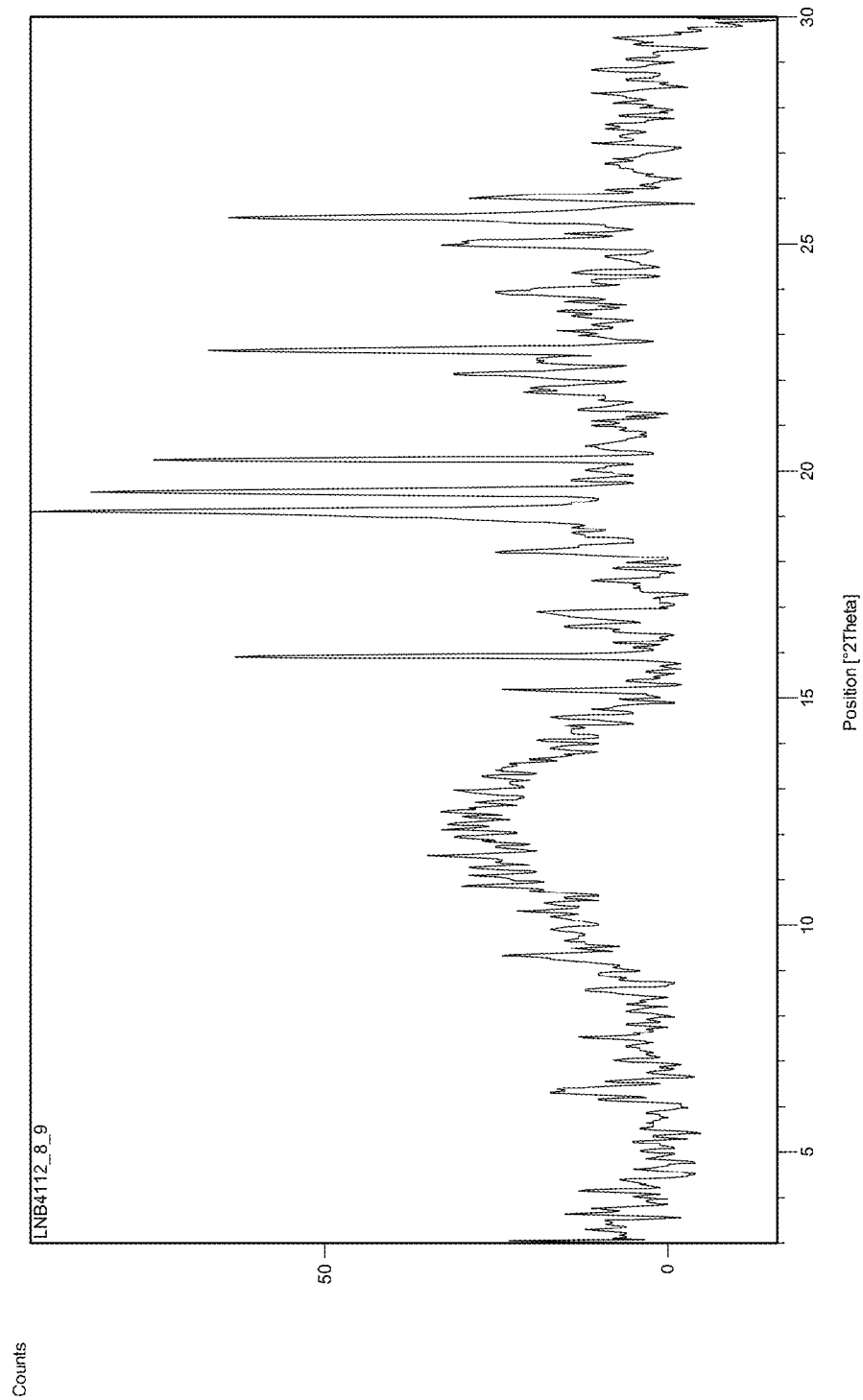
FIG. 75 depicts the XRPD pattern for a Form VII hydrobromide salt of Compound 1.

In some embodiments, compound 2 is a Form VII hydrobromide salt. In some such embodiments, a Form VII hydrobromide salt is a dimethylsulfoxide (DMSO) solvate. In some embodiments, a Form VII hydrobromide salt is characterized by a powder X-ray diffraction pattern substantially similar to that depicted in FIG. 75. According to one embodiment, a Form VII hydrobromide salt is characterized by one or more peaks in its powder X-ray diffraction pattern selected from those at about 15.91, about 19.10, about 19.53, about 20.24, about 22.64 and about 25.58 degrees 2-theta. In some embodiments, a Form VII hydrobromide salt is characterized by two or more peaks in its powder X-ray diffraction pattern selected from those at about 15.91, about 19.10, about 19.53, about 20.24, about 22.64 and about 25.58 degrees 2-theta. In certain embodiments, a Form VII hydrobromide salt is characterized by three or more peaks in its powder X-ray diffraction pattern selected from those at about 15.91, about 19.10, about 19.53, about 20.24, about 22.64 and about 25.58 degrees 2-theta. In some embodiments, a Form VII hydrobromide salt is characterized by four or more peaks in its powder X-ray diffraction pattern selected from those at about 15.91, about 19.10, about 19.53, about 20.24, about 22.64 and about 25.58 degrees 2-theta. In some embodiments, a Form VII hydrobromide salt is characterized by five or more peaks in its powder X-ray diffraction pattern selected from those at about 15.91, about 19.10, about 19.53, about 20.24, about 22.64 and about 25.58 degrees 2-theta. In particular embodiments, a Form VII hydrobromide salt is characterized by an X-ray powder diffraction pattern which includes the peaks at about 15.91, about 19.10, about 19.53, about 20.24, about 22.64 and about 25.58 degrees 2-theta. In an exemplary embodiment, a Form VII hydrobromide salt is characterized by substantially all of the peaks in its X-ray powder diffraction pattern selected from those at about

| °2-Theta |
| --- |
| 6.35 |
| 8.88 |
| 9.29 |
| 15.18 |
| 15.91 |
| 16.54 |
| 16.88 |
| 17.56 |
| 18.22 |
| 19.10 |
| 19.53 |
| 20.24 |
| 21.78 |
| 22.12 |
| 22.64 |
| 23.93 |
| 24.37 |
| 25.00 |
| 25.58 |
| 26.00 |

Figure 76:
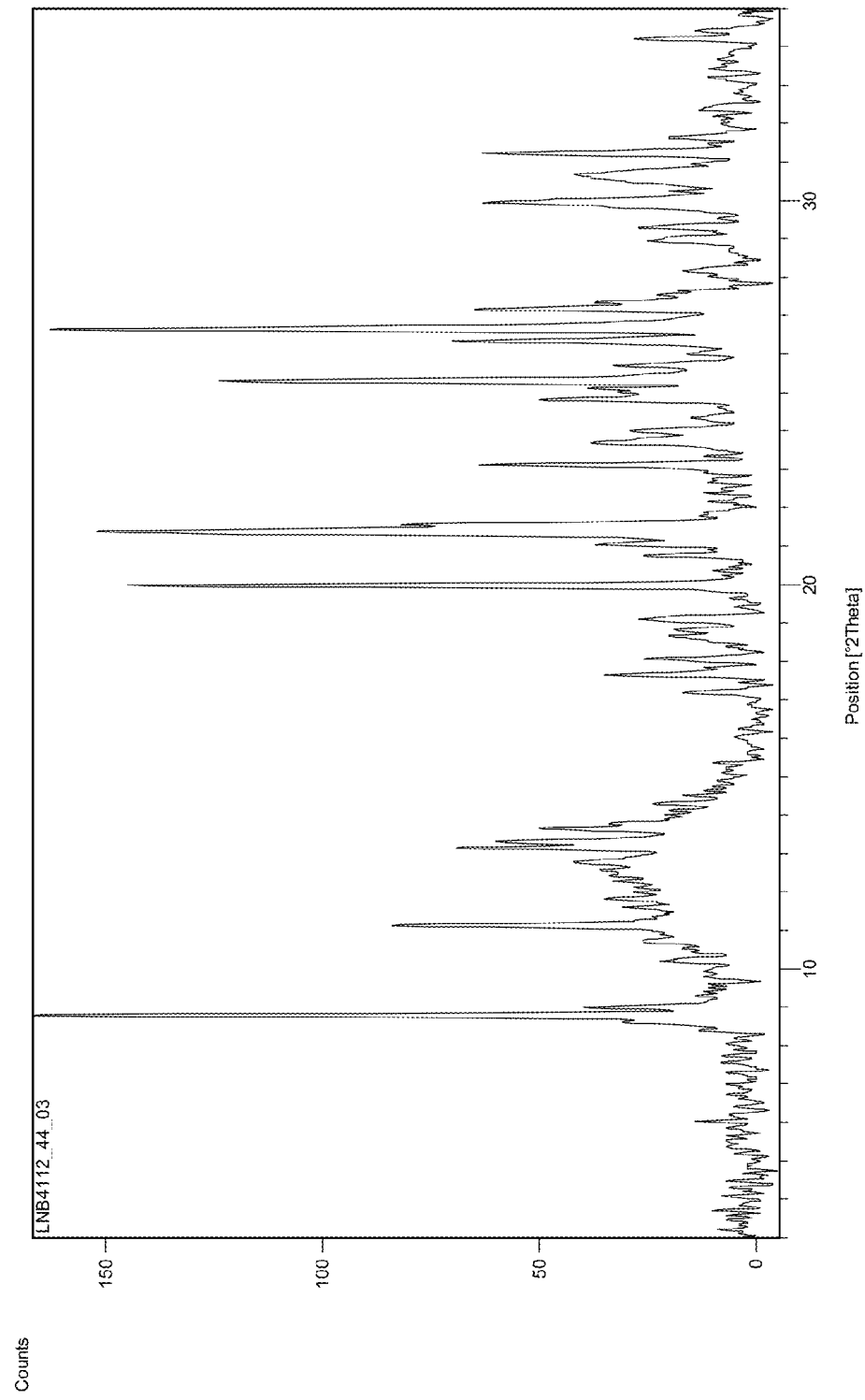
FIG. 76 depicts the XRPD pattern for a Form VIII hydrobromide salt of Compound 1.

In some embodiments, compound 2 is a Form VIII hydrobromide salt. In some such embodiments, a Form VIII hydrobromide salt is a hydrate. In some embodiments, a Form VIII hydrobromide salt is characterized by a powder X-ray diffraction pattern substantially similar to that depicted in FIG. 76. According to one embodiment, a Form VIII hydrobromide salt is characterized by one or more peaks in its powder X-ray diffraction pattern selected from those at about 8.79, about 11.13, about 19.97, about 21.31, about 21.56, about 25.30 and about 26.65 degrees 2-theta. In some embodiments, a Form VIII hydrobromide salt is characterized by two or more peaks in its powder X-ray diffraction pattern selected from those at about 8.79, about 11.13, about 19.97, about 21.31, about 21.56, about 25.30 and about 26.65 degrees 2-theta. In certain embodiments, a Form VIII hydrobromide salt is characterized by three or more peaks in its powder X-ray diffraction pattern selected from those at about 8.79, about 11.13, about 19.97, about 21.31, about 21.56, about 25.30 and about 26.65 degrees 2-theta. In some embodiments, a Form VIII hydrobromide salt is characterized by four or more peaks in its powder X-ray diffraction pattern selected from those at about 8.79, about 11.13, about 19.97, about 21.31, about 21.56, about 25.30 and about 26.65 degrees 2-theta. In some embodiments, a Form VIII hydrobromide salt is characterized by five or more peaks in its powder X-ray diffraction pattern selected from those at about 8.79, about 11.13, about 19.97, about 21.31, about 21.56, about 25.30 and about 26.65 degrees 2-theta. In some embodiments, a Form VIII hydrobromide salt is characterized by six or more peaks in its powder X-ray diffraction pattern selected from those at about 8.79, about 11.13, about 19.97, about 21.31, about 21.56, about 25.30 and about 26.65 degrees 2-theta. In particular embodiments, a Form VIII hydrobromide salt is characterized by an X-ray powder diffraction pattern which includes the peaks at about 8.79, about 11.13, about 19.97, about 21.31, about 21.56, about 25.30 and about 26.65 degrees 2-theta. In an exemplary embodiment, a Form VIII hydrobromide salt is characterized by substantially all of the peaks in its X-ray powder diffraction pattern selected from those at about

| °2-Theta |
| --- |
| 8.79 |
| 9.00 |
| 10.22 |
| 11.13 |
| 13.15 |
| 13.30 |
| 13.65 |
| 17.19 |
| 17.65 |
| 18.07 |
| 18.69 |
| 19.09 |
| 19.97 |
| 20.75 |
| 21.05 |
| 21.31 |
| 21.56 |
| 23.12 |
| 23.71 |
| 24.00 |
| 24.82 |
| 25.30 |
| 25.71 |
| 26.34 |
| 26.65 |
| 27.17 |
| 28.18 |
| 28.97 |
| 29.31 |
| 29.96 |
| 30.65 |
| 31.23 |
| 31.64 |
| 34.21 |
| 34.43 |

Figure 77:
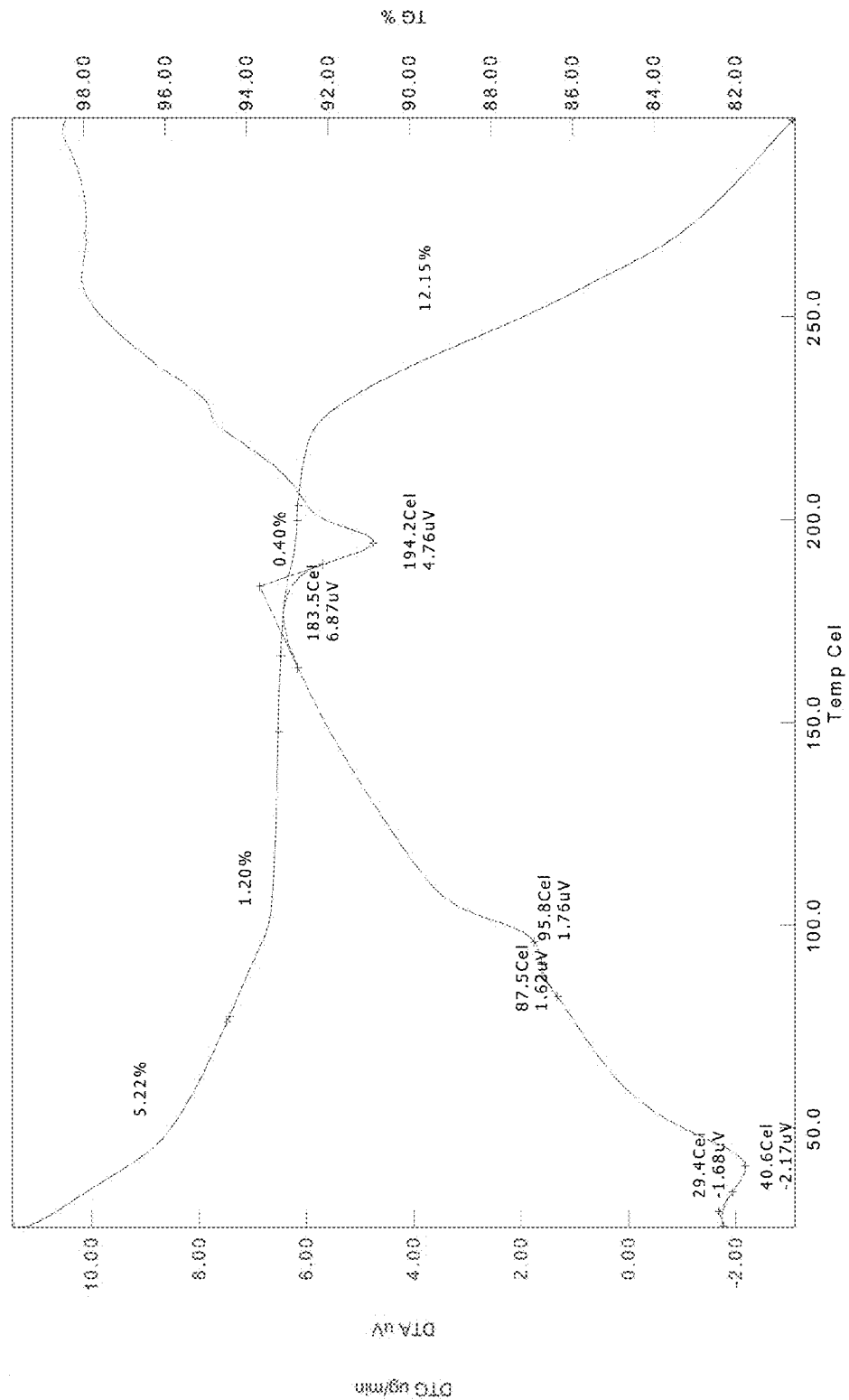
FIG. 77 depicts the TGA pattern for a Form VIII hydrobromide salt of Compound 1.
Figure 78:
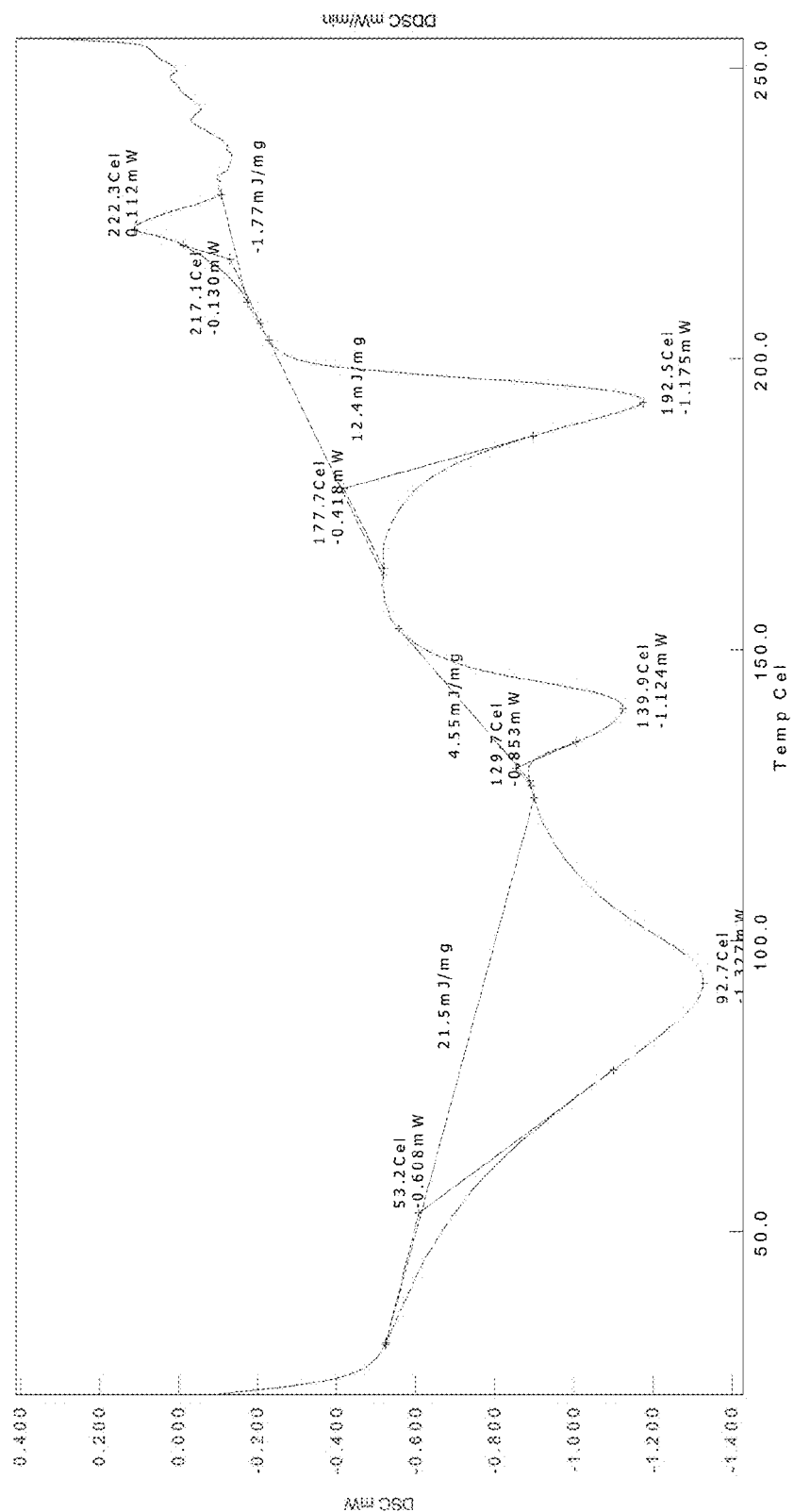
FIG. 78 depicts the DSC pattern for a Form VIII hydrobromide salt of Compound 1.

In some embodiments, a Form VIII hydrobromide salt has a thermogravimetric analysis pattern substantially similar to that depicted in FIG. 77. In some embodiments, a Form VIII hydrobromide salt has a differential scanning calorimetry pattern substantially similar to that depicted in FIG. 78. In some embodiments, a Form VIII hydrobromide salt is characterized by substantial similarity to two or more of these figures simultaneously.

In certain embodiments, compound 2 is a hydrochloric acid salt. In some embodiments, compound 2 is a monohydrochloric acid salt. In some embodiments, compound 2 is a bis-hydrochloric acid salt.

Figure 28:
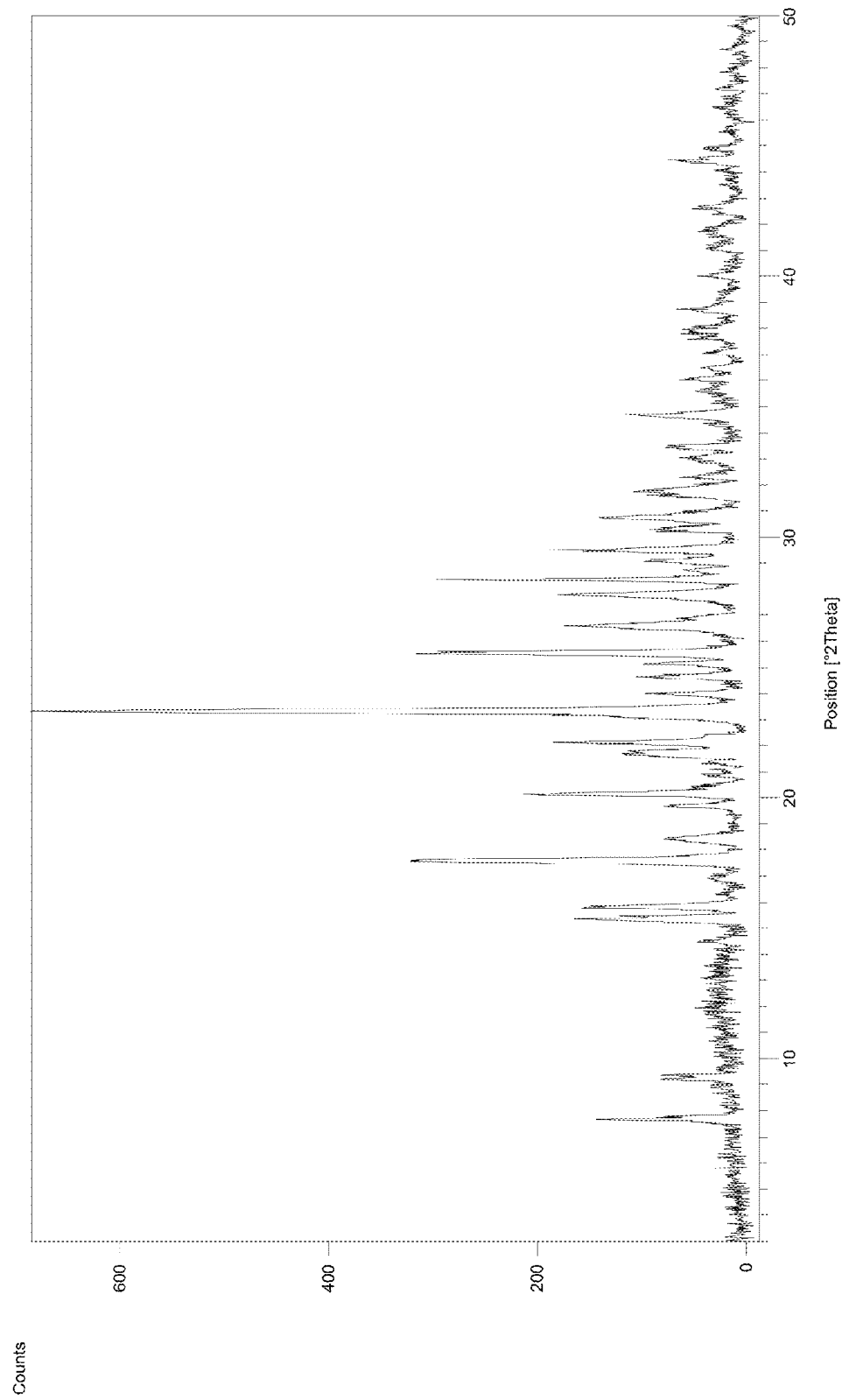
FIG. 28 depicts the XRPD pattern for a bis-hydrochloride salt of Compound 1.

According to one aspect, a bis-hydrochloride salt has a powder X-ray diffraction pattern substantially similar to that depicted in FIG. 28. According to one embodiment, a bis-hydrochloride salt is characterized by one or more peaks in its powder X-ray diffraction pattern selected from those at about 17.58, about 23.32, about 25.53 and about 28.37 degrees 2-theta. In some embodiments, a bis-hydrochloride salt is characterized by two or more peaks in its powder X-ray diffraction pattern selected from those at about 17.58, about 23.32, about 25.53 and about 28.37 degrees 2-theta. In certain embodiments, a bis-hydrochloride salt is characterized by three or more peaks in its powder X-ray diffraction pattern selected from those at about 17.58, about 23.32, about 25.53 and about 28.37 degrees 2-theta. In particular embodiments, a bis-hydrochloride salt is characterized by substantially all of the peaks in its X-ray powder diffraction pattern selected from those at about 17.58, 20.13, 22.14, 23.32, 25.53, 26.60, 27.80 and 28.37 degrees 2-theta. In an exemplary embodiment, a bis-hydrochloride salt is characterized by substantially all of the peaks in its X-ray powder diffraction pattern selected from those at about

| °2-Theta |
| --- |
| 3.04 |
| 3.84 |
| 5.40 |
| 6.34 |
| 7.67 |
| 9.20 |
| 9.37 |
| 10.62 |
| 14.48 |
| 15.34 |
| 15.47 |
| 15.81 |
| 16.34 |
| 16.87 |
| 17.58 |
| 18.44 |
| 19.68 |
| 20.13 |
| 20.86 |
| 21.38 |
| 21.67 |
| 22.14 |
| 23.32 |
| 23.99 |
| 24.63 |
| 25.15 |
| 25.53 |
| 26.60 |
| 27.80 |
| 28.37 |
| 28.73 |
| 29.08 |
| 29.50 |
| 30.21 |
| 30.74 |
| 31.56 |
| 31.79 |
| 32.29 |
| 33.03 |
| 33.46 |
| 34.66 |
| 35.62 |
| 36.07 |
| 36.47 |
| 37.08 |
| 37.91 |
| 38.71 |
| 40.02 |
| 41.01 |
| 41.78 |
| 42.64 |
| 44.43 |
| 44.89 |
| 45.62 |
| 46.46 |
| 46.87 |
| 47.18 |
| 47.88 |
| 48.14 |
| 48.72 |
| 49.63 |

Figure 29:
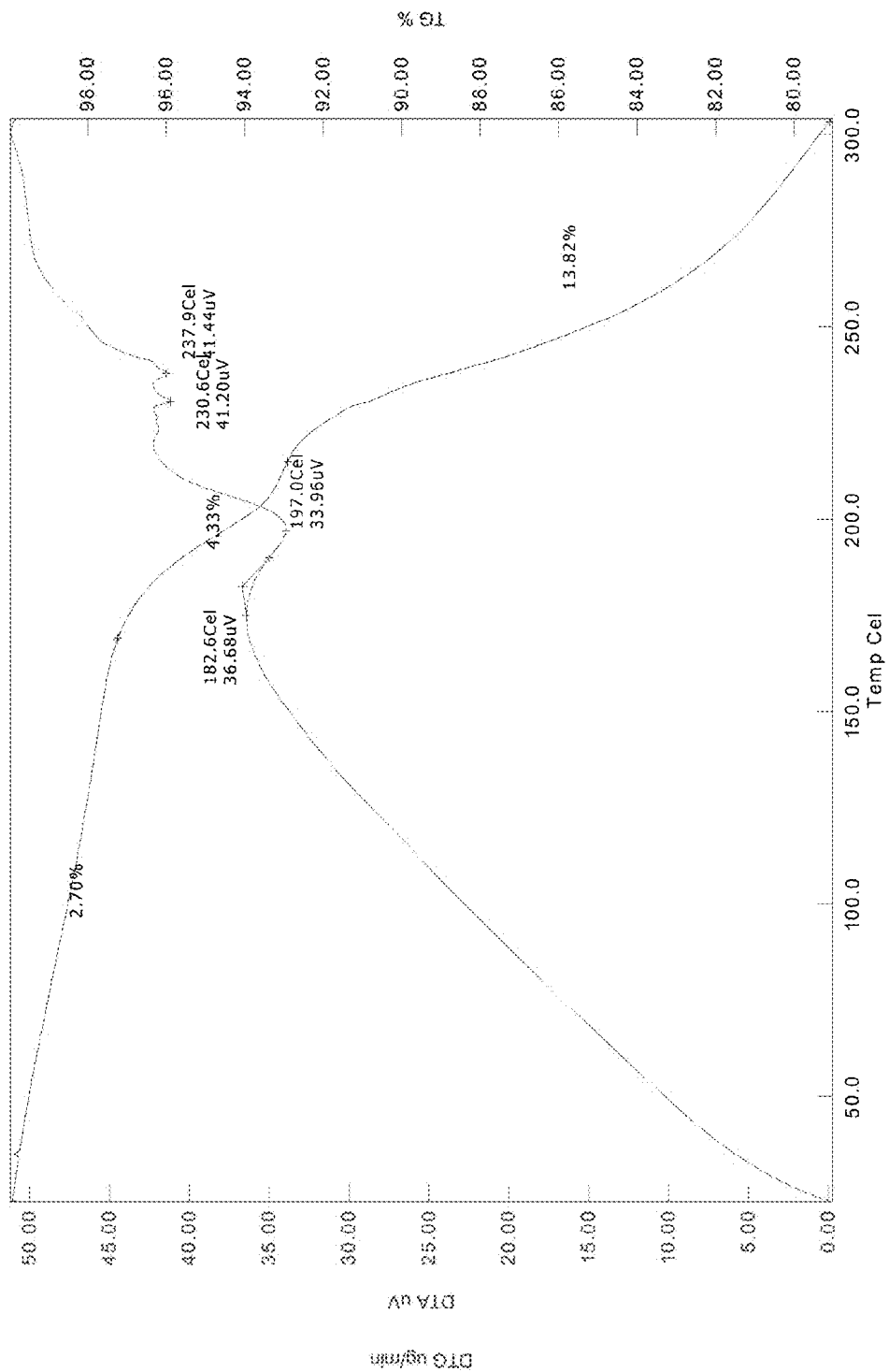
FIG. 29 depicts the TGA pattern for a bis-hydrochloride salt of Compound 1.

According to another aspect, a bis-hydrochloride salt has a thermogravimetric analysis pattern substantially similar to that depicted in FIG. 29. According to yet another aspect, a bis-hydrochloride salt has a differential scanning calorimetry pattern substantially similar to that depicted in FIG. 30. According to another embodiment, a bis-hydrochloride salt has an $^1$H-NMR spectrum substantially similar to that depicted in FIG. 31.

In certain embodiments, compound 2 is a maleic acid salt. In some embodiments, compound 2 is a mono-maleic acid salt. In some embodiments, compound 2 is a bis-maleic acid salt.

Figure 24:
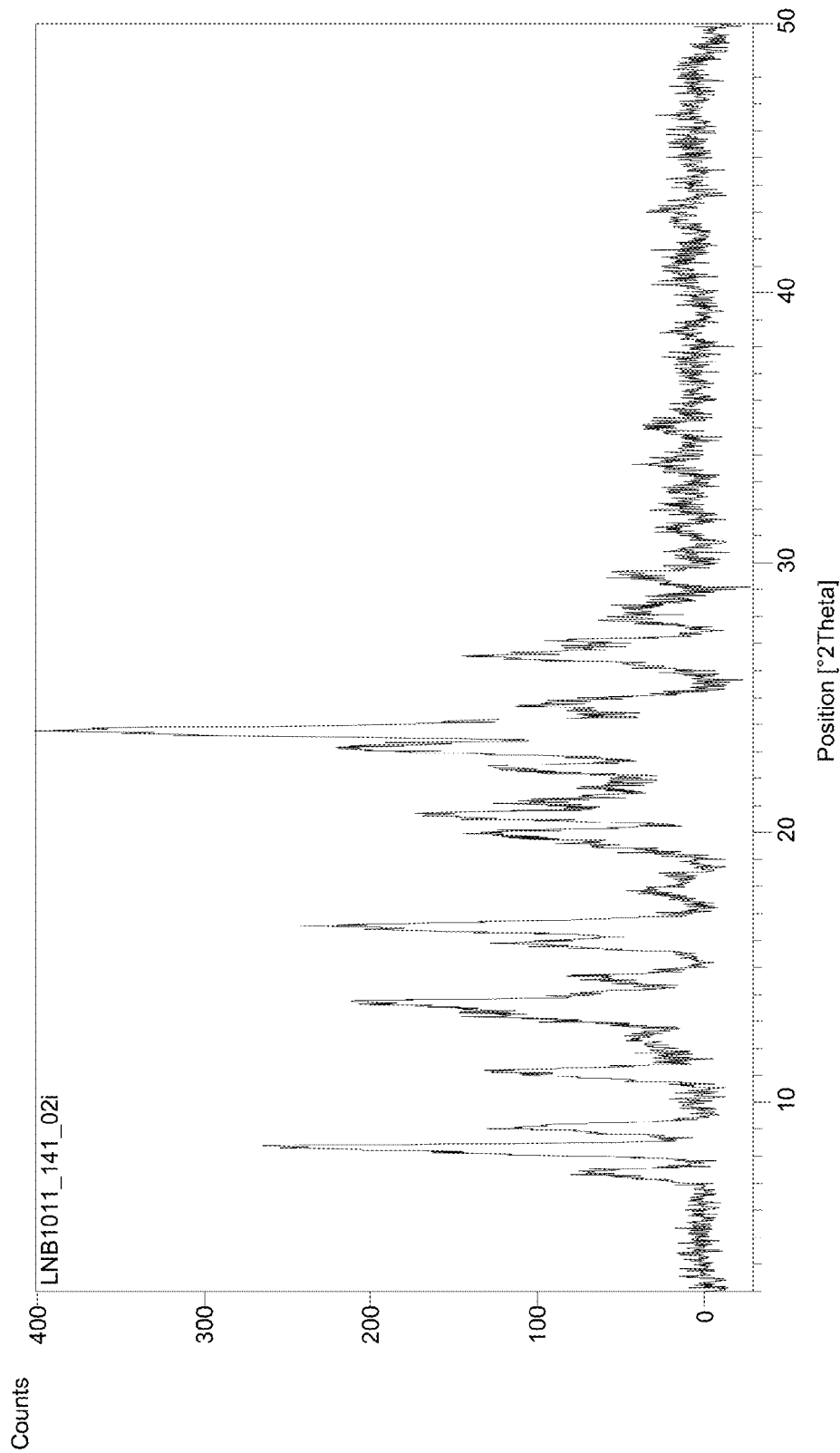
FIG. 24 depicts the XRPD pattern for a mono-maleate salt of Compound 1.

According to one aspect, a mono-maleate salt has a powder X-ray diffraction pattern substantially similar to that depicted in FIG. 24. According to one embodiment, a mono-maleate salt is characterized by one or more peaks in its powder X-ray diffraction pattern selected from those at about 8.38, about 23.59 and about 23.80 degrees 2-theta. In some embodiments, a mono-maleate salt is characterized by two or more peaks in its powder X-ray diffraction pattern selected from those at about 8.38, about 23.59 and about 23.80 degrees 2-theta. In certain embodiments, a mono-maleate salt is characterized by three peaks in its powder X-ray diffraction pattern selected from those at about 8.38, about 23.59 and about 23.80 degrees 2-theta. In particular embodiments, a mono-maleate salt is characterized by substantially all of the peaks in its X-ray powder diffraction pattern selected from those at about 8.38, 13.74, 16.35, 16.54, 20.67, 23.15, 23.59 and 23.80 degrees 2-theta. In an exemplary embodiment, a mono-maleate salt is characterized by substantially all of the peaks in its X-ray powder diffraction pattern selected from those at about

| °2-Theta |
| --- |
| 7.42 |
| 8.38 |
| 9.06 |
| 9.91 |
| 10.13 |
| 10.45 |
| 10.62 |
| 11.16 |
| 12.40 |
| 13.15 |
| 13.74 |
| 14.65 |
| 15.91 |
| 16.35 |
| 16.54 |
| 17.86 |
| 19.96 |
| 20.67 |
| 22.50 |
| 23.15 |
| 23.59 |
| 23.80 |
| 24.75 |
| 26.52 |
| 27.13 |
| 27.90 |
| 29.53 |
| 30.37 |
| 31.30 |
| 32.04 |
| 33.68 |
| 35.05 |
| 38.51 |
| 41.05 |
| 43.03 |
| 45.85 |
| 46.06 |
| 46.44 |
| 46.69 |
| 48.23 |

Figure 25:
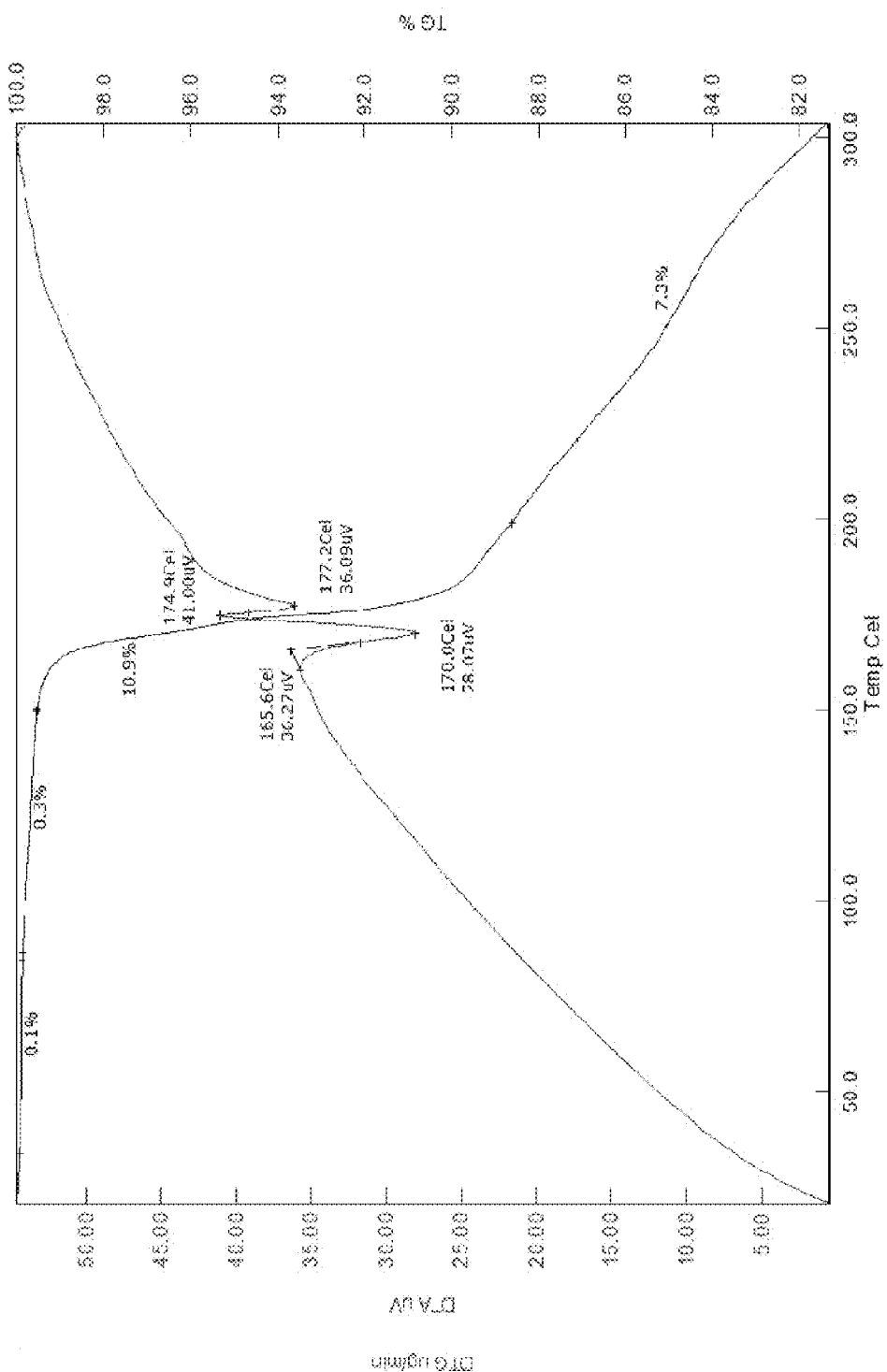
FIG. 25 depicts the TGA pattern for a mono-maleate salt of Compound 1.

According to another aspect, a mono-maleate salt has a thermogravimetric analysis pattern substantially similar to that depicted in FIG. 25. According to yet another aspect, a mono-maleate salt has a differential scanning calorimetry pattern substantially similar to that depicted in FIG. 26. According to another embodiment, a mono-maleate salt has an $^1$H-NMR spectrum substantially similar to that depicted in FIG. 27.

It will be appreciated that any of the above-described polymorph forms can be characterized, for example, by reference to any of the peaks in their respective X-ray diffraction patterns. Accordingly, in some embodiments, a polymorph described herein is characterized by one, two, three, four, five, six, seven, eight, nine, ten, eleven, twelve, thirteen, fourteen, fifteen, sixteen, seventeen, eighteen, nineteen, twenty or more XRPD peaks (°2θ).

In certain embodiments, compound 2 is a methanesulfonic acid salt. In some embodiments, compound 2 is a mono-methansulfonic acid salt. In some embodiments, compound 2 is a bis-methanesulfonic acid salt.

In certain embodiments, compound 2 is a naphthalene-2-sulfonic acid salt. In some embodiments, compound 2 is a mono-naphthalene-2-sulfonic acid salt. In some embodiments, compound 2 is a bis-naphthalene-2-sulfonic acid salt.

In certain embodiments, compound 2 is a 1,5-naphthalene disulfonic acid salt. In some embodiments, compound 2 is a mono-1,5-naphthalene disulfonic acid salt. In some embodiments, compound 2 is a bis-1,5-naphthalene disulfonic acid salt.

In certain embodiments, compound 2 is an oxalic acid salt. In some embodiments, compound 2 is a mono-oxalic acid salt. In some embodiments, compound 2 is a bis-oxalic acid salt.

In certain embodiments, compound 2 is a p-toluenesulfonic acid (tosylate) salt. In some embodiments, compound 2 is a mono-p-toluenesulfonic acid salt. In some embodiments, compound 2 is a bis-p-toluenesulfonic acid salt.

In certain embodiments, compound 2 is a 2,4,6-trihydroxybenzoic acid salt. In some embodiments, compound 2 is a mono-2,4,6-trihydroxybenzoic acid salt. In some embodiments, compound 2 is a bis-2,4,6-trihydroxybenzoic acid salt.

According to another embodiment, the present invention provides compound 2 as an amorphous solid. Amorphous solids are well known to one of ordinary skill in the art and are typically prepared by such methods as lyophilization, melting, and precipitation from supercritical fluid, among others.

General Methods of Providing Compound 2:

Compound 1 is prepared according to the methods described in detail in the '061 application, the entirety of which is hereby incorporated herein by reference. Compound 2 is prepared from Compound 1, according to the Scheme below.

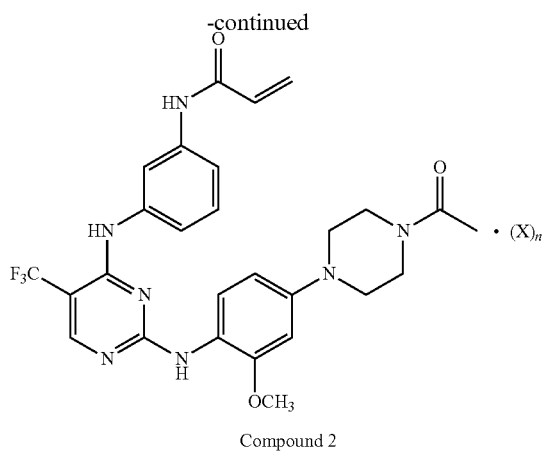

Compound 2

As depicted in the general Scheme above, Compound 2 is prepared from Compound 1 by combining Compound 1 with either one or two equivalents of benzenesulfonic acid, camphor sulfonic acid, 1,2-ethane disulfonic acid, hydrobromic acid, hydrochloric acid, maleic acid, methanesulfonic acid, naphthalene-2-sulfonic acid, 1,5-naphthalene disulfonic acid, oxalic acid, 4-toluenesulfonic acid or 2,4,6-trihydroxybenzoic acid to form the salt thereof. Thus, another aspect of the present invention provides a method for preparing Compound 2:

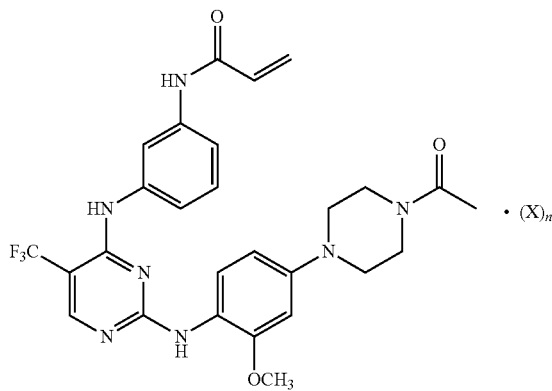

Compound 2 comprising the steps of:
providing Compound 1:

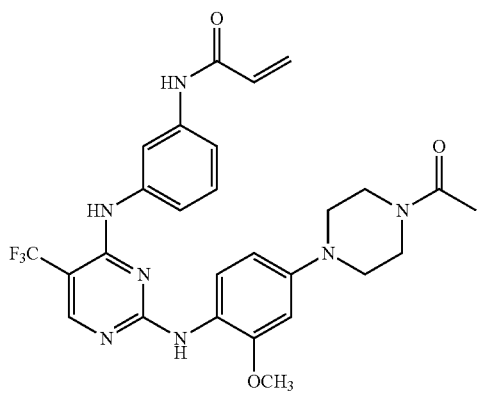

Compound 1

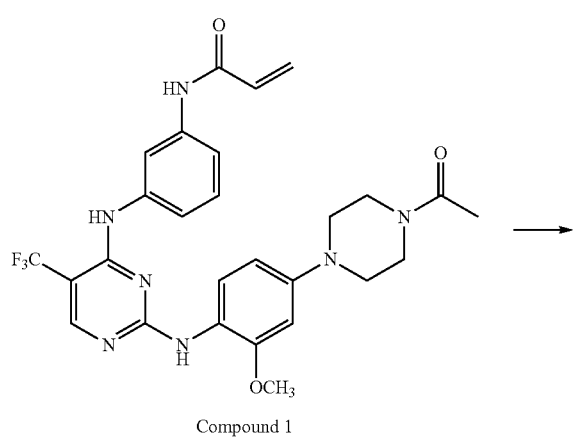

Compound 1 combining Compound 1 with one or two equivalents of benzenesulfonic acid, camphor sulfonic acid, 1,2-ethane disulfonic acid, hydrobromic acid, hydrochloric acid, maleic acid, methanesulfonic acid, naphthalene-2-sulfonic acid, 1,5-naphthalene disulfonic acid, oxalic acid, 4-toluenesulfonic acid or 2,4,6-trihydroxybenzoic acid in a suitable solvent; and optionally isolating Compound 2.

A suitable solvent may solubilize one or more of the reaction components, or, alternatively, the suitable solvent may facilitate the agitation of a suspension of one or more of the reaction components. Examples of suitable solvents useful in the present invention are a protic solvent, a polar aprotic solvent, a nonpolar solvent or mixtures thereof. In certain embodiments, suitable solvents include water, an ether, an ester, an alcohol, a halogenated solvent, a ketone, or a mixture thereof. In certain embodiments, the suitable solvent is methanol, ethanol, isopropanol, ethyl acetate, isopropyl acetate, methyl ethyl ketone, methyl isobutyl ketone or acetone. In certain embodiments, the suitable solvent is dichloromethane. In other embodiments, suitable solvents include tetrahydrofuran, dimethylformamide, dimethylsulfoxide, glyme, diglyme, methyl t-butyl ether, t-butanol, n-butanol, and acetonitrile. In some embodiments, the suitable solvent is cyclohexane.

According to another embodiment, the present invention provides a method for preparing Compound 2:

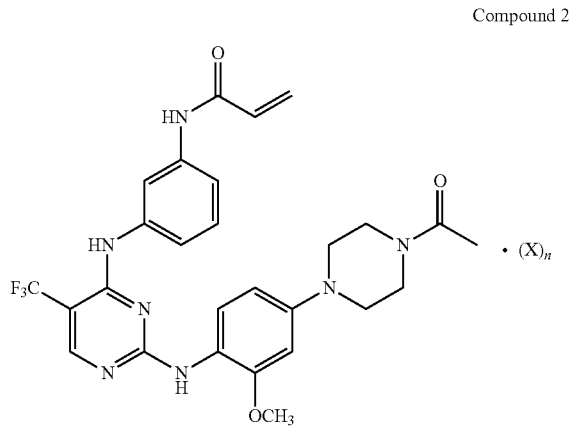 [SMILES: C=CC(=O)Nc1cccc(Nc2nc(Nc3ccc(N4CCN(C(C)=O)CC4)cc3OC)ncc2C(F)(F)F)c1]

Compound 2 comprising the steps of:
combining Compound 1:

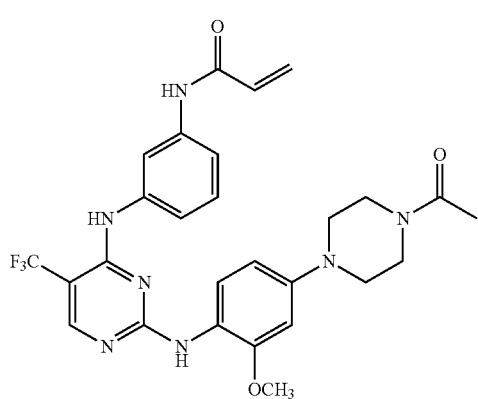

Compound 1 with a suitable solvent and optionally heating to form a solution thereof;

adding one or two equivalents of benzenesulfonic acid, camphor sulfonic acid, 1,2-ethane disulfonic acid, hydrobromic acid, hydrochloric acid, maleic acid, methanesulfonic acid, naphthalene-2-sulfonic acid, 1,5-naphthalene disulfonic acid, oxalic acid, 4-toluenesulfonic acid or 2,4,6-trihydroxybenzoic acid to said solution; and optionally isolating Compound 2.

As described generally above, Compound 1 is dissolved or suspended in a suitable solvent, optionally with heating. In certain embodiments Compound 1 is dissolved at about 20 to about 60° C. In other embodiments, Compound 1 is dissolved at about 20 to about 25° C., such as about ambient temperature. In still other embodiments, compound 1 is dissolved at the boiling temperature of the solvent. In other embodiments, compound 1 is dissolved without heating.

In certain embodiments, about 1 equivalent of benzenesulfonic acid, camphor sulfonic acid, 1,2-ethane disulfonic acid, hydrobromic acid, hydrochloric acid, maleic acid, methanesulfonic acid, naphthalene-2-sulfonic acid, 1,5-naphthalene disulfonic acid, oxalic acid, 4-toluenesulfonic acid or 2,4,6-trihydroxybenzoic acid is added to Compound 1 to afford Compound 2. In other embodiments, about 2 equivalents of benzenesulfonic acid, camphor sulfonic acid, 1,2-ethane disulfonic acid, hydrobromic acid, hydrochloric acid, maleic acid, methanesulfonic acid, naphthalene-2-sulfonic acid, 1,5-naphthalene disulfonic acid, oxalic acid, 4-toluenesulfonic acid or 2,4,6-trihydroxybenzoic acid is added to Compound 1 to afford Compound 2. In yet other embodiments, greater than 2 equivalents of benzenesulfonic acid, camphor sulfonic acid, 1,2-ethane disulfonic acid, hydrobromic acid, hydrochloric acid, maleic acid, methanesulfonic acid, naphthalene-2-sulfonic acid, 1,5-naphthalene disulfonic acid, oxalic acid, 4-toluenesulfonic acid or 2,4,6-trihydroxybenzoic acid is added to Compound 1 to afford Compound 2. In still other embodiments, about 0.9 to about 1.1 equivalents of benzenesulfonic acid, camphor sulfonic acid, 1,2-ethane disulfonic acid, hydrobromic acid, hydrochloric acid, maleic acid, methanesulfonic acid, naphthalene-2-sulfonic acid, 1,5-naphthalene disulfonic acid, oxalic acid, 4-toluenesulfonic acid or 2,4,6-trihydroxybenzoic acid is added to Compound 1 to afford Compound 2. In another embodiment, about 0.99 to about 1.01 equivalents of benzenesulfonic acid, camphor sulfonic acid, 1,2-ethane disulfonic acid, hydrobromic acid, hydrochloric acid, maleic acid, methanesulfonic acid, naphthalene-2-sulfonic acid, 1,5-naphthalene disulfonic acid, oxalic acid, 4-toluenesulfonic acid or 2,4,6-trihydroxybenzoic acid is added to Compound 1 to afford Compound 2. In further embodiments, about 1.8 to about 2.2 equivalents, such as about 1.98 to 2.02 equivalents, of benzenesulfonic acid, camphor sulfonic acid, 1,2-ethane disulfonic acid, hydrobromic acid, hydrochloric acid, maleic acid, methanesulfonic acid, naphthalene-2-sulfonic acid, 1,5-naphthalene disulfonic acid, oxalic acid, 4-toluenesulfonic acid or 2,4,6-trihydroxybenzoic acid is added to Compound 1 to afford Compound 2.

It will be appreciated that the acid may be added to the mixture of Compound 1 and a suitable solvent in any suitable form. For example, the acid may be added in solid form or as a solution or a suspension in a suitable solvent. The suitable solvent may be the same suitable solvent as that which is combined with Compound 1 or may be a different solvent. According to one embodiment, the acid is added in solid form. In certain embodiments, the acid is combined with a suitable solvent prior to adding to Compound 1. According to another embodiment, the acid is added as a solution in a suitable solvent. In certain embodiments, suitable solvents include water, an ether, an ester, an alcohol, a halogenated solvent, a ketone, or a mixture thereof. In certain embodiments, the suitable solvent is methanol, ethanol, isopropanol, ethyl acetate, isopropyl acetate, methyl ethyl ketone, methyl isobutyl ketone or acetone. In certain embodiments, the suitable solvent is dichloromethane. In other embodiments, suitable solvents include tetrahydrofuran, dimethylformamide, dimethylsulfoxide, glyme, diglyme, methyl t-butyl ether, t-butanol, n-butanol, and acetonitrile. In some embodiments, the suitable solvent is cyclohexane. In certain embodiments the suitable solvent is selected from those above and is anhydrous.

In certain embodiments, the resulting mixture containing Compound 2 is cooled. In other embodiments, the mixture containing Compound 2 is cooled below 20° C., such as below 10° C.

In certain embodiments, Compound 2 precipitates from the mixture. In another embodiment, Compound 2 crystallizes from the mixture. In other embodiments, Compound 2 crystallizes from solution following seeding of the solution (i.e., adding crystals of Compound 2 to the solution).

Crystalline Compound 2 can precipitate out of the reaction mixture, or be generated by removal of part or all of the solvent through methods such as evaporation, distillation, filtration (e.g., nanofiltration, ultrafiltration), reverse osmosis, absorption and reaction, by adding an anti-solvent such as water, MTBE or heptane, by cooling or by different combinations of these methods.

As described generally above, Compound 2 is optionally isolated. It will be appreciated that Compound 2 may be isolated by any suitable physical means known to one of ordinary skill in the art. In certain embodiments, precipitated solid compound 2 is separated from the supernatant by filtration. In other embodiments, precipitated solid Compound 2 is separated from the supernatant by decanting the supernatant.

In certain embodiments, precipitated solid Compound 2 is separated from the supernatant by filtration.

In certain embodiments, isolated Compound 2 is dried in air. In other embodiments isolated Compound 2 is dried under reduced pressure, optionally at elevated temperature.

Uses, Formulation and Administration
Pharmaceutically Acceptable Compositions

According to another embodiment, the invention provides a composition comprising Compound 2 and a pharmaceutically acceptable carrier, adjuvant, or vehicle. The amount of Compound 2 in compositions of this invention it is such that is effective to measurably inhibit a protein kinase, particularly an EGFR kinase, or a mutant thereof, in a biological sample or in a patient. In certain embodiments, a composition of this invention is formulated for administration to a patient in need of such composition. In some embodiments, a composition of this invention is formulated for oral administration to a patient.

The term "patient", as used herein, means an animal, preferably a mammal, and most preferably a human.

The term "pharmaceutically acceptable carrier, adjuvant, or vehicle" refers to a nontoxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, Vitamin E polyethylene glycol succinate (d-alpha tocopheryl polyethylene glycol 1000 succinate), sodium carboxymethylcellulose, polyacrylates, waxes, polyethylene-polyoxypropylene-block polymers, gelatine, polyvinyl pyrrolidone vinyl acetate, hydroxypropyl methyl cellulose, madnesium stearate, steric acid, citric acid, mannitol, and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be an aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous and non-aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is typically combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of Compound 2 include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In some embodiments, pharmaceutically acceptable compositions of this invention are formulated for oral administration.

The amount of Compound 2 that may be combined with the carrier materials to produce a composition in a single dosage form will vary depending upon the host treated, the particular mode of administration. In certain embodiments, provided compositions are formulated so that a dosage of between 0.01-100 mg/kg body weight/day of Compound 2 can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated.
Uses of Compounds and Pharmaceutically Acceptable Compositions Compound 2 and compositions described herein are generally useful for the inhibition of protein kinase activity of one or more enzymes. Examples of kinases that are inhibited by Compound 2 and compositions described herein and against which the methods described herein are useful include EGFR kinase or a mutant thereof. It has been found that Compound 2 is a selective inhibitor of at least one mutation of EGFR, as compared to wild-type ("WT") EGFR. In certain embodiments, an at least one mutation of EGFR is T790M. In certain embodiments, the at least one mutation of EGFR is a deletion mutation. In some embodiments, the at least one mutation of EGFR is an activating mutation. In certain embodiments, Compound 2 selectively inhibits at least one resistant mutation and at least one activating mutation as compared to WT EGFR. In some embodiments, Compound 2 selectively inhibits at least one deletion mutation and/or at least one point mutation, and is sparing as to WT EGFR inhibition.

A mutation of EGFR can be selected from T790M (resistant or oncogenic), L858R (activating), delE746-A750 (activating), G719S (activating), or a combination thereof.

As used herein, the term "selectively inhibits," as used in comparison to inhibition of WT EGFR, means that Compound 2 inhibits at least one mutation of EGFR (i.e., at least one deletion mutation, at least one activating mutation, at least one resistant mutation, or a combination of at least one deletion mutation and at least one point mutation) in at least one assay described herein (e.g., biochemical or cellular). In some embodiments, the term "selectively inhibits," as used in comparison to WT EGFR inhibition means that Compound 2 is at least 50 times more potent, at least 45 times, at least 40, at least 35, at least 30, at least 25, or at least 20 times more potent as an inhibitor of at least one mutation of EGFR, as defined and described herein, as compared to WT EGFR.

As used herein, the term "sparing as to WT EGFR" means that a selective inhibitor of at least one mutation of EGFR, as defined and described above and herein, inhibits EGFR at the upper limit of detection of at least one assay, such as those described in the '061 application (e.g., biochemical or cellular as described in detail in Examples 56-58). In vitro assays include assays that determine inhibition of the phosphorylation activity and/or the subsequent functional consequences, or ATPase activity of activated EGFR (WT or mutant). Alternate in vitro assays quantitate the ability of the inhibitor to bind to EGFR (WT or mutant). Inhibitor binding may be measured by radiolabeling the inhibitor prior to binding, isolating the inhibitor/EGFR (WT or mutant) complex and determining the amount of radiolabel bound. Alternatively, inhibitor binding may be determined by running a competition experiment where new inhibitors are incubated with EGFR (WT or mutant) bound to known radioligands. In some embodiments, the term "sparing as to WT EGFR" means that Compound 2 inhibits WT EGFR with an $IC_{50}$ of at least 10 µM, at least 9 µM, at least 8 µM, at least 7 µM, at least 6 µM, at least 5 µM, at least 3 µM, at least 2 µM, or at least 1 µM.

In certain embodiments, Compound 2 selectively inhibits (a) at least one activating mutation; and (b) T790M; and (c) is sparing as to WT. In some embodiments, an at least one activating mutation is a deletion mutation. In some embodiments, an at least one activating mutation is a point mutation. In some embodiments, an activating mutation is delE746-A750. In some embodiments, an activating mutation is L858R. In some embodiments, an activating mutation is G719S.

In some embodiments, the at least one mutation of EGFR is L858R and/or T790M.

Without wishing to be bound by any particular theory, it is believed that administration of Compound 2 to a patient having at least one activating mutation may preempt formation of the T790M resistance mutation. Thus, in certain embodiments, the present invention provides a method for inhibiting an activating mutation in a patient comprising administering to the patient Compound 2 or composition thereof, as described herein.

One of ordinary skill in the art will appreciate that certain patients have an oncogenic form of the T790M mutation, i.e., the T790M mutation is present prior to administrating any EGFR kinase inhibitor to a patient and is therefore oncogenic. Accordingly, in some embodiments, the present invention provides a method for inhibiting oncogenic T790M in a patient comprising administering to the patient a provided compound or composition thereof, as described herein.

In certain embodiments, the amount of Compound 2 in a composition is effective to measurably inhibit at least one mutant of EGFR selectively as compared to WT EGFR and other protein kinases (e.g., ErbB2, ErbB4, a TEC-kinase, and/or JAK3), in a biological sample or in a patient.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Compound 2 is an inhibitor of at least one mutant of EGFR and is therefore useful for treating one or more disorders associated with activity of one of more EGFR mutants (e.g., a deletion mutation, an activating mutation, a resistant mutation, or combination thereof). Thus, in certain embodiments, the present invention provides a method for treating a mutant EGFR-mediated disorder comprising the step of administering to a patient in need thereof Compound 2 or pharmaceutically acceptable composition thereof.

As used herein, the term "mutant EGFR-mediated" disorders or conditions as used herein means any disease or other deleterious condition in which at least one mutant of EGFR is known to play a role. In certain embodiments, an at least one mutant of EGFR is T790M. In some embodiments, the at least one mutant of EGFR is a deletion mutation. In certain embodiments, the at least one mutant of EGFR is an activating mutation. In some embodiments, the at least one mutant of EGFR is L858R and/or T790M. In certain embodiments, a provided compound selectively inhibits (a) at least one activating mutation, (b) T790M, and (c) is sparing as to WT. In some embodiments, an at least one activating mutation is a deletion mutation. In some embodiments, an at least one activating mutation is a point mutation. In some embodiments, an activating mutation is delE746-A750. In some embodiments, an activating mutation is L858R. In some embodiments, an activating mutation is G719S.

Accordingly, another embodiment of the present invention relates to treating or lessening the severity of one or more diseases in which at least one mutant of EGFR is known to play a role. Specifically, the present invention relates to a method of treating or lessening the severity of a disease or condition selected from a proliferative disorder, wherein said method comprises administering to a patient in need thereof a compound or composition according to the present invention.

In some embodiments, the present invention provides a method for treating or lessening the severity of one or more disorders selected from a cancer. In some embodiments, the cancer is associated with a solid tumor. In certain embodiments, the cancer is breast cancer, glioblastoma, lung cancer, cancer of the head and neck, colorectal cancer, bladder cancer, or non-small cell lung cancer. In some embodiments, the present invention provides a method for treating or lessening the severity of one or more disorders selected from squamous cell carcinoma, salivary gland carcinoma, ovarian carcinoma, or pancreatic cancer.

In certain embodiments, the present invention provides a method for treating or lessening the severity of neurofibromatosis type I (NF1), neurofibromatosis type II (NF2) Schwann cell neoplasms (e.g. MPNST's), or Schwannomas.

Compound 2 and compositions thereof, according to the method of the present invention, may be administered using any amount and any route of administration effective for treating or lessening the severity of a cancer. The exact amount required will vary from subject to subject, depending on the species, age, and general condition of the subject, the severity of the infection, the particular agent, its mode of administration, and the like. Compound 2 is preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, Compound 2 may be administered orally or parenterally at dosage levels of about 0.01 mg/kg to about 60 mg/kg, or about 0.1 mg/kg to about 50 mg/kg, or about 0.25 mg/kg to about 45 mg/kg and preferably from about 0.5 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to Compound 2, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, polyethylene glycol (e.g., PEG 200, PEG 400, PEG 1000, PEG 2000), propylene glycol, 1,3-butylene glycol, dimethylformamide, oils (in particular, cottonseed, groundnut, corn, germ, olive, castor, and sesame oils), glycerol, tetrahydrofurfuryl alcohol, Vitamin E polyethylene glycol succinate (d-alpha tocopheryl polyethylene glycol 1000 succinate), polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. The liquid forms above can also be filled into a soft or hard capsule to form a solid dosage form. Suitable capsules can be formed from, for example, gelatin, starch and cellulose derivatives (e.g., hydroxycellulose, hydropropylmethylcellulose).

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of Compound 2 of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing Compound 2 of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, Compound 2 is mixed with at least one inert, pharmaceutically acceptable excipient or carrier such as sodium citrate, Avicel, hydroxypropyl cellulose or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, PVP vinyl acetate, and acacia, c) humectants such as glycerol, d) disintegrating agents such as agar-agar, calcium carbonate, potato or tapioca starch, alginic acid, certain silicates, sodium croscarmellose and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, i) lubricants such as talc, calcium stearate, magnesium stearate, solid polyethylene glycols, sodium lauryl sulfate, j) solubilising agents such as Vitamin E polyethylene glycol succinate (d-alpha tocopheryl polyethylene glycol 1000 succinate), steric acid, and mixtures thereof. In the case of capsules, tablets and pills, the dosage form may also comprise buffering agents.

Solid compositions of a similar type may also be employed as fillers in soft and hard-filled capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled capsules using such excipients as lactose or milk sugar as well as high molecular weight polyethylene glycols and the like.

Compound 2 can also be in micro-encapsulated form with one or more excipients as noted above. The solid dosage forms of tablets, dragees, capsules, pills, and granules can be prepared with coatings and shells such as cosmetic coatings, enteric coatings, release controlling coatings and other coatings well known in the pharmaceutical formulating art. In such solid dosage forms the active compound may be admixed with at least one inert diluent such as a polymer, sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of Compound 2 include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with Compound 2 or a composition comprising said compound.

According to another embodiment, the invention relates to a method of inhibiting at least one mutant of EGFR (e.g., a deletion mutation, an activating mutation, a resistant mutations, or combination thereof) activity in a biological sample comprising the step of contacting said biological sample with Compound 2, or a composition comprising the compound. In certain embodiments, the invention relates to a method of irreversibly inhibiting at least one mutant of EGFR (e.g., a deletion mutation, an activating mutation, a resistant mutation, or combination thereof) activity in a biological sample comprising the step of contacting the biological sample with Compound 2, or a composition comprising the compound.

In certain embodiments, Compound 2 selectively inhibits in a biological sample (a) at least one activating mutation, (b) T790M, and (c) is sparing as to WT. In some embodiments, an at least one activating mutation is a deletion mutation. In some embodiments, an at least one activating mutation is a point mutation. In some embodiments, an activating mutation is delE746-A750. In some embodiments, an activating mutation is L858R. In some embodiments, an activating mutation is G719S.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of at least one mutant of EGFR (e.g., a deletion mutation, an activating mutation, a resistant mutation, or combination thereof) activity in a biological sample is useful for a variety of purposes that are known to one of skill in the art. Examples of such purposes include, but are not limited to, blood transfusion, organ transplantation, biological specimen storage, and biological assays.

Another embodiment of the present invention relates to a method of inhibiting at least one mutant of EGFR (e.g., a deletion mutation, an activating mutation, a resistant mutation, or combination thereof) activity in a patient comprising the step of administering to the patient Compound 2 or a composition comprising the compound. In certain embodiments, the present invention provides a method for inhibiting (a) at least one activating mutation, and (b) T790M in a patient, and (c) is sparing as to WT, wherein the method comprises administering to the patient Compound 2 or composition thereof. In some embodiments, an at least one activating mutation is a deletion mutation. In some embodiments, an at least one activating mutation is a point mutation. In some embodiments, the present invention provides a method for inhibiting at least one mutant of EGFR in a patient, wherein an activating mutation is delE746-A750. In some embodiments, the present invention provides a method for inhibiting at least one mutant of EGFR in a patient, wherein an activating mutation is L858R. In some embodiments, the present invention provides a method for inhibiting at least one mutant of EGFR in a patient, wherein an activating mutation is G719S.

According to another embodiment, the invention relates to a method of inhibiting at least one mutant of EGFR (e.g., a deletion mutation, an activating mutation, a resistant mutation, or combination thereof) activity in a patient comprising the step of administering to the patient Compound 2 or a composition comprising the compound. According to certain embodiments, the invention relates to a method of irreversibly inhibiting at least one mutant of EGFR activity (e.g., a deletion mutation, an activating mutation, a resistant mutation, or combination thereof) in a patient comprising the step of administering to said patient Compound 2 or a composition comprising the compound. In certain embodiments, the present invention provides a method for irreversibly inhibiting (a) at least one activating mutation, and (b) T790M in a patient, and (c) is sparing as to WT, wherein said method comprises administering to the patient Compound 2 or composition thereof. In some embodiments, an irreversibly inhibited at least one activating mutation is a deletion mutation. In some embodiments, an irreversibly inhibited at least one activating mutation is a point mutation. In some embodiments, the present invention provides a method for irreversibly inhibiting at least one mutant of EGFR in a patient, wherein an activating mutation is delE746-A750. In some embodiments, the present invention provides a method for irreversibly inhibiting at least one mutant of EGFR in a patient, wherein an activating mutation is L858R. In some embodiments, the present invention provides a method for irreversibly inhibiting at least one mutant of EGFR in a patient, wherein an activating mutation is G719S.

In other embodiments, the present invention provides a method for treating a disorder mediated by one or more of at least one mutant of EGFR (e.g., a deletion mutation, an activating mutation, a resistant mutation, or combination thereof) in a patient in need thereof, comprising the step of administering to said patient Compound 2 or pharmaceutically acceptable composition thereof. Such disorders are described in detail herein.

Depending upon the particular condition, or disease, to be treated, additional therapeutic agents, which are normally administered to treat that condition, may also be present in the compositions of this invention or as part of a treatment regimen including Compound 2. As used herein, additional therapeutic agents that are normally administered to treat a particular disease, or condition, are known as "appropriate for the disease or condition being treated."

For example, Compound 2 or a pharmaceutically acceptable composition thereof is administered in combination with chemotherapeutic agents to treat proliferative diseases and cancer. Examples of known chemotherapeutic agents include, but are not limited to, Adriamycin, dexamethasone, vincristine, cyclophosphamide, fluorouracil, topotecan, taxol, interferons, platinum derivatives, taxane (e.g., paclitaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, campthothecin, cisplatin, metronidazole, and Gleevec™, among others. In other embodiments, Compound 2 is administered in combination with a biologic agent, such as Avastin or VECTIBIX.

In certain embodiments, Compound 2 or a pharmaceutically acceptable composition thereof is administered in combination with an antiproliferative or chemotherapeutic agent selected from any one or more of abarelix, aldesleukin, alemtuzumab, alitretinoin, allopurinol, altretamine, amifostine, anastrozole, arsenic trioxide, asparaginase, azacitidine, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, erlotinib, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, or zoledronic acid.

Other examples of agents the inhibitors of this invention may also be combined with include, without limitation: treatments for Alzheimer's Disease such as donepezil hydrochloride (Aricept®) and rivastigmine (Exelon®); treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), glatiramer acetate (Copaxone®), and mitoxantrone; treatments for asthma such as albuterol and montelukast (Singulair®); agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anticonvulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

In certain embodiments, Compound 2 or a pharmaceutically acceptable composition thereof is administered in combination with a monoclonal antibody or an siRNA therapeutic.

The additional agents may be administered separately from a Compound 2-containing composition, as part of a multiple dosage regimen. Alternatively, those agents may be part of a single dosage form, mixed together with Compound 2 in a single composition. If administered as part of a multiple dosage regime, the two active agents may be submitted simultaneously, sequentially or within a period of time from one another (e.g., one hour, two hours, six hours, twelve hours, one day, one week, two weeks, one month).

As used herein, the terms "combination," "combined," and related terms refer to the simultaneous or sequential administration of therapeutic agents in accordance with this invention. For example, Compound 2 may be administered with another therapeutic agent simultaneously or sequentially in separate unit dosage forms or together in a single unit dosage form. Accordingly, the present invention provides a single unit dosage form comprising Compound 2, an additional therapeutic agent, and a pharmaceutically acceptable carrier, adjuvant, or vehicle.

The amount of Compound 2 and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of Compound 2 can be administered.

In those compositions that include an additional therapeutic agent, that additional therapeutic agent and Compound 2 may act synergistically. Therefore, the amount of additional therapeutic agent in such compositions may be less than that required in a monotherapy utilizing only that therapeutic agent. In such compositions, a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Compound 2 or pharmaceutical compositions thereof may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with Compound 2 are another embodiment of the present invention.

All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Preparation of Compound 1

The synthesis of Compound 1 is described in detail at Example 3 of the '061 application.

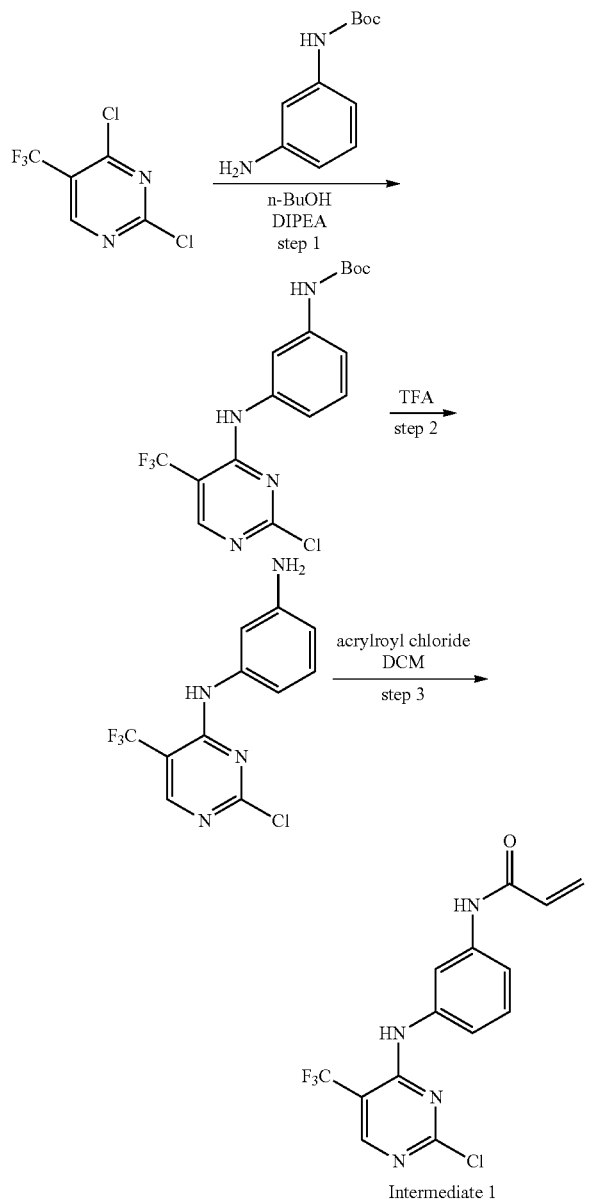

Intermediate 1

Step 1:

In a 25 mL 3-neck round-bottom flask previously equipped with a magnetic stirrer, Thermo pocket and $CaCl_2$ guard tube, N-Boc-1,3-diaminobenzene (0.96 g) and n-butanol (9.00 mL) were charged. The reaction mixture was cooled to 0° C. 2,4-Dichloro-5-trifluoromethylpyrimidine (1.0 g) was added dropwise to the above reaction mixture at 0° C. Diisopropylethylamine (DIPEA) (0.96 mL) was dropwise added to the above reaction mixture at 0° C. and the reaction mixture was stirred for 1 hr at 0° C. to 5° C. Finally, the reaction mixture was allowed to warm to room temperature. The reaction mixture was stirred for another 4 hrs at room temperature. Completion of reaction was monitored by TLC using hexane:ethyl acetate (7:3). The solid precipitated out was filtered off and washed with 1-butanol (2 mL). The solid was dried under reduced pressure at 40° C. for 1 hr. $^1$H-NMR (DMSO-d6, 400 MHz) δ 1.48 (S, 9H), 7.02 (m, 1H), 7.26 (m, 2H), 7.58 (S, 1H), 8.57 (S, 1H), 9.48 (S, 1H), 9.55 (S, 1H).

Step 2:

To the above crude (3.1 g) in dichloromethane (DCM) (25 mL) was added trifluoroacetic acid (TFA) (12.4 mL) slowly at 0° C. The reaction mixture was allowed to warm to room temperature. The reaction mixture was stirred for another 10 min at room temperature. The crude was concentrated under reduced pressure.

Step 3:

The concentrated crude was dissolved in DIPEA (2.0 mL) and dichloromethane (25 mL), and then cooled to −30° C. To the reaction mixture was slowly added acryloyl chloride (0.76 g) at −30° C. The reaction mass was warmed to room temperature stirred at room temperature for 1.0 hr. The reaction was monitored on TLC using hexane:ethyl acetate (7:3) as mobile phase. The reaction was completed after 1 hr. Step 3 yielded intermediate 1.

Step 4:

To obtain a salt of compound 1, a mixture of intermediate 1 (16 mg) and 2-methoxy-4-(4-acetylpiperazinyl)aniline in dioxane (1.0 mL) with catalytic trifluoroacetic acid was stirred overnight at 50° C. The crude was concentrated under reduced pressure and purified using HPLC (TFA modifier) to give compound 1 as a TFA salt. $^1$H-NMR (DMSO-d6, 400 MHz) δ 10.2 (S, 1H), 8.2 (br, 1H), 8.30 (S, 1H), 7.73 (br, 1H), 7.52 (d, J=7.8 Hz, 1H), 7.45 (d, J=7.8 Hz, 1H), 7.26 (J=8.2 Hz, 1H), 7.14 (be, 1H), 6.60 (S, 1H), 6.42 (dd, J=11.4, 16.9 Hz, 1H), 6.24 (d, J=16.9 Hz, 1H), 5.75 (d, J=11.4 Hz, 1H), 3.76 (S, 3H), 3.04 (br, 4H), 2.04 (S, 3H); calculated mass for $C_{27}H_{28}F_3N_7O_3$: 555.2, found: 556.2 (M+H$^+$).

Step 5:

To obtain the free base form of Compound 1 from the TFA salt, the salt was added to DCM and cooled to 0° C. $Na_2CO_3$ solution (9.6% w/w) was added at 0° C. The mixture was warmed to 20° C. and stirred for 35 min. The pH of the aqueous layer was >8. The layers were separated. Extraction of the aqueous layer was performed using DCM. The organic layers were combined and washed with brine. The organic layer was collected and evaporated to yield a solid of Compound 1.

General Preparation of Compound 2

For each counterion and solvent system, ca. 25 or 50 mg of the free base of Compound 1 was slurried in 200-300 µl of the allocated solvent. The solvents included acetone, dichloromethane, cyclohexane, ethyl acetate, methanol (methyl ethyl ketone for sulfonic acid-containing counterions), methyl isobutyl ketone, 2-propanol (isopropyl acetate for sulfonic acid-containing counterions), tetrahydrofuran and acetonitrile:water (90:10). The respective counterion was also dissolved/slurried in 200-300 µl of the allocated solvent. The counterions included benzenesulfonic acid, camphor sulfonic acid, 1,2-ethane disulfonic acid, hydrobromic acid, hydrochloric acid, maleic acid, methanesulfonic acid, naphthalene-2-sulfonic acid, 1,5-naphthalene disulfonic acid, oxalic acid, 4-toluenesulfonic acid and 2,4,6-trihydroxybenzoic acid. One equivalent of each counterion was used and additional experiments with two equivalents of benzenesulfonic acid, hydrochloric acid, sulphuric acid and p-toluenesulfonic acid were performed. The acid solution/slurry was then added to the slurry of Compound 1 in small aliquots in order to minimize the risk of degradation. The pH of the reaction was then checked using universal indicator paper.

The mixtures of Compound 1/counterion/solvent created using the procedure above were temperature cycled between ca. 0° C. and ambient (ca. 22° C.) whilst stirring in 1 hour cycles for a period of 1-2 days. Overnight, samples were kept at ca. 2-5° C. The mixtures were visually checked for any obvious signs of degradation (i.e. color changes) and then, if not visually degraded, any solids present were isolated and allowed to dry at ambient conditions prior to analysis. The solids represent isolated Compound 2.

General Procedures

The solubility of the potential salts was tested using a shake flask method whereby a slurry of each salt was prepared in deionized water and the pH of the reaction was reduced to below pH 2 by adding a small amount of the counterion used for salt formation. The pH was tested using universal indicator paper. After ca. 24 hours of shaking, the slurries were filtered for the solubility determination using HPLC analysis.

X-Ray Powder Diffraction.

X-ray powder diffraction (XRPD) analysis was carried out on a Siemens D5000, scanning the samples between 3 and 30, 35 or 50 °2θ. For samples <100 mg, ca. 5-10 mg of sample was gently compressed onto a glass slide which fitted into the sample holder. For samples >100 mg, ca. 100 mg of sample was gently compressed into a plastic sample holder, so that the sample surface was smooth and just above the level of the sample holder. Measurements were made using the following experimental conditions:

| | |
|---|---|
| start position | 3.00 °2Θ |
| end position | 30, 35 or 50 °2Θ |
| step size | 0.02 °2Θ |
| scan step time | 1 s |
| scan type | continuous |
| offset | 0 °2Θ |
| divergence slit type | fixed |
| divergence slit size | 2.0000° |
| receiving slit size | 0.2 mm |
| temperature | 20° C. |
| anode material | copper (Cu) |
| K-Alpha1 | 1.54060 Angstroms |
| K-Alpha2 | 1.54443 Angstroms |
| K-Beta | 1.39225 Angstroms |
| K-A2/K-A1 Ratio | 0.50000 |
| Generator settings | 40 mA, 40 kV |
| goniometer radius | 217.50 |

Polarized Light Microscopy.

In polarized light microscopy (PLM), the presence of crystallinity (birefringence) was determined using an Olympus BX50 polarising microscope, equipped with a Motic camera and image capture software (Motic Images Plus 2.0). All images were recorded using the 20x objective, unless otherwise stated.

Thermogravimetric Analysis.

For thermogravimetric analysis (TGA), approximately 5-10 mg of material was accurately weighed into an open aluminium pan and loaded into a simultaneous thermogravimetric/differential thermal analyser (TG/DTA) and held at room temperature. The sample was then heated at a rate of 10° C./min from 25° C. to 300° C. during which time the change in sample weight was recorded along with any differential thermal events (DTA). Nitrogen was used as the purge gas, at a flow rate of 100 cm$^3$/min.

Differential Scanning Calorimetry.

For differential scanning calorimetry (DSC), approximately 5-10 mg of material was weighed into an aluminium DSC pan and sealed non-hermetically with a pierced aluminium lid. The sample pan was then loaded into a Seiko DSC6200 (equipped with a cooler) cooled and held at 25° C. Once a stable heat-flow response was obtained, the sample and reference were heated to ca. 260° C.-280° C. at scan rate of 10° C./min and the resulting heat flow response monitored.

Nuclear Magnetic Resonance Spectroscopy.

$^1$H-NMR experiments were performed on a Bruker AV400 CH frequency: 400 MHz). $^1$H experiments of each sample were performed in deuterated DMSO and each sample was prepared to ca. 1 mg/mL concentration.

Dynamic Vapour Sorption.

For dynamic vapour sorption (DVS), approximately 10-20 mg of sample was placed into a wire mesh vapour sorption balance pan and loaded into a DVS-1 dynamic vapour sorption balance by Surface Measurement Systems. The sample was subjected to a ramping profile from 20-90% relative humidity (RH) at 10% increments, maintaining the sample at each step until a stable weight had been achieved (99.5% step completion). After completion of the sorption cycle, the sample was dried using the same procedure, but all the way down to 0% RH and finally taken back to the starting point of 20% RH. The weight change during the sorption/desorption cycles were plotted, allowing for the hygroscopic nature of the sample to be determined.

Infrared Spectroscopy.

Infrared spectroscopy (IR) was carried out on a Bruker ALPHA P spectrometer. Sufficient material was placed onto the centre of the plate of the spectrometer and the spectra were obtained using the following parameters:

| | |
|---|---|
| resolution | 4 cm$^{-1}$ |
| background scan time | 16 scans |
| sample scan time | 16 scans |
| data collection | 4000 to 400 cm$^{-1}$ |
| result spectrum | transmittance |
| software | OPUS version 6 |

For Karl Fischer (KF) Coulometric titration, 10-15 mg of solid material was accurately weighed into a vial. The solid was then manually introduced into the titration cell of a Mettler Toledo C30 Compact Titrator. The vial was back-weighed after the addition of the solid and the weight of the added solid entered on the instrument. Titration was initiated once the sample had fully dissolved in the cell. The water content was calculated automatically by the instrument as a percentage and the data printed.

Reverse-phase gradient high performance liquid chromatography (HPLC) was performed on an Agilent 1100 instrument fitted with a C18, 3.0×100 mm×3.5 μm column. The detection wavelength was 240 nm.

A Sotax AT7 dissolution bath (USP 2, EP 2 apparatus) was used for the dissolution study in which paddles were used to stir the media. All tests were carried out at 37° C. and a paddle speed of 100 rpm.

Example 1

Primary Salt Screen

The results of the primary salt screen, based on the general preparation of Compound 2, are shown in Table 1. Table 1 indicates the counterion, the solvent and the solid form(s) obtained.

TABLE 1

Results of Primary Salt Screen

| Counterion | Equivalents of Acid | Solvent | | | | | | | | |
|---|---|---|---|---|---|---|---|---|---|---|
| | | Acetone | Dichloromethane | Cyclohexane | Ethyl Acetate | Methanol or MEK | Methylisobutyl Ketone | 2-Propanol (IPA) or Isopropyl acetate | Tetrahydrofuran | Acetonitrile:Water (10%) |
| 2,4,6-Trihydroxybenzoic | 1 | FC | FC FA | FC FA | AM | S1 | FC | FC | S2 | S2 |
| Benzenesulfonic acid | 1 | S1 | XR | FC | FC | S1 S2 | S2 | S2 | S1 FC | XR |
| Benzenesulfonic acid | 2 | S1 | AM | FC | S1 | S1 | FC | FC | S1 | S2 |
| Hydrochloric acid | 1 | AM | FC | FC | FC | FC | AM | FC | FC | S1 |
| Hydrochloric acid | 2 | AM | S1 | FC | XR | S1 XR | S1 S2 | S XR | AM | S1 |
| Maleic acid | 1 | XR | S1 | FC FA | XR XR | S2 | FC | FC | S3 | S2 XR |
| Methanesulfonic acid | 2 | S1 | AM | FC | AM | S1 | AM | AM | S1 | AM |
| Oxalic acid | 1 | S1 | AM | FC FA | S1 | S1 | AM | AM | AM | S2 |
| Sulfuric acid | 1 | S1 | GM | FC | FC | AM | FC | AM | FC SP | AM |
| Sulfuric acid | 2 | FC | FC | FC | FC | FC | FC | FC | FC | FC |
| p-Toluenesulfonic acid monohydrate | 1 | S1 | S1 | FC | S1 | S1 | S1 | FC | S2 | AM |
| p-Toluenesulfonic acid monohydrate | 2 | S1 | S1 | FC | S1 | S2 | AM | AM | S2 XR | AM |
| 1,2-Ethane disulfonic acid dehydrate | 1 | AM | AM | FC | FC | S1 | FC | FC | AM | S2 |
| 1,2-Ethane disulfonic acid dehydrate | 2 | AM | AM | FC | AM | S1 | FC | FC | AM | S2 |
| Hydrobromic acid | 1 | AM | S1 | FC/S1 | S1 | S1(?) | S1 | S1 | S1 | S1 |
| Hydrobromic acid | 2 | S1/XR | S1 | S1 | S1 | S1 | S1 | S1 | S2 | S1 |
| Naphthalene-2-sulfonic acid | 1 | S1 | S1 | FC | S1 | S1 | S1 | S1 | AM | S1 |
| Naphthalene-2-sulfonic acid | 2 | S1 | S2 | FC | AM | S2 | XR | AM | S3 | S4 |
| 1,5-Naphthalene disulfonic acid | 1 | AM | FC | FC | FC | XR | FC | FC | FC | S1 |
| 1,5-Naphthalene disulfonic acid | 2 | XR | AM | FA | FA/FC | FA/FC | XR | FA | AM | S1 |
| Camphor-10-sulfonic acid | 1 | S1 | S1 | FC | S1 | S1 | S1 | S1 | S1 | S2 |
| Camphor-10-sulfonic acid | 2 | AM | AM | FA/FC | XR/S1 | S1/XR | AM | FC | AM | AM |

S1 = salt, polymorphic form 1
S2 = salt, polymorphic form 2
S3 = salt, polymorphic form 3
S4 = salt, polymorphic form 4
SP = salt, partially crystalline
FA = free acid
FC = free Compound 1
XR = different XRPD pattern, but only a few peaks in the diffractogram (possibly indicating degradation)
AM = amorphous
GM = solid that rapidly converts to gum upon isolation Example 2

Primary Salt Screen

For the potential salts obtained during the primary salt screen in Example 1, the samples were set-up for 1 week stability studies at 40° C./75% RH (open vials) and 80° C. (open vials). TGA was carried out after the stability studies for samples containing sufficient material. The solubility of the samples was also tested in an aqueous medium (pH<2). The results for the stability and solubility studies are indicated in Table 2.

TABLE 2

Stability and solubility results from potential salts obtained in the primary salt screen

| Potential Salt | Form | Approximate Solubility (mg/ml) | 40° C./75% RH (open conditions) | 80° C. (open conditions) |
|---|---|---|---|---|
| 2,4,6-Trihydroxybenzoate | Form I | Below LOQ | No form change, remains predominantly crystalline | No form change, remains predominantly crystalline |
| 2,4,6-Trihydroxybenzoate | Form II | Below LOQ | No form change, but poor crystallinity | No form change, but poor crystallinity |
| Besylate (1 equiv.) | Form I | 0.047 | No form change, remains predominantly crystalline | No form change, remains predominantly crystalline |
| Besylate (1 equiv.) | Form II | 0.055 | No form change, some decline in crystallinity. | No form change, some decline in crystallinity. |
| Besylate (2 equiv.) | Form I | 4.264 | Solid/gum present. Change in polymorphic form (likely hydrated), but poor crystallinity. | No form change, remains predominantly crystalline. TGA shows initial 1.95% weight |

TABLE 2-continued

Stability and solubility results from potential salts obtained in the primary salt screen

| Potential Salt | Form | Approximate Solubility (mg/ml) | 40° C./75% RH (open conditions) | 80° C. (open conditions) |
|---|---|---|---|---|
| | | | | loss likely due to unbound volatiles. No further weight losses present prior to likely degradation. |
| Besylate (2 equiv.) | Form II | 0.044 | No form change, remains predominantly crystalline | No form change, remains predominantly crystalline |
| Hydrochloride (1 equiv.) | Form I | 0.400 | No form change, partially crystalline. | No form change, poorly crystalline |
| Hydrochloride (2 equiv.) | Form I | 0.196 | No form change, remains predominantly crystalline. TGA shows initial weight loss of ca. 2% likely due to unbound volatiles. A further ca. 8% weight loss from ca. 150° C., directly followed by further weight loss likely due to degradation. Likely hydrated or solvated. | No form change, remains predominantly crystalline |
| Maleate | Form I | 0.168 | No form change, remains predominantly crystalline. TGA shows a weight loss of ca. 11% from ca. 160° C. The required DCM content for a mono DCM solvate is 11.23%. | No form change, remains predominantly crystalline. |
| Maleate | Form II | 0.271 | No form change, remains predominantly crystalline. TGA shows an initial 1.76% weight loss likely due to unbound volatiles. A further ca. 6.3% weight loss is seen from ca. 130° C., likely due to bound solvent/water. | No form change, remains predominantly crystalline |
| Maleate | Form III | 0.251 | No clear form change but poorly crystalline (brown) | No clear form change but poorly crystalline (brown) |
| Mesylate | Form I | 7.286 | Gum formed | Amorphous solid |
| Oxalate | Form I | 0.158 | No form change, remains predominantly crystalline. TGA shows a weight loss of ca. 14.4% associated with an endotherm at ca. 200° C. | No form change, remains predominantly crystalline. |
| Oxalate | Form II | 0.22 | No form change, remains predominantly crystalline | Amorphous brown solid |
| Tosylate (1 equiv.) | Form I | 0.104 | No form change, remains predominantly crystalline | No form change, partially crystalline |
| Tosylate (1 equiv.) | Form II | 0.422 | Gum formed | Possible form change, partially crystalline |
| Tosylate (2 equiv.) | Form I | 0.089 | No form change, remains predominantly crystalline | No form change, remains predominantly crystalline |
| Tosylate (2 equiv.) | Form II | 0.303 | Gum formed | Possible form change, partially crystalline |
| 1,2-Ethane disulfonic acid (1 eq.) | Form I | 0.21 | Significant loss in crystallinity | Significant loss in crystallinity |
| 1,2-Ethane disulfonic acid (1 eq.) | Form II | 0.62 | No form change but some loss in crystallinity | Significant loss in crystallinity |
| 1,2-Ethane disulfonic acid (2 eq.) | Form I | 0.34 | No form change, remains partially crystalline. | No form change, remains partially crystalline. TGA showed an initial weight loss of 6.28% |

TABLE 2-continued

Stability and solubility results from potential salts obtained in the primary salt screen

| Potential Salt | Form | Approximate Solubility (mg/ml) | 40° C./75% RH (open conditions) | 80° C. (open conditions) |
|---|---|---|---|---|
| | | | | which could indicate potential solvation (8.4% required for 1 equiv. of MEK). No other weight losses prior to degradation. |
| 1,2-Ethane disulfonic acid (2 eq.) | Form II | 0.25 | XRPD predominantly similar to input material. | XRPD predominantly similar to input material. Partially crystalline. TGA showed an initial weight loss of 3.7%, which could indicate potential hydration or hygroscopic material (monohydrate would have 2.23% water). No other weight losses prior to degradation. |
| HBr (1 eq.) (Form I for both 1 and 2 equiv. was the same form) | Form I | 1.27 | No form change, slight loss in crystallinity. | No Form change. Slight loss in crystallinity. TGA showed an initial weight loss of 0.83% probably due to unbound volatiles. No other weight losses prior to degradation. |
| HBr (2 eq.) | Form II | 2.38 | Changed to Form I, poorly crystalline. | Potential new form, but poorly crystalline |
| Naphthalene-2-sulfonic acid (1 eq.) | Form I | 0.34 | No form change, small loss in crystallinity | No form change, small loss in crystallinity TGA showed an initial weight loss of 1.86% probably due to unbound volatiles. No other weight losses prior to degradation. |
| Naphthalene-2-sulfonic acid (2 eq.) | Form I | 0.87 | No form change, poor crystallinity. | No form change, poor crystallinity |
| Naphthalene-2-sulfonic acid (2 eq.) | Form II | 0.86 | No form change, remains partially crystalline. TGA showed an initial weight loss of 0.71% probably due to unbound volatiles and a second loss of 1.61% associated with the melt (ca. 138° C.) which could indicate some bound water or solvent (monohydrate would lave 1.82 wt % water). | No form change, but loss of crystallinity |
| Naphthalene-2-sulfonic acid (2 eq.) | Form III | 0.74 | Converted to Form II, but partially crystalline. | Converted to Form II, but partially crystalline. TGA showed an initial weigh loss of 1.41% probably due to unbound volatiles and a second loss of 1.32% associated with the melt (ca. 135° C.). Could indicate some bound water or solvent. |

TABLE 2-continued

Stability and solubility results from potential salts obtained in the primary salt screen

| Potential Salt | Form | Approximate Solubility (mg/ml) | 40° C./75% RH (open conditions) | 80° C. (open conditions) |
|---|---|---|---|---|
| Naphthalene-2-sulfonic acid (2 eq.) | Form IV | 0.76 | Converted to Form II, but poorly crystalline. | Converted to Form II, but poorly crystalline. |
| 1,5 Naphthalene disulfonic acid (1 eq.) | Form I | Below LOQ | No form change, remains partially crystalline. TGA showed an initial weight loss of 2.94% probably due to unbound volatiles and another weight loss of 6.00%, which could indicate potential salvation (mono acetonitrile solvate would have ca. 4.29 wt %). No other weight loss prior to degradation. | Possible form change, but poorly crystalline. |
| 1,5 Naphthalene disulfonic acid (2 eq.) | Form I | Below LOQ | No form change, but loss in crystallinity. | Predominantly amorphous. |
| Camphor-10-sulfonic acid (1 eq.) | Form I | 1.05 | No form change, slight loss in crystallinity TGA showed an initial weight loss of 2.13% probably due to unbound volatiles. No other weight loss prior to degradation. | No form change, slight loss in crystallinity |
| Camphor-10-sulfonic acid (1 eq.) | Form II | 0.58 | Mixture of Form I and Form II. Some loss in crystallinity. TGA showed a 3.3% weight loss between 25-120° C. Possible bound and unbound water/solvent present. No other weight losses prior to degradation. | Converted to Form I, partially crystalline. |
| Camphor-10-sulfonic acid (2 eq.) | Form I | 0.89 | Amorphous | Amorphous |

From these results the bis-besylate salt was selected to be scaled up, using acetone as the solvent. In addition, the hydrobromide salt was selected to be scaled up, using acetonitrile:water (90:10) as the solvent. The mono-maleate and bis-hydrochloride salts were also selected for scale-up experiments to assess whether these are solvated/hydrated.

Example 3

Secondary Screen of Bis-Besylate Salt

Approximately 5 mL of acetone was added to approximately 800 mg of Compound 1 to form a slurry. In a separate vial, approximately 3 mL acetone was added to 2 equivalents of benzenesulfonic acid to dissolve the acid. The acid solution was then added in small aliquots to the free base slurry while stirring. After the complete addition of the acid, a gum/oil-like material initially formed, however, this converted to a solid after ca. 30 minutes of stirring. The reaction was stirred for ca. 1.5 days before being isolated and dried. The material was initially dried at ambient under vacuum (ca. 22° C.) for 3 days, however, approximately 6.7% acetone was still present at this stage. A portion was then dried for a further 2 days at 40° C. under vacuum after which ca. 2.7% acetone remained. The material was then dried for a further 2 days at 60° C. under vacuum. The yield was 1.1 g of material (86%).

To examine whether the citric acid in the buffers was having an effect on the solubility values obtained for pH 3, 4.5 and 6.6, the thermodynamic solubility experiments were repeated at these pH values using KHP/HCl for pH 3, KHP/NaOH for pH 4.5 and phosphate/NaOH for pH 6.6. The remaining solids were also analysed by XRPD analysis to establish if any changes in the solid form occurred.

XRPD analysis (FIG. 1) showed the material to be crystalline. The diffractogram is consistent with the small scale bis-besylate Form I diffractograms obtained during the primary salt screen.

TGA/DTA was carried after 3 days of drying at ambient under vacuum as well as after further drying for 2 days at 40° C. under vacuum and 2 days at 60° C. under vacuum. After the ambient drying process, the TGA showed a 6.7% weight loss between ca. 50-150° C. (FIG. 2) (for an acetone solvate, 1 mole equivalent of acetone would be ca. 6.3 wt %). After further drying, the TGA showed a 0.47% weight loss from the outset, likely due to unbound moisture or solvent. A further small 0.16% weight loss corresponded with the endotherm at onset ca. 142° C. (FIG. 3).

DSC analysis (FIG. 4) indicated a broad endotherm from the outset likely due to unbound solvent. A second endotherm was present at onset ca. 139.4° C. (peak 146.1° C.).

Polarised Light Microscopy (not shown) showed birefringent particles with no clearly defined morphology present.

IR spectroscopy (FIG. 5) showed a number of differences and shifts in comparison with the freebase and benzenesulfonic acid.

$^1$H NMR spectroscopy (FIG. 6) indicated that a number of the Compound 1 and benzenesulfonic acid peaks appear to be overlapping, however, the stoichiometry is approximately 2:1 benzenesulfonic acid: Compound 1. The acetone present does not appear to be a stoichiometric amount.

DVS analysis (FIG. 7) showed a water uptake of ca. 2.2% between 20 and 70% RH. The difference between the mass of the first sorption cycle and the desorption and second sorption cycle at 20% RH is likely due to the loss of excess acetone in the first cycle. The material also appears to hydrate during DVS analysis as indicated by the change in polymorphic form seen by post DVS XRPD analysis (not shown). The XRPD diffractogram also showed some loss in crystallinity.

Karl Fischer Coulometry indicated a ca. 0.77% water content (Note: due to the manual introduction of the solid material into the titration cell, measured values below 1% are generally slightly higher than the actual water content).

The HPLC purity evaluation (not shown) indicated a purity of ca. 97.6% for the bis-besylate salt with the main peak eluting at a retention time of ca. 13.05 minutes.

Figure 8:
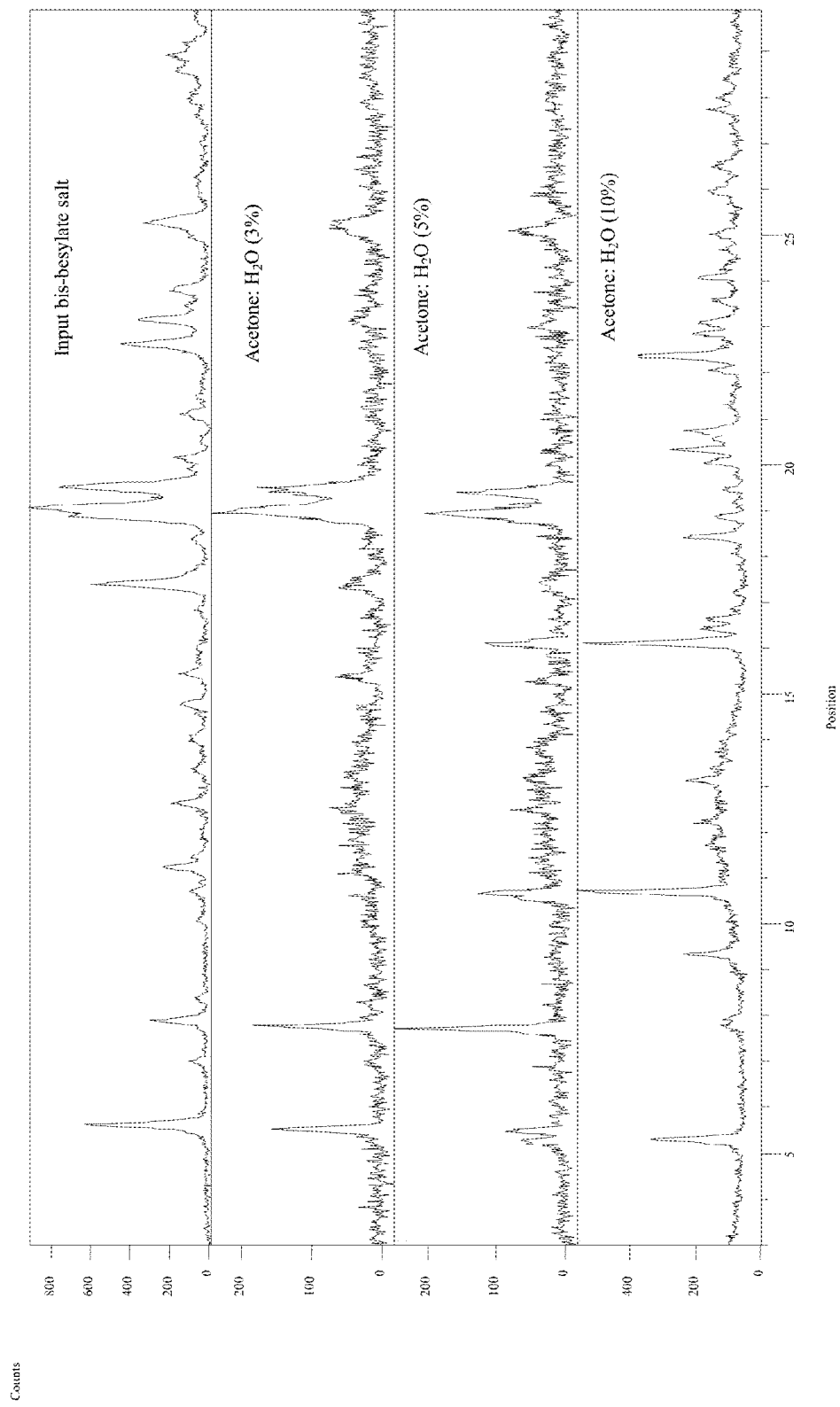
FIG. 8 depicts the results of a hydration study of a bis-besylate salt of Compound 1, as analyzed by the XRPD patterns.

Slurries of the bis-besylate salt were created in acetone:water mixtures (3%, 5% and 10%) and stirred at ambient for ca. 4 days. The resulting solids were then analyzed by XRPD to determine if any changes had occurred on slurrying. The hydration study results from XRPD analysis (FIG. 8) are summarised in Table 3.

TABLE 3

Hydration Study Results

| Solvent System | Result of slurrying |
|---|---|
| Acetone:water (3%) | Corresponds with the input bis-besylate salt material. |
| Acetone:water (5%) | Appears to be a mixture of the input material and a possible hydrate. |
| Acetone:water (10%) | Different from the bis-besylate input material, likely hydrated. Peaks correspond with post DVS XRPD peaks. |

Figure 9:
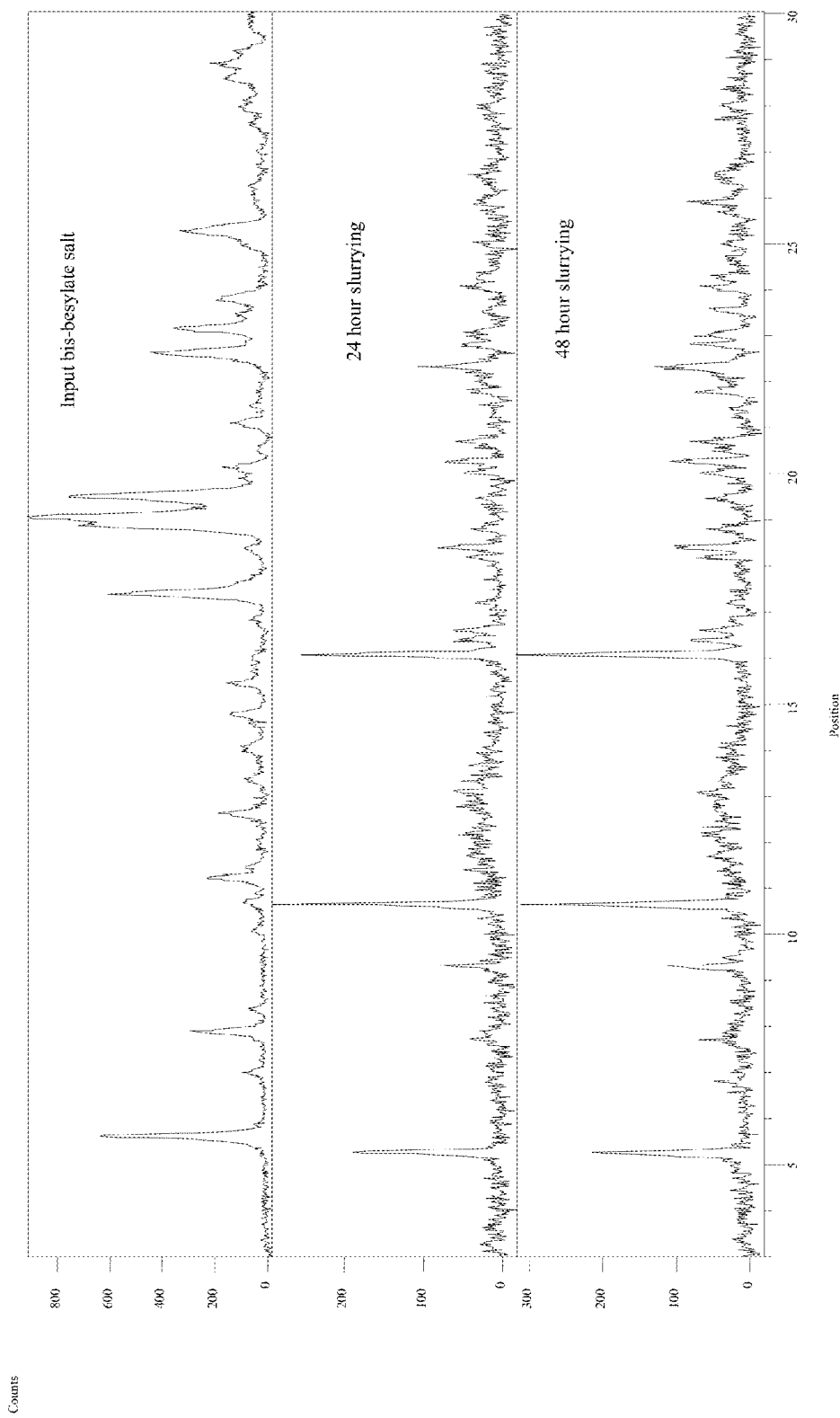
FIG. 9 depicts the results of a disproportionation study of a bis-besylate salt of Compound 1, as analyzed by the XRPD patterns.

The bis-besylate salt was slurried in deionized water at ambient temperature (ca. 22° C.). A sample of solid was taken at 24 & 48 hours and analysed by XRPD. The pH of the supernatant was also monitored. The Salt Disproportionation study results from XRPD analysis (FIG. 9) are summarised in Table 4.

TABLE 4

Disproportionation Study Results

| Timepoint | Solvent System | Result of slurrying |
|---|---|---|
| 1 hr | pH 2-3 | Yellow gum present. |
| 24 hrs | pH 1-2 | Different from starting material, appears to have hydrated (corresponds with Acetone:water (90:10%) hydration sample). |
| 48 hrs | pH 1-2 | Different from starting material, appears to have hydrated (corresponds with Acetone:water (90:10%) hydration sample). |

Figure 10:
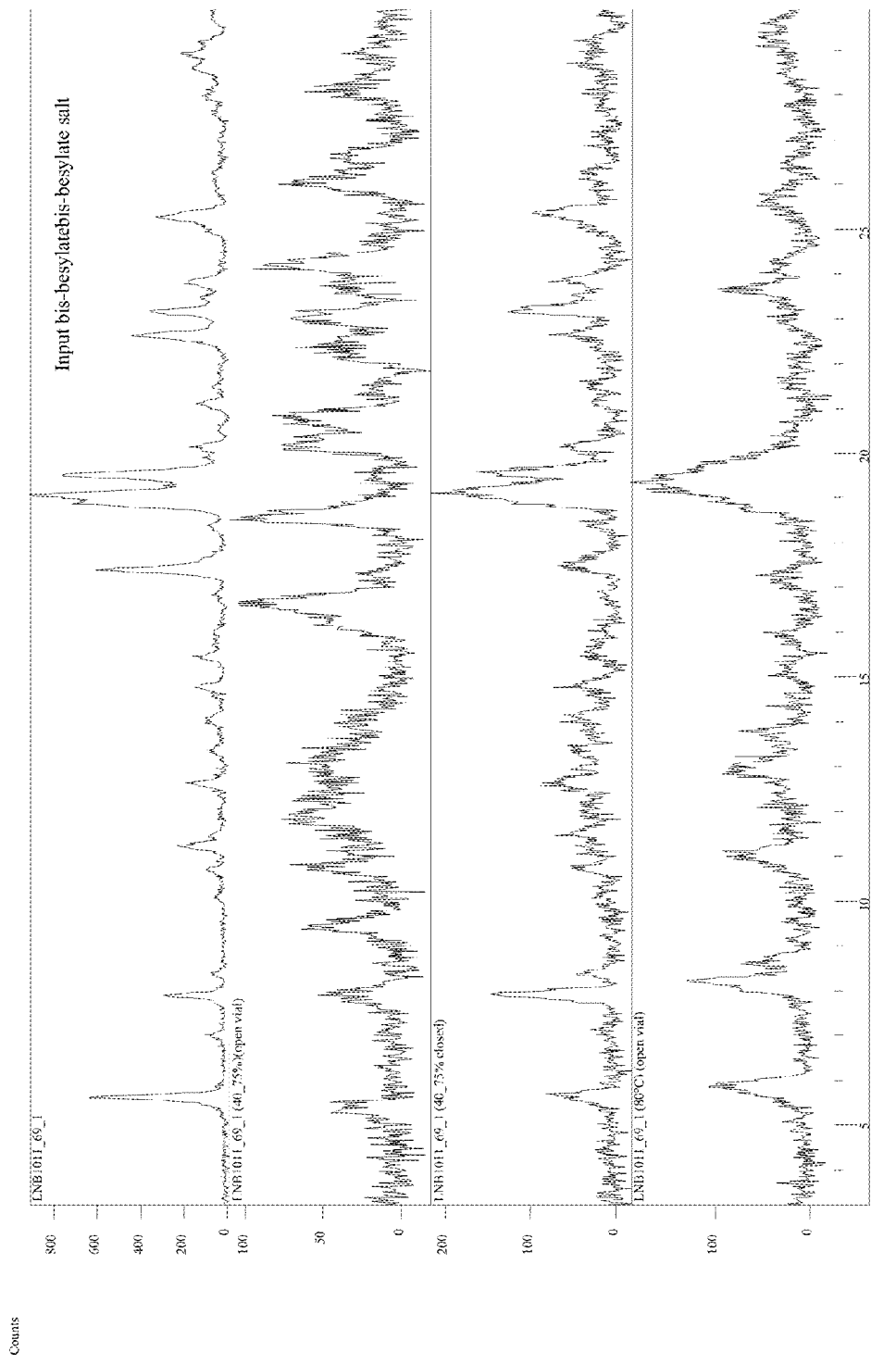
FIG. 10 depicts the results of a stability study of a bis-besylate salt of Compound 1, as analyzed by the XRPD patterns.

The bis-besylate salt was exposed to environments of 40° C./75% RH (relative humidity, open and closed vial) and 80° C. (open vial) for 1 week to determine stability. Resulting solids were analysed by XRPD and HPLC to establish if any changes had occurred. The 1 Week stability study results from XRPD (FIG. 10) and HPLC analysis (not shown) at 40° C./75% RH using an open and closed vial and 80° C. using an open vial are indicated Table 5.

TABLE 5

1 Week Stability Study Results

| Storage Condition | HPLC | XRPD |
|---|---|---|
| 40° C./75% RH (open vial) | 97.22% | Change in polymorphic form, likely due to hydration. |
| 40° C./75% RH (crimped vial) | 97.35% | No change in polymorphic form. |
| 80° C. (open vial) | 97.20% | Corresponds predominantly with input material, with loss in crystallinity. |

Slurries of the bis-besylate salt were created in media of various pH (pH 1; pH 3; pH 4.5 and pH 6.6) and shaken for ca. 24 hours. After 24 hours, the slurries were filtered and the solution analysed by HPLC in order to determine the solubility at the various pH levels. The remaining solids were also analysed by XRPD analysis to establish if any changes in the solid form occurred. For the buffer solutions, KCl/HCl was used for pH 1 and citrate/phosphate combinations for pH 3, 4.5 and 6.6. Thermodynamic solubility studies indicated the results shown in Table 6.

TABLE 6

Thermodynamic Solubility Results

Figure 11:
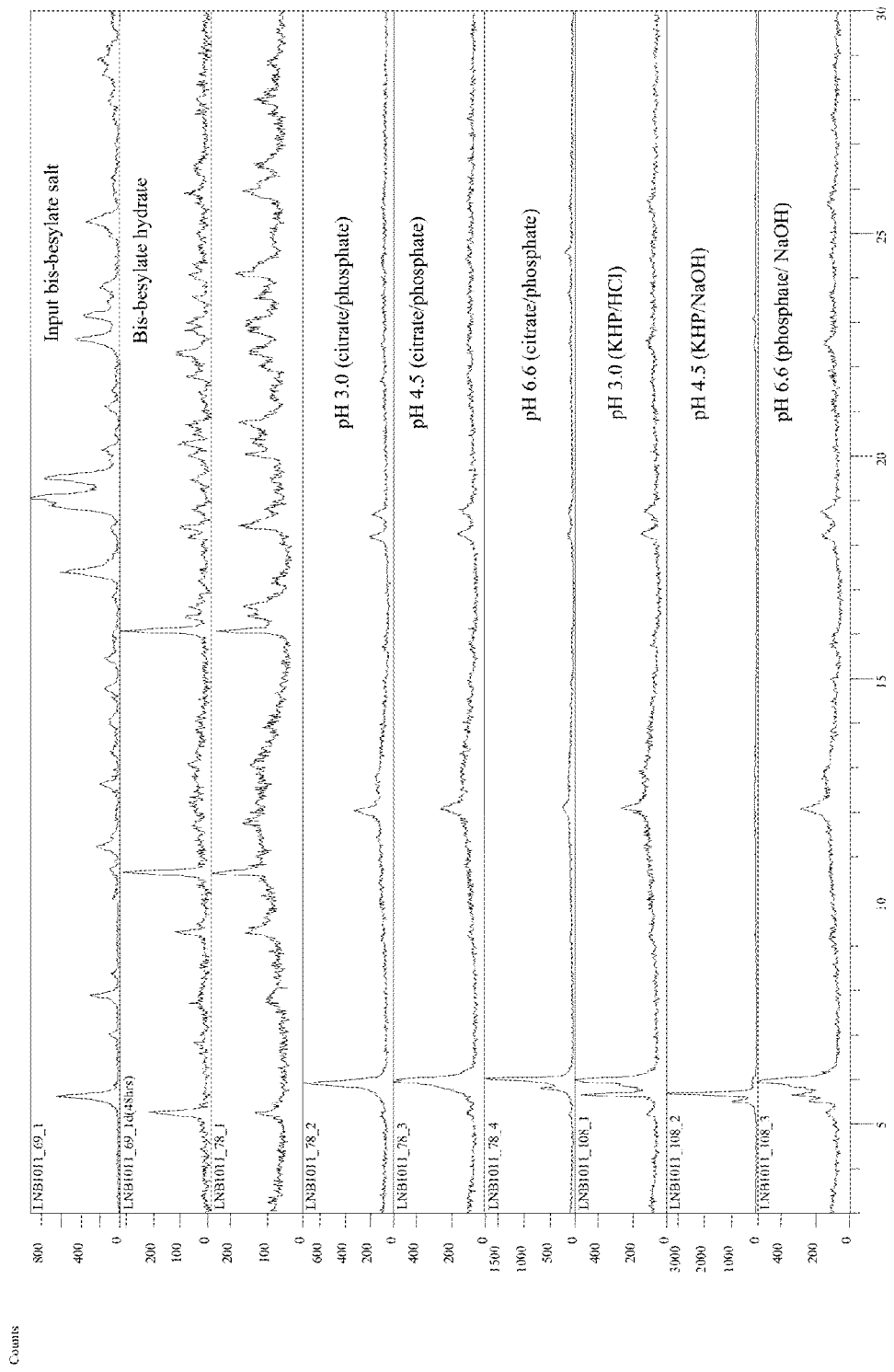
FIG. 11 depicts the results of a thermodynamic solubility study of a bis-besylate salt of Compound 1, as analyzed by the XRPD patterns.

| pH | Buffers used | Solubility (mg/ml) | XRPD of excess solids (FIG. 11) |
|---|---|---|---|
| pH 1.0 | KCl/HCl | 4.93 mg/ml | Diffractogram corresponds with the hydrated bis-besylate. |
| pH 3.0 | Citrate/Phosphate | 0.24 mg/ml | Change in diffractogram - does not correspond with any known forms of the bis-besylate or Compound 1. Does not correspond with the solids used in the buffers. |
| pH 4.5 | Citrate/Phosphate | 0.43 mg/ml | Change in diffractogram - does not correspond with any known forms of the bis-besylate or Compound 1. Does not correspond with the solids used in the buffers. |
| pH 6.6 | Citrate/Phosphate | 0.66 mg/ml | Change in diffractogram - does not correspond with any known forms of the bis-besylate or Compound 1. Does not correspond with the solids used in the buffers. |
| pH 3.0 | KHP/HCl | 0.26 mg/ml | Change in diffractogram - does not correspond with any known forms of the bis-besylate or Compound 1. Does not correspond with the solids used in the buffers. |

TABLE 6-continued

Thermodynamic Solubility Results

| pH | Buffers used | Solubility (mg/ml) | XRPD of excess solids (FIG. 11) |
|---|---|---|---|
| pH 4.5 | KHP/ NaOH | 0.10 mg/ml | Change in diffractogram - does not correspond with any known forms of the bis-besylate or Compound 1. Does not correspond with the solids used in the buffers. |
| pH 6.6 | Phosphate/ NaOH | 0.17 mg/ml | Change in diffractogram - does not correspond with any known forms of the bis-besylate or Compound 1. Does not correspond with the solids used in the buffers. |

When initially setting up the slurries for thermodynamic solubility determinations, gums were obtained in all of the pH media used, however, upon shaking, the gums converted to solids after ca. 2 hours. The XRPD analysis of the excess solid from the slurries after the solubility experiments, indicate that for pH 1, the bis-besylate salt hydrates while slurrying. Hence, the solubility value obtained is likely an indication of the solubility of the hydrated material. The diffractograms for the remaining samples appear different from the input material as well as all identified forms of the bis-besylate and Compound 1 free base. The diffractograms also appear different from the diffractograms of the solids used to make up the buffers. The solubility values obtained using these pH buffers are likely not representative of the bis-besylate salt which was initially placed into the solutions.

Approximately 100-120 mg of each form was compressed into discs by placing the material into a die (diameter: 13 mm) and compressing the die under 5 tons of pressure in a hydraulic press for ca. 2 minutes. A Sotax AT7 (conformed to EP2 and USP2) dissolution instrument was used containing paddles to stir the media at 100 rpm. Dissolution media of pH 3 (1% SDS) and pH 4.5 (1% SDS) were prepared using citrate/phosphate buffer. All materials were tested in 750 ml of the buffer medium. Discs were added at time=0 seconds and allowed to sink to the bottom of the dissolution vessel before stirring began. ca. 1 ml aliquots of media were extracted from the dissolution vessels at times 1, 5, 10, 15, 30, 60, 120, 240 minutes and 24 hours, and tested for dissolved salt concentration by HPLC-UV. The dissolution tests were carried out in duplicate. For both dissolution media, the peak areas for the initial time points (up to 15 minutes), fell below the limit of quantification, however, when plotting Dissolution rate vs. time, the steepest part of the curve occurs during these early time points.

Figure 12:
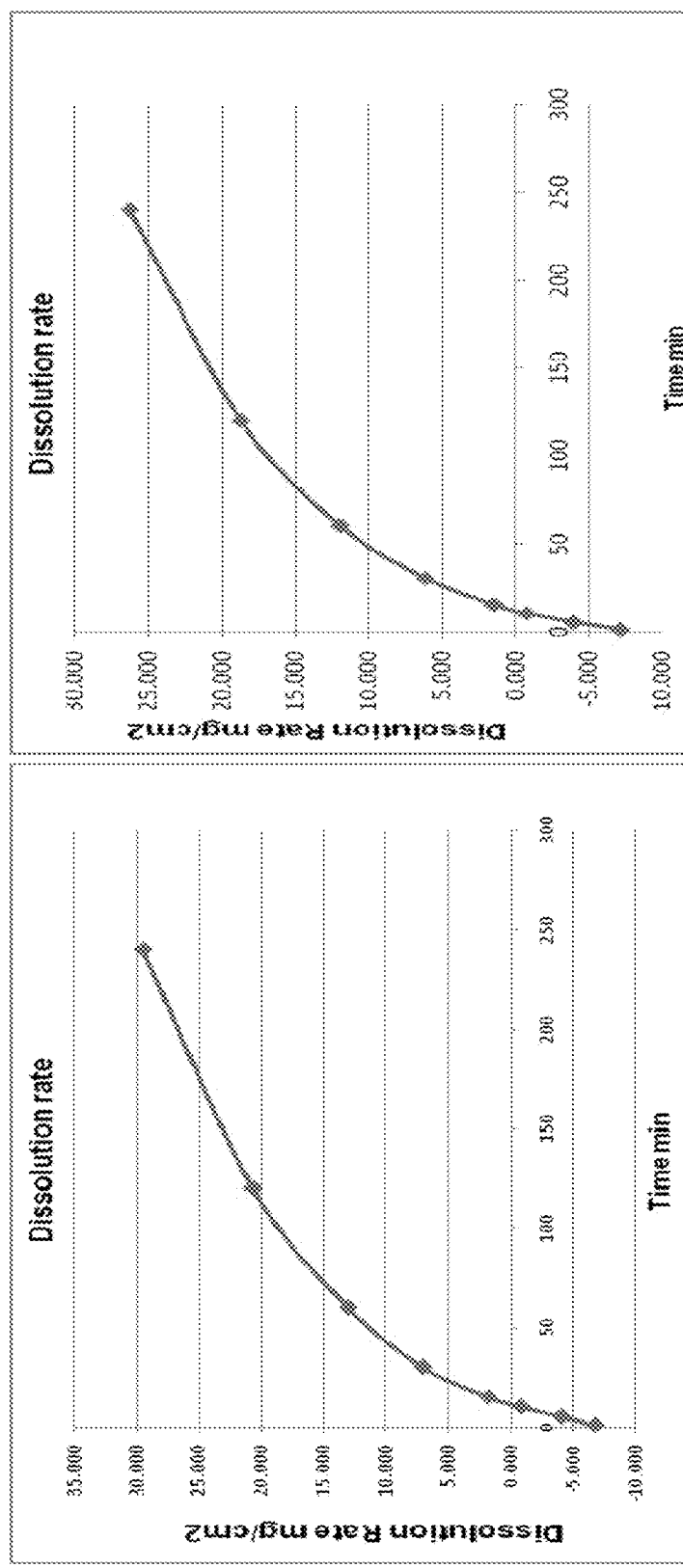
FIG. 12 depicts the dissolution at pH 4.5 of a compressed disc of a bis-besylate salt of Compound 1.

For pH 4.5, when plotting the curve of Dissolution rate vs. Time (FIG. 12), the intrinsic dissolution values obtained from the early time points on the curve (steepest part of the curve) were approximately 0.61 mg/cm$^2$/min for both tablets 1 and 2. At the later time points, intrinsic dissolution values of 0.09 mg/cm$^2$/min and 0.08 mg/cm$^2$/min were obtained for tablets 1 and 2, respectively.

Figure 13:
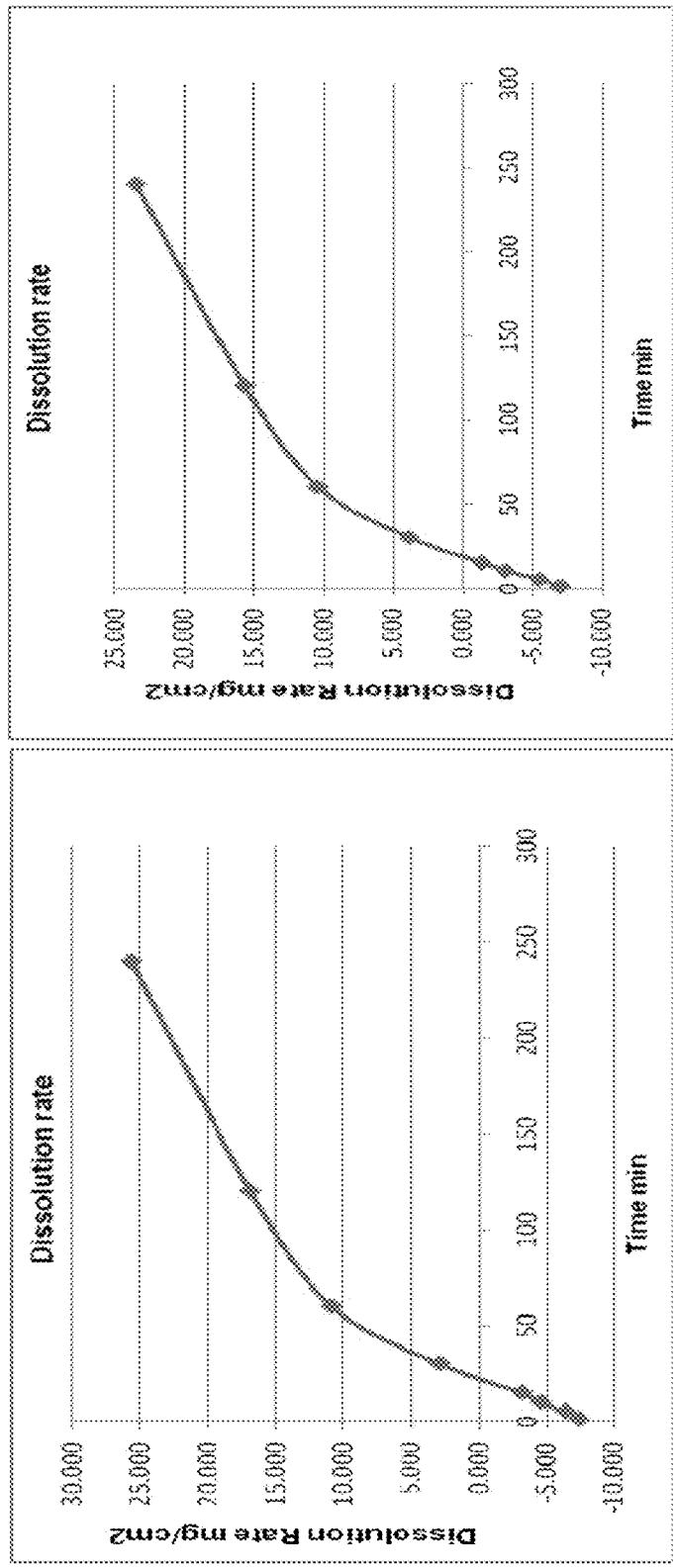
FIG. 13 depicts the dissolution at pH 3.0 of a compressed disc of a bis-besylate salt of Compound 1.

For pH 3.0, when plotting the curve of Dissolution rate vs. Time (FIG. 13), the intrinsic dissolution values obtained from the early time points on the curve (steepest part of the curve) were approximately 0.36 mg/cm$^2$/min for tablet 1 and 0.38 mg/cm$^2$/min for tablet 2. At the later time points, intrinsic dissolution values of 0.08 mg/cm$^2$/min and 0.07 mg/cm$^2$/min were obtained for tablets 1 and 2, respectively.

Example 4

Secondary Screen of Bis-Besylate Hydrate Salt

Approximately 3 mL of acetone was added to ca. 500 mg of Compound 1 to form a slurry. In a separate vial, ca. 1 mL of acetone was added to 2 equivalents of benzenesulfonic acid in order to dissolve the acid. The acid solution was then added in small aliquots to the freebase slurry while stirring. The reaction was stirred for ca. 1 day while temperature cycling between 0 and ambient temperature (ca. 22° C.). After 1 day, deionized water was added to the reaction mixture and the slurry was allowed to stir for ca. 3 hours before being isolated and dried at ambient under vacuum.

XRPD analysis (FIG. 14) showed the material to be crystalline. The diffractogram is consistent with the bis-besylate hydrate obtained from the hydration studies of the bis-besylate salt.

TGA/DTA indicated a weight loss of ca. 2.1% between ca. 70-100° C. (FIG. 15). This corresponds approximately with the 2.03 wt % water required for a monohydrate. A ca. 2.2% weight loss was present from the outset to ca. 70° C., likely due to unbound water. Although the total ca. 4.2% weight loss corresponds approximately with a dihydrate, the first weight loss occurs from the outset followed by a second clear weight loss corresponding with mono amounts of water. As the first weight loss occurs from ca. 25° C., this would likely be due to unbound water.

Figure 16:
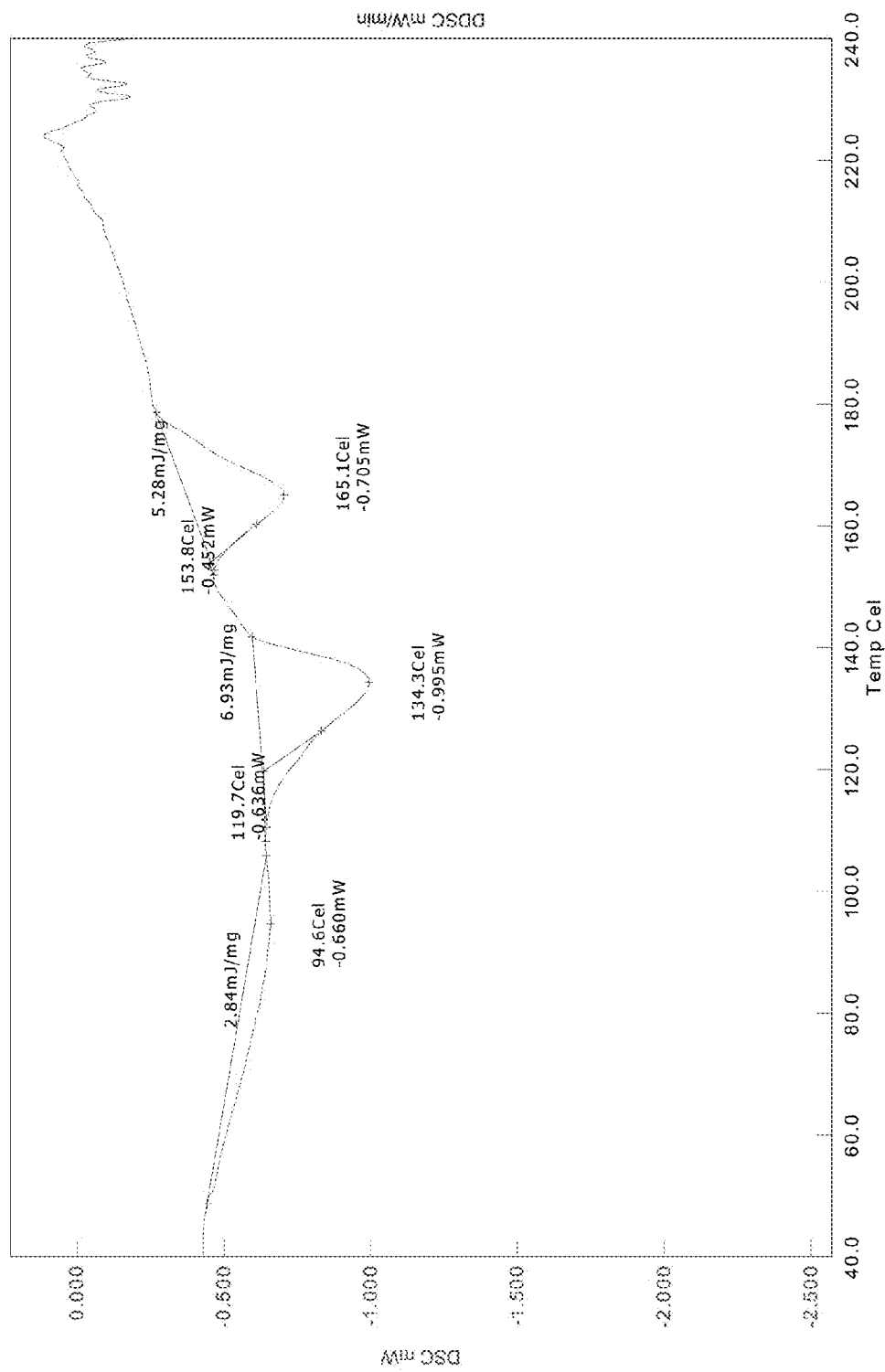
FIG. 16 depicts the DSC pattern for a bis-besylate hydrate salt of Compound 1.

DSC analysis indicated a broad endotherm between ca. 40-115° C. Two further endotherms were then present at onset 119.7° C. (peak 134.3° C.) and onset 153.8° C. (peak 165.1° C.) (FIG. 16).

PLM analysis showed some birefringence, however the particle size is very small and no clear morphology could be seen (not shown). Hot-stage microscopy was carried out on a sample of the bis-besylate hydrate. No visual changes could be observed prior to the material melting and degrading (turned brown) at ca. 160° C.

IR analysis (FIG. 17) showed differences from both the free base and benzenesulfonic acid spectra as well as some differences when comparing the spectra of the input bis-besylate salt with that of the hydrated material.

$^1$H NMR spectroscopy (FIG. 18) indicated that a number of the Compound 1 and benzenesulfonic acid peaks appear to be overlapping, however, the stoichiometry appears to be approximately 2:1 benzenesulfonic acid: Compound 1. A small non-stoichiometric amount of acetone was present in the spectrum.

DVS analysis (FIG. 19) showed a water uptake of ca. 1.3% between 20 and 70% RH. No hysteresis was seen between the sorption and desorption cycles. The XRPD diffractogram of the material post DVS analysis was consistent with the diffractogram of the input bis-besylate hydrate material (not shown).

Figure 20:
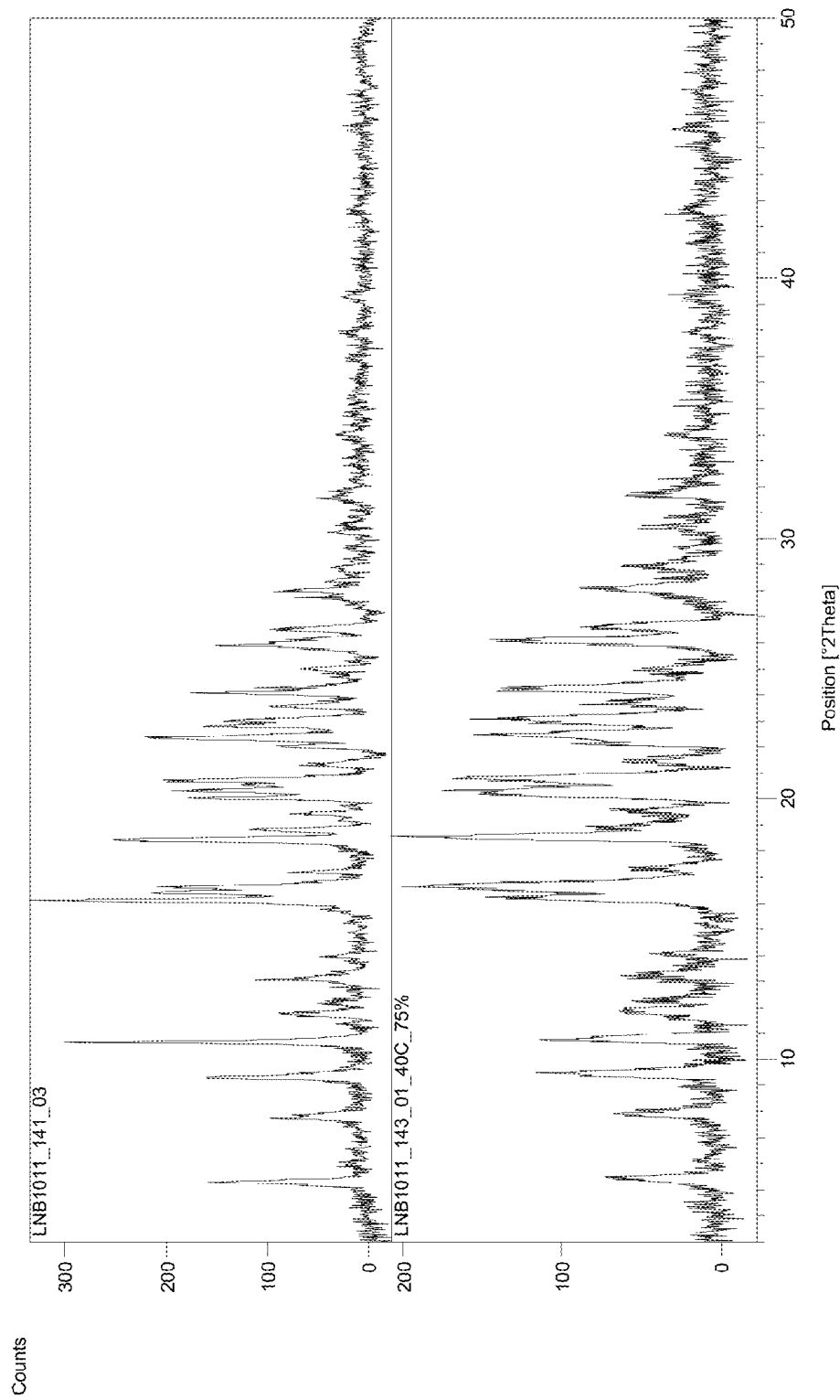
FIG. 20 depicts the results of a stability study of a bis-besylate hydrate salt of Compound 1, as analyzed by the XRPD patterns.

The 1 week stability data at 40° C./75% RH (open container) indicated that by XRPD, the material remained consistent with the input material with no changes in polymorphic form (FIG. 20).

HPLC purity determinations indicated an initial purity of ca. 98.4% and a purity of ca. 98.3% after 1 week storage at 40° C./75% RH.

Thermodynamic solubility studies of the bis-besylate hydrate indicated the results shown in Table 7.

TABLE 7

Thermodynamic Solubility Results

Figure 21:
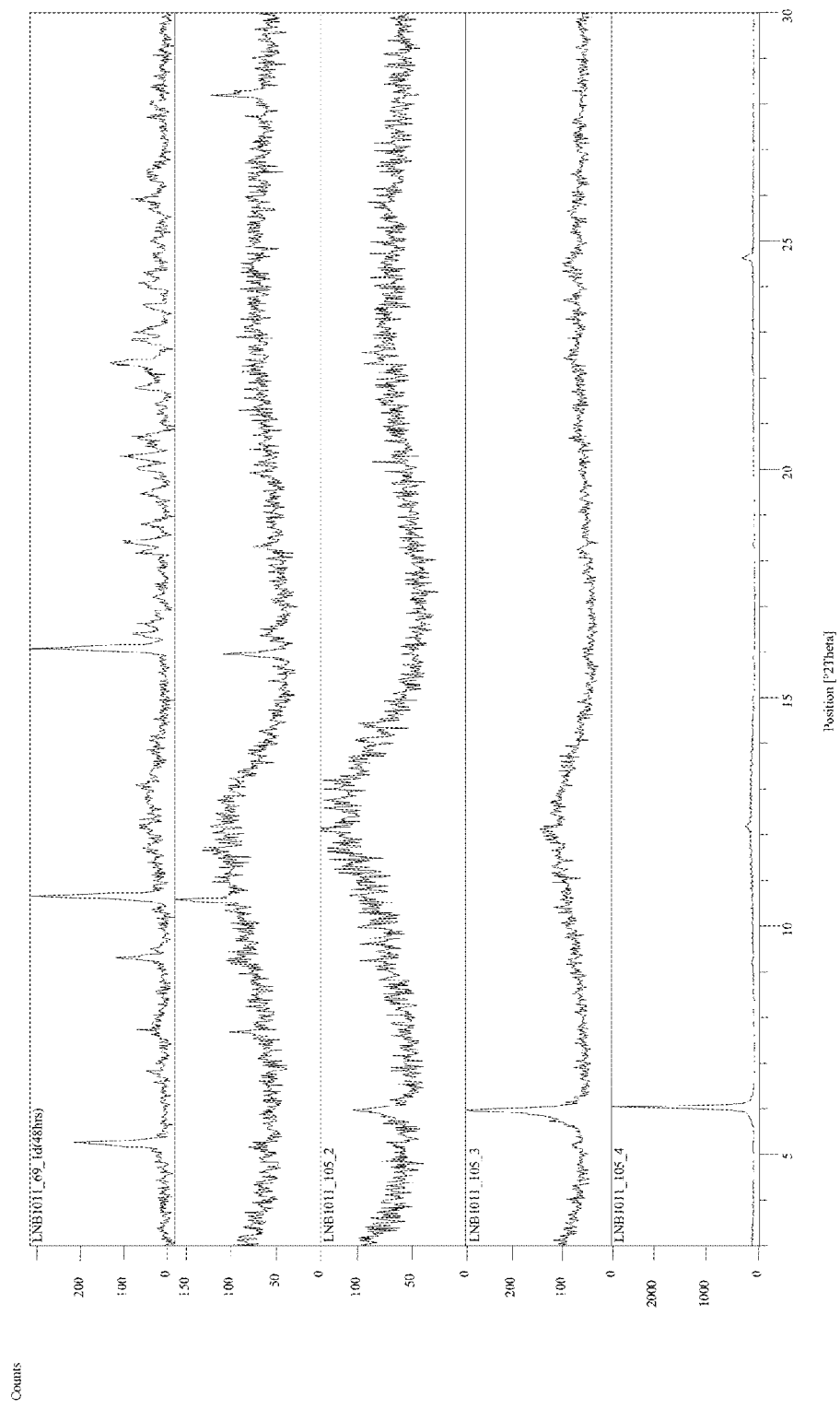
FIG. 21 depicts the results of a thermodynamic solubility study of a bis-besylate salt of Compound 1, as analyzed by the XRPD patterns.

| pH | Buffers | Solubility (mg/ml) | XRPD of excess solids (FIG. 21) |
|---|---|---|---|
| pH 1.0 | KCl/ HCl | 4.39 mg/ml | Very little solid present for XRPD, however the peaks which are visible in the diffractogram appear to correspond with the hydrated bis-besylate diffractogram. |
| pH 3.0 | Citrate/ Phosphate | 0.016 mg/ml | Very little solid present for XRPD, however, a change in the diffractogram is seen where it does not correspond with any identified forms of the bis-besylate salt or Compound 1. It also does not correspond with the solids used in the buffers. |
| pH 4.5 | Citrate/ Phosphate | Below LOQ | Very little solid present for XRPD, however, a change in the diffractogram is seen where it does not correspond with any identified forms of the bis-besylate salt or Compound 1. It also does not correspond with the solids used in the buffers. |
| pH 6.6 | Citrate/ Phosphate | Not detected by HPLC | Very little solid present for XRPD, however, a change in the diffractogram is seen where it does not correspond with any identified forms of the bis-besylate salt or Compound 1. It also does not correspond with the solids used in the buffers. |

Figure 22:
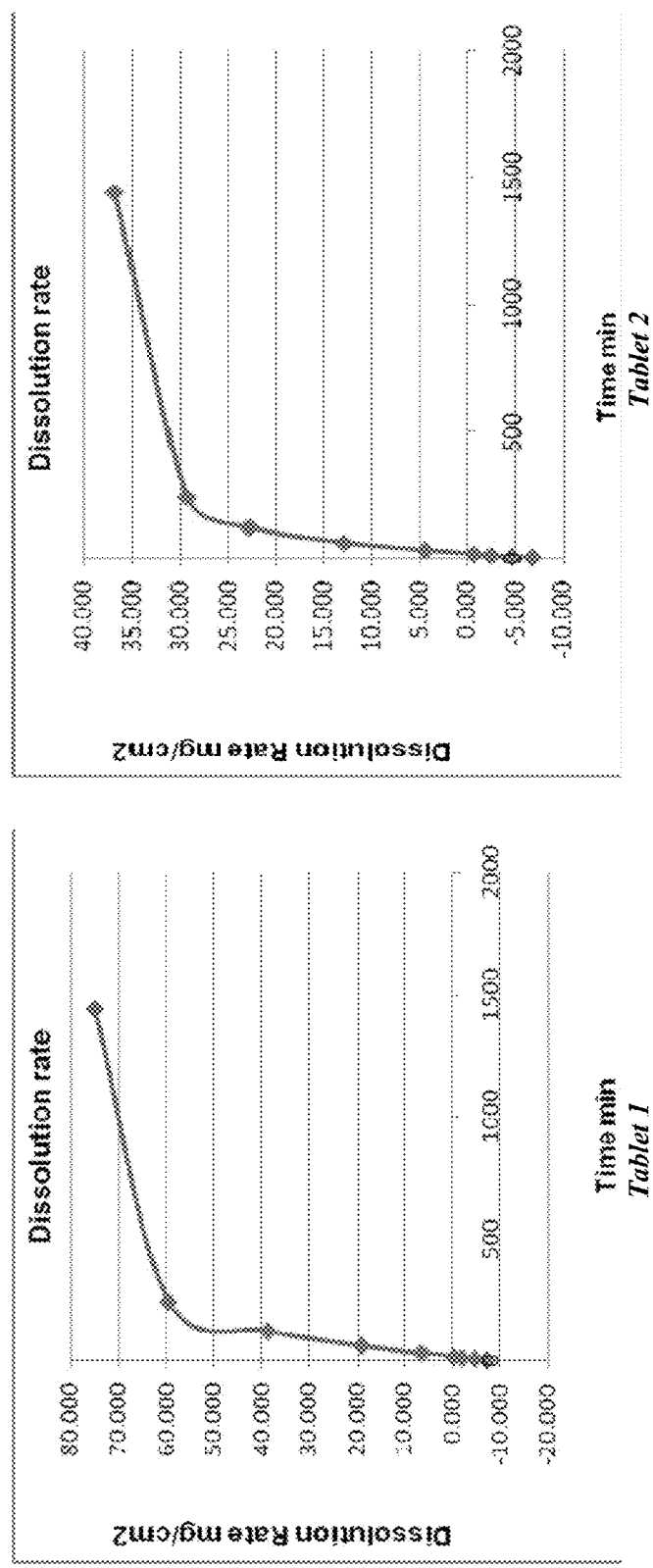
FIG. 22 depicts the dissolution at pH 4.5 of a compressed disc of a bis-besylate hydrate salt of Compound 1.

Intrinsic dissolution tests were carried out using pH 4.5 (1% SDS) and pH 3.0 (1% SDS). For both dissolution media, the peak areas for the initial time points (up to 15 minutes), fell below the limit of quantification, however when plotting Dissolution rate vs. time, the steepest part of the curve occurs during these early time points. For pH 4.5, when plotting the curve of Dissolution rate vs. Time (FIG. 22), the intrinsic dissolution values obtained from the early time points on the curve (steepest part of the curve) were approximately 0.43 mg/cm$^2$/min for tablet 1 and 0.44 mg/cm$^2$/min for tablet 2. At the later time points (toward the end of the dissolution study), intrinsic dissolution values of 0.012 mg/cm$^2$/min and 0.006 mg/cm$^2$/min were obtained for tablets 1 and 2, respectively.

Figure 23:
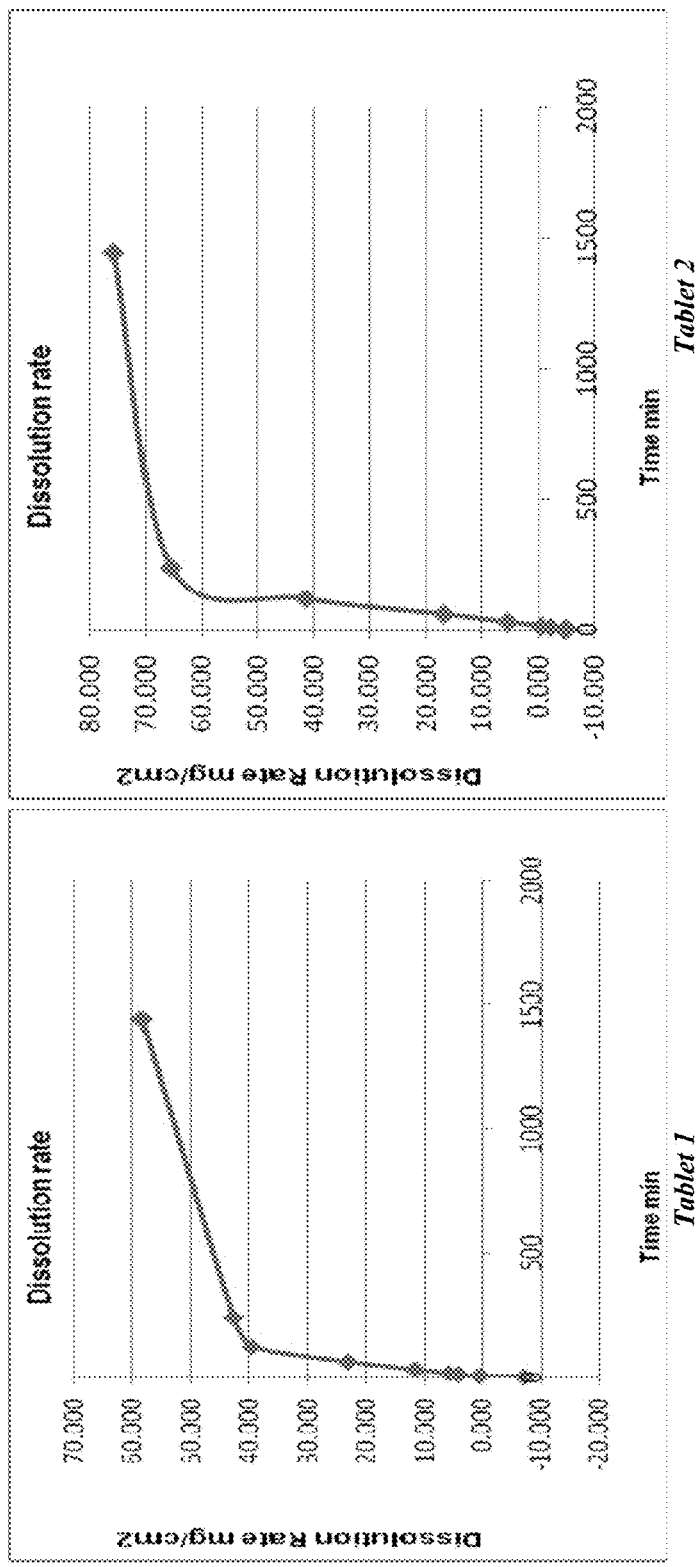
FIG. 23 depicts the dissolution at pH 3.0 of a compressed disc of a bis-besylate hydrate salt of Compound 1.

For pH 3.0, when plotting the curve of Dissolution rate vs. Time (FIG. 23), the intrinsic dissolution values obtained from the early time points on the curve (steepest part of the curve) were approximately 0.38 mg/cm$^2$/min for tablet 1 and 0.39 mg/cm$^2$/min for tablet 2. At the later time points, intrinsic dissolution values of 0.01 mg/cm$^2$/min for both tablets 1 and 2 were obtained.

A larger batch of the bis-besylate hydrate salt was prepared using the following procedure. Approximately 20 mL of acetone was added to ca. 14 g of Compound 1 in a round bottomed flask to form a slurry. In a separate flask, ca. 10 mL of acetone was added to 2 equivalents of benzenesulfonic acid in order to dissolve the acid. The acid solution was then added in small aliquots to the freebase slurry whilst stirring at ca. 0° C. The resulting slurry was then allowed to stir at ambient for ca. 2 hours. It was then placed at ca. 5° C. for 2 days before stirring for a further 3 hours at ambient temperature. The acetone was then removed and ca. 20 mL of water was added to the material. The slurry was temperature cycled (0° C.—ambient temperature (ca. 22° C.)) in 2 hour cycles for ca. 1 day. The solid was then isolated by filtration and allowed to dry at ambient conditions under vacuum before analysis. The drying was continued for ca. 10 days.

The properties of the material from this larger batch were similar to those described above. In addition to those properties, it was noted that when the bis-besylate hydrate was left on the bench for 2 hours and TGA was again carried out, the sample seemed to pick up the water to have a total ca. 4.5% weight loss in the final TGA. It does not appear to be possible to remove the remaining 2% of unbound water by drying as this is regained when exposed to ambient conditions. Also, KF titration determined the water content of the material to be ca. 3.97%. While the ca. 4 wt % water would correspond theoretically with a dihydrate, the weight loss in the TGA appears to start from the outset followed by a more clear second weight loss which corresponds approximately with 1 equivalent of water. The material likely shows some hygroscopicity resulting in the initial TGA weight loss.

Example 5

Secondary Screen of Mono-Maleate Salt

Approximately 3 mL of dichloromethane was added to ca. 200 mg of Compound 1 to form a slurry. In a separate vial, ca. 1 mL of dichloromethane was added to 1 equivalent of maleic acid in order to dissolve the acid. The acid solution was then added in small aliquots to the freebase slurry while stirring. The slurry obtained was yellow in color. The reaction was stirred for ca. 1.5 days between 0° C. and ambient temperature (ca. 22° C.) and remained at ca. 4° C. for a further 2 days before being isolated and dried at ambient. The material was dried at ambient temperature under vacuum (ca. 22° C.) for ca. 2 days.

XRPD analysis (FIG. 24) showed the material to be crystalline. The diffractogram is consistent with the small scale mono-maleate Form I diffractogram obtained during the primary salt screen.

TGA/DTA was carried after 2 days of drying at ambient under vacuum. The TGA showed a 0.4% weight loss from the outset, likely due to unbound moisture or solvent. A large 10.9% weight loss is associated with endothermic/exothermic events in the DTA between ca. 145-185° C., followed by further weight losses due to likely degradation (FIG. 25).

Figure 26:
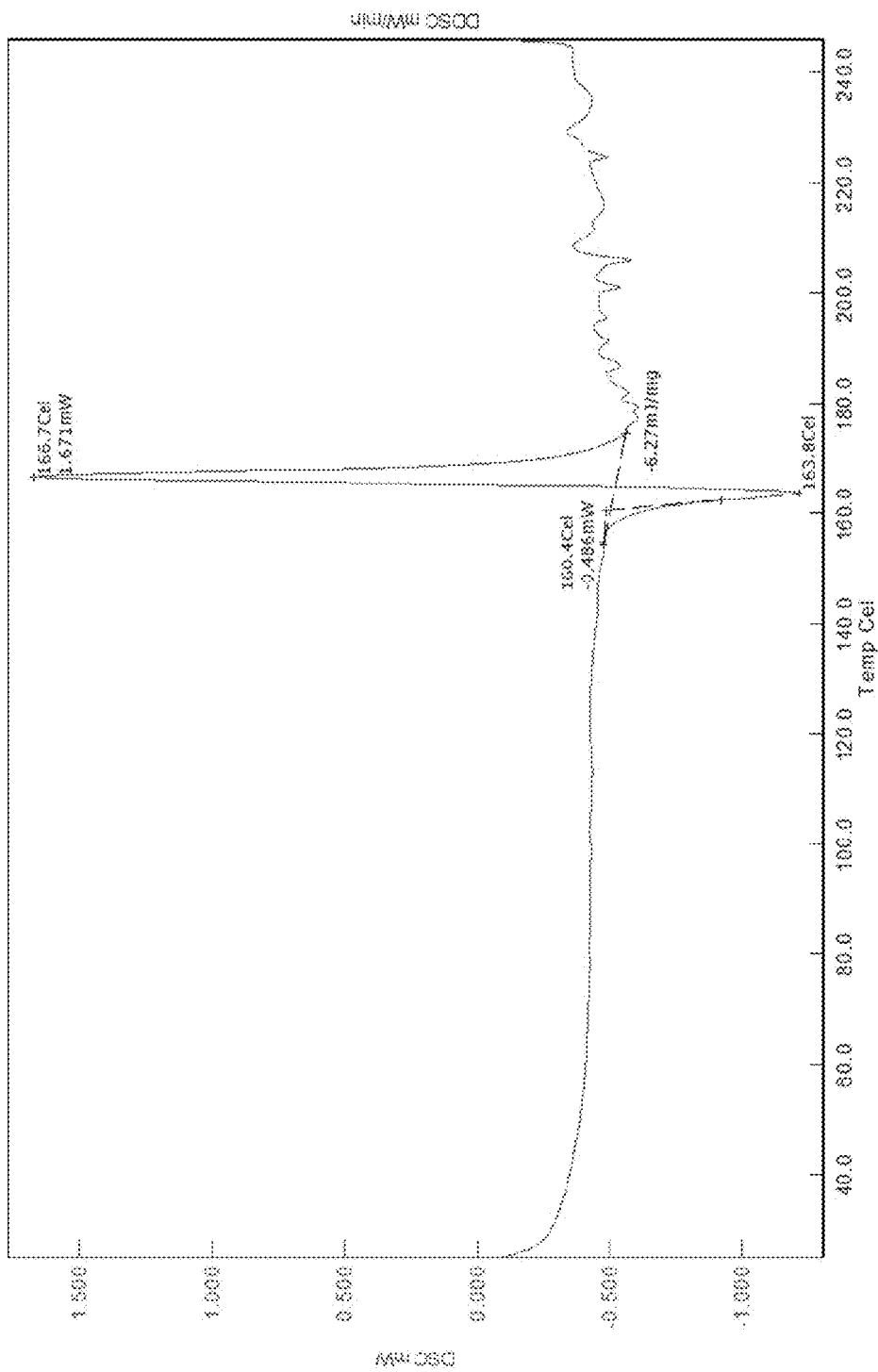
FIG. 26 depicts the DSC pattern for a mono-maleate salt of Compound 1.
Figure 27:
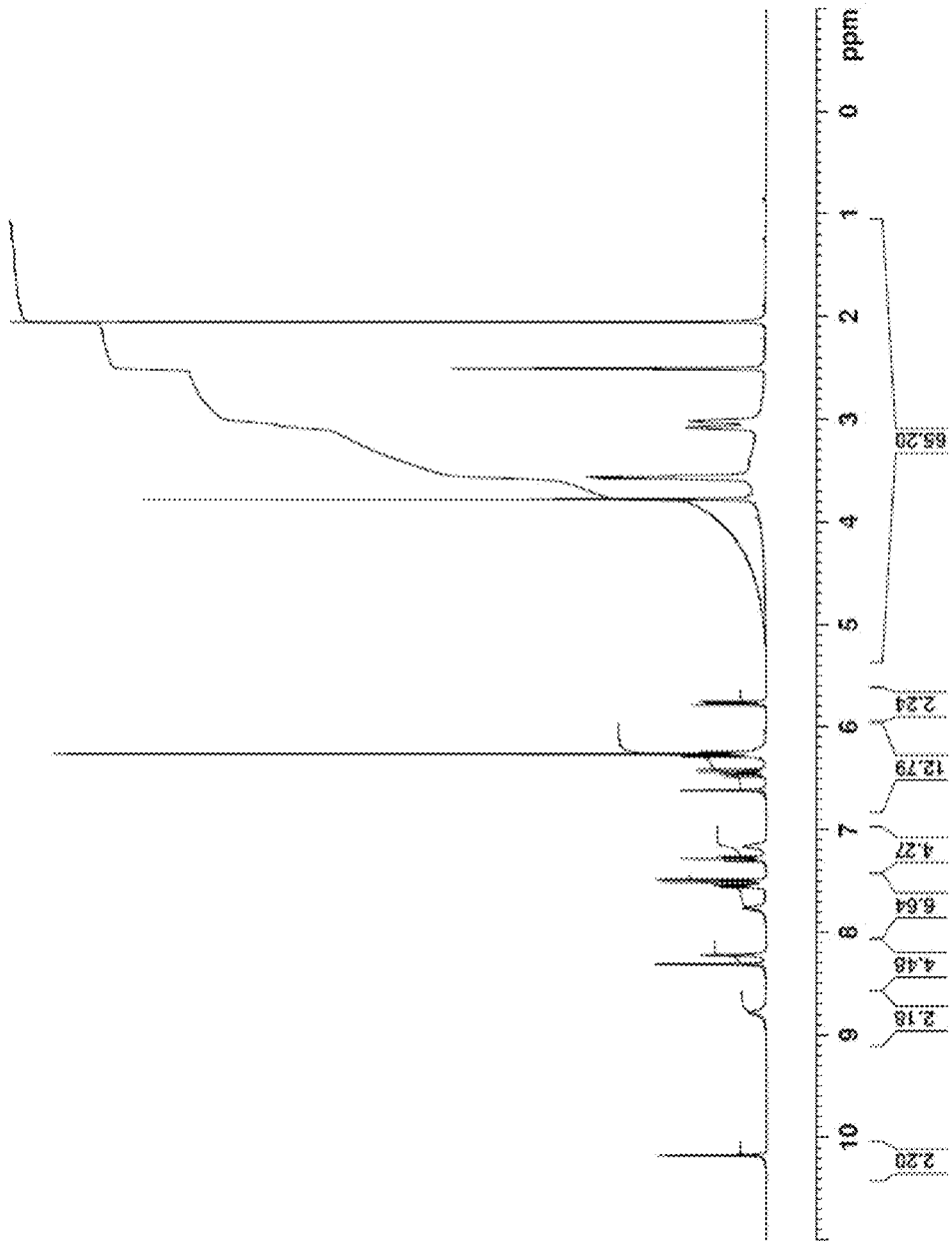
FIG. 27 depicts the $^1$H-NMR spectrum of a mono-maleate salt of Compound 1.

DSC analysis indicated an endotherm at onset 160.4° C. (peak 163.8° C.), directly followed by an exotherm, likely due to recrystallisation and then final degradation (FIG. 26).

$^1$H NMR spectroscopy (FIG. 27) indicated approximately 1:1 stoichiometry of Compound 1: maleic acid. Dichloromethane was not present in the spectrum. Therefore, the mono-maleate salt does not appear to be solvated.

Example 6

Secondary Screening of Bis-Hydrochloride Salt (Form I)

Approximately 1.5 mL of acetonitrile:H$_2$O (90:10) was added to ca. 200 mg of Compound 1 to form a slurry. In a separate vial, ca. 1 mL of acetonitrile:H$_2$O (90:10) was added to 2 equivalents of hydrochloric acid. The acid solution was then added in small aliquots to the freebase slurry while stirring. The reaction was stirred for ca. 1.5 days between 0° C. and ambient temperature (ca. 22° C.) and remained at ca. 4° C. for a further 2 days before being isolated and dried at ambient temperature. The material was dried at ambient temperature under vacuum (ca. 22° C.) for ca. 2 days.

XRPD analysis (FIG. 28) showed the material to be crystalline. The diffractogram is consistent with the small scale bis-hydrochloride Form I diffractogram obtained during the primary salt screen.

TGA/DTA was carried after 2 days of drying at ambient under vacuum. The TGA showed a 2.7% gradual weight loss from the outset to ca. 180° C. A further 4.3% weight loss is seen between ca. 180-210° C., which corresponds with an endotherm in the DTA trace (FIG. 29).

Figure 30:
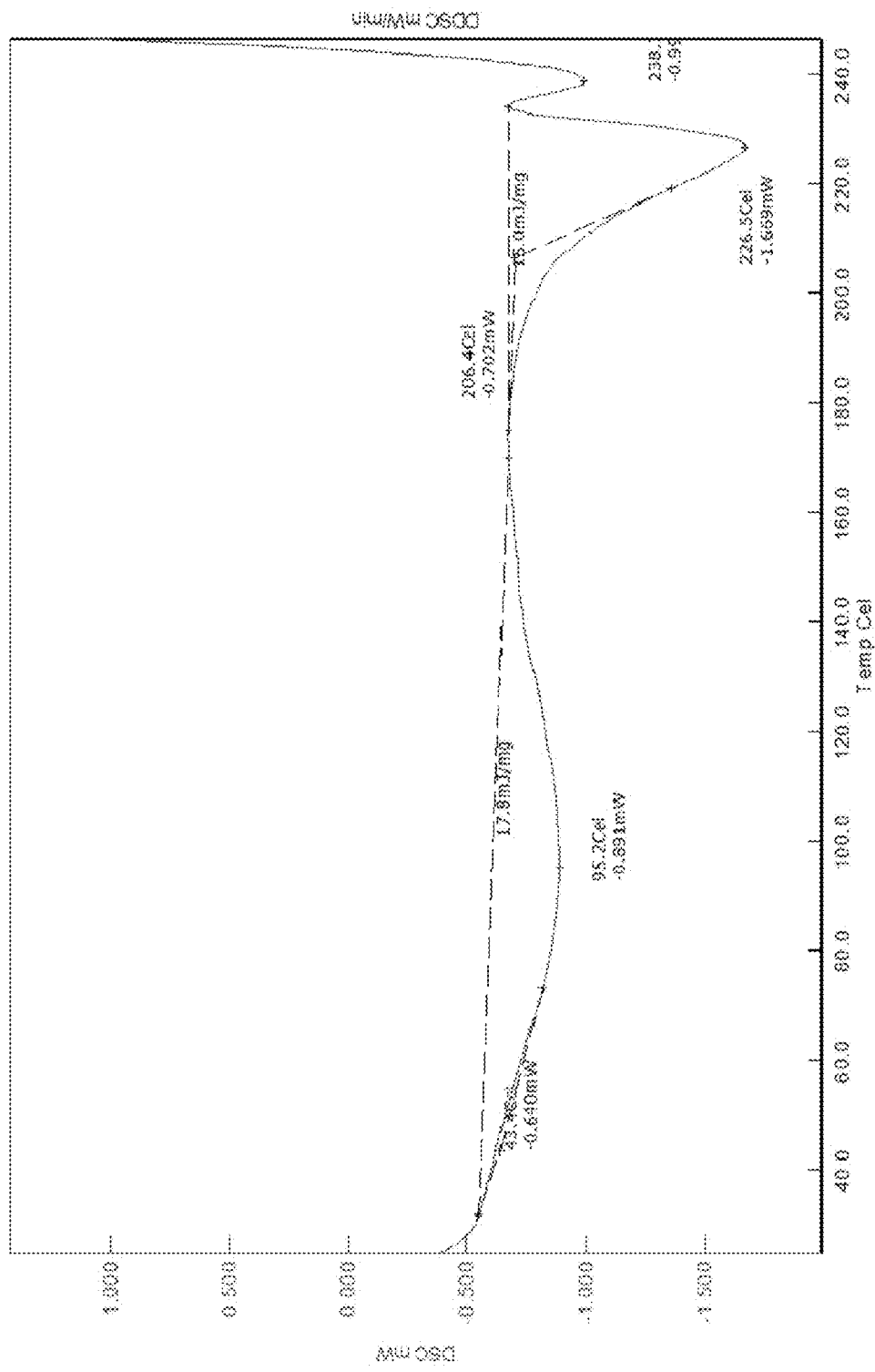
FIG. 30 depicts the DSC pattern for a bis-hydrochloride salt of Compound 1.
Figure 31:
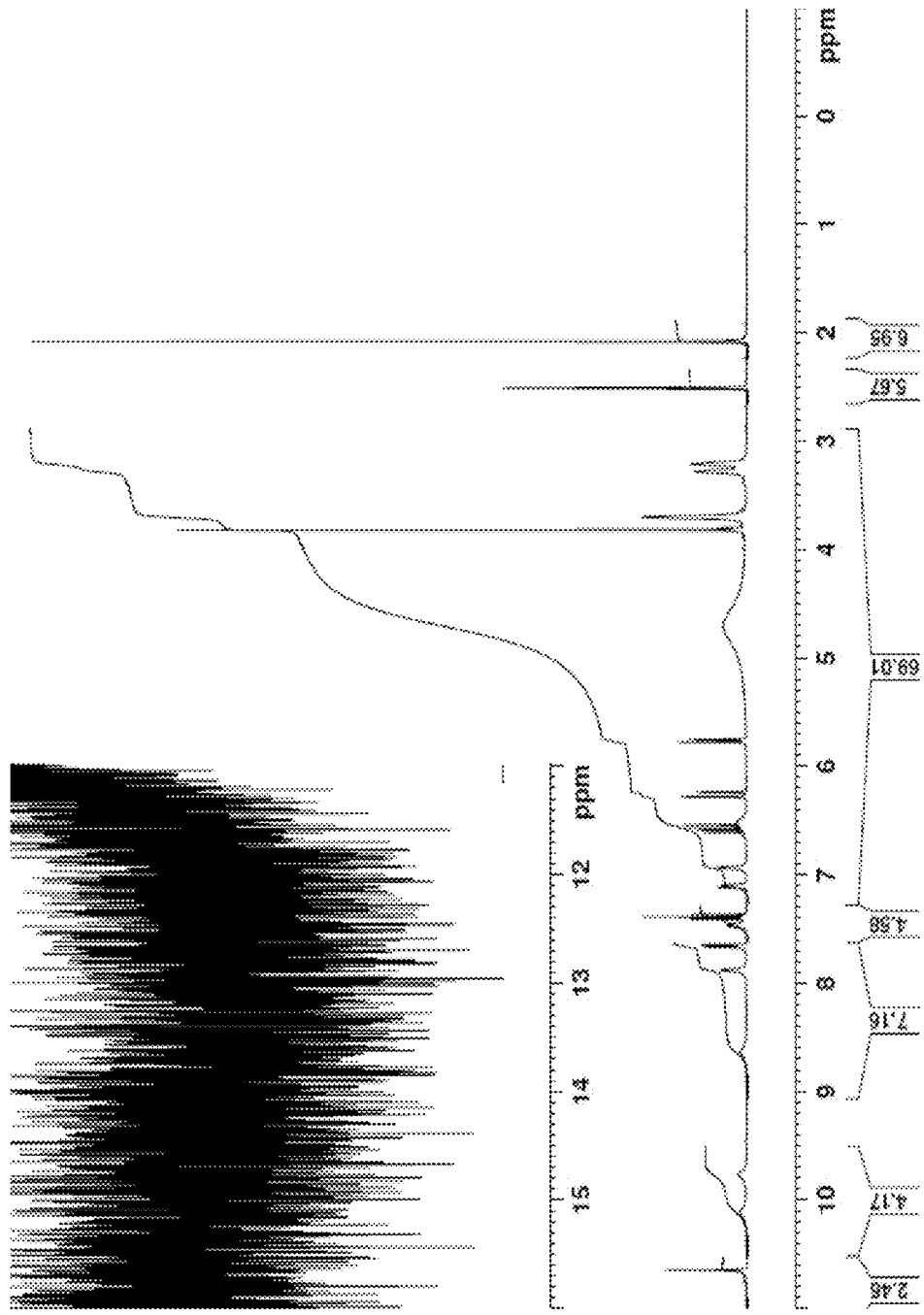
FIG. 31 depicts the $^1$H-NMR spectrum of a bis-hydrochloride salt of Compound 1.

DSC analysis indicated a broad endotherm between ca. 30-160° C. A further endotherm is then present at onset 206.4° C. (peak 226.5° C.), directly followed by a smaller endotherm at peak 238.2° C. (FIG. 30).

Karl Fischer analysis showed ca. 3.3% water content (ca. 2.8% water required for a monohydrate).

$^1$H NMR spectroscopy (FIG. 31) indicated that the spectrum had shifted in comparison with Compound 1, indicating likely salt formation. No signs of degradation could be seen. The free base peak appears to be partially overlapping with the region for acetonitrile, however, no significant amounts of acetonitrile appear to be present.

Example 7

Secondary Screening of Hydrobromide Salt (1 Equiv.)

Approximately ca. 5 mL of acetonitrile:water (10%) was added to ca. 1 g of Compound 1 free base to form a slurry. In a separate vial, ca. 3 mL of acetonitrile:water (10%) was added to 1 equivalent of hydrobromic acid (48%). The acid solution was then added dropwise over a 1 hour period to the free base slurry whilst stirring and maintaining a temperature between 0-5° C. After the complete addition of the acid, a further 3 mL of acetonitrile:water (10%) was added. The reaction was stirred for ca. 1 day before being isolated and dried under vacuum at ambient (ca. 22° C.). A yield of ca. 79% was obtained.

Figure 32:
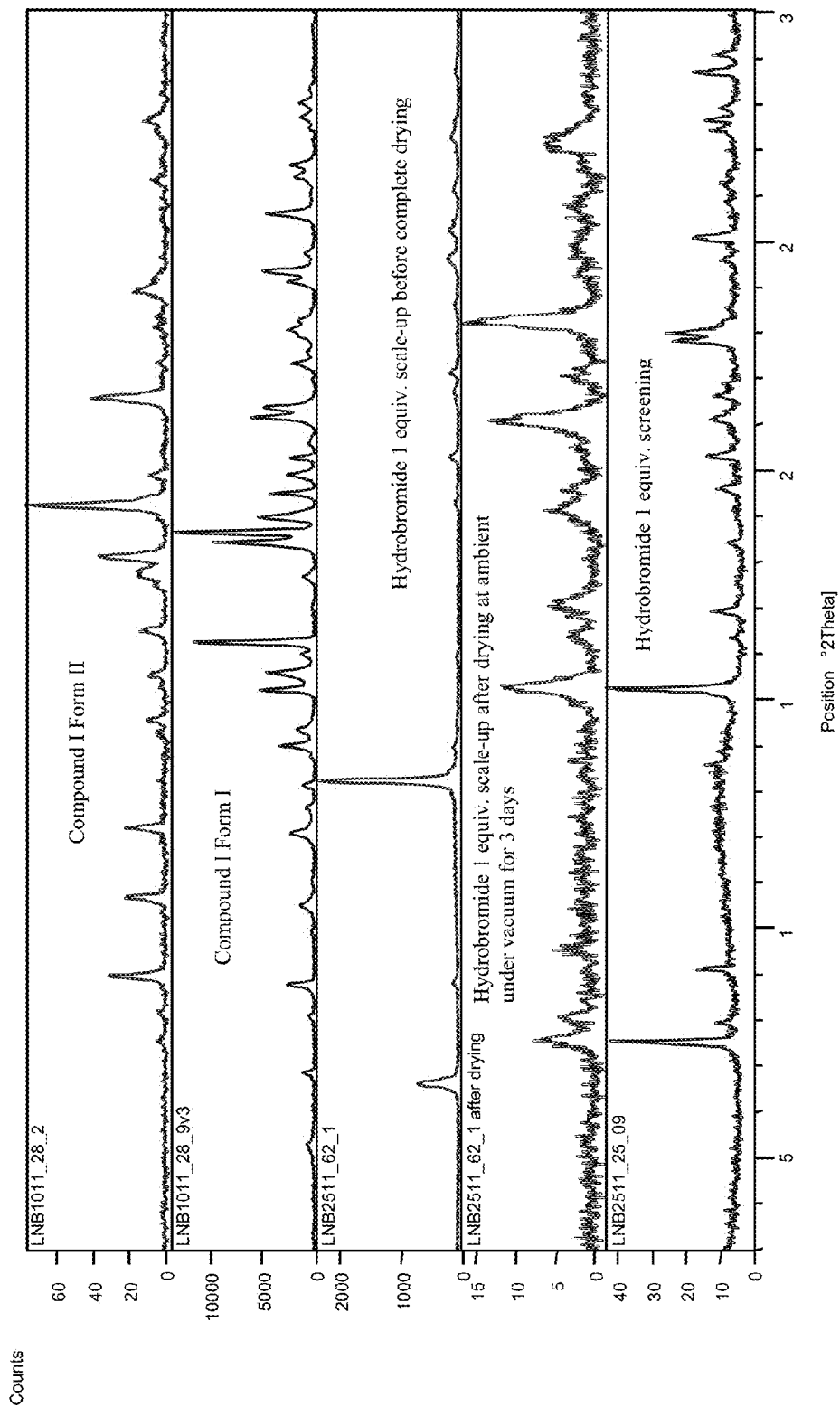
FIG. 32 depicts the XRPD pattern for a Form I hydrobromide salt of Compound 1.

XRPD analysis (FIG. 32) was carried out on the wet sample and after drying. The analysis indicated that the material undergoes a form change upon drying. The diffractogram of the scaled up material, both before and after drying, was different from the diffractogram of the primary screen hydrobromide sample.

Figure 33:
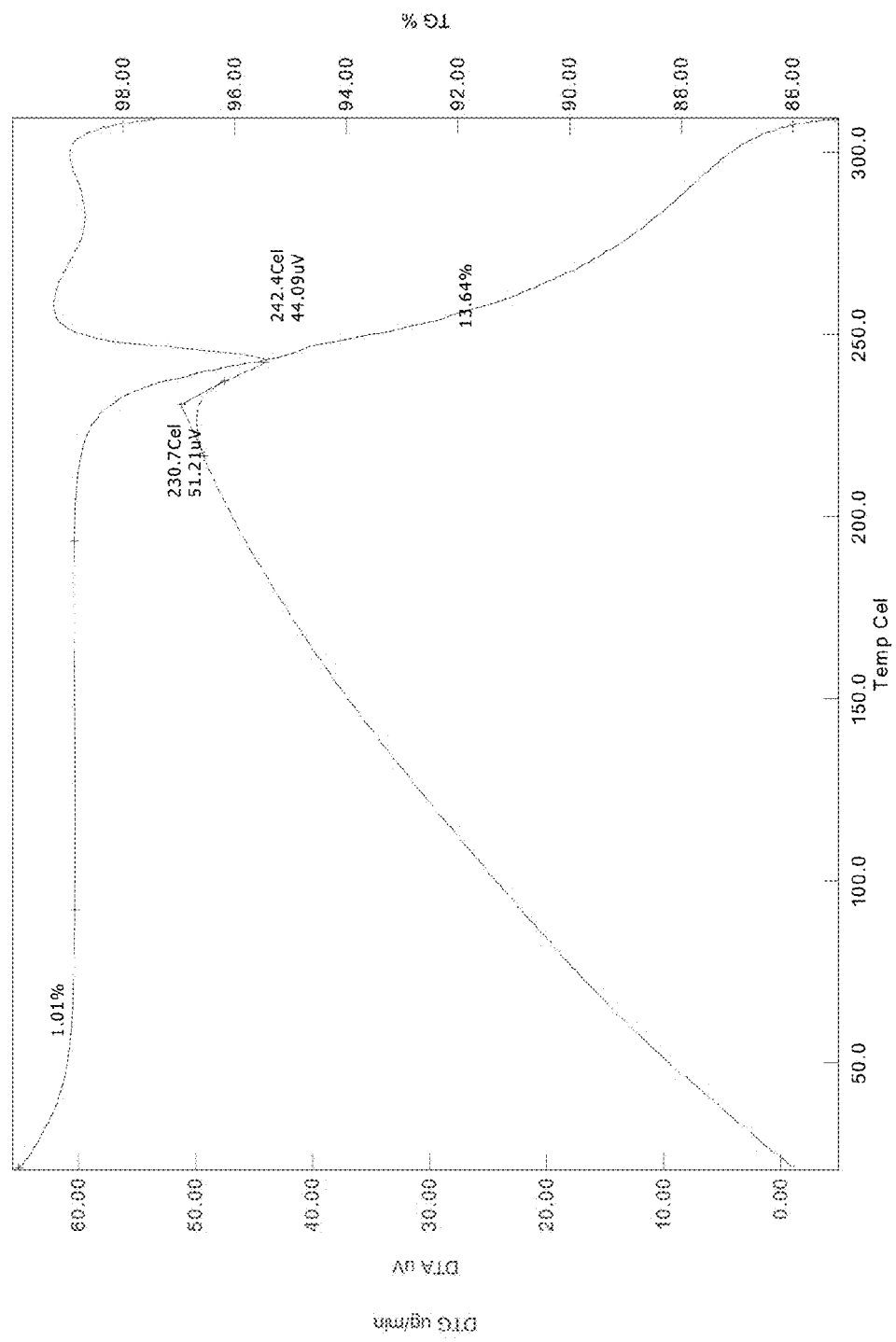
FIG. 33 depicts the TGA pattern for a Form I hydrobromide salt of Compound 1.

TGA/DTA showed a 1.01% weight loss from the outset, likely due to unbound moisture or solvent. No further weight losses were seen prior to degradation at onset ca. 230° C. (FIG. 33).

Figure 34:
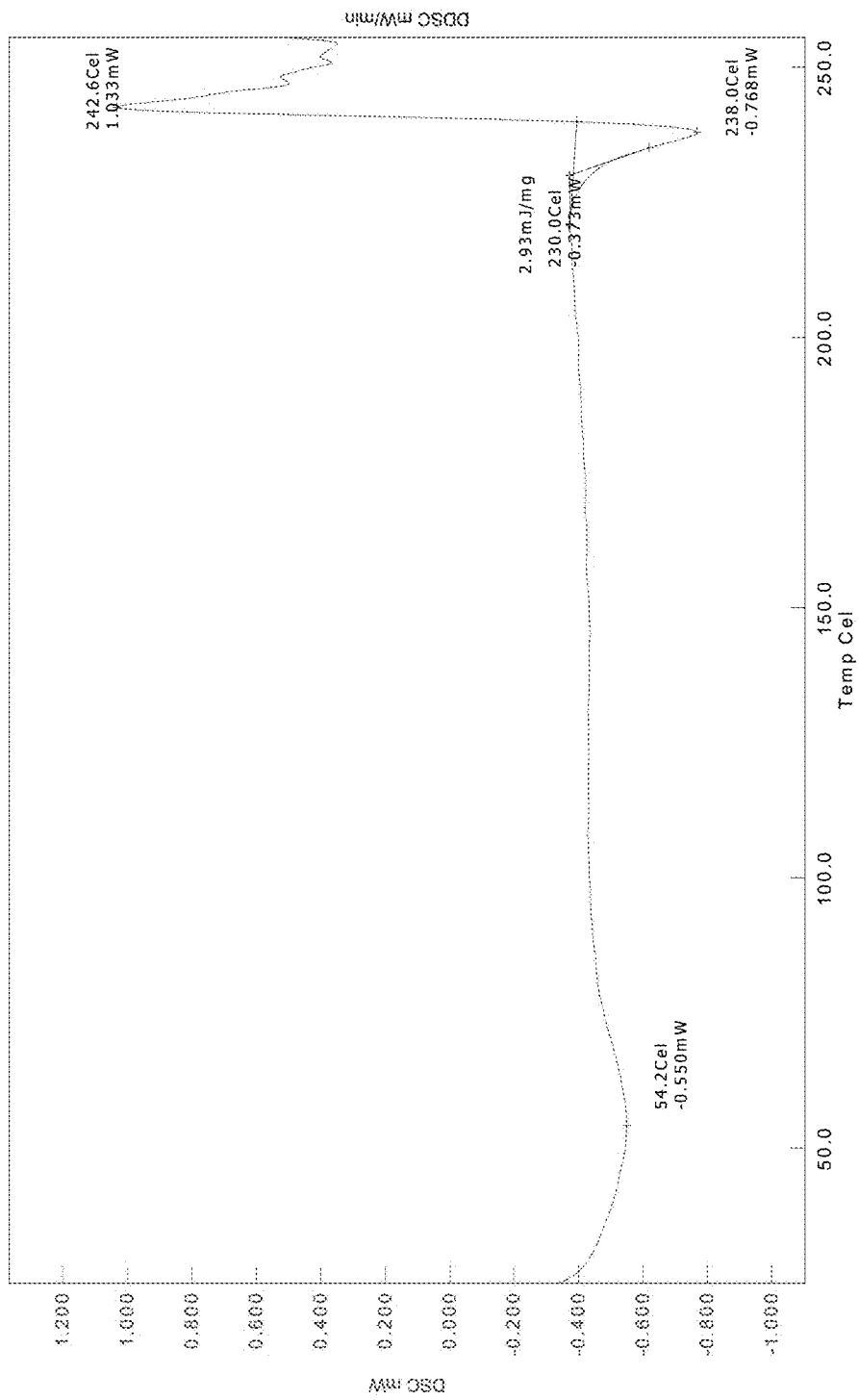
FIG. 34 depicts the DSC pattern for a Form I hydrobromide salt of Compound 1.

DSC analysis (FIG. 34) indicated a broad endotherm from the outset likely due to unbound solvent/water. A second endotherm was then seen at onset ca. 230° C. (peak 238° C.), followed by likely degradation.

Polarised Light Microscopy showed very small particles with no clearly defined morphology present (not shown).

Figure 35:
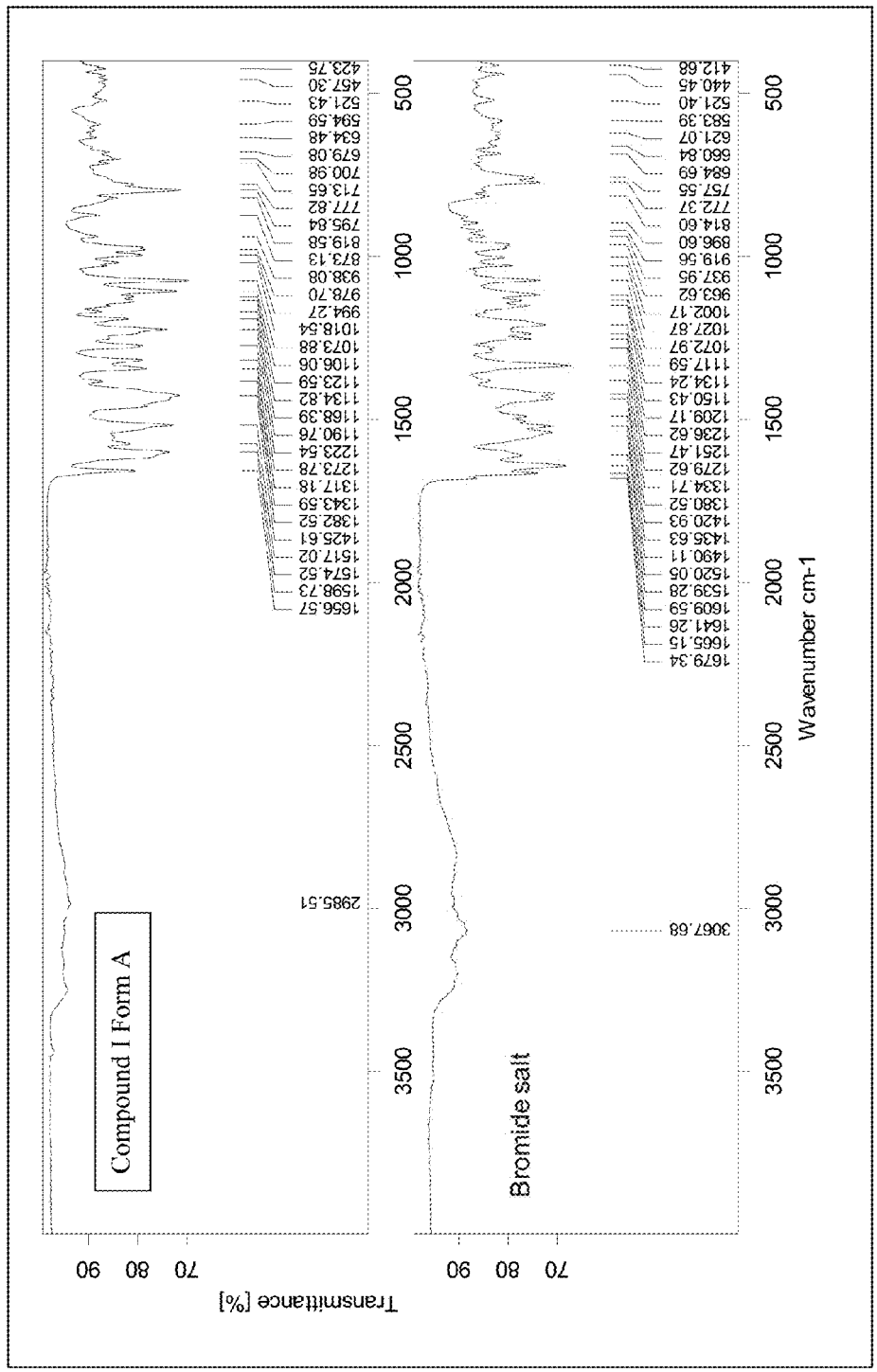
FIG. 35 depicts the IR spectrum of a Form I hydrobromide salt of Compound 1.

IR spectroscopy (FIG. 35) showed a number of differences and shifts in comparison with the freebase.

Figure 36:
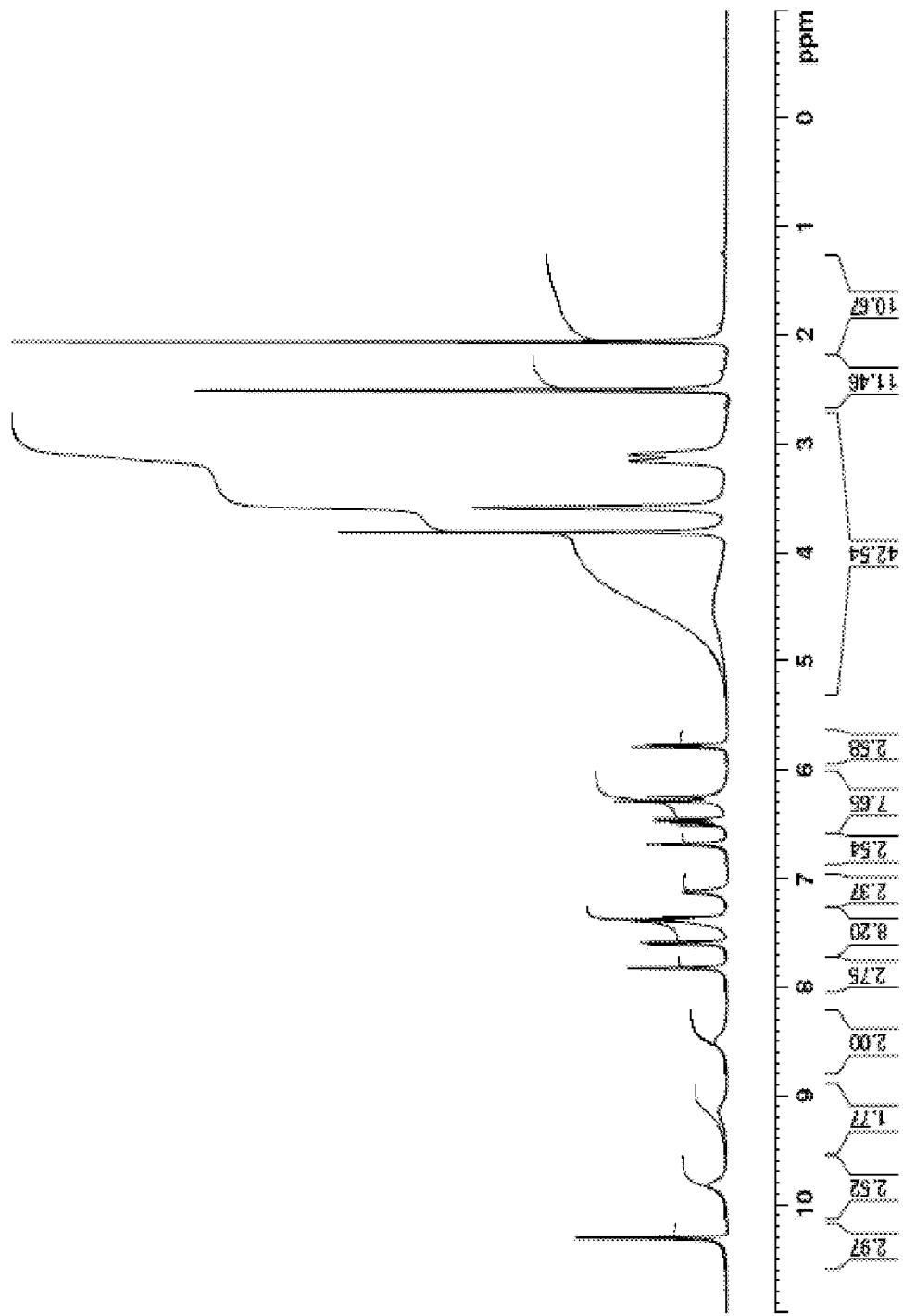
FIG. 36 depicts the $^1$H-NMR spectrum of a Form I hydrobromide salt of Compound 1.

$^1$H NMR spectroscopy (FIG. 36) indicated a number of peak shifts in comparison with the freebase.

Figure 37:
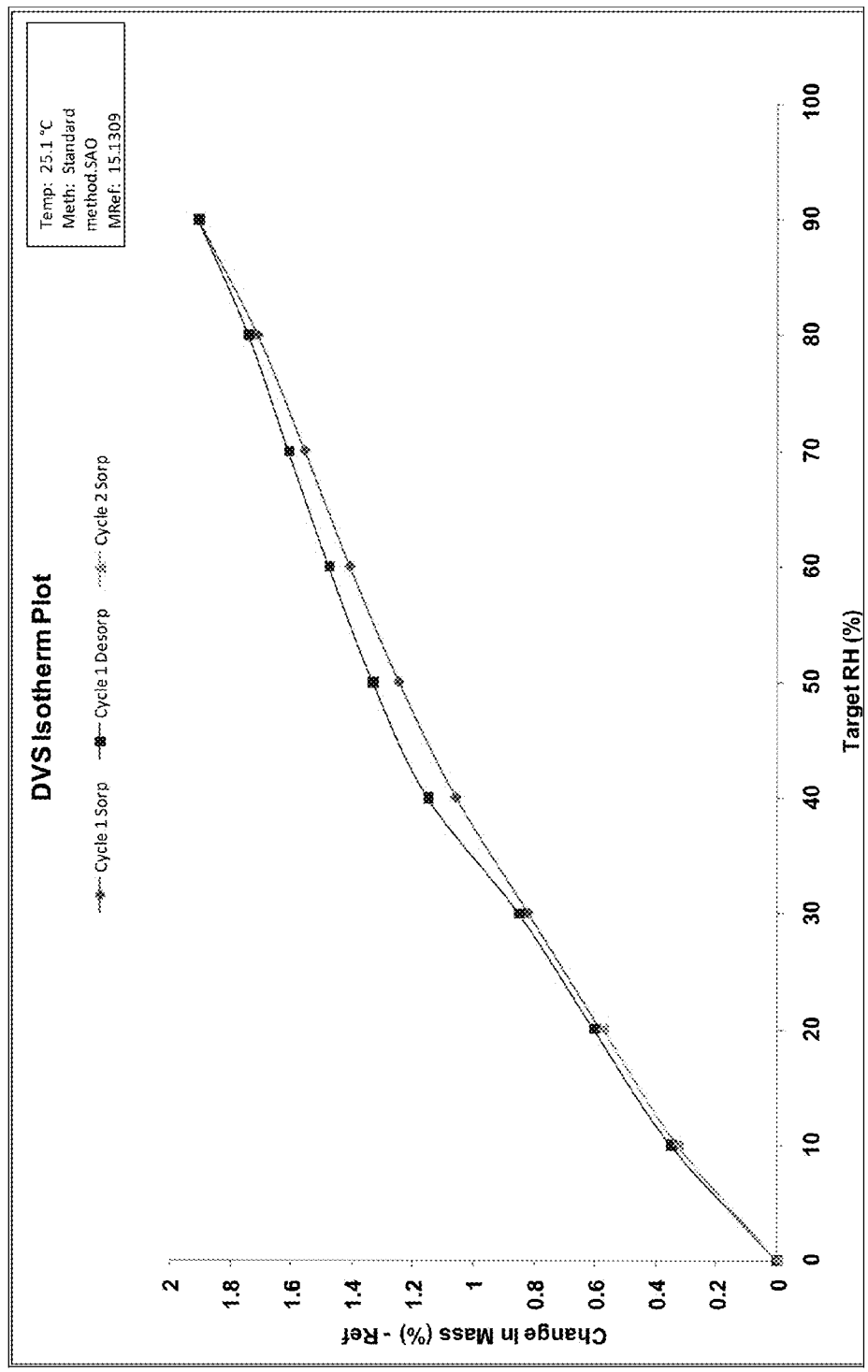
FIG. 37 depicts the DVS pattern of a Form I hydrobromide salt of Compound 1.

DVS analysis (FIG. 37) showed a water uptake of 0.97% between 20 and 70% RH. The water uptake between 0-90% RH is reversible showing very little hysteresis. Post DVS XRPD analysis indicated that the polymorphic form appears to remain consistent after exposure to varying RH % conditions (not shown).

Karl Fischer Coulometry indicated a ca. 1.65% water content.

The HPLC purity evaluation indicated a purity of ca. 97.5% for the hydrobromide salt with the main peak eluting at a retention time of ca. 13 minutes.

Figure 38:
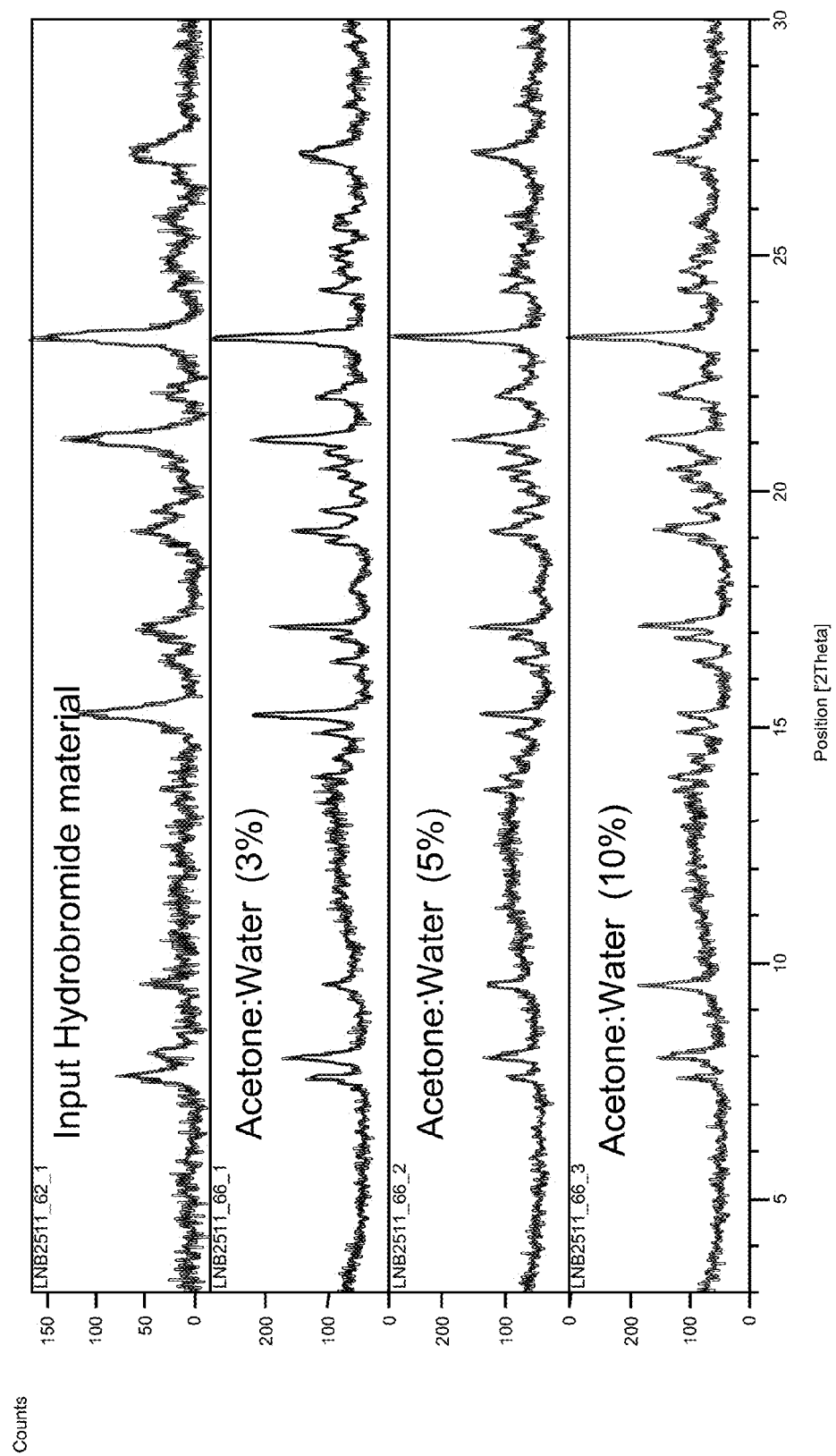
FIG. 38 depicts the results of a hydration study of a Form I hydrobromide salt of Compound 1, as analyzed by the XRPD patterns.

Slurries of the hydrobromide salt were created in acetone:water mixtures (3%, 5% and 10%) and stirred at ambient for ca. 3 days. The resulting solids were then analysed by XRPD to determine if any changes had occurred on slurrying. The hydration study results from XRPD analysis (FIG. 38) are summarised in Table 8.

TABLE 8

Hydration Study Results

| Solvent System | Result of slurrying |
|---|---|
| Acetone:water (3%) | Corresponds with the input hydrobromide form. Improvement in crystallinity. |
| Acetone:water (5%) | Corresponds with the input hydrobromide form. Improvement in crystallinity. |
| Acetone:water (10%) | Corresponds with the input hydrobromide form. Improvement in crystallinity. |

Figure 39:
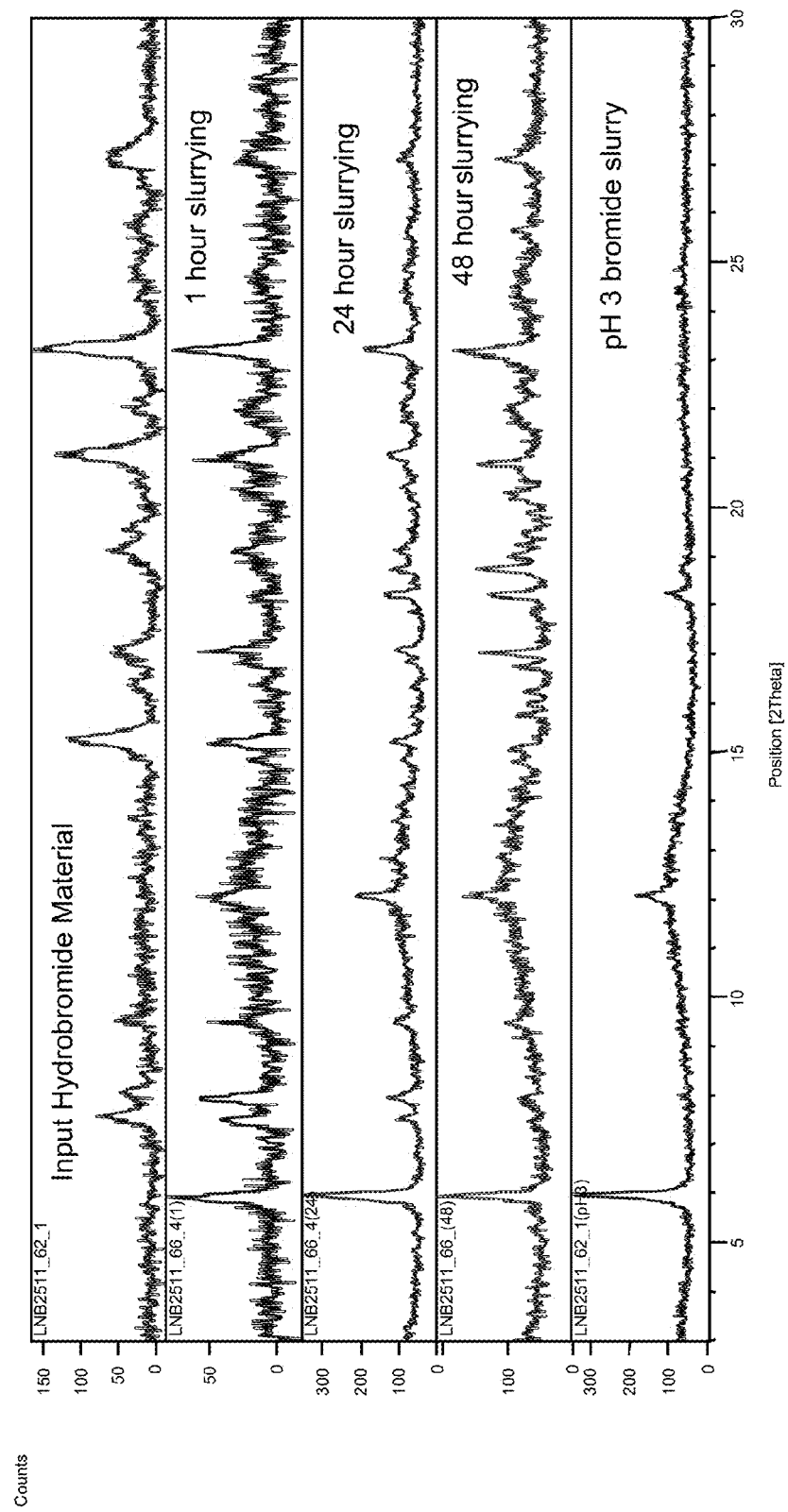
FIG. 39 depicts the results of a disproportionation study of a Form I hydrobromide salt of Compound 1, as analyzed by the XRPD patterns.

The hydrobromide salt was slurried in deionised water at ambient temperature (ca. 22° C.). A sample of solid was taken at 1, 24 & 48 hours and analysed by XRPD. The pH of the supernatant was also monitored. The Salt Disproportionation study results from XRPD analysis (FIG. 39) are summarised in Table 9.

TABLE 9

Disproportionation Study Results

| Time point | pH | XRPD |
|---|---|---|
| 1 hr | pH 1 | The material appears to be a mixture of the input hydrobromide material and a solid form that was also obtained from slurrying the material in the various pH solutions during thermodynamic solubility studies. |
| 24 hrs | pH 1 | The material appears to be a mixture of the input hydrobromide material and a solid form which was obtained from slurrying the material in the various pH solutions during thermodynamic solubility studies. |
| 48 hrs | pH 1 | The material appears to be a mixture of the input hydrobromide material and a solid form which was obtained from slurrying the material in the various pH solutions during thermodynamic solubility studies. |

Figure 40:
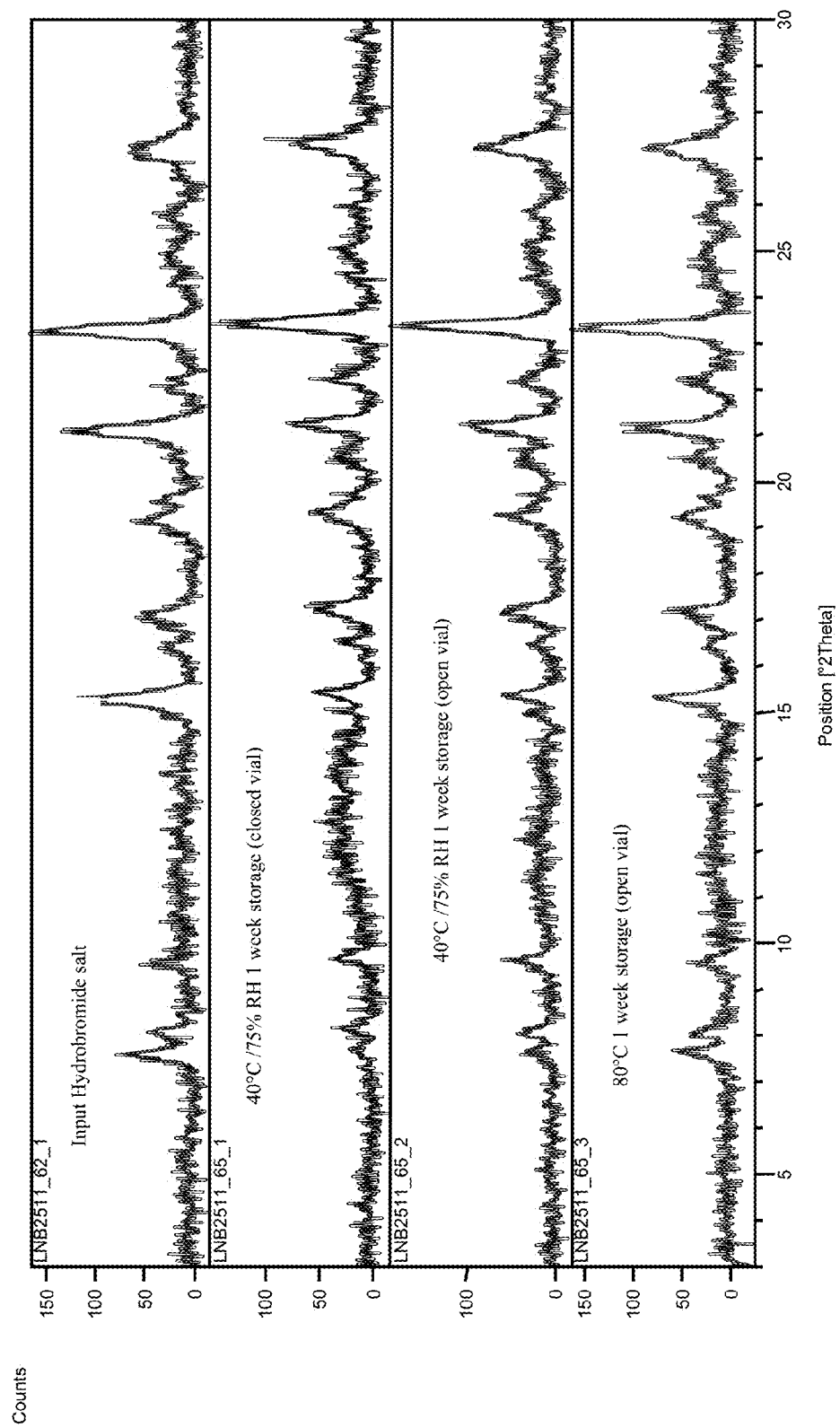
FIG. 40 depicts the results of a stability study of a Form I hydrobromide salt of Compound 1, as analyzed by the XRPD patterns.

The hydrobromide salt was exposed to environments of 40° C./75% RH (open and closed vial) and 80° C. (open vial) for 1 week to determine stability. Resulting solids were analysed by XRPD and HPLC to establish if any changes had occurred. The 1 Week stability study results from XRPD (FIG. 40) and HPLC analysis at 40° C./75% RH using an open and closed vial and 80° C. using an open vial are indicated Table 10.

TABLE 10

1 Week Stability Study Results

| Condition | HPLC | XRPD |
|---|---|---|
| 40° C./75% RH (closed vial) | 97.2% | No polymorphic form changes observed during storage. |
| 40° C./75% RH (open vial) | 97.2% | No polymorphic form changes observed during storage. |
| 80° C. open vial | 97.1% | No polymorphic form changes observed during storage. |

Slurries of the hydrobromide salt were created in media of various pH (pH 1; pH 3; pH 4.5 and pH 6.2) and shaken for ca. 24 hours. After 24 hours, the slurries were filtered and the solution analyzed by HPLC in order to determine the solubility at the various pH levels. The remaining solids were also analysed by XRPD analysis to establish if any changes in the solid form occurred. For the buffer solutions, KCl/HCl was used for pH 1 and citric acid/sodium citrate combinations for pH 3, 4.5 and 6.2. The thermodynamic solubility studies indicated the results shown in Table 11.

TABLE 11

Thermodynamic Solubility Results

Figure 41:
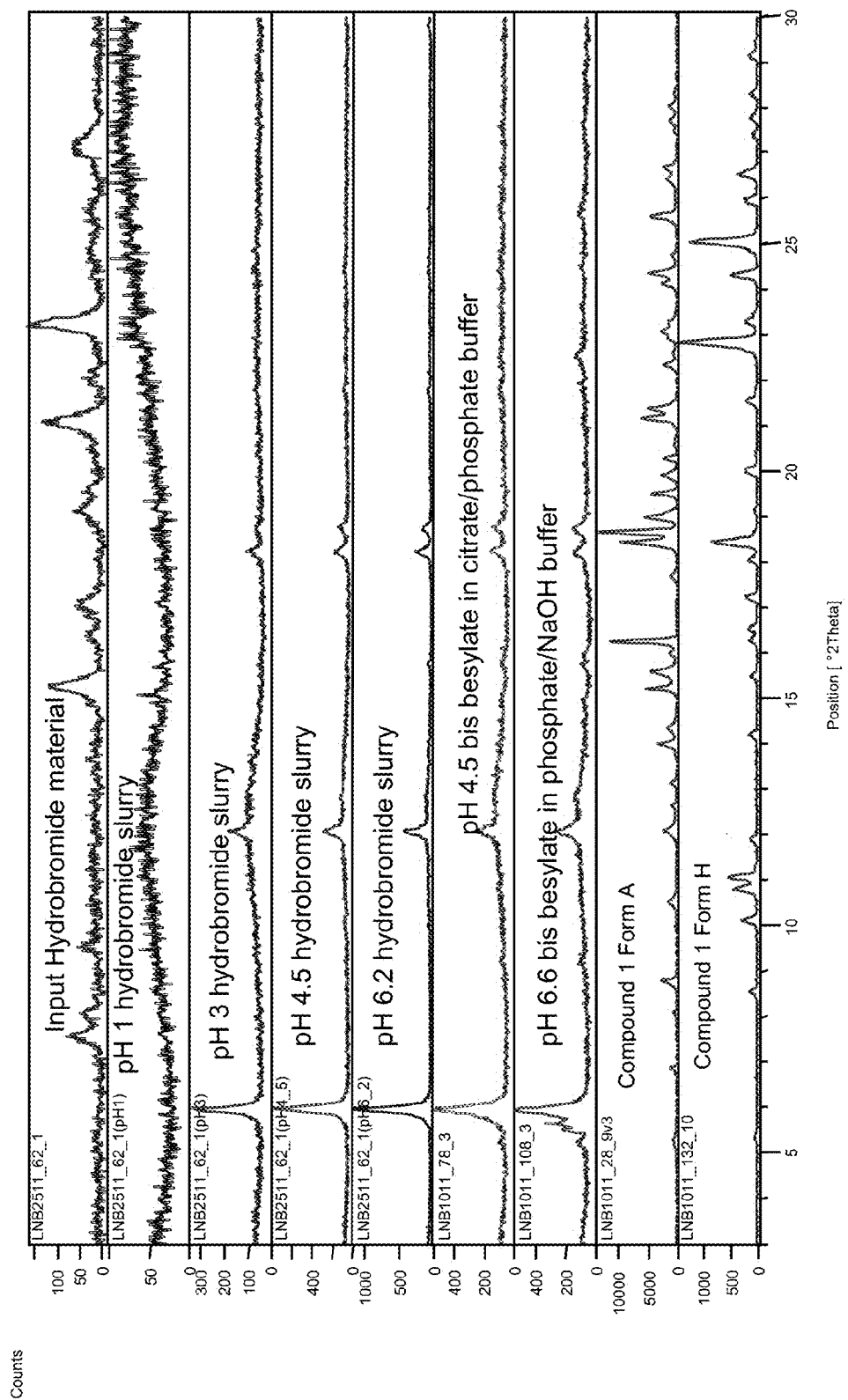
FIG. 41 depicts the results of a thermodynamic solubility study of a Form I hydrobromide salt of Compound 1, as analyzed by the XRPD patterns.

| pH | Buffers used | Solubility (mg/ml) | XRPD of excess solids (FIG. 41) |
|---|---|---|---|
| pH 1.0 | KCl/HCl | 3.78 | Appears predominantly amorphous by XRPD analysis. Solid material converted to a gum after being placed onto an XRPD sample holder as a slurry. |
| pH 3.0 | Citric acid/ Sodium Citrate | 0.21 | The diffractogram appears different from the input hydrobromide material, all known forms of the Compound 1 free base and the citric acid used in buffer preparation. The diffractogram also appears to correspond with the diffractograms obtained for the thermodynamic solubility experiments carried out on the bis-besylate salt. |
| pH 4.5 | Citric acid/ Sodium Citrate | 0.08 | The diffractogram appears different from the input hydrobromide material, all known forms of the Compound 1 free base and the citric acid used in buffer preparation. The diffractogram also appears to correspond with the diffractograms obtained for the thermodynamic solubility experiments carried out on the bis-besylate salt. |
| pH 6.2 | Citric acid/ Sodium Citrate | 0.03 | The diffractogram appears different from the input hydrobromide material, all known forms of the Compound 1 free base and the citric acid used in buffer preparation. The diffractogram also appears to correspond with the diffractograms obtained for the thermodynamic solubility experiments carried out on the bis-besylate salt. |

The diffractograms for the pH 3.0, 4.5 and 6.2 experiments appeared different from the input material as well as all identified forms of the hydrobromide salt and Compound 1 free base. The diffractograms also appeared different from the diffractograms of the solids used to make up the buffers. The solubility values obtained using these pH buffers are therefore likely not representative of the hydrobromide salt which was initially placed into the solutions.

Approximately 100-120 mg of material was compressed into discs by placing the material into a die (diameter: 13 mm) and compressing the die under 5 tons of pressure in a hydraulic press for ca. 2 minutes. A Sotax AT7 (conformed to EP2 and USP2) dissolution instrument was used containing paddles to stir the media at 100 rpm. Dissolution media of pH 3 (1% SDS) and pH 4.5 (1% SDS) were prepared using citrate/phosphate buffer. All materials were tested in 750 ml of the buffer medium. Discs were added at time=0 seconds and allowed to sink to the bottom of the dissolution vessel before stirring began. ca. 1 ml aliquots of media were extracted from the dissolution vessels at times 1, 5, 10, 15, 30, 60, 120, 240 minutes and 24 hours, and tested for API concentration by HPLC-UV. The dissolution tests were carried out in duplicate. For both dissolution media, the peak areas for the initial time points (up to 15 minutes), fell below the limit of quantification, however, when plotting Dissolution rate vs. time, the steepest part of the curve occurs during these early time points.

Figure 42:
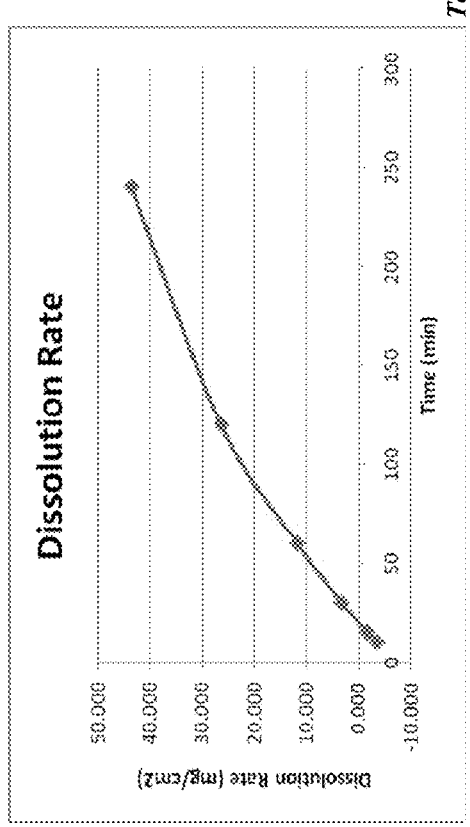
FIG. 42 depicts the dissolution at pH 4.5 of a compressed disc of a Form I hydrobromide salt of Compound 1.
Figure 42:
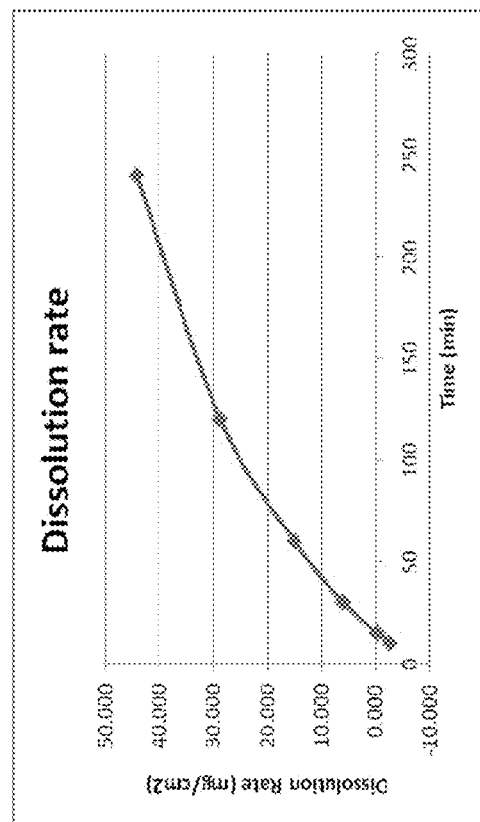

For pH 4.5, when plotting the curve of Dissolution rate vs. Time (FIG. 42), the intrinsic dissolution values obtained from the early time points on the curve (steepest part of the curve) were approximately 0.27 mg/cm$^2$/min for tablet 1 and 0.28 mg/cm$^2$/min for tablet 2.

Figure 43:
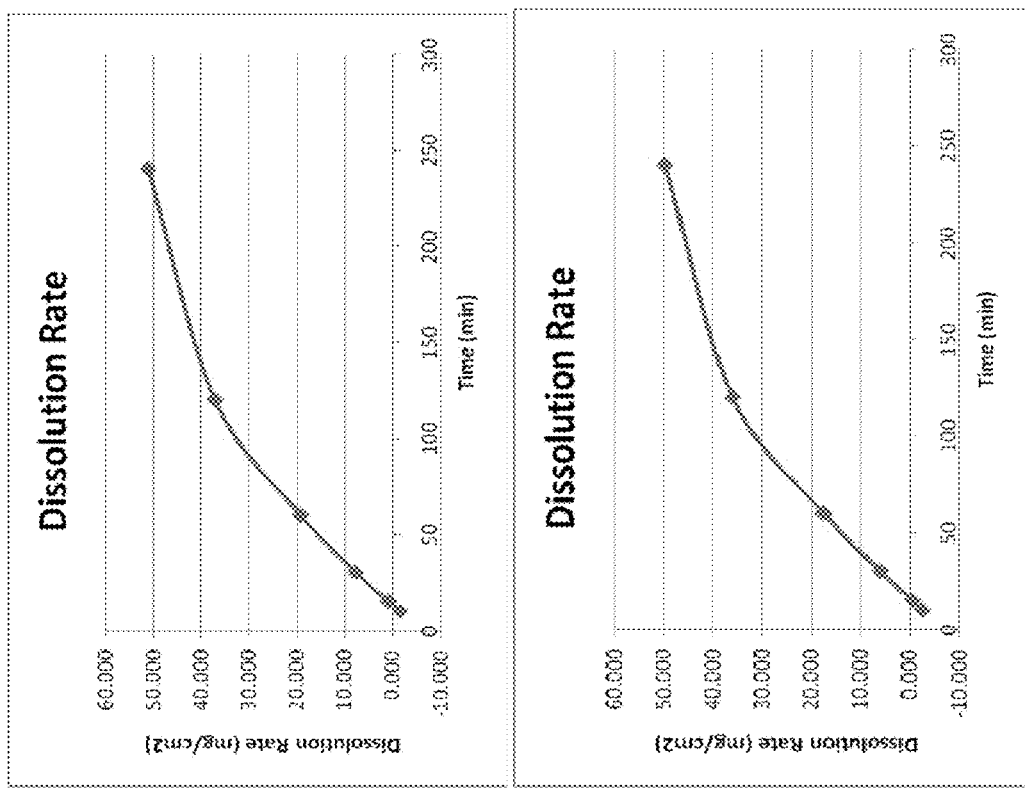
FIG. 43 depicts the dissolution at pH 3.0 of a compressed disc of a Form I hydrobromide salt of Compound 1.

For pH 3.0, when plotting the curve of Dissolution rate vs. Time (FIG. 43), the intrinsic dissolution values obtained from the early time points on the curve (steepest part of the curve) were approximately 0.35 mg/cm$^2$/min for both tablets 1 and 2.

Example 8

Secondary Screening of Hydrobromide Salt (2 Equiv.)

Approximately 1 ml of methanol was added to ca. 200 mg of Compound 1 to form a slurry. In a separate vial, ca. 1 mL of methanol was added to 2 equivalents of hydrobromic acid (48%). The acid solution was then added dropwise over a 1 hour period to the free base slurry whilst stirring and maintaining a temperature between 0-5° C. After the complete addition of the acid, a further 1 mL of methanol was added. The reaction was stirred for ca. 3 hours before being isolated and dried. A yield of approximately 68% was obtained.

Figure 44:
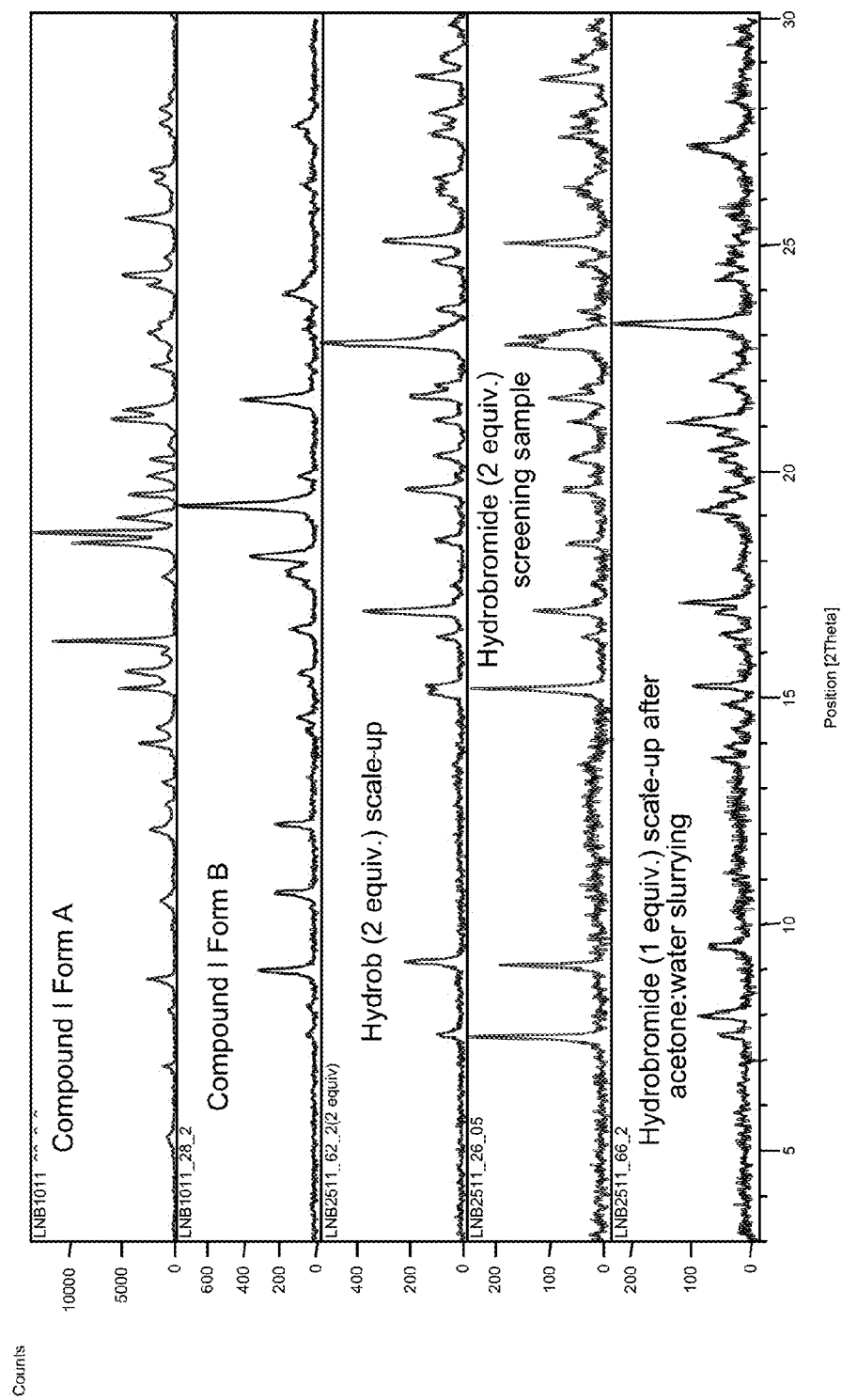
FIG. 44 depicts the XRPD pattern for a Form I hydrobromide salt of Compound 1.

XRPD analysis (FIG. 44) was carried out after filtration and the diffractogram obtained was consistent with the Form I material obtained using both 1 and 2 equivalents of HBr in the primary salt screen.

Figure 45:
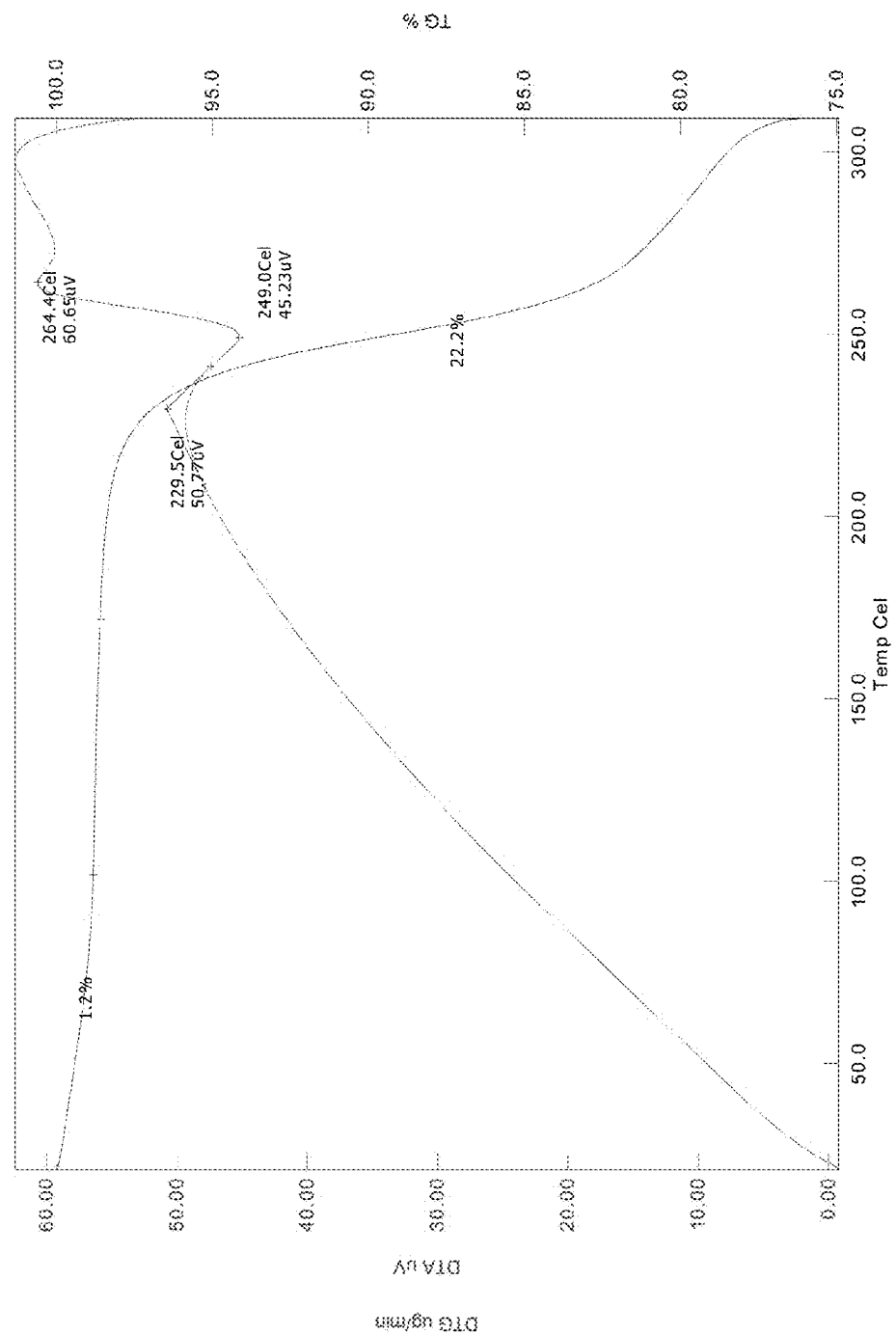
FIG. 45 depicts the TGA pattern for a Form I hydrobromide salt of Compound 1.

TGA/DTA (FIG. 45) showed a 1.2% weight loss from the outset to ca. 100° C., likely due to unbound moisture or solvent. No further weight losses were seen prior to degradation at onset ca. 230° C. The TGA/DTA is similar to the trace obtained for the 1 equivalent scaled-up form of Example 6.

Figure 46:
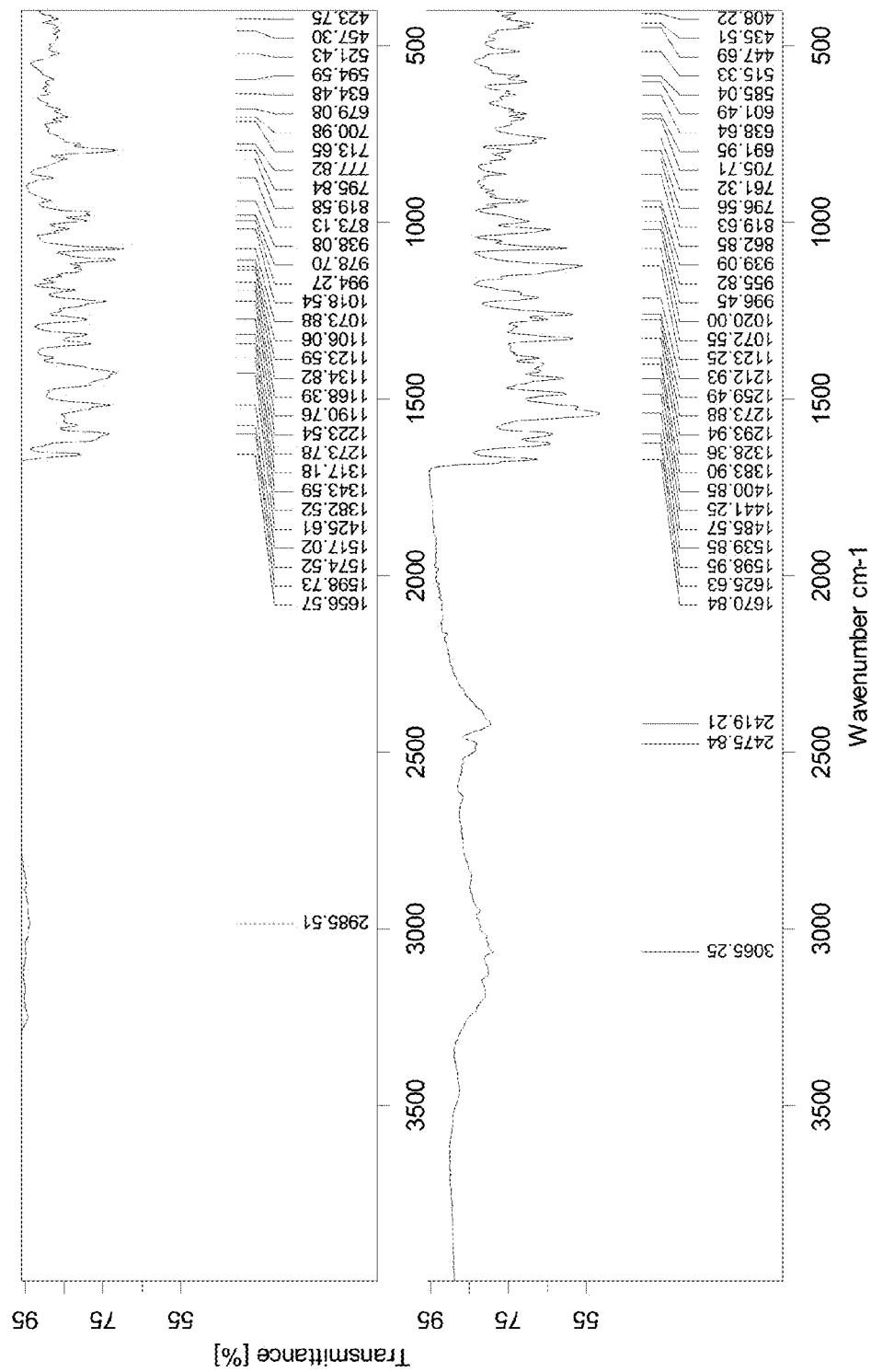
FIG. 46 depicts the IR spectrum of a Form I hydrobromide salt of Compound 1.

IR spectroscopy (FIG. 46) showed a number of differences and shifts in comparison with the free base and the hydrobromide (1 equiv.) scaled-up salt.

Example 9

Secondary Screening of Hydrobromide Salt (Unknown Form)

The thermodynamic solubility experiments carried out on the hydrobromide salt resulted in the formation of an unknown solid form. In attempts to characterize this form, as well as establish the rate of conversion to this form while slurrying the material, the following experiments were carried out. Initially, approximately 100 mg of the hydrobromide (1 equiv.) material was slurried in a pH 6.2 aqueous solution at ambient and XRPD analysis was carried out at time points 5 min., 1 hr, 2 hrs, 4 hrs and 8 hrs. Further analysis was then also carried out on the converted material.

Figure 47:
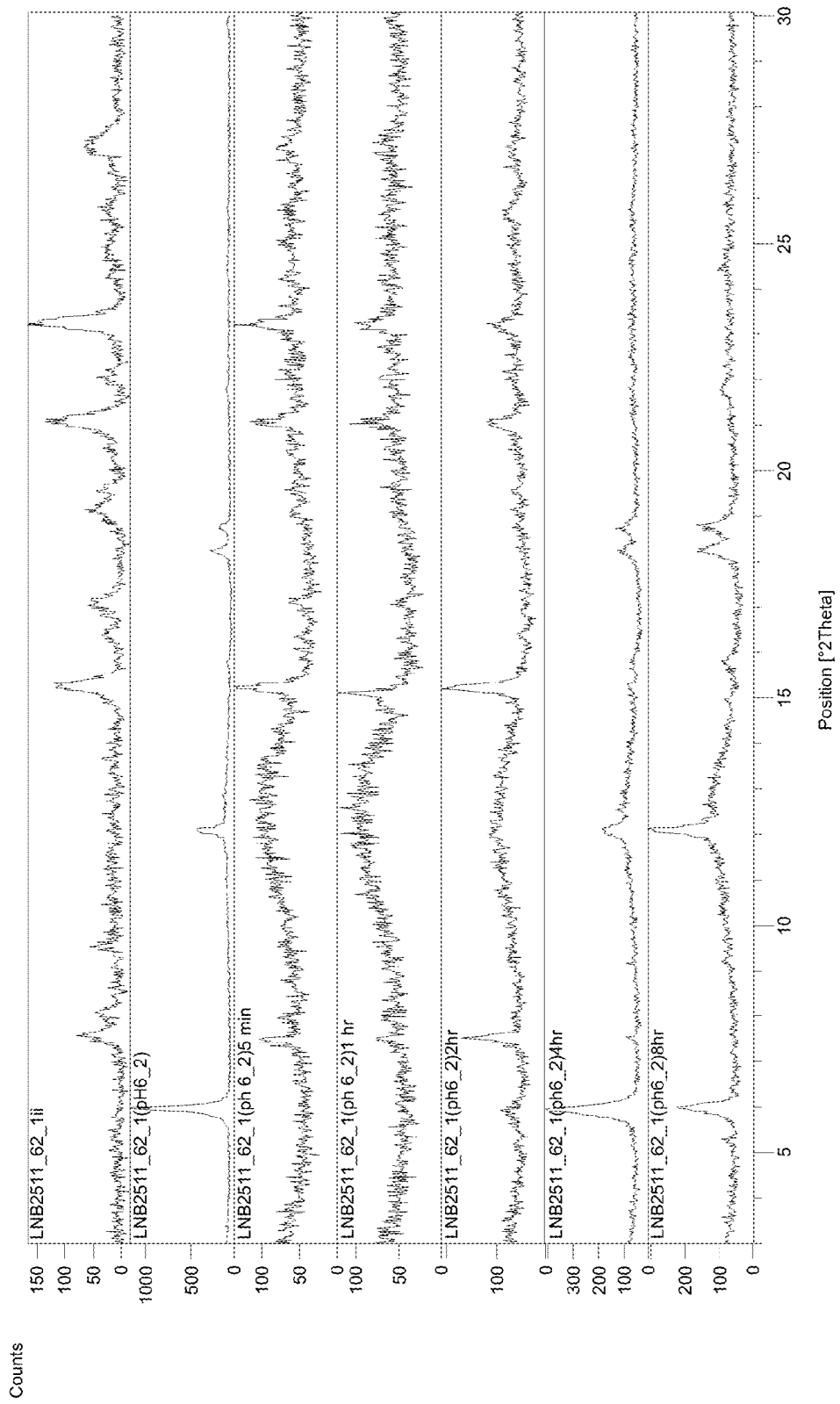
FIG. 47 depicts the XRPD pattern for a Form I hydrobromide salt of Compound 1.

The XRPD analysis (FIG. 47) carried out on the hydrobromide (1 equiv.) salt sample after slurrying the solid in an aqueous pH 6.2 medium for 5 min, 1 hr, 2 hrs, 4 hrs and 8 hrs indicated that conversion to the unknown solid form occurs between 2-4 hours.

PLM analysis carried out on a slurry of the material indicated a very small particle size. Some birefringence was observed (not shown). Upon drying the material became glass-like.

Figure 48:
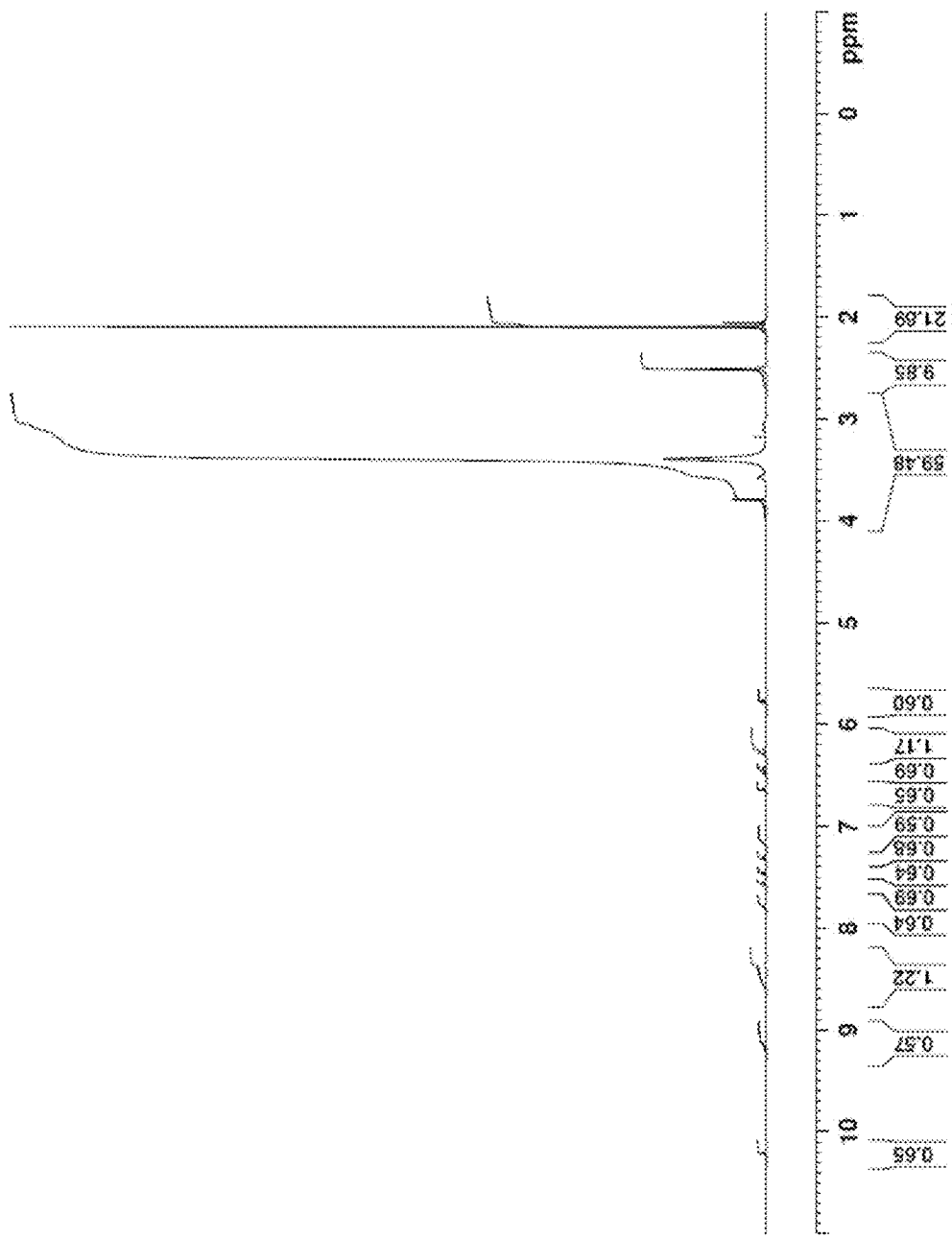
FIG. 48 depicts the $^1$H-NMR spectrum for a Form I hydrobromide salt of Compound 1.

$^1$H NMR analysis was carried out on this material which showed a spectrum which was different in terms of peak positions from both the free base spectrum and the hydrobromide spectrum (FIG. 48).

Figure 49:
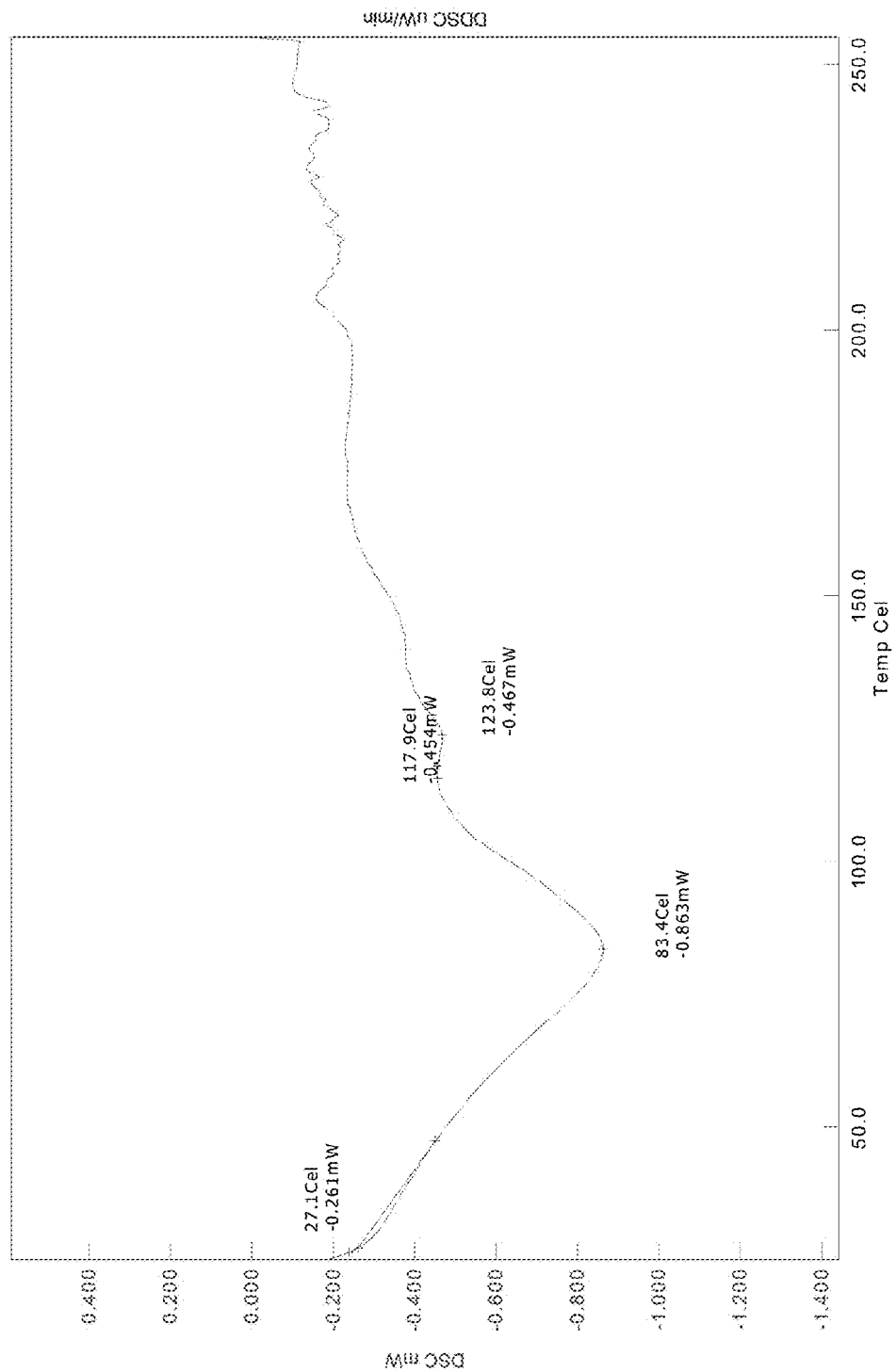
FIG. 49 depicts the DSC pattern of a Form I hydrobromide salt of Compound 1.

DSC analysis was also attempted on the glass-like material, however, a large broad endotherm is seen from the outset to ca. 110° C., followed by a pattern characteristic of amorphous material (FIG. 49).

Figure 50:
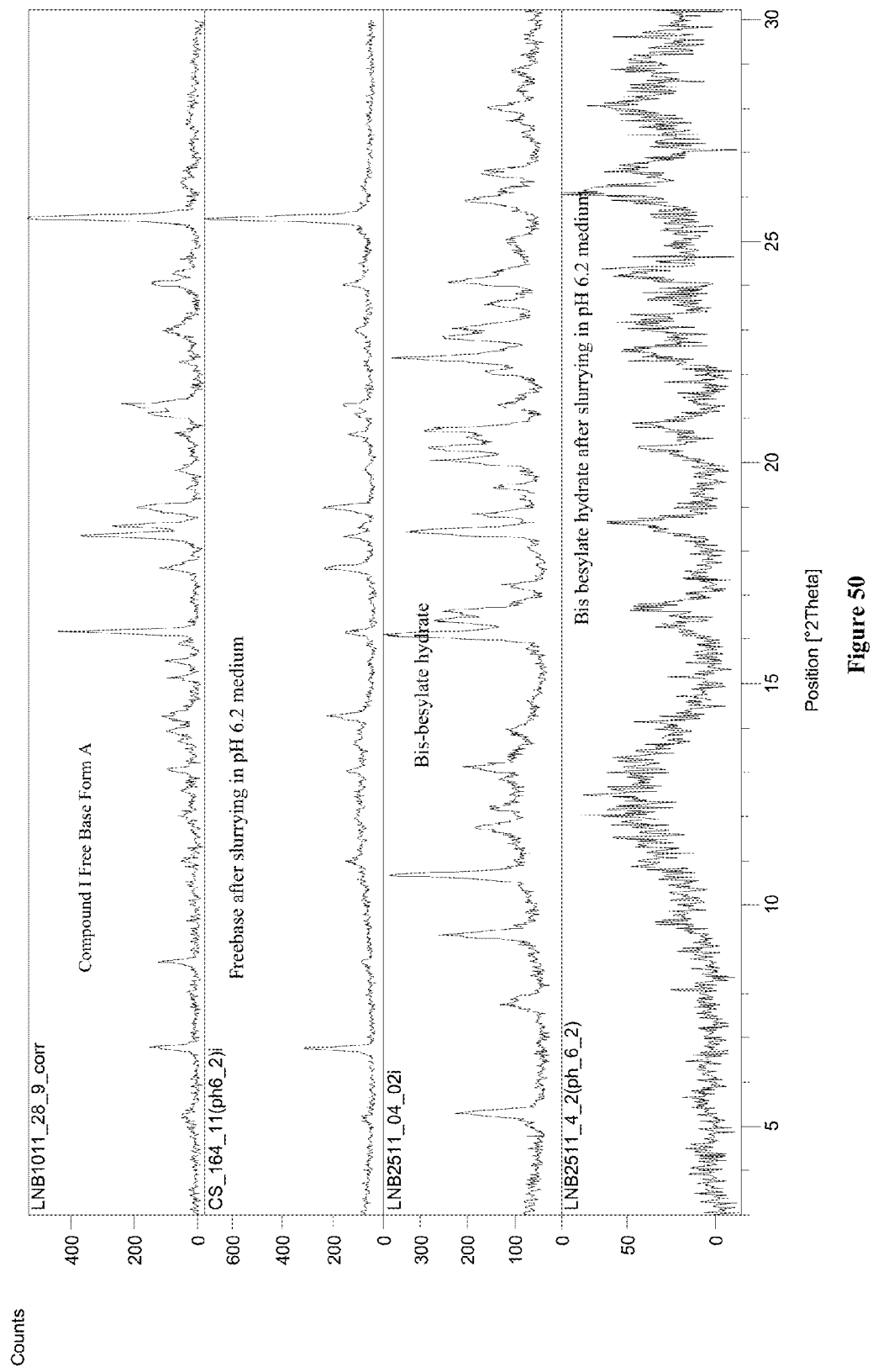
FIG. 50 depicts the results of a slurry experiment involving a form of the free base of Compound 1 and a bis-besylate hydrate.

The slurry experiment of Compound 1 free base and the bis-besylate hydrate (carried out in attempts to produce more of this form for analysis) were unsuccessful in producing this unknown solid form. For the free base slurry, the material remained as the free base Form I and for the bis-besylate hydrate slurry, the material lost some crystallinity, but remained as the bis-besylate hydrate (FIG. 50).

Figure 51:
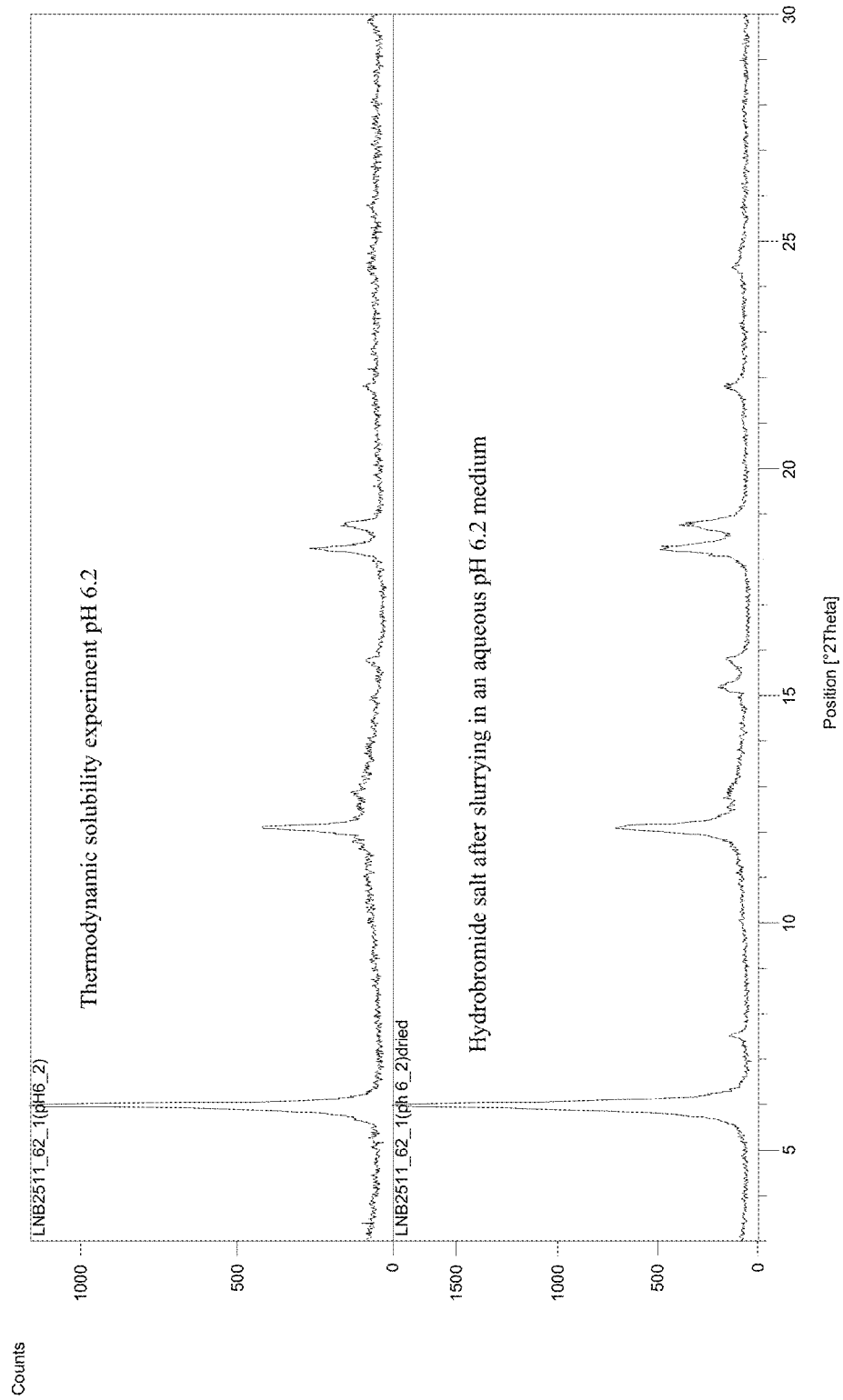
FIG. 51 depicts the results of a slurry experiment involving a Form I hydrobromide salt of Compound 1 at pH 6.2.

The further scale-up of the hydrobromide (1 equiv.) salt and subsequent slurrying in a pH 6.2 aqueous medium resulted in this unknown solid form being obtained (FIG. 51), however, all attempts at filtering the material were unsuccessful with the solid going through a sintered filter and multiple sheets of filter paper, due to the small particle size. Again, attempts at evaporating off the solvent resulted in a glass-like material being obtained. This appears to indicate that the unknown form is unstable when isolated.

Example 10

Tertiary Screening of Hydrobromide Salt (1 Equiv.)

Approximately 85 mL of acetonitrile:water (90:10) was added to ca. 20 g of Compound 1 in a round bottomed flask to form a slurry. In a separate flask, 1 equivalent of hydrogen bromide (ca. 4.073 mL) was added to ca. 70 mL of acetonitrile:water (90:10). The acid solution was then added in small aliquots to the free base slurry while stirring at ca. 4° C. The resulting slurry was then allowed to stir at ambient temperature for ca. 2 hours. It was then placed at ca. 5° C. for 1 day before stirring for a further 4 hours at ambient temperature. The reaction was then filtered and the solid dried under vacuum at ambient temperature (ca. 22° C.). The drying was continued for ca. 2 days. Due to the partially crystalline nature of the material after drying, the material was then slurried in ca. 50 mL of an acetone:water (90:10) mixture. The reaction was temperature cycled between ca. 4-22° C. in 1 hour cycles while stirring for ca. 2 days. The reaction was then filtered and dried at ambient for ca. 4 days before being analyzed. The yield after the further slurrying was 16.4 g (63%).

Figure 52:
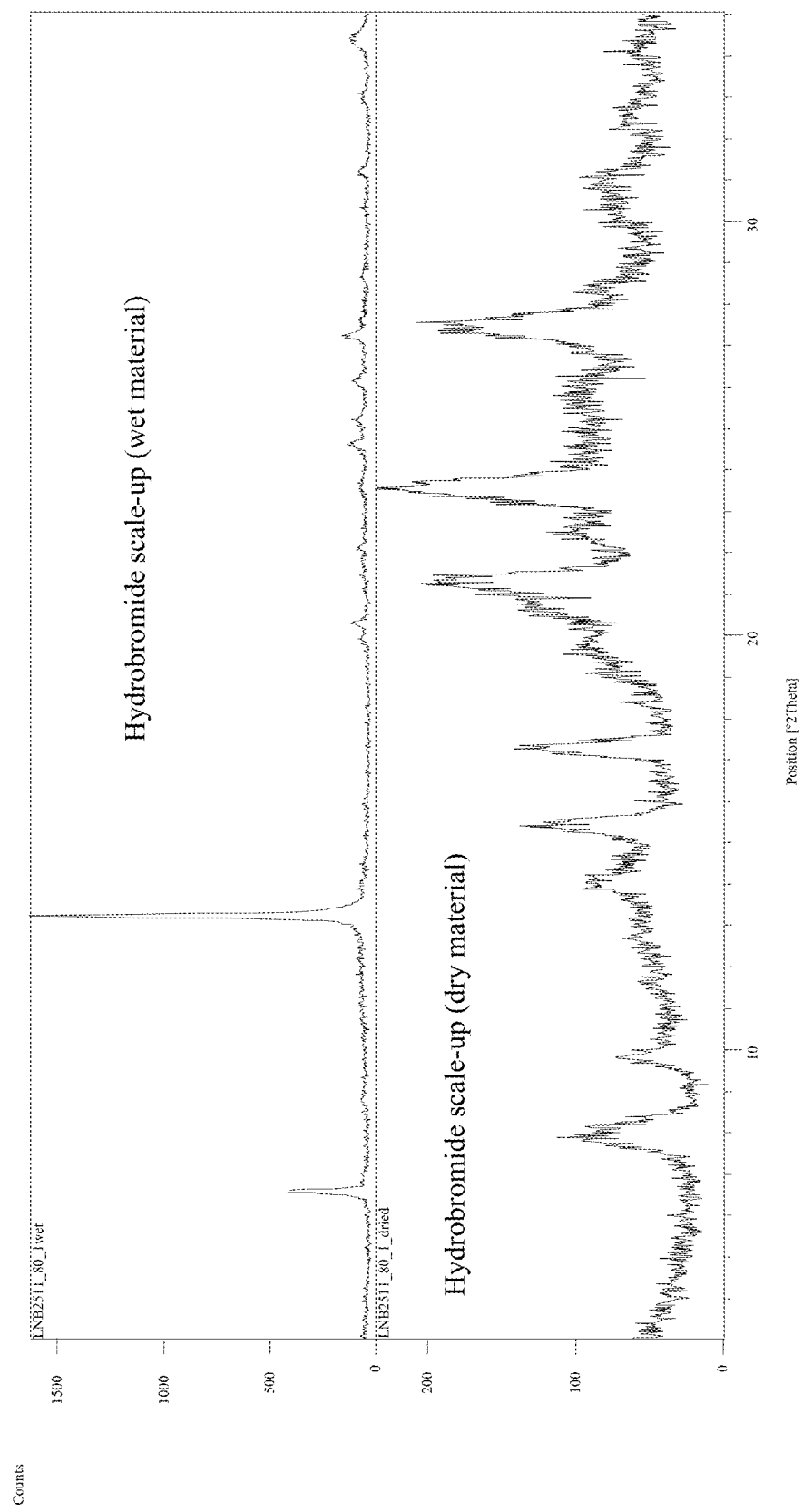
FIG. 52 depicts the XRPD pattern for a Form I hydrobromide salt of Compound 1.
Figure 53:
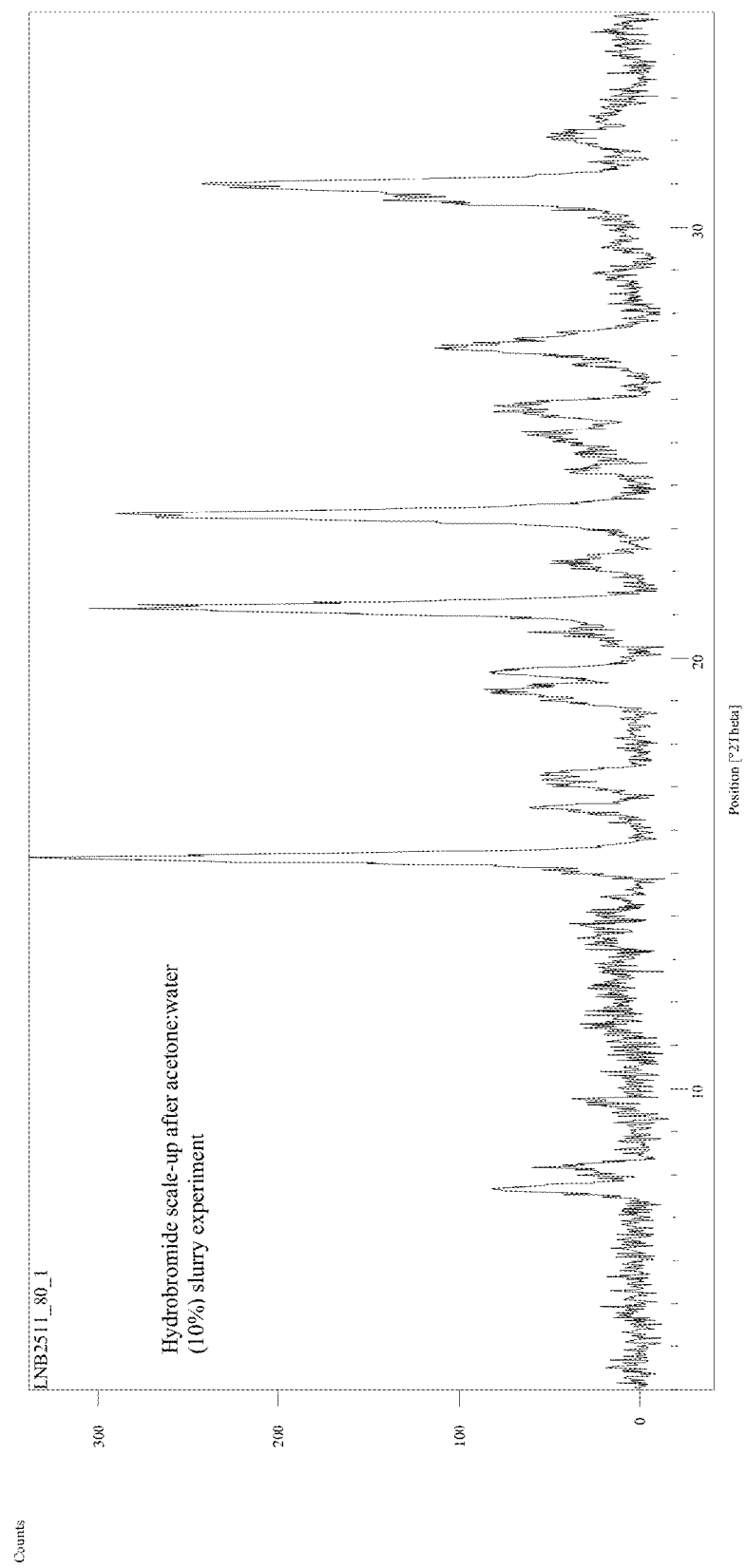
FIG. 53 depicts the XRPD pattern for a Form I hydrobromide salt of Compound 1.

XRPD analysis (FIG. 52) carried out on the initial scale-up material while wet, showed the sample to be highly crystalline. After drying, the solid converted to a different polymorphic form and also lost some crystallinity. XRPD analysis (FIG. 53) on the material after further slurrying in acetone:water (10%) and subsequent drying indicated a crystalline material. The diffractogram corresponded with the smaller scale hydrobromide sample obtained after drying during Example 1.

Figure 54:
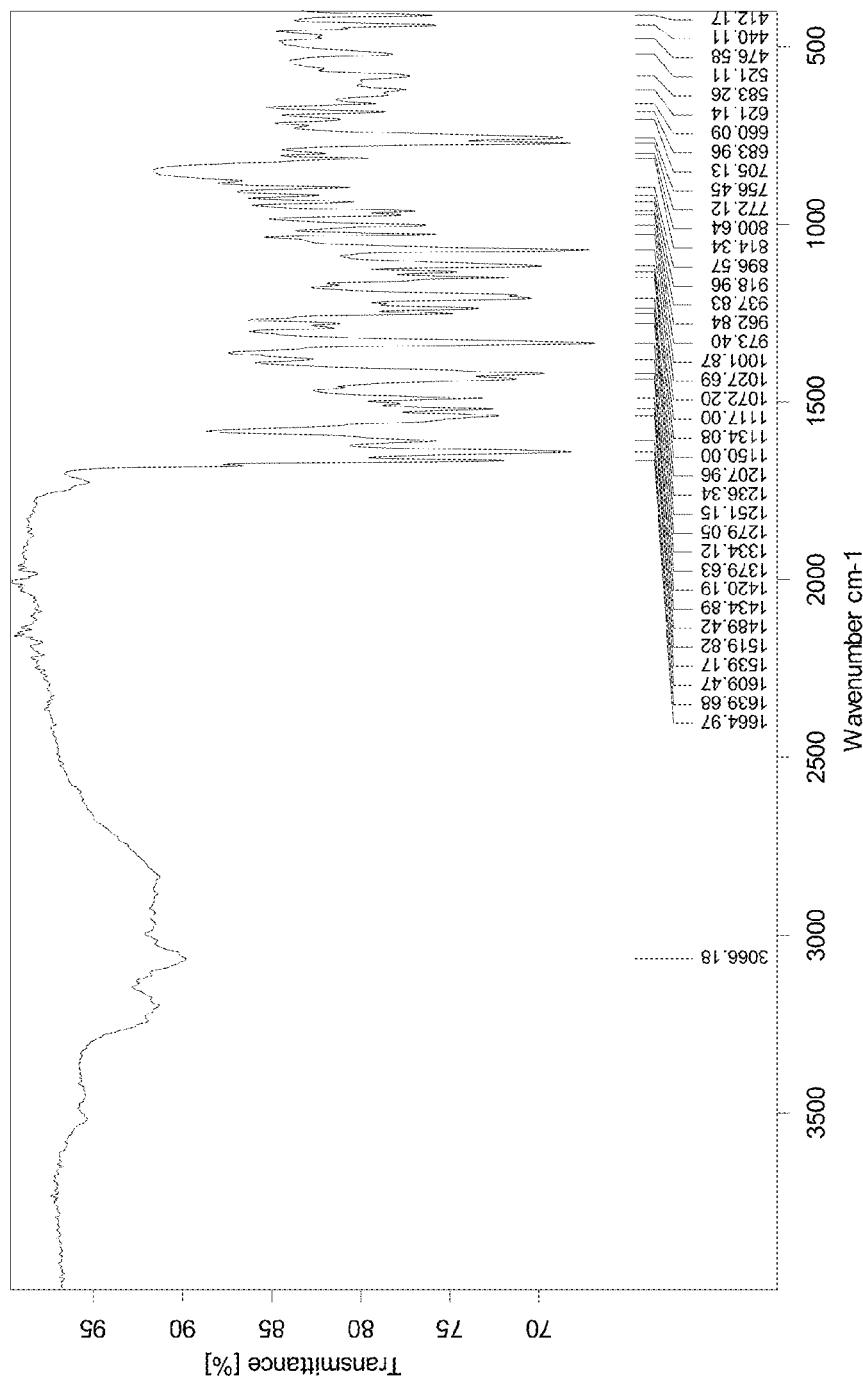
FIG. 54 depicts the IR spectrum of a Form I hydrobromide salt of Compound 1.

IR Spectroscopy (FIG. 54) showed differences when compared with the free base spectrum. The spectrum also appeared consistent with the spectrum obtained for the hydrobromide salt in Example 1.

PLM (not shown) showed small particles with no defined morphology and little birefringence.

Figure 55:
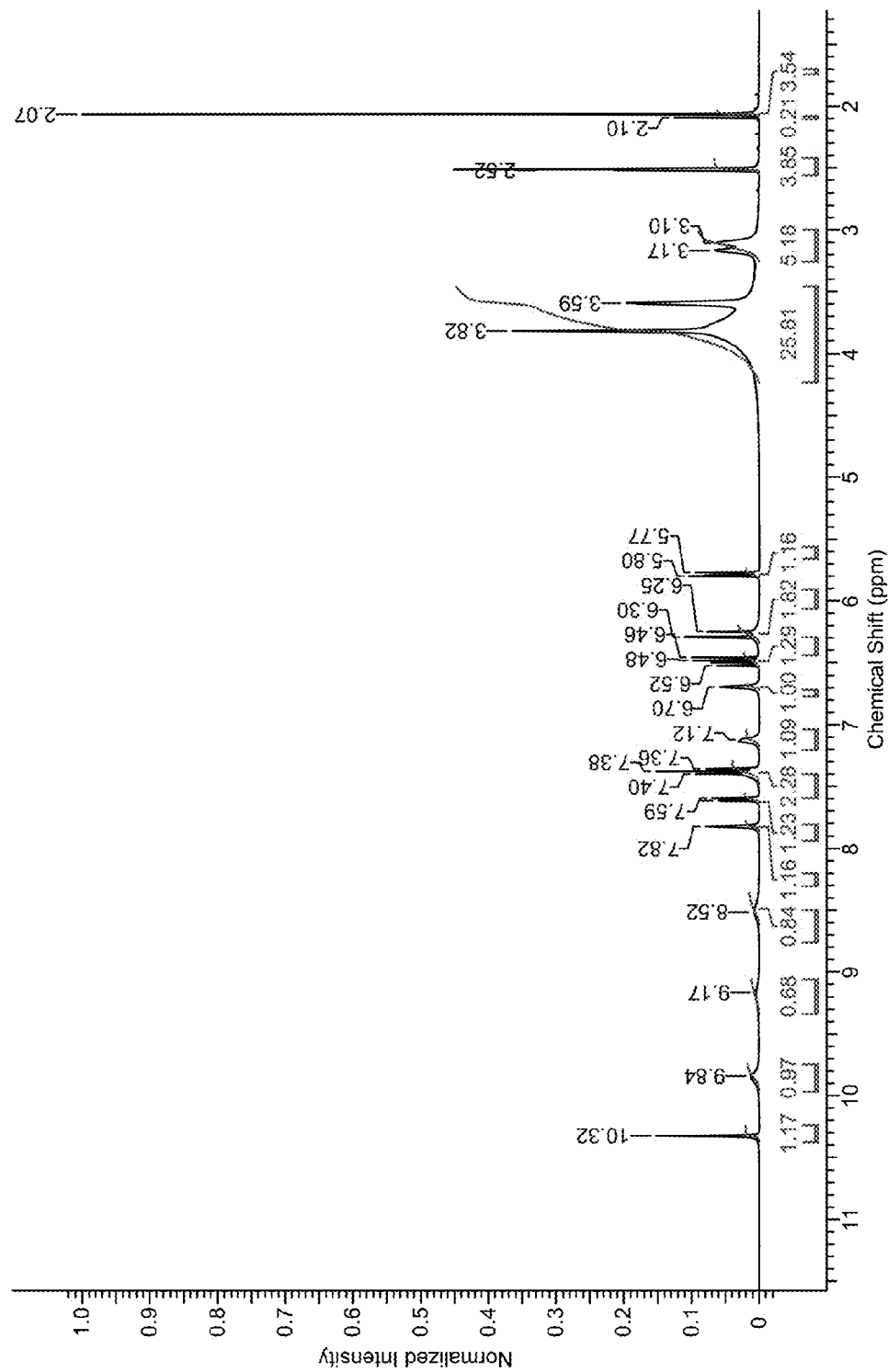
FIG. 55 depicts the $^1$H-NMR spectrum of a Form I hydrobromide salt of Compound 1.

$^1$H NMR (FIG. 55) indicated a number of peak shifts in comparison with the free base. A small non-stoichiometric amount of acetone was present in the spectrum.

Figure 56:
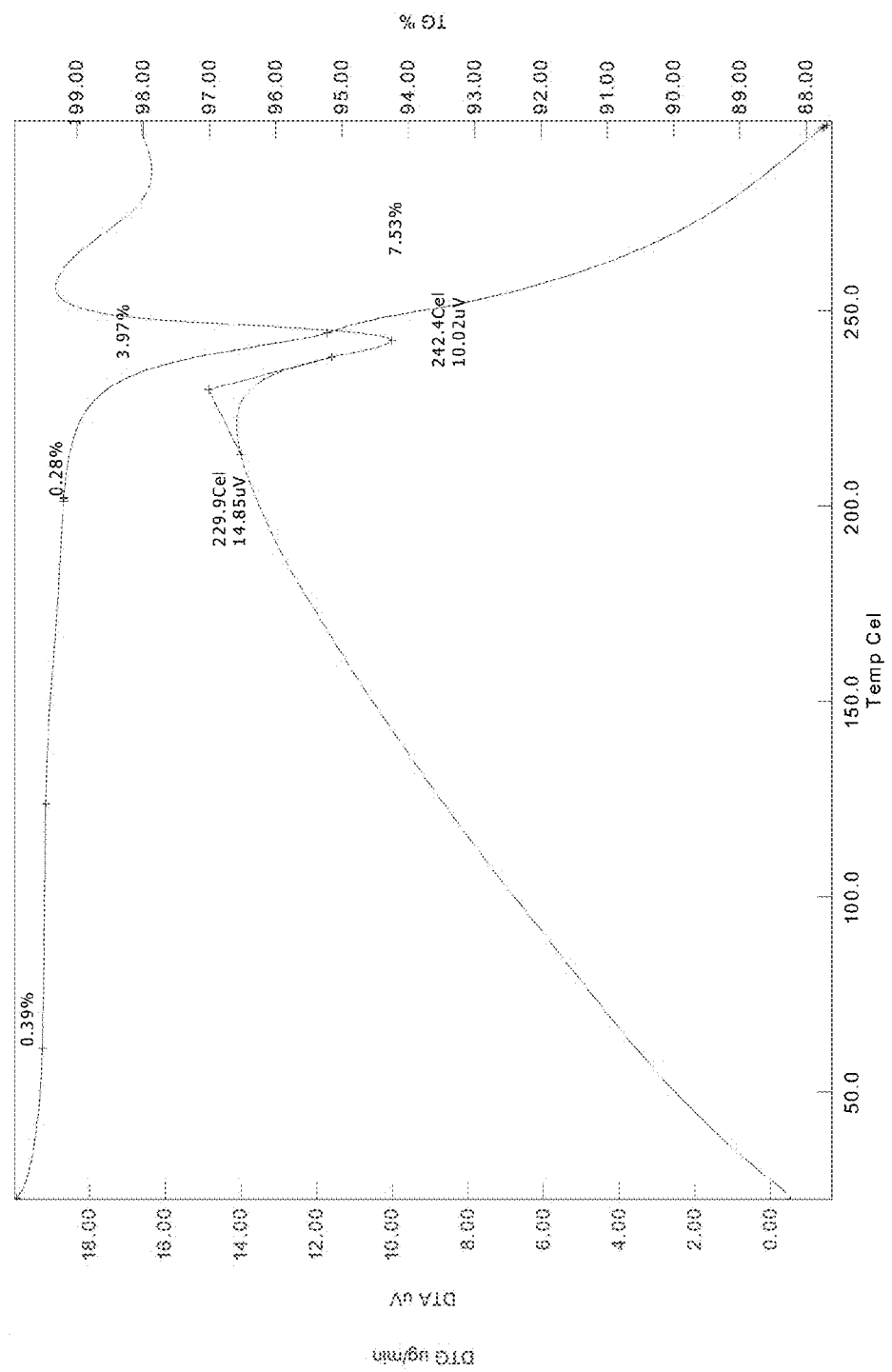
FIG. 56 depicts the TGA pattern for a Form I hydrobromide salt of Compound 1.

TGA/DTA (FIG. 56) showed a weight loss from the outset of ca. 0.4%, likely due to unbound moisture or solvent. No further significant weight losses were seen prior to degradation at onset ca. 230° C.

Figure 57:
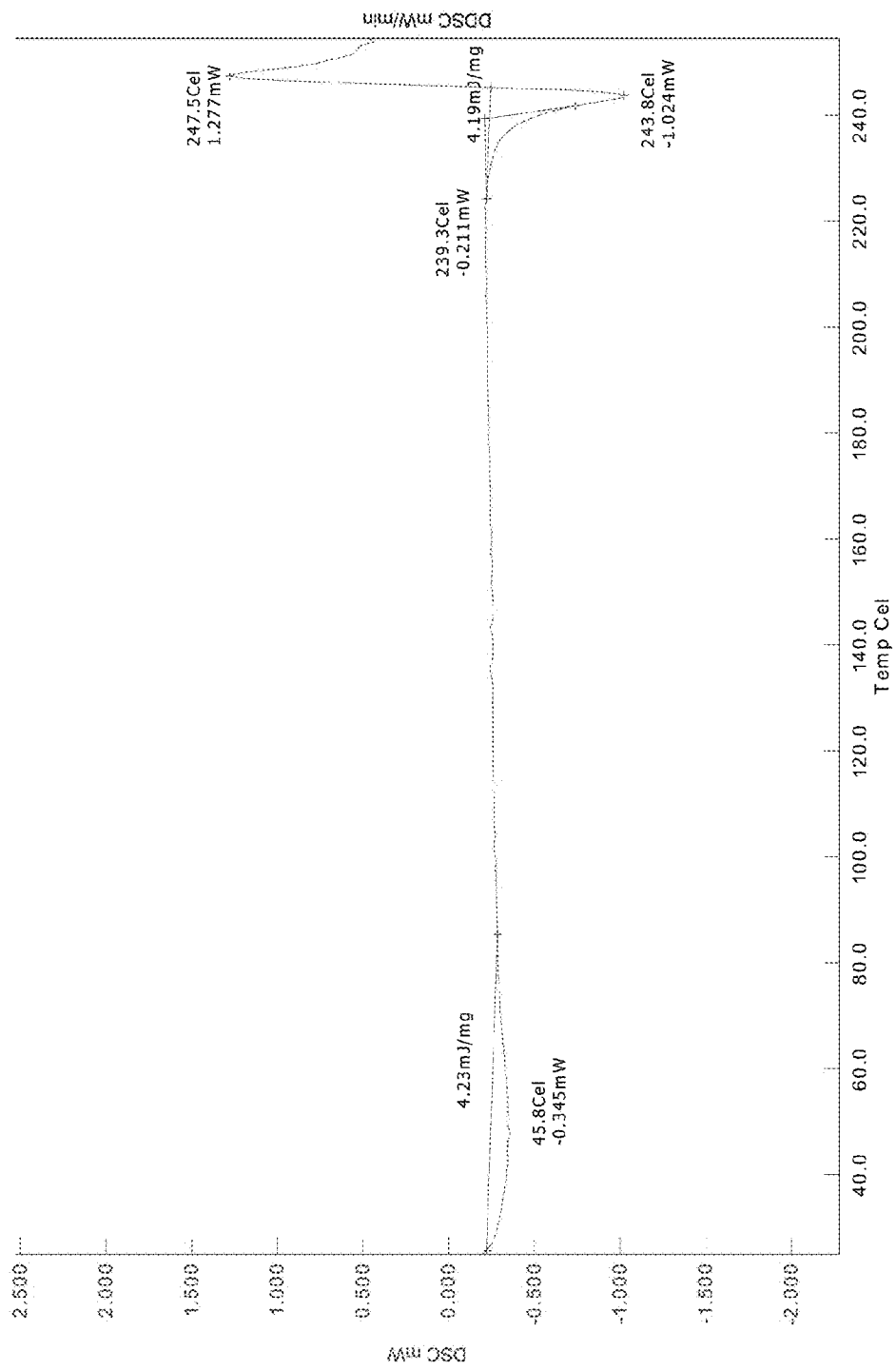
FIG. 57 depicts the DSC pattern for a Form I hydrobromide salt of Compound 1.

DSC analysis (FIG. 57) indicated a shallow, broad endotherm from the outset likely due to unbound solvent/water. A second endotherm was then present at onset ca. 240° C. (peak 244° C.), followed by likely degradation.

KF analysis determined the water content of the material to be ca. 0.76%.

HPLC purity determination indicated a purity of ca. 98.1%.

The content of carbon, hydrogen and nitrogen in the material was determined by placing the samples into a tin capsule, placed inside an autosampler drum of an elemental analysis system. The sample environment was purged by a continuous flow of helium and the samples dropped at pre-set intervals into a vertical quartz tube maintained at 900° C. The mixture of combustion gases was separated and detected by a thermal conductivity detector giving a signal proportional to the concentration of the individual components of the mixture. The content of bromine in the material was determined by oxygen flask combustion of the sample. Once the combustion and absorption into solution had occurred, the samples were titrated using a calibrated Mercuric Nitrate solution. Elemental analysis (CHN and bromide) indicated the following percentages:

| | ELEMENT | | | |
|---|---|---|---|---|
| | C | H | N | Br |
| % Theory | 51.03 | 4.44 | 15.42 | 12.57 |
| % Found | 50.36 | 4.32 | 16.47 | 12.11 |

Ion chromatography was carried out using a Metrohm 761 Compact Ion Chromatograph for the analysis of ions in aqueous solutions. Calibration standards were prepared from certified 1000 ppm stock solutions. Ion chromatography showed the presence of 12.38% bromide.

Figure 58:
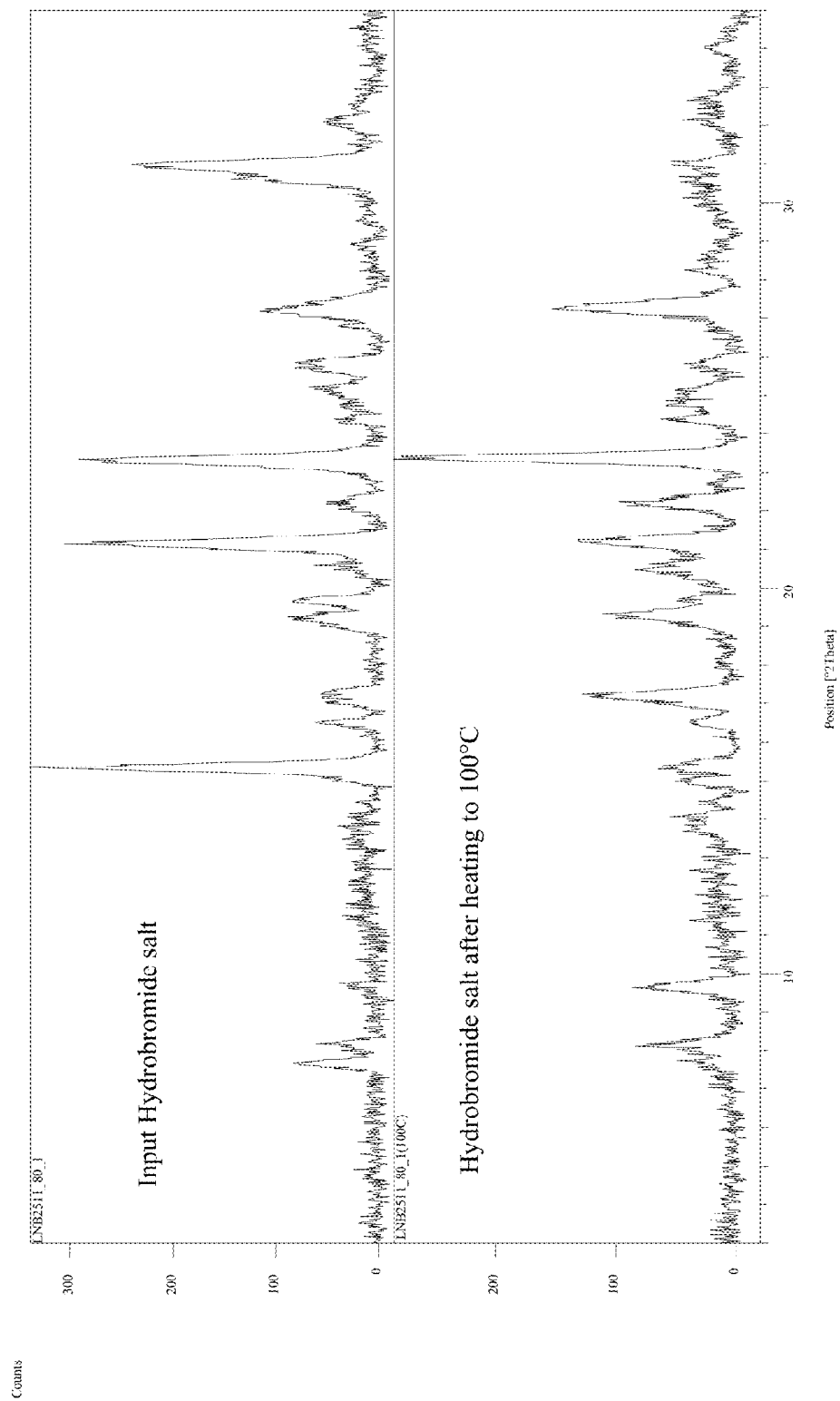
FIG. 58 depicts the XRPD pattern for a Form I hydrobromide salt of Compound 1 after heating.

In order to examine the effect of removing the water which is retained by the material, (despite extended periods of drying) a small sample was heated to 100° C. in a TGA pan and XRPD analysis was then carried out (FIG. 58). The analysis indicates some loss in crystallinity, however, the polymorphic form remains consistent after removing the ca. 0.5% water by heating. Nevertheless, the material appears to be slightly hygroscopic.

Example 11

Large-Scale Preparation of Hydrobromide Salt (1 Equiv.)

Approximately 1 L of acetone:water (90:10) was added to ca. 319 g of Compound 1 in a 5 L reaction vessel with the reactor temperature set to 4° C. A suspension was obtained. The suspension was stirred at 450 rpm. In a separate flask, 1 equivalent of hydrogen bromide (48%) (ca. 65 mL) was added to ca. 750 mL of acetone:water (90:10). The acid solution was then added to the 5 L reactor over a 1 hour period, while maintaining a temperature of ca. 4° C. After 30 minutes, a further 700 mL of acetone:water (90:10) was added to the reactor. After the complete addition of the HBr solution, the reactor temperature was raised to 20° C. for 2 hours. The reaction was then again cooled to ca. 4° C. and maintained at this temperature for a further 3 hours. The reaction mixture was then filtered and dried under vacuum at ambient temperature (ca. 22° C.) for 3 days. The solid was stirred periodically during the drying process. The yield after drying was 258.1 g (71%).

Figure 60:
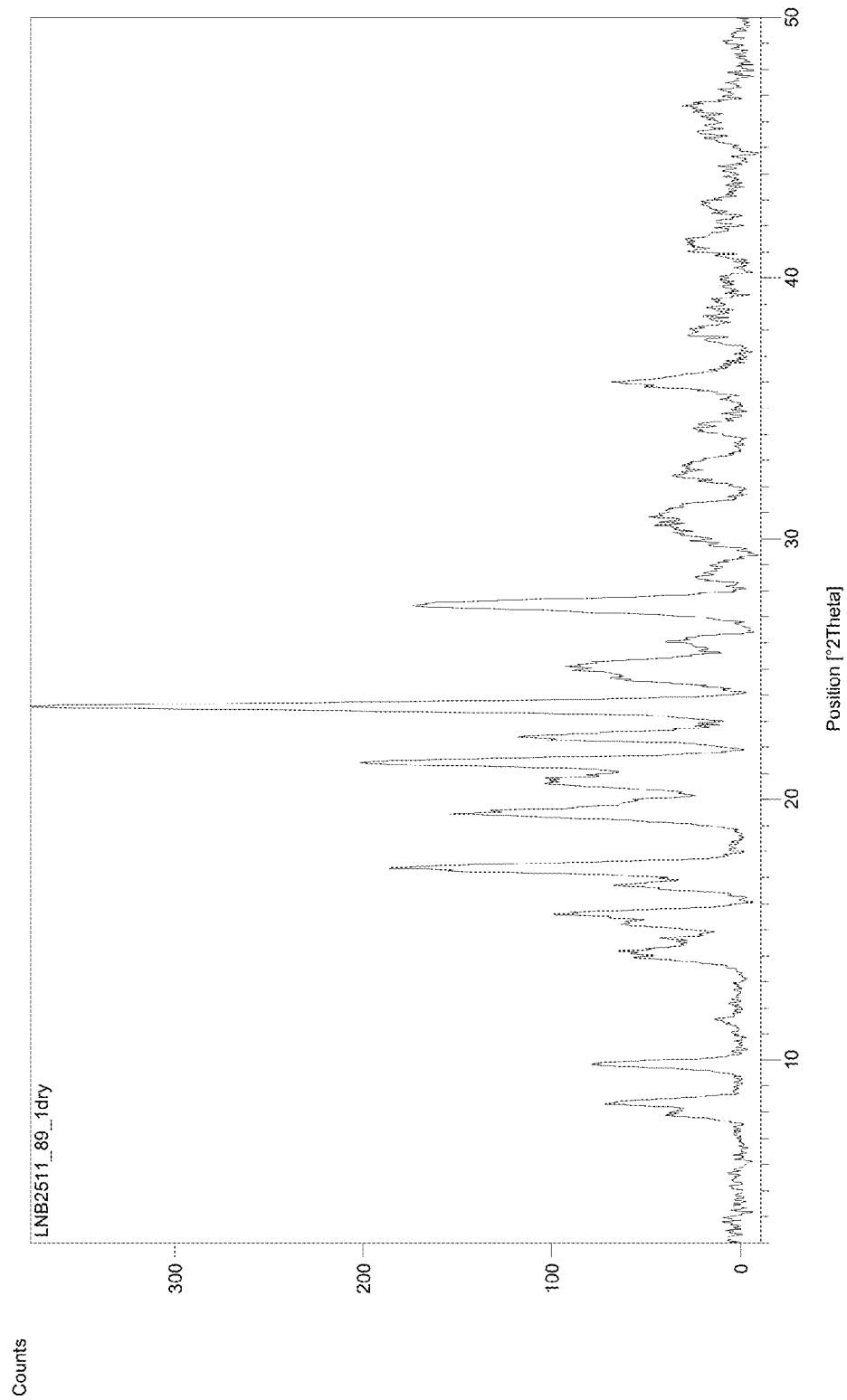
FIG. 60 depicts the XRPD pattern for a Form I hydrobromide salt of Compound 1.

XRPD analysis (FIG. 59) carried out on the initial scale-up material while wet, showed the sample to be highly crystalline. After drying, the solid converted to a different polymorphic form (FIG. 60). The dried material is the same form as that obtained from the primary salt screen.

IR Spectroscopy (FIG. 61) showed differences when compared with the freebase spectrum. The spectrum also appeared consistent with the spectra obtained for the hydrobromide salt prepared in Examples 1 and 7.

PLM analysis showed a needle-like, fibrous morphology when wet (not shown). Upon drying and hence polymorph conversion, the needle-like morphology was lost with small particles resulting.

$^1$H NMR (FIG. 62) indicated a number of peak shifts in comparison with the free base. Trace amounts of acetone were present in the spectrum.

TGA/DTA (FIG. 63) showed a weight loss from the outset of ca. 0.4%, likely due to unbound moisture or solvent. No further significant weight losses were seen prior to degradation at onset ca. 230° C. Thus, the material appears to retain ca. 0.5% water at ambient conditions despite extended periods of drying and therefore appears to be slightly hygroscopic.

DSC analysis (FIG. 64) indicated a shallow, broad endotherm from the outset likely due to unbound solvent/water. A second endotherm was then present at onset ca. 241° C. (peak 245° C.), followed by likely degradation.

KF analysis determined the water content of the material to be ca. 0.74%.

HPLC purity determination indicated a purity of ca. 99.1%.

Slurries of the hydrobromide salt were prepared in buffered aqueous media at pH 1.0 (HCl/KCl buffer), pH 3.0 (citrate buffer), pH 4.5 (citrate buffer) and pH 6.2 (citrate buffer) as well as in an aqueous solution with pH reduced to below 2 using HBr (48%). The respective slurries were shaken for a period of 24 hours at 22° C. The solids were then removed by filtration and tested by XRPD analysis. The mother liquors were analyzed by HPLC to determine API solubility. HPLC solubility determination in various pH media showed the following results:

| pH condition | Conc. (mg/mL) |
| --- | --- |
| Aqueous solution with pH reduced to below 2 using HBr. | 3.52 |
| pH 1.0 (HCl/KCl buffer) | 4.09 |
| pH 3.0 (citrate buffer) | 0.20 |
| pH 4.5 (citrate buffer) | 0.17 |
| pH 6.2 (citrate buffer) | 0.04 |

Figure 65:
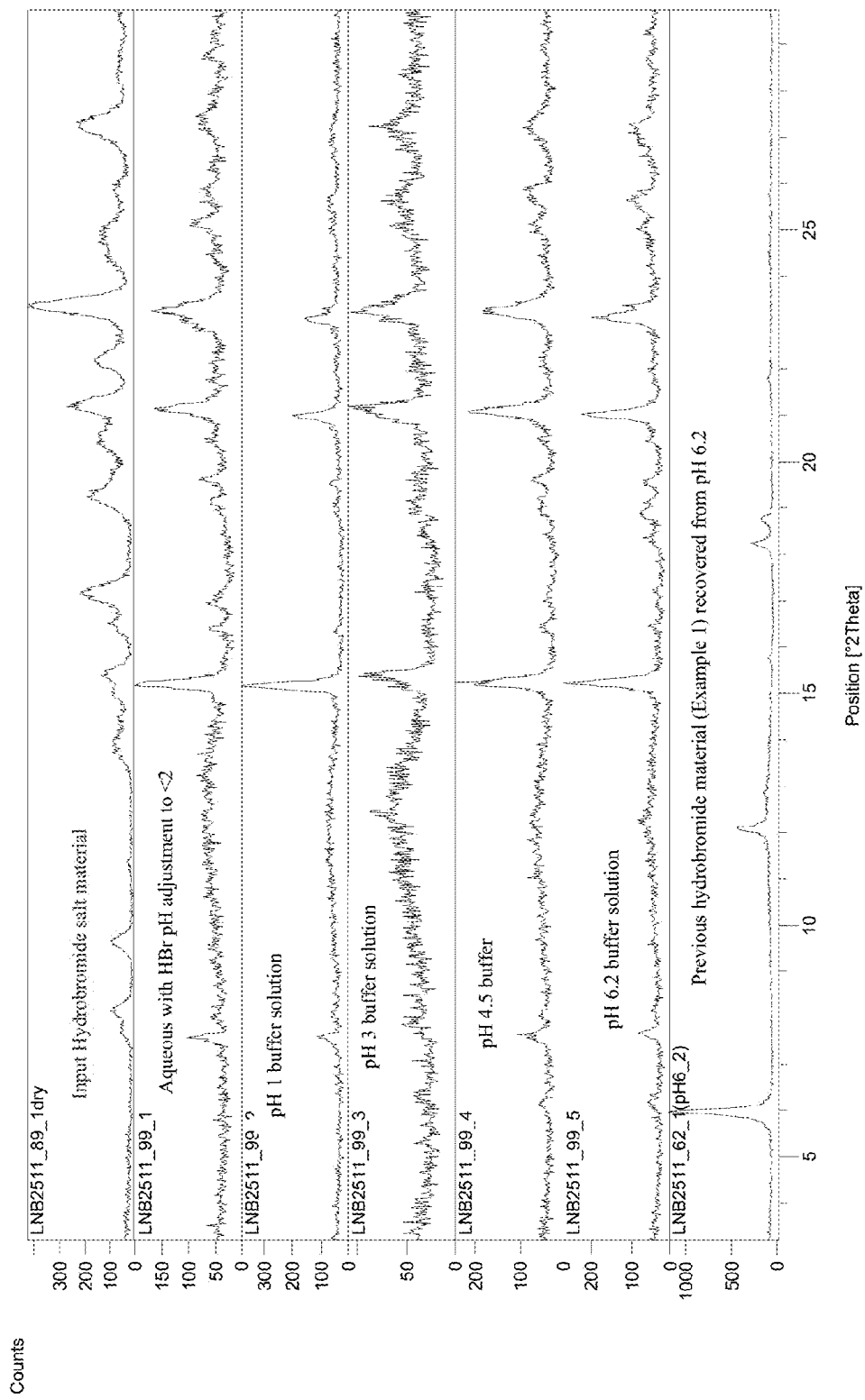
FIG. 65 depicts the results of a thermodynamic solubility study of a Form I hydrobromide salt of Compound 1, as analyzed by the XRPD patterns.

XRPD analysis of the solids recovered after the solubility experiments (FIG. 65) showed all samples to correspond predominantly with the input hydrobromide salt material, with the samples in the pH 3.0, 4.5 and 6.2 buffers showing traces of a form previously identified from disproportionation studies and previous slurring of the hydrobromide salt in pH buffers >pH 3.

Elemental analysis (CHN and bromide) indicated the following percentages:

| | ELEMENT | | | |
| --- | --- | --- | --- | --- |
| | C | H | N | Br |
| % Theory | 51.03 | 4.44 | 15.43 | 12.57 |
| % Found | 50.42 | 4.60 | 15.14 | 12.54 |

Figure 66:
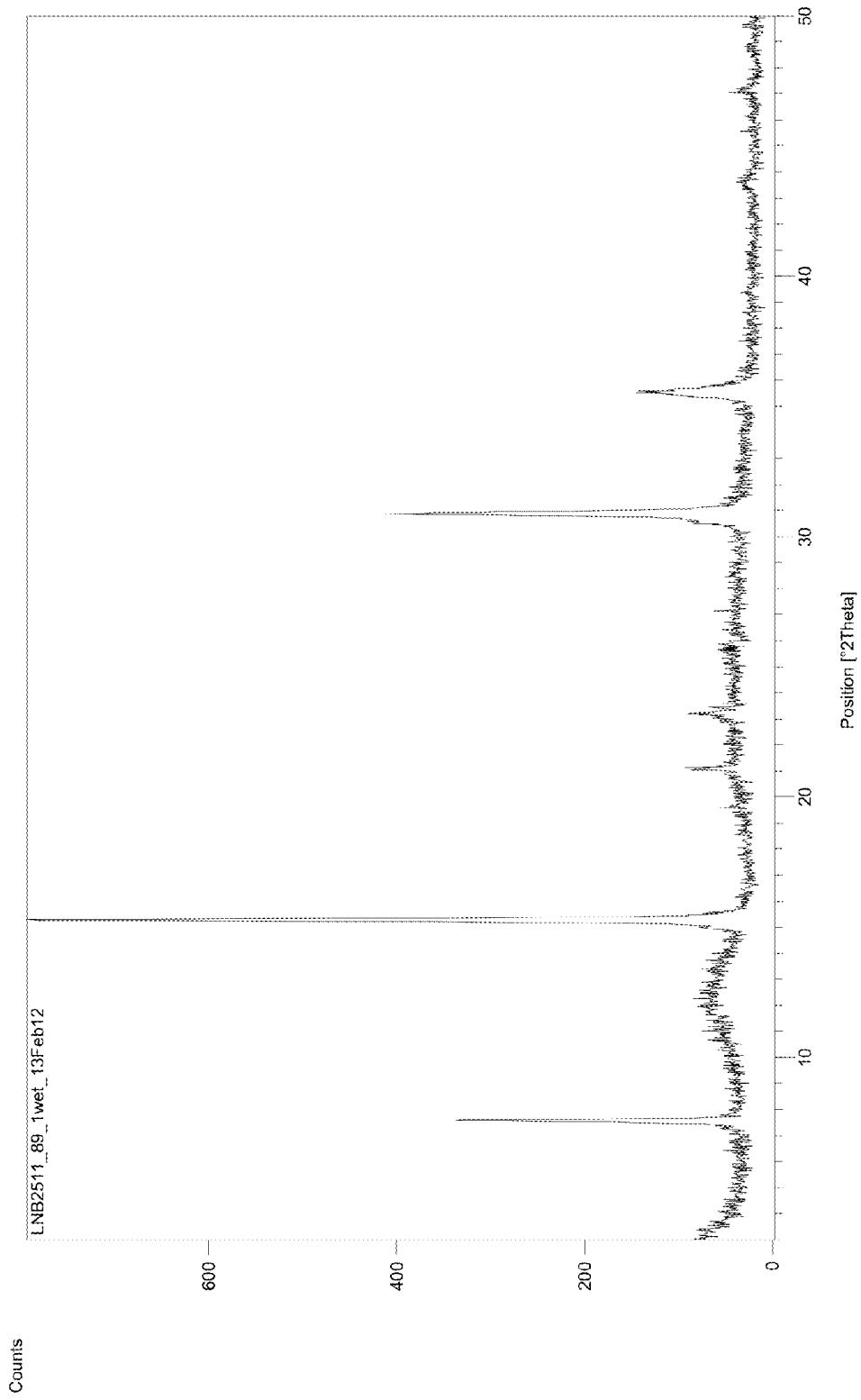
FIG. 66 depicts the XRPD pattern for a Form I hydrobromide salt of Compound 1, after storage for 1.5 months.

A small slurry of the scale-up material was stored for ca. 1.5 months at ca. 4° C. Upon re-analyzing the material by PLM analysis, the crystals appeared as very flat, rod-shaped particles in comparison to the fibrous, needle-like particles previously observed (not shown). The material converted to the same form as the one obtained upon drying with a change in crystal morphology from fibrous needle-like crystals to flat, rod-like crystals. XRPD analysis (FIG. 66) indicated a diffractogram which corresponded with the dry hydrobromide salt material (peaks at 7.59, 15.28, 21.10, 23.21, 30.88, 35.54, 43.58 and 47.13 °2-theta). The peaks appear very sharp with some preferred orientation in the diffractogram.

Example 12

Primary Polymorph Screening of Hydrobromide Salt

Preparation of Amorphous Material.

Figure 79:
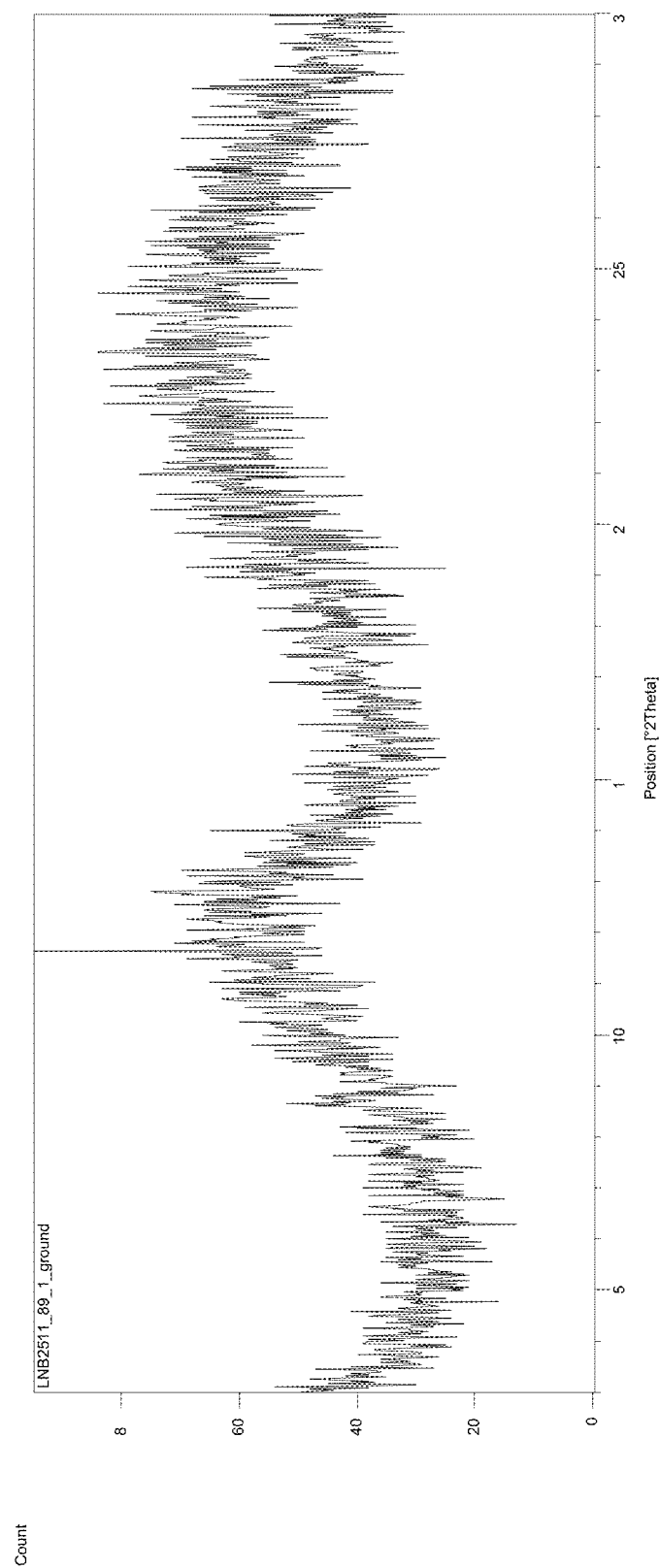
FIG. 79 depicts the XRPD of an amorphous hydrobromide salt of Compound 1.

Hydrobromide salt material was ground using a Retsch Ball Mill for ca. 25 minutes, with a 5 minute break midway to prevent the sample from overheating. The sample was then analysed by XRPD to determine form and by HPLC to check for degradation. Post grinding XRPD analysis showed the hydrobromide salt material to be amorphous with an HPLC purity of ca. 99.5%. (FIG. 79). Amorphous material was desired in order to both increase the solubility and not to bias the screening study towards one particular form.

Solvent Solubility Screen.

Approximately 10 mg of amorphous hydrobromide salt was placed in each of 24 vials and 5 volume aliquots of the appropriate solvent system was added to the vial. Between each addition, the mixture was checked for dissolution. This procedure was continued until dissolution was observed or until 100 volumes of solvent had been added. Amorphous hydrobromide salt material was found to be highly soluble in 3 of the 24 solvent systems but exhibited low solubility in the remaining solvents. The approximate solubility values of the amorphous hydrobromide salt in the 24 solvent systems are presented in Table 12:

TABLE 12

Approximate Solubility in Selected Solvents

| Solvent | Approximate Solubility (mg/mL) |
|---|---|
| Acetone | <10 |
| Acetone:Water (10%) | <10 |
| Acetonitrile | <10 |
| 1-Butanol | <10 |
| Cyclohexane | <10 |
| Dichloromethane | <10 |
| Diisopropyl ether | <10 |
| Dimethylformamide | ca. 67 |
| Dimethylsulfoxide | ca. 50 |
| 1,4-Dioxane | <10 |
| Ethanol | <10 |
| Ethyl acetate | <10 |
| Heptane | <10 |
| Isopropyl acetate | <10 |
| 3-Methyl-1-butanol | <10 |
| Methylethyl ketone | <10 |
| Methyl isobutyl ketone | <10 |
| N-Methyl-2-pyrrolidone | ca. 20 |
| Nitromethane | <10 |
| 2-Propanol | <10 |
| tert-Butylmethyl ether | <10 |
| Tetrahydrofuran | <10 |
| Toluene | <10 |
| Water | <10 |

Temperature Cycling Experiments.

The results obtained from the solubility approximation experiments were used to prepare slurries for temperature cycling. The slurries were temperature cycled between 4° C. and 25° C. in 4 hour cycles for a period of 72 hours (slurries were held at 4° C. for 4 hours followed by a hold at ambient for 4 hours, the cooling/heating rates after the 4 hour hold periods was ca. 1° C./min). Solid material was then recovered for analysis.

Crash Cooling Experiments.

Crash cooling experiments were performed by placing saturated solutions of the material, in each of the 24 selected solvent systems, in environments of 2° C. and −18° C. for a minimum of 48 hours. Any solid material was then recovered for analysis.

Rapid Evaporation Experiments.

Rapid evaporation experiments were conducted by evaporating the solvents from saturated, filtered solutions of the material, in each of the 24 solvent systems, under vacuum. Any solid material was then recovered and analysed after the solvent had evaporated to dryness.

Anti-Solvent Addition Experiments.

Anti-solvent addition experiments were conducted at ambient temperature by adding the selected anti-solvent to saturated, filtered solutions of the material, in each of the 24 selected solvent systems. The anti-solvent selected was heptane, with tert-butylmethyl ether and water being used for solvents immiscible with heptane. Addition of anti-solvent was continued until there was no further precipitation or until no more anti-solvent could be added. Any solid material was recovered and analysed quickly in order to prevent form changes.

Slow Evaporation Experiments.

Slow evaporation experiments were conducted by evaporating the solvents from saturated, filtered solutions of the material, in each of the 24 solvent systems at ambient conditions. Any solid material was then recovered and analysed after the solvent had evaporated to dryness.

Desolvation of Solvated Forms.

Figure 80:
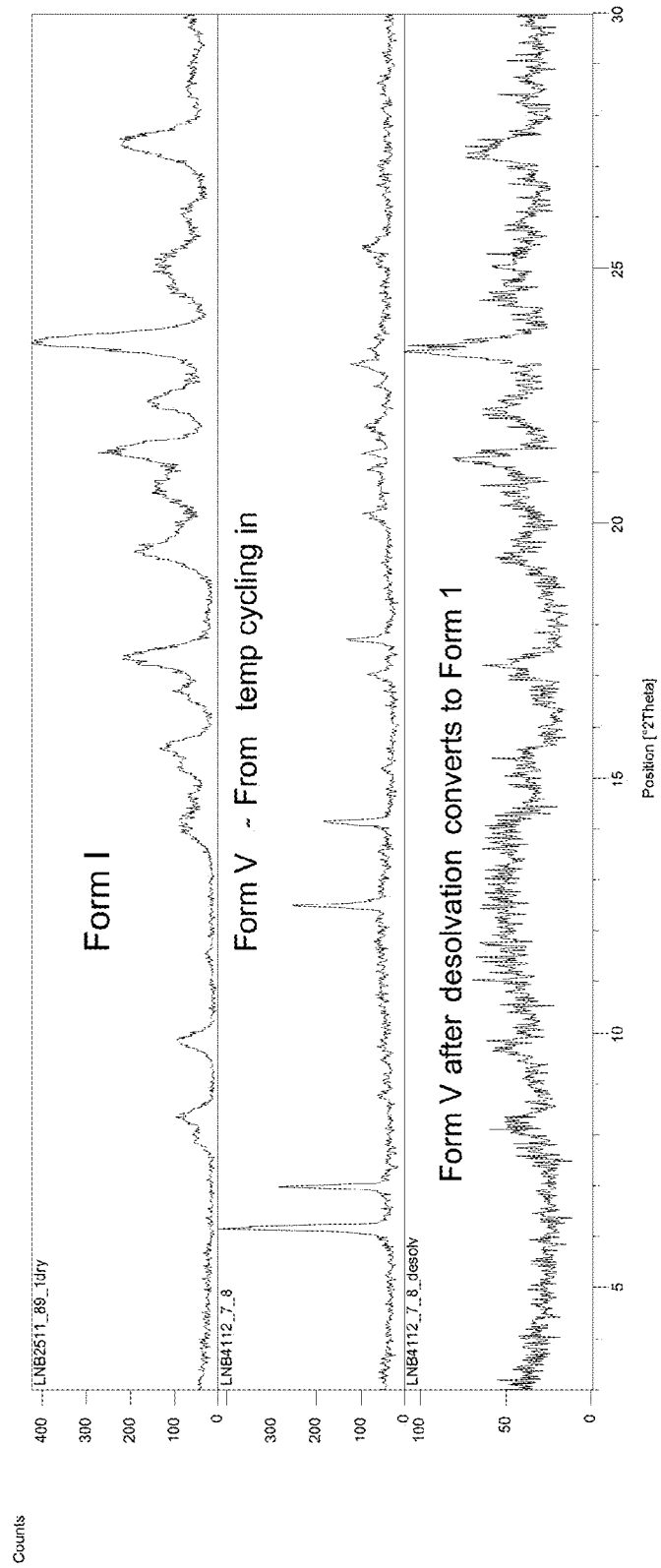
FIG. 80 depicts the XRPD of Form V hydrobromide salt of Compound 1 following desolvation conditions.

Potential solvated forms were subjected to heating on a TGA instrument to a temperature slightly beyond the initial weight loss. It could then be determined by subsequent XRPD analysis whether the form had changed as a result of the loss of solvent molecules. After heating to 180° C. using TGA instrumentation, Form V solvate was found to have reverted to Form I by XRPD analysis. The resultant diffractogram is shown in FIG. 80. The attempted desolvation of Form VII resulted in a gum following heating.

Investigation into Wet and Dry Samples of Form I.

Figure 81:
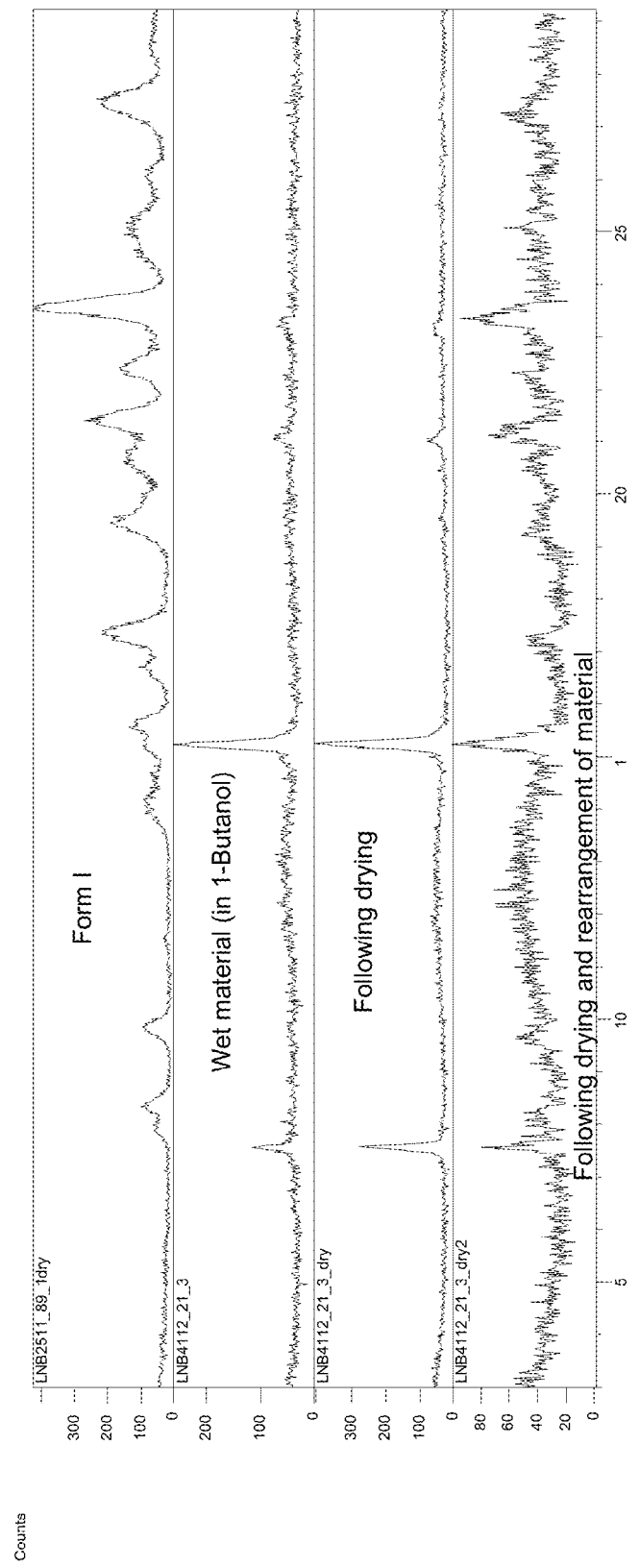
FIG. 81 depicts input material Form I hydrobromide salt of Compound 1 compared with a wet sample, and after stages of drying.

Initially, wet samples of Form 1 showed some differences in the XRPD diffractograms to those of the dry samples. Further investigation, including drying studies followed by XRPD analysis, TGA, and XRPD analysis with spinning were carried out. For Form I, the wet material showed significant preferred orientation and shifting was observed in the diffractograms when compared to the dry material. FIG. 81 shows input material Form I compared with a wet sample, and after stages of drying.

The results from the experiments conducted during the primary polymorph screen are shown in Table 13. Results were obtained from PLM and XRPD analysis. Overall it can be seen that multiple potential polymorphic forms were identified during the screening experiments.

Form I was obtained from multiple temperature cycling experiments.

Form III, an anhydrous form, was obtained from rapid evaporation of DMSO, crash cooling to 2° C. in ethanol, and anti-solvent addition from acetone, acetonitrile, and ethanol.

Form IV, a 1,4-dioxane solvate, was obtained from temperature cycling in 1,4-dioxane.

Form V, a DMF solvate, was obtained from temperature cycling and rapid evaporation from DMF.

Form VI, a DMSO solvate, was obtained from temperature cycling in DMSO.

Form VII, a DMSO solvate, was obtained from slow evaporation from DMSO.

TABLE 13

Results of Primary Hydrobromide Salt Screen

| | Solvent | Temperature Cycling | Evaporation | Rapid Evaporation | Crash Cool (2° C.) | Crash Cool (−18° C.) | Anti-Solvent Addition |
|---|---|---|---|---|---|---|---|
| 1 | Acetone | Form I | AM/PLM+ | AM/PLM+ | NS | NS | Form III (heptane) |
| 2 | Acetone:Water (10%) | FB | Form I | FB§ | FB§ | FB | NS (heptane) |
| 3 | Acetonitrile | Form I* | AM/PLM+ | AM/PLM+ | NS | NS | Form III (tBME) |

TABLE 13-continued

Results of Primary Hydrobromide Salt Screen

| Solvent | Temperature Cycling | Rapid Evaporation | Evaporation | Crash Cool (2° C.) | Crash Cool (−18° C.) | Anti-Solvent Addition |
|---|---|---|---|---|---|---|
| 4 1-Butanol | Form I | NS | AM/PLM$^+$ | NS | NS | AM/PLM (heptane) |
| 5 Cyclohexane | AM | NS | NS | NS | NS | NS (heptane) |
| 6 Dichloromethane | Form I | AM/PLM$^+$ | AM | NS | PLM | AM/PLM (heptane) |
| 7 Diisopropyl ether | Form I | NS | NS | NS | NS | NS (heptane) |
| 8 Dimethylformamide | Form V | Form I | Form V | NS | NS | WD (tBME) |
| 9 Dimethylsulfoxide | Form VI | Form VII | Form III (WD) | NS | AM/PLM$^{\#\dagger}$ | AM (water) |
| 10 1,4-Dioxane | Form IV | NS | AM/PLM$^+$ | NS | NS | NS (heptane) |
| 11 Ethanol | Form I | AM/PLM$^\ddagger$ | AM | Form III$^\wedge$ | PLM | Form III (heptane) |
| 12 Ethyl acetate | Form I | NS | NS | NS | NS | AM/PLM (heptane) |
| 13 Heptane | AM | NS | NS | NS | NS | NS (tBME) |
| 14 Isopropyl acetate | Form I | NS | NS | NS | NS | AM/PLM (heptane) |
| 15 3-Methyl-1-butanol | Form I | AM/PLM$^+$ | AM/PLM$^+$ | NS | NS | AM/PLM (heptane) |
| 16 Methylethyl ketone | Form I | AM/PLM$^+$ | AM | NS | NS | AM (heptane) |
| 17 Methyl isobutyl ketone | Form I | NS | NS | NS | NS | AM/PLM (heptane) |
| 18 N-Methyl-2-pyrrolidone | Form I | NS | NS | NS | NS | AM (tBME) |
| 19 Nitromethane | Form I | AM/PLM | AM/PLM | NS | PLM | AM (tBME) |
| 20 2-Propanol | Form I | AM | AM | NS | NS | AM/PLM (heptane) |
| 21 tert-Butylmethyl ether | Form I | NS | NS | NS | NS | NS (heptane) |
| 22 Tetrahydrofuran | Form I | AM/PLM$^\#$ | AM/PLM$^\#$ | NS | NS | AM (heptane) |
| 23 Toluene | Form I | NS | NS | NS | NS | NS (heptane) |
| 24 Water | FB | NS | NS | NS | NS | NS |

AM - amorphous solid
NS - no solid observed
AM/PLM - amorphous by XRPD, birefringence observed by PLM
FB - Compound 1 free base
PLM - birefringence by PLM
WD - weak data
*poorly crystalline
$^+$no clear morphology
$^\wedge$only 2 peaks present; needle-like morphology
$^\#$plate-like morphology
$^\dagger$similar to Form VI
$^\ddagger$rod-like morphology
$^\S$missing peaks Example 13

Secondary Polymorph Screening of Hydrobromide Salt and Developability Assessment Form III hydrobromide salt of Compound 1 (1 equiv.) was obtained during the primary polymorph screen from multiple experiments. This form was therefore progressed for scale-up and further analysis.

Form III Hydrobromide Salt Preparation.

Approximately 500 mg of amorphous Compound 2 HBr salt material was slurried in ca. 6 mL of acetonitrile. The suspension was then temperature cycled between 4 and 25° C. in four hour cycles for ca. 2 days. The secondary screen analysis was carried out on the material when it was damp, due to the instability of Form III.

During the scale-up of the Form III hydrobromide salt, the material remained yellow in colour. XRPD analysis showed the material produced from scale-up to be crystalline and consistent with the small scale Form III hydrobromide salt diffractogram. PLM analysis indicated birefringent, needle-like crystals when wet. Hot stage microscopy indicated that as the solvent dried off between 40 and 50° C., the crystal morphology changed to more rod-like crystals. By ca. 250° C., the material was observed to melt. For TGA/DTA analysis, a damp sample of Form III was placed into the TGA pan. An initial 10.3% weight loss was observed due to the unbound solvent. The form change which occurs between 40 and 50° C. by hotstage microscopy was masked by the solvent loss. A further endotherm corresponding with Form I hydrobromide salt was observed at onset ca. 239° C.

(peak ca. 245° C.). DSC analysis indicated an initial endotherm from the outset up to approximately 100° C. A final endotherm was observed at onset ca. 233° C. (peak ca. 247° C.), which appears consistent with the Form I melt. IR spectroscopy indicated very small differences between the IR spectrums of Forms I and III.

DVS analysis showed the following observations:
Cycle 1—Sorption 20-90% RH
Sample gradually takes up ca. 1.045% mass.
Cycle 2—Desorption 90-0% RH
Between 90-0% RH, sample mass decreases gradually by ca. 1.983%.
Cycle 3—Sorption 0-20% RH
Moisture uptake of ca. 0.535% between 0-20% RH.

The material was observed to be slightly hygroscopic. Post DVS XRPD indicated that the material converted to Form I hydrobromide salt during DVS analysis. $^1$H NMR spectroscopy carried out in deuterated DMSO showed a spectrum which corresponded with the Form I hydrobromide salt. KF analysis indicated the presence of 1.4% water. HPLC purity analysis indicated a purity of ca. 99.43%. Ion chromatography indicated the presence of 12.17% bromide (ca. 12.57% required for 1 equivalent).

XRPD analysis carried out on the thermodynamic solubility experiment solids remaining after 24 hours, indicated that for the pH 6.6 and 4.5 experiments, the Form III hydrobromide salt converted to a freebase hydrate form, the solid from the pH 3.0 experiment became amorphous and the solid from the pH 1 experiment remained predominantly consistent with the Form III hydrobromide, with some loss in crystallinity.

7 Day Stability Studies at 25° C., 80° C., 40° C./75% RH (Open and Closed Conditions).

Approximately 15 mg of Form III was placed into vials and then exposed to 25° C., 80° C. and 40° C./75% RH environments (open and closed vials) for 1 week to determine stability. The resulting solids were analysed by XRPD and HPLC to establish if any changes had occurred. The 1 week stability studies carried out in open and closed vials at 25° C., 80° C. and 40° C./75% RH indicated the following results:

TABLE 14

7 day stability studies (open container)

| Condition | Purity | XRPD analysis |
|---|---|---|
| 40° C./75% RH | 98.3% | Form I |
| 80° C. | 98.7% | Form I (some loss in crystallinity) |
| 25° C. | 98.2% | Form I |

TABLE 15

7 day stability studies (closed container)

| Condition | Purity | XRPD analysis |
|---|---|---|
| 40° C./75% RH | 99.0% | Form I |
| 80° C. | 99.0% | Form I |
| 25° C. | 98.9% | Form I |

From the characterisation carried out on Form III, this form was determined to be a metastable, likely anhydrous form of the hydrobromide salt. Form III was observed to be very unstable with conversion to Form I occurring upon isolation and drying of the material.

Thermodynamic Solubility Studies.

Slurries of Form III were created in media of various pH (pH 1; pH 3; pH 4.5 and pH 6.6) and shaken for ca. 24 hours. After 24 hours, the slurries were filtered and the solution analysed by HPLC in order to determine the solubility at the various pH levels. For the buffer solutions, KCl/HCl was used for pH 1 and citrate/phosphate combinations for pH 3, 4.5 and 6.6 (10 mM). The pH of the solutions was also measured prior to HPLC analysis. XRPD analysis was carried out on the remaining solids after 24 hours of shaking.

Thermodynamic solubility experiments carried out in buffers pH 1, 3.0, 4.5 and 6.6 indicated the following result:

TABLE 16

Thermodynamic Solubility Studies

| Buffer pH | pH prior to analysis | Solubility (mg/mL) |
|---|---|---|
| 1 | 0.95 | 13.88 |
| 3 | 1.53 | 0.84 |
| 4.5 | 1.79 | 0.28 |
| 6.6 | 1.79 | 0.42 |

Competitive Slurry Experiments.

Figure 82:
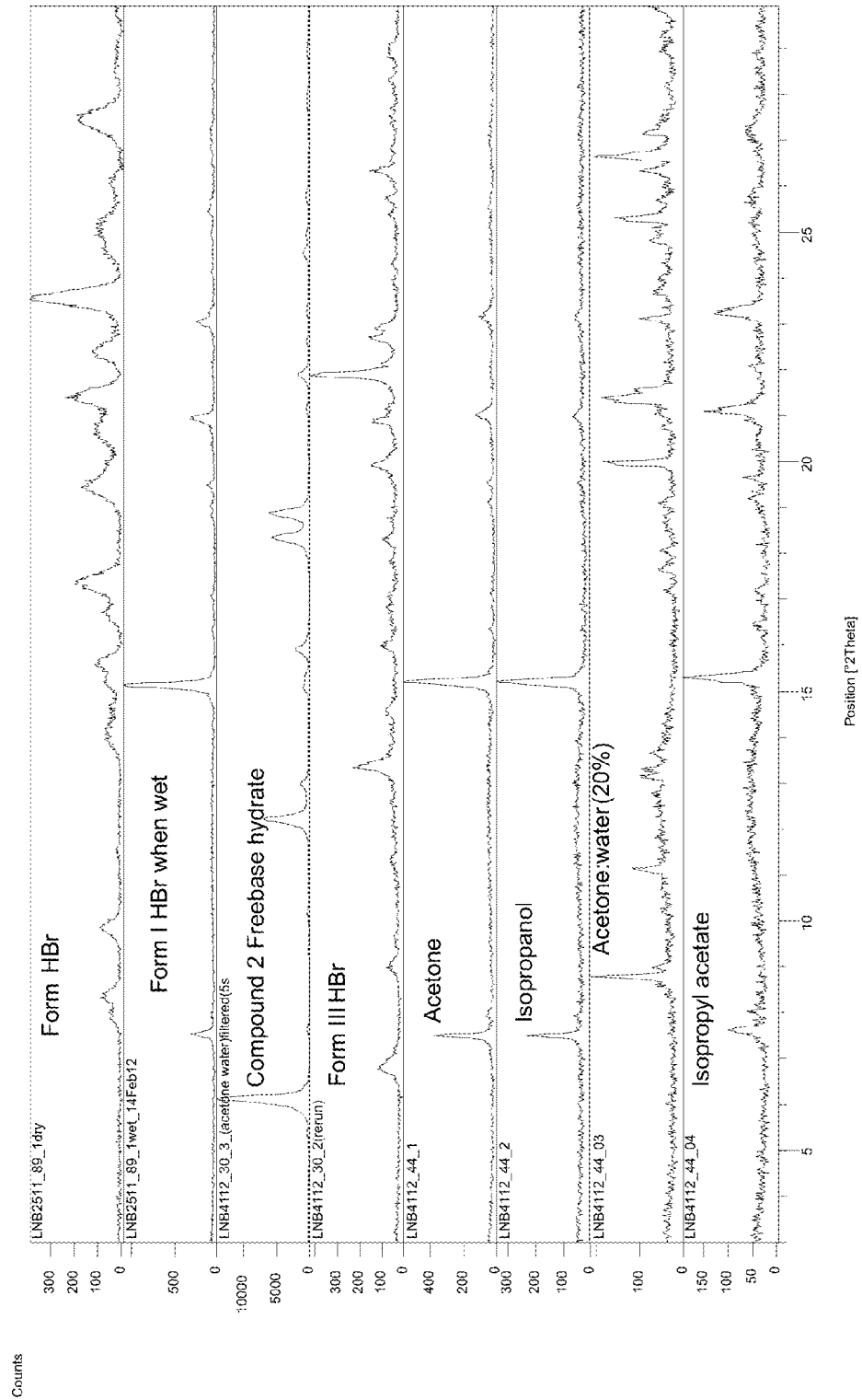
FIG. 82 depicts the XRPD analysis of hydrobromide salt Forms I and III resulting from competitive slurry experiments at ambient temperature (22° C.).
Figure 83:
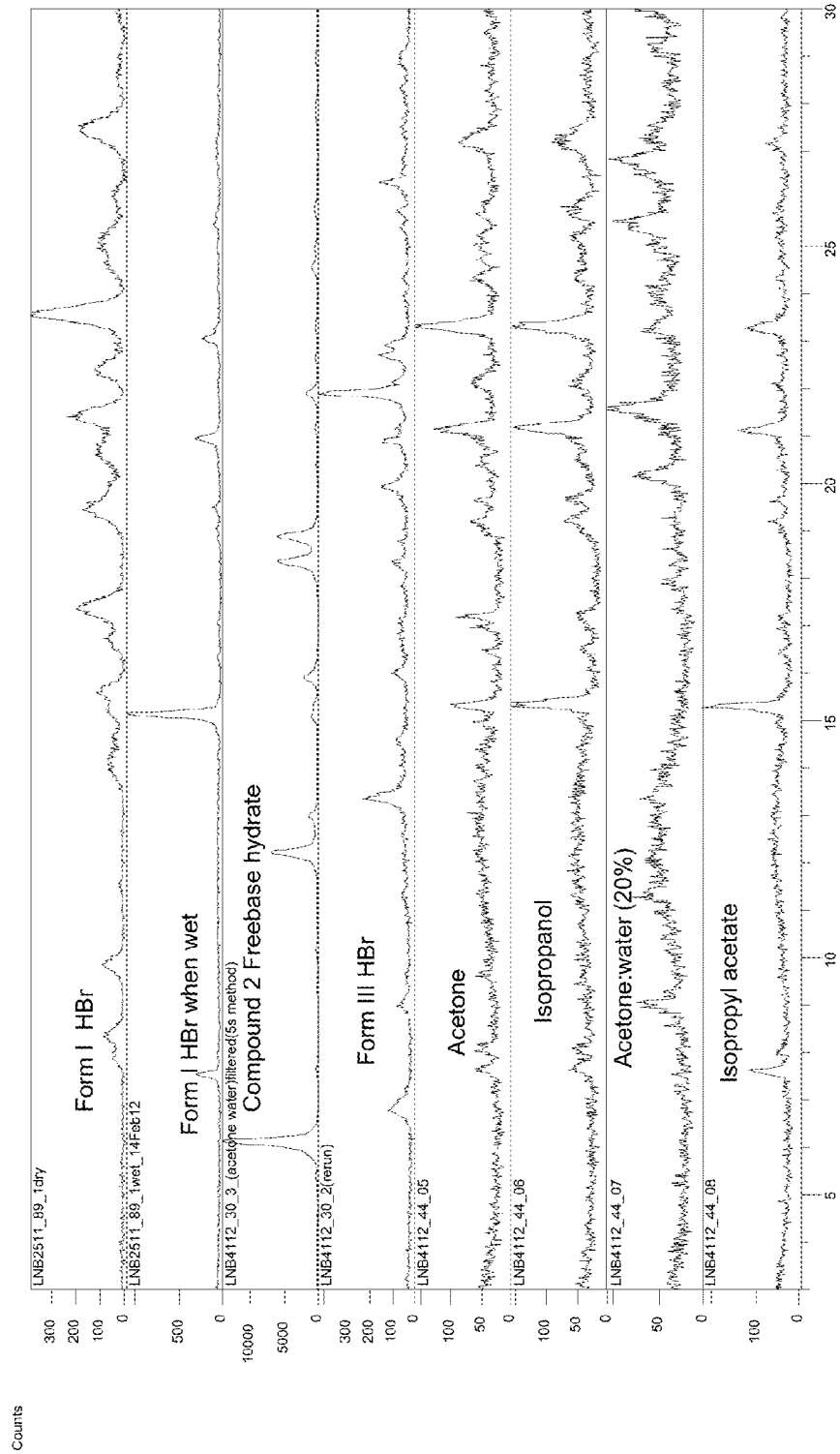
FIG. 83 depicts the XRPD analysis of hydrobromide salt Forms I and III resulting from competitive slurry experiments at 60° C.

Competitive slurry experiments were set up in acetone, isopropanol, acetone:water (80:20) and isopropyl acetate at both room temperature (ca. 22° C.) and 60° C. Approximately 200 mg of each of Forms I and III material was placed into a vial and 4 mL of the appropriate solvent system was added to produce a slurry. For each experiment, the slurries were allowed to stir for ca. 3 days. Analysis by XRPD was then conducted to determine the form of the resultant solid. Competitive slurry experiments of Form I vs. Form III were carried out in 4 solvent systems and resulting solids were analysed by XRPD analysis (FIG. 82 and FIG. 83). Results are summarised in Table 17.

TABLE 17

Summary of results from competitive slurry experiments

| Ingoing Forms | Solvent | Temperature | Result |
|---|---|---|---|
| I and III | Acetone | RT (ca. 22° C.) | Form I |
| I and III | Acetone | 60° C. | Form I |
| I and III | Isopropanol | RT (ca. 22° C.) | Form I |
| I and III | Isopropanol | 60° C. | Form I |
| I and III | Acetone:water (80:20) | RT (ca. 22° C.) | Form VIII |
| I and III | Acetone:water (80:20) | 60° C. | Form VIII |
| I and III | Isopropyl acetate | RT (ca. 22° C.) | Form I |
| I and III | Isopropyl acetate | 60° C. | Form I |

From the competitive slurry experiments, Form I was found to be the thermodynamically most stable form in acetone, isopropanol and isopropyl acetate at both ambient and 60° C. In acetone:water (80:20), conversion to an unidentified form resulted (labelled as Form VIII).

Characterization of Form VIII.

An initial assessment of Form VIII, obtained from competitive slurry experiments of Forms I and III in acetone:water (80:20), was made in order to determine the nature of the form and evaluate whether it is consistent with freebase material or the HBr salt. The material resulting from the competitive slurry experiments appeared light yellow in colour. PLM analysis indicated birefringent material with no clearly defined morphology. After drying under vacuum for ca. 24 hours, the TGA/DTA indicated a weight loss of 5.2% from the outset followed by a second weight loss of 1.2%, with endotherms in the DTA trace at ca. 40° C. and ca. 96°

C. A final endotherm was observed in the DTA trace at onset ca. 184° C. (peak ca. 194° C.). Very little change was observed by hotstage microscopy prior to the melt at ca. 197° C. DSC analysis indicated a broad endotherm starting from the outset (peak ca. 93° C.) followed by a second endotherm at peak ca. 140° C. and a third endotherm at onset ca. 178° C. (peak ca. 193° C.). Ion chromatography indicated a bromide content of 12.8% (approximately 1 equivalent).

In order to examine the effect of desolvating/dehydrating Form VIII, the material was heated to 150° C. in a TGA pan and XRPD analysis was then carried out. The polymorphic form appeared to remain the same. After heating to 150° C. and carrying out XRPD analysis, TGA analysis was again carried out on the same material and showed a weight loss of 6.0% from the outset followed by a second weight loss of 0.9%, with endotherms in the DTA trace at ca. 42° C. and 96° C. A final endotherm was observed in the DTA trace at onset ca. 186° C. (peak ca. 194° C.). The sample appeared to re-hydrate when exposed to atmospheric conditions. This would likely explain the consistency between the XRPD diffractograms before and after desolvation/dehydration.

Hydration Studies at 55° C.

Slurries were created using ca. 200 mg of Form I salt material in 2 mL of the appropriate solvent system. These were stirred at ca. 55° C. for 6 hours. The solvent systems used are listed in Table 18.

TABLE 18

| Solvent Systems for Hydration Studies at 55° C. Solvent System |
|---|
| Ethanol:Water (1%) |
| Ethanol:Water (2%) |
| Ethanol:Water (5%) |
| Ethanol:Water (10%) |
| IPA/Acetone (9:1):Water (1%) |
| IPA/Acetone (9:1):Water (2%) |
| IPA/Acetone (9:1):Water (5%) |
| IPA/Acetone (9:1):Water (10%) |

Figure 84:
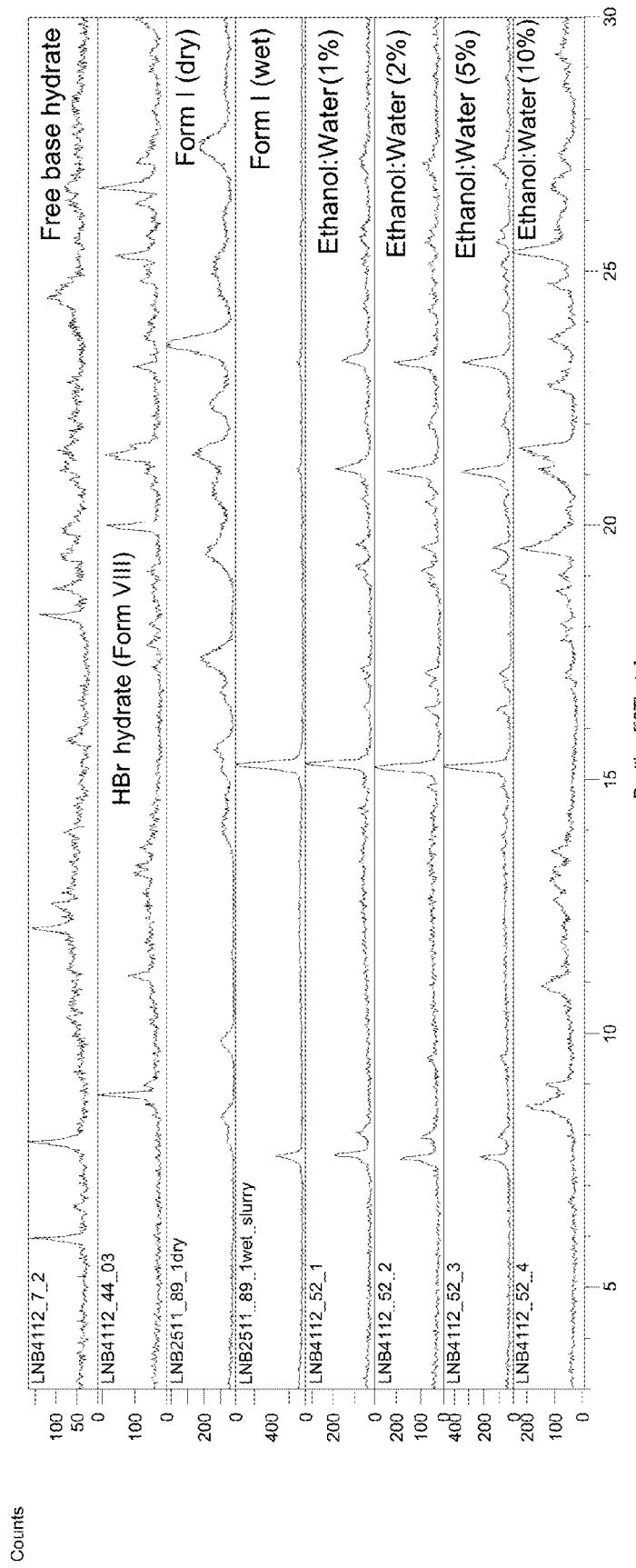
FIG. 84 depicts the XRPD analysis of Form I hydrobromide salt of Compound 1 slurried in EtOH:water mixtures.
Figure 85:
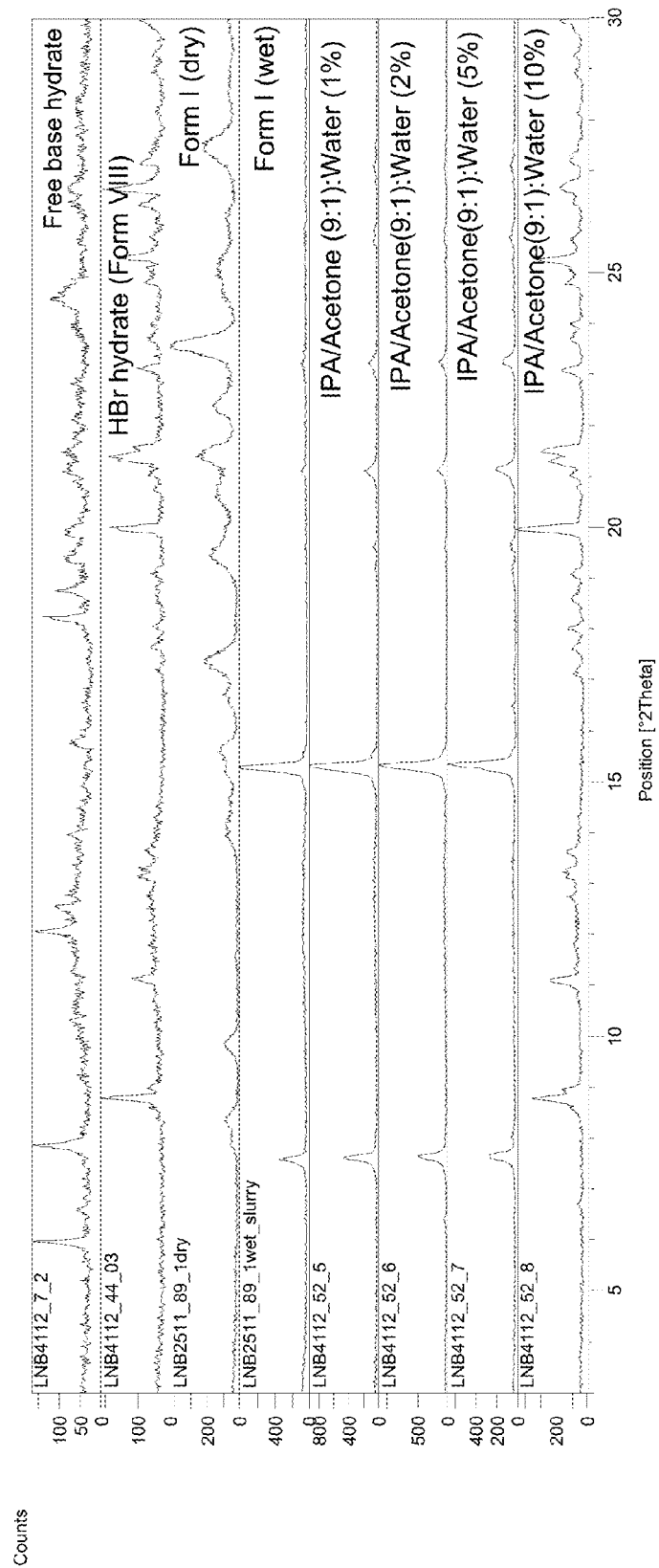
FIG. 85 depicts the XRPD analysis of material slurried in IPA/acetone (9:1):water mixtures.

Following the hydration studies, material was analysed by XRPD to determine whether hydration or disproportionation had occurred at the various water activity levels. XRPD analysis of EtOH:Water samples revealed that, at 1, 2, and 5% water, the resultant diffractograms corresponded with the Form I input HBr salt material. At 10% water, the HBr hydrate was formed. The same pattern emerged for samples slurried in IPA/Acetone (9:1):Water mixtures, where at 1, 2, and 5% water the resultant diffractograms corresponded with the input Form I HBr salt, however, at 10% water, the HBr hydrate was obtained. The diffractograms can be seen in FIG. 84 and FIG. 85.

Hydration Studies at 15° C. and 35° C.

Slurries were created using ca. 200 mg of Form I salt material in 2 mL of the appropriate solvent system. These were stirred at ca. 15° C. and ca. 35° C. for 24 hours. The solvent systems used are listed in Table 19.

TABLE 19

| Solvent Systems for Hydration Studies at 15° C. and 35° C. | |
|---|---|
| Solvent System | Temperature |
| Ethanol:Water (2%) | 35° C. |
| Ethanol:Water (2%) | 15° C. |

TABLE 19-continued

| Solvent Systems for Hydration Studies at 15° C. and 35° C. | |
|---|---|
| Solvent System | Temperature |
| IPA/Acetone (9:1):Water (2%) | 35° C. |
| IPA/Acetone (9:1):Water (2%) | 15° C. |

Figure 86:
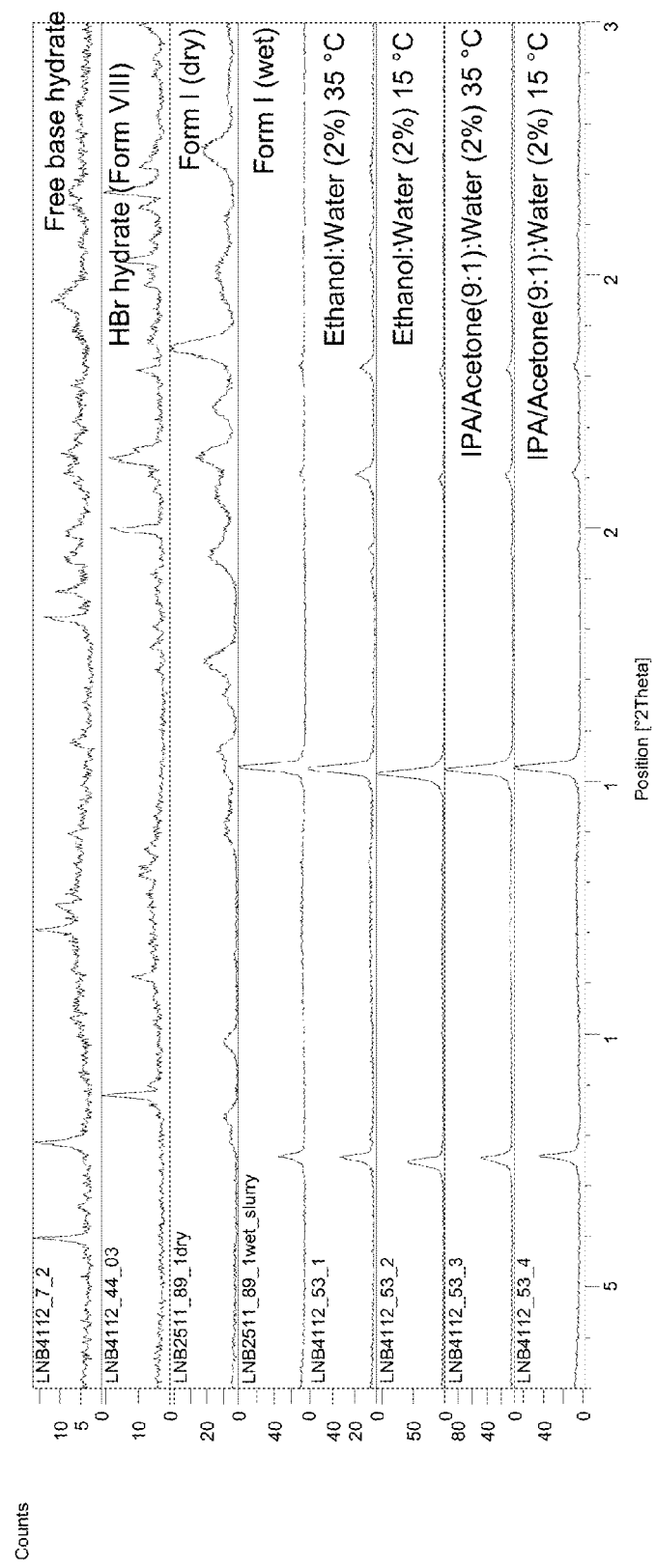
FIG. 86 depicts the XRPD analysis following hydration studies at 15° C. and 35° C.

Following the hydration studies, XRPD analysis of samples revealed that the resultant diffractograms corresponded with the Form I HBr salt and hydration did not occur at the 2% water level. The diffractograms can be seen in FIG. 86.

Figure 87:
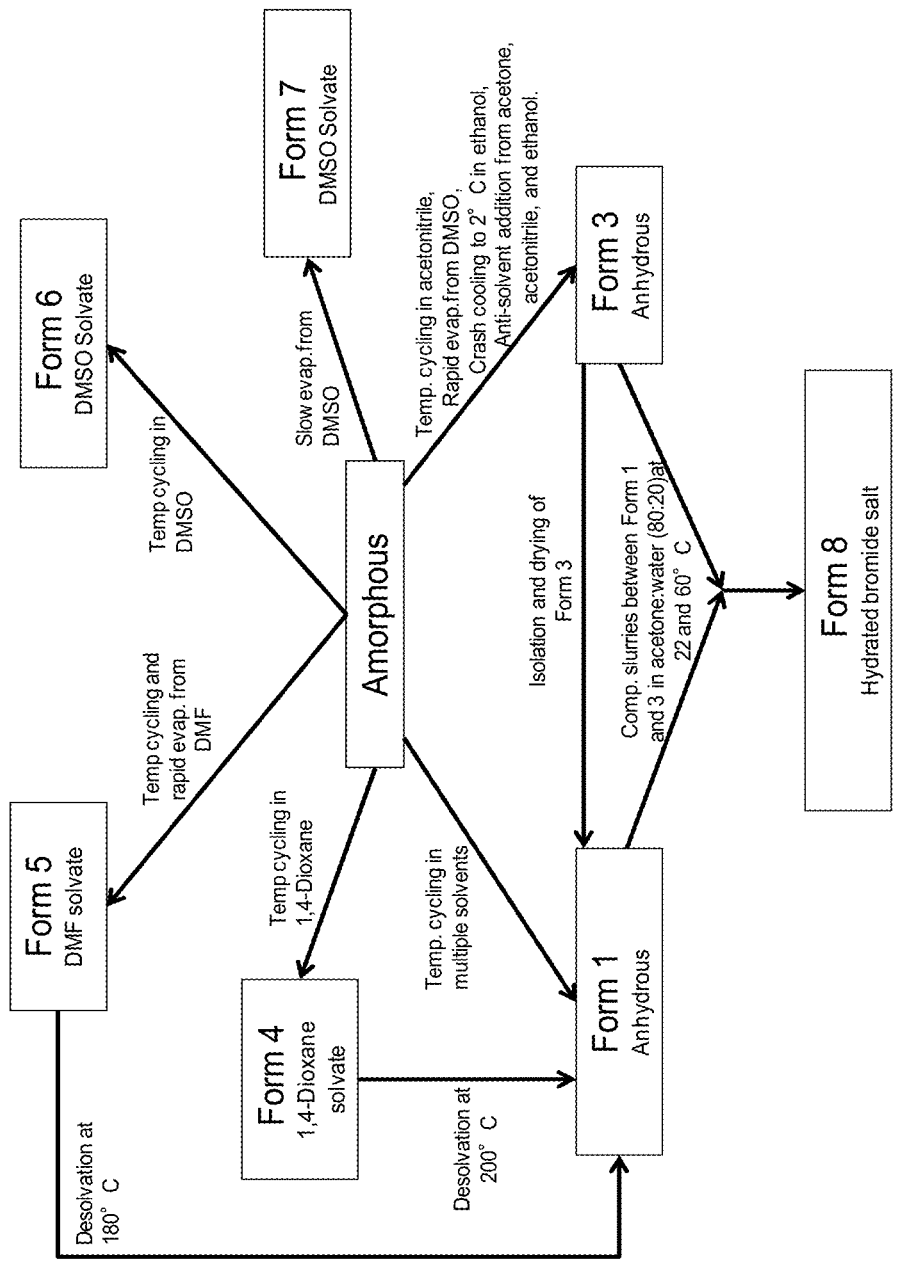
FIG. 87 depicts the form diagram for the hydrobromide salt, including 7 different forms and the relationship between such forms.

The results of the polymorph screen for the hydrobromide salt of compound 1 (compound 2 hydrobromide) is depicted in FIG. 87. Compound 2 hydrobromide exists in eight (8) different solid forms, including amorphous, anhydrous, solvated and hydrated forms. FIG. 87 illustrates the interconversion between several of the identified forms, with Form I exhibiting particular stability under a variety of conditions.

Example 14

Dog PK Study 1

Compound 1 free base and compound 2, as the Form I monohydrobromide (HBr) salt, were evaluated in a crossover dog PK study. Compound 1 free base capsule consisted of compound 1 free base in Vitamin E TPGS and PEG 400 filled into a capsule. The Form I hydrobromide salt capsule consisted of Form I HBr alone filled into a capsule.

Compound 1 free base capsule and Form I HBr capsule were dosed orally at 28.5 and 24.5 mg/kg (as active) QD, respectively, to three fasted male non-naïve beagle dogs (body weight range: 10.1-10.8 kg) with a 5-day washout period. Approximately 5 mL of tap water was orally administered to encourage swallowing and ensure delivery of capsules into the stomach. Plasma samples were collected at pre-dose and 0.5, 1, 2, 4, 6, 8, 12 and 24 hours post dose. The plasma concentrations of compound 1 were determined by a liquid chromatography-tandem mass spectrometry (LC/MS/MS) method. The results are provided in Table 20.

When compound 1 is administered orally to fasted dogs at 24.5-28.5 mg/kg QD, compound 1 exposure (based on AUC and $C_{max}$) is significantly higher when drug is administered as the Form I HBr salt compared to the free base form.

TABLE 20

Mean pharmacokinetic parameters (% CV) of compound 1 in fasted dogs (n = 3) receiving compound 1 (free base) capsule and compound 2 (Form I hydrobromide) capsule orally

| | PK Values (% CV) | |
|---|---|---|
| Dog PK Parameters | Compound 1 (Free Base) Capsule 28.5 mg/kg | Compound 2 (Form I Hydrobromide) Capsule 24.5 mg/kg |
| $C_{max}$ (ng/mL) | 120* | 1420 (47%) |
| $T_{max}$ (h) | 1* (median) | 2 (median) |
| $AUC_{0-24}$ (ng · h/mL) | 278* | 5260 (74%) |
| $T_{1/2}$ (h) | 2.1* | 2.4 |

*Dog #3 had emesis at 30 min post dose. At the 1 h time point, a partial capsule was found under its cage. Thus, data from dog #3 was not included in the calculation of PK parameters.

Example 15

Dog PK Study 2

Compound 1 free base and compound 2, as the Form I monohydrobromide (HBr) salt, were evaluated in a crossover dog PK study in which male dogs were pre-treated with either pentagastrin (to decrease gastric pH) or famotidine (to increase gastric pH) prior to oral dosing to control gastric pH. In addition, the effect of food on the systemic exposure to compound 1 was also evaluated in dogs receiving Form I HBr with pentagastrin pre-treatment. Compound 1 free base capsule consisted of compound 1 free base in Vitamin E TPGS and PEG 400 filled into a capsule. The Form I hydrobromide salt capsule consisted of Form I HBr alone filled into a capsule.

Compound 1 free base and Form I HBr capsules were dosed orally at 30 mg/kg (as active) QD to three non-naïve male beagle dogs (body weight range: 9.6-10.5 kg) that were treated prior to dosing with 1) pentagastrin and fasted, 2) famotidine and fasted, or 3) pentagastrin and fed. There was a minimum 6-day washout between dosing. On the day of dosing under fed condition, dogs were given 60 gram of a high fat diet (Harlan Teklad 2027C) and allowed to consume all of the food within 15-20 minutes. The animals were given a 10-minute rest period and then the capsule doses were administered. Plasma samples were collected at pre-dose and 0.5, 1, 2, 4, 6, 8, 12 and 24 hours post dose. The results are provided in Table 21.

When compound 1 was administered orally to dogs at 30 mg/kg QD, compound 1 exposure was significantly higher when drug is administered as the HBr salt compared to the free base form under both low and high gastric pH conditions. In dogs receiving the free base capsules under high gastric pH condition, a 32- to 48-fold reduction in compound 1 exposure was observed compared to that under low pH condition. The effect of varying gastric pH on the systemic exposure to compound 1, measured as $C_{max}$ and AUC, was greatly minimized when Form I HBr was administered. Administering Form I HBr with food resulted in an increase in $C_{max}$ and AUC of compound 1 in dogs.

TABLE 21

Mean pharmacokinetic parameters (% CV) of compound 1 in dogs (n = 3) receiving compound 1 (free base) capsule and compound 2 (Form I hydrobromide) capsule orally following gastric pH adjustment treatment

| | PK Values (% CV) | | | |
|---|---|---|---|---|
| | Compound 1 (Free Base) Capsule | | Compound 2 (Form I Hydrobromide) Capsule | |
| Treatment of Dogs Prior to Dosing | $C_{max}$ (ng/mL) | $AUC_{0-24}$ (ng · h/mL) | $C_{max}$ (ng/mL) | $AUC_{0-24}$ (ng · h/mL) |
| Pentagastrin, fasted | 1820 (20%) | 7810 (73%) | 2860 (39%) | 9450 (31%) |
| Famotidine, fasted | 57 (24%) | 163 (3%) | 1180 (20%) | 4010 (54%) |
| Pentagastrin, fed | Not Dosed | Not Dosed | 3970 (28%) | 13900 (26%) |

Example 16

Administration to Healthy Volunteers

The primary objective of the study is to compare the compound 1 pharmacokinetic (PK) profiles of single doses of Form I monohydrobromide formulations with that of the compound 1 free base in healthy adult males.

This is a single centre non-randomised, open-label, single dose study in healthy male subjects. Subjects will be screened for eligibility to participate in the study up to 28 days before dosing. The subjects will be admitted to the clinical unit at approximately 09:00 in the morning on the day prior to dosing (Day-1) and will remain on site until 24 h after each dose. Each subject will attend a follow-up visit 4 to 6 days after the final dose.

One group of 12 subjects will be dosed in an effort to obtain the data described above. Each subject will receive the following formulations in a crossover investigation. Dosing will be separated by at least 7 days.

Regimen A: 150 mg compound 1 (free base) capsule
Regimen B: 50 mg as active compound 2 (Form I HBr) tablet formulation
Regimen C: ≤150 mg as active compound 2 (Form I HBr) tablet formulation All formulations will be dosed in the morning, following an overnight fast. Subjects will be allowed water up to 2 h before the scheduled dosing time and will be provided with 240 mL of water at 2 h post-dose. Decaffeinated fluids will be allowed ad libitum from lunch time on the day of dosing.

If, for technical reasons, dosing is delayed for more than 2 h beyond the expected dosing time, subjects will receive 200 mL of Lucozade Sport at the originally scheduled dosing time, or earlier if possible.

Subjects will be provided with a light snack and then fast from all food and drink (except water) for a minimum of 8 h on the day prior to dosing until approximately 4 h post-dose at which time lunch will be provided. An evening meal will be provided at approximately 9 h post-dose and an evening snack at approximately 14 h post-dose. On subsequent days, meals will be provided at appropriate times.

Venous blood samples will be withdrawn via an indwelling cannula or by venepuncture at the following times after dosing (hours): 0.5, 1, 1.5, 2, 4, 8, and 12.

The primary endpoint of the study is to compare the PK profiles of a formulation of Form I HBr with that of compound 1 as a free base by measuring the following parameters: $T_{lag}$, $C_{max}$, $T_{max}$, $AUC_{(0-last)}$, $AUC_{(0-inf)}$, $AUC_{\% \, extrap}$, $F_{rel}$, lambda-z, $T_{1/2}$el. The secondary endpoint of the study is to collect information about the safety and tolerability of compound 1 (free base) and compound 2 (Form I HBr salt) by assessing: physical examinations, safety laboratory tests, vital signs, electrocardiograms (ECGs), body temperature and AEs.

Plasma concentration data will be tabulated and plotted for each subject for whom concentrations are quantifiable. PK analysis of the concentration time data obtained will be performed using appropriate non-compartmental techniques to obtain estimates of the following PK parameters (where relevant).

$T_{lag}$ the sampling time before the first quantifiable concentration of compound 1 in a concentration vs time profile $C_{max}$ the maximum observed plasma concentration $T_{max}$ the time from dosing at which $C_{max}$ occurs $AUC_{(0-last)}$ the area under the concentration vs time curve from time zero to the last measured time point $AUC_{(0-inf)}$ the area under the concentration vs time curve from time zero extrapolated to infinity $AUC_{\% \, extrap}$ the percentage of $AUC_{(0-inf)}$ accounted for by extrapolation $AUC_{(0-tau)}$ the area under the concentration vs time curve within the dosing interval, estimated using the [linear or linear/log down] trapezoidal rule $AUC_{(0-24)}$ the area under the concentration vs time curve from time zero to 24 hour post morning dose RA relative accumulation $F_{rel}$ relative bioavailability of the test formulations compared with the reference formulation eg Regimens B, or C (test) compared with Regimen A (reference)

lambda-z slope of the regression line passing through the apparent elimination phase in a concentration vs time plot $T_{1/2}$el the apparent elimination half-life Assessment of dose proportionality, as appropriate eg $C_{max}$/D; AUC/D The initial 50 mg HBr dose selected for Regimen B (determined by AUC) is anticipated to be that which is expected to give a similar exposure to the 150 mg free base. This dose is also expected to provide less patient-to-patient variability.

There will be an interim analysis after completion of Regimens A and B during which the safety, tolerability and PK data will be reviewed. These data will be used to assess whether dose adjustment is needed. For dose selection to proceed, safety data from a minimum of 8 evaluable subjects (defined as subjects who have received study drug and have completed all safety assessments up to 24 h) in a group must be available for review. The dose selected for Regimen C will be that which is expected to give a similar exposure to the 150 mg free base. However, if the 50 mg HBr dose used in Regimen B exceeds the exposure of the 150 mg free base, and is well tolerated and within the limits defined within the protocol, Regimen C will not occur.

If the dose is changed, the Form I HBr formulation will be dosed again at the revised dose (Regimen C). There will then follow a further period of interim analysis to confirm that the Regimen C dose provides either, 1) a lower active dose as compared to Regimen A that provides an equivalent or higher exposure and/or provide less patient-to-patient variability, or 2) an active dose similar to that of Regimen A with a higher exposure and/or provide less patient-to-patient variability.

We claim:

1. A composition comprising Compound 2:

[Chemical structure of Compound 2] · (X)$_n$ wherein:
n is 1 or 2;
X is hydrobromic acid, benzenesulfonic acid, camphor sulfonic acid, 1,2-ethane disulfonic acid, hydrochloric acid, maleic acid, methanesulfonic acid, naphthalene-2-sulfonic acid, 1,5-naphthalene disulfonic acid, oxalic acid, 4-toluenesulfonic acid or 2,4,6-trihydroxybenzoic acid; and
wherein the composition is substantially free of impurities.

2. The composition of claim 1, wherein the composition comprises at least about 90% by weight of Compound 2.

3. The composition of claim 2, wherein the composition comprises at least about 95% by weight of Compound 2.

4. The composition of claim 3, wherein the composition comprises at least about 97% by weight of Compound 2.

5. The composition of claim 4, wherein the composition comprises at least about 98% by weight of Compound 2.

6. The composition of claim 5, wherein the composition comprises at least about 99% by weight of Compound 2.

7. The composition of claim 1, wherein the composition contains no more than 5.0 area percent HPLC of total organic impurities relative to the total area of an HPLC chromatogram of Compound 2.

8. The composition of claim 7, wherein the composition contains no more than 3.0 area percent HPLC of total organic impurities relative to the total area of an HPLC chromatogram of Compound 2.

9. The composition of claim 8, wherein the composition contains no more than 1.5 area percent HPLC of total organic impurities relative to the total area of an HPLC chromatogram of Compound 2.

10. The composition of claim 9, wherein the composition contains no more than 1.0 area percent HPLC of total organic impurities relative to the total area of an HPLC chromatogram of Compound 2.

11. The composition of claim 1, wherein X is hydrobromic acid.

12. A composition comprising Compound 2:

[Chemical structure of Compound 2] · (X)$_n$ wherein:
n is 1 or 2;
X is hydrobromic acid, benzenesulfonic acid, camphor sulfonic acid, 1,2-ethane disulfonic acid, hydrochloric acid, maleic acid, methanesulfonic acid, naphthalene-2-sulfonic acid, 1,5-naphthalene disulfonic acid, oxalic acid, 4-toluenesulfonic acid or 2,4,6-trihydroxybenzoic acid; and
wherein Compound 2 is a crystalline solid substantially free of an amorphous form of Compound 2.

13. The composition of claim 12, wherein Compound 2 is at least 90% crystalline.

14. The composition of claim 13, wherein Compound 2 is at least 95% crystalline.

15. The composition of claim 14, wherein Compound 2 is at least 97% crystalline.

16. The composition of claim 15, wherein Compound 2 is at least 98% crystalline.

17. The composition of claim 16, wherein Compound 2 is at least 99% crystalline.

18. The composition of claim 12, wherein X is hydrobromic acid.

19. A composition comprising Compound 2:

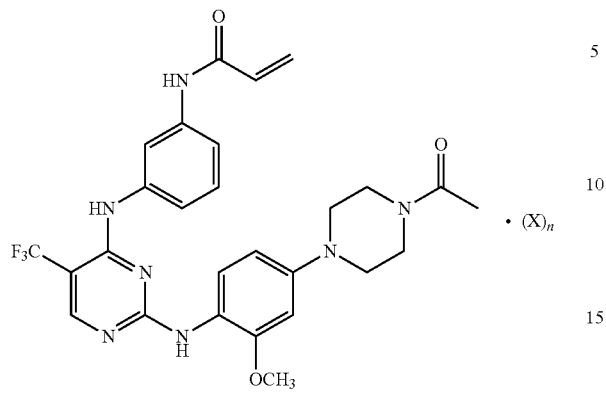

· (X)$_n$ wherein:
  n is 1 or 2;
  X is hydrobromic acid, benzenesulfonic acid, camphor sulfonic acid, 1,2-ethane disulfonic acid, hydrochloric acid, maleic acid, methanesulfonic acid, naphthalene-2-sulfonic acid, 1,5-naphthalene disulfonic acid, oxalic acid, 4-toluenesulfonic acid or 2,4,6-trihydroxybenzoic acid; and
a pharmaceutically acceptable carrier, adjuvant, or vehicle.

20. The composition of claim 19, wherein X is hydrobromic acid.

* * * * *